US007776577B2

(12) United States Patent
Kapeller-Libermann et al.

(10) Patent No.: US 7,776,577 B2
(45) Date of Patent: Aug. 17, 2010

(54) UBIQUITIN PROTEASE

(75) Inventors: Rosanna Kapeller-Libermann, Chestnut Hill, MA (US); John J. Hunter, Newton, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/316,681

(22) Filed: Dec. 16, 2008

(65) Prior Publication Data

US 2009/0269350 A1 Oct. 29, 2009

Related U.S. Application Data

(60) Division of application No. 11/313,836, filed on Dec. 21, 2005, now Pat. No. 7,482,147, which is a division of application No. 10/426,776, filed on Apr. 30, 2003, now Pat. No. 7,029,895, which is a continuation-in-part of application No. 10/229,662, filed on Aug. 28, 2002, now Pat. No. 7,060,476, which is a division of application No. 09/795,691, filed on Feb. 28, 2001, now Pat. No. 6,465,230, said application No. 10/229, 662 is a continuation-in-part of application No. 10/105,992, filed on Mar. 25, 2002, now abandoned, which is a continuation of application No. 09/406,045, filed on Sep. 27, 1999, now Pat. No. 6,451,994, said application No. 10/229,662 is a continuation-in-part of application No. 10/314,881, filed on Dec. 9, 2002, which is a continuation of application No. 09/773,426, filed on Jan. 31, 2001, which is a continuation-in-part of application No. 09/495,823, filed on Jan. 31, 2000, said application No. 10/229,662 is a continuation-in-part of application No. 09/692,785, filed on Oct. 20, 2000, now abandoned, said application No. 10/229, 662 is a continuation-in-part of application No. 10/284,014, filed on Oct. 30, 2002, said application No. 10/229,662 is a continuation-in-part of application No. 10/284,059, filed on Oct. 30, 2002.

(60) Provisional application No. 60/335,037, filed on Oct. 31, 2001, provisional application No. 60/335,003, filed on Oct. 31, 2001, provisional application No. 60/185,517, filed on Feb. 28, 2000, provisional application No. 60/161,188, filed on Oct. 22, 1999.

(51) Int. Cl.

| | |
|---|---|
| ***C12N 9/48*** | (2006.01) |
| ***C12P 21/04*** | (2006.01) |
| ***C12Q 1/00*** | (2006.01) |
| ***C12Q 1/37*** | (2006.01) |
| ***A01N 25/00*** | (2006.01) |
| *C07H 21/04* | (2006.01) |
| *C12Q 1/68* | (2006.01) |
| *C12N 15/00* | (2006.01) |
| *C12N 1/20* | (2006.01) |

(52) U.S. Cl. .............................. 435/212; 435/4; 435/6; 435/69.1; 435/71.1; 435/23; 435/252.3; 435/320.1; 514/789; 536/23.2

(58) Field of Classification Search ...................... None
See application file for complete search history.

(56) References Cited

FOREIGN PATENT DOCUMENTS

| | | |
|---|---|---|
| WO | WO 00/01817 | 1/2000 |
| WO | WO 00/28033 | 5/2000 |
| WO | WO 00/28033 A2 | 5/2000 |
| WO | WO 00/58473 A2 | 10/2000 |

OTHER PUBLICATIONS

Henchoz, et al., *Molecular and Cellular Biology*, vol. 16, No. 10, (Oct. 1996), pp. 5717-5725.
Hershko, et al., *Annual Review in Biochemistry*, vol. 67, (1998), pp. 425-479.
Wall, et al., *Journal of Dairy Science*, vol. 80, (1997), pp. 2213-2224.
Hammer, et al., *Journal of Animal Science*, vol. 63, (1986), pp. 269-278.
Verma, et al., *Nature*, vol. 389, (Sep. 1997), pp. 239-242.
Anderson, W., *Nature*, vol. 392, (Apr. 1998), pp. 25-30.
Schwer, Heinz, et al., "Cloning and Characterization of a Novel Human Ubiquitin-Specific Protease, A Homologue of Murine UBP43 (Usp18)," *Genomics*, vol. 65, No. 1, (Apr. 1, 2000), pp. 44-52.
Li, Xiao-Ling, et al., "RNase L-Dependent Destabilization of Interferon-Induced mRNAs: A Role for the 2-5A System in Attenuation of the Interferon Response," *The Journal of Biological Chemistry*, vol. 275, No. 12, (Mar. 24, 2000), pp. 8880-8888.
Zhu, et al., "DUB-2 Is a Member of a Novel Family of Cytokine-Inducible Deubiquitinating Enzymes," *The Journal of Biological Chemistry*, vol. 272, No. 1, (1997), pp. 51-57.
Jensen, et al., "BAP1: A Novel Ubiquitin Hydrolase Which Binds to the BRCA1 Ring Finger and Enhances BRCA1-Mediated Cell Growth Suppression," *Oncogene*, vol. 16, (1998), pp. 1097-1112.
Lucero, et al., "Catabolite Inactivation of the Yeast Maltose Transporter Requires Ubiquitin-Ligase npil/rsp5 and Ubiquitin-Hydrolase npi2/doa4," *FEMS Microbiology Letters*, vol. 147, (1997), pp. 273-277.
Swanson, et al., "A Ubiquitin C-Terminal Hydrolasse Gene on the Proximal Short Arm of the X Chromosome: Implications for X-Linked Retinal Disorders," *Human Molecular Genetics*, vol. 5, No. 4, (1996), pp. 533-538.

(Continued)

*Primary Examiner*—Yong D Pak

(57) ABSTRACT

The invention provides isolated nucleic acids molecules and proteins, designated 27411, 23413, 22438, 23553, 25278, 26212, NARC SC1, NARC 10A, NARC 1, NARC 12, NARC 13, NARC17, NARC 25, NARC 3, NARC 4, NARC 7, NARC 8, NARC 11, NARC 14A, NARC 15, NARC 16, NARC 19, NARC 20, NARC 26, NARC 27, NARC 28, NARC 30, NARC 5, NARC 6, NARC 9, NARC 10C, NARC 8B, NARC 9, NARC2A, NARC 16B, NARC 1C, NARC 1A, NARC 25, 86604 and 32222 nucleic acid molecules and proteins. The invention also provides antisense nucleic acid molecules, recombinant expression vectors containing said nucleic acid molecules, host cells into which the expression vectors have been introduced, nonhuman transgenic animals in which a said genes have been introduced or disrupted, fusion proteins, antigenic peptides and antibodies to said proteins. Diagnostic and therapeutic methods utilizing compositions of the invention are also provided.

5 Claims, No Drawings

OTHER PUBLICATIONS

Branden, Carl et al., "Introduction to Protein Structure," *Garland Publishing, Inc., New York*, (1991), pp. 247.

Li, X.L.. et al., "*Homo sapiens* Ubiquitin-specific protease ISG43 (ISG43) mRNA, complete cds.," Aug. 17, 1999, (sequence), EMBL Database [online], Hinxton, Cambridge, U.K., European Bioinformatics Institute, [retrieved on Feb. 9, 2010]. Retrieved from the Internet: URL: http://www.ebi.ac.uk/embl/>, EMBL Accession No. AF176642.

UBIQUITIN PROTEASE

RELATED APPLICATIONS

The present application is a divisional of U.S. patent application Ser. No. 11/313,836, filed Dec. 21, 2005, now U.S. Pat. No. 7,482,147, which is a divisional of U.S. patent application Ser. No. 10/426,776, filed Apr. 30, 2003, now U.S. Pat. No. 7,029,895, which is a continuation-in-part of U.S. patent application Ser. No. 10/229,662, filed Aug. 28, 2002, now U.S. Pat. No. 7,060,476, which is a divisional of U.S. patent application Ser. No. 09/795,691, filed Feb. 28, 2001, now U.S. Pat. No. 6,465,230, which claims the benefit of Provisional Application Ser. No. 60/185,517, filed Feb. 28, 2000 (abandoned). U.S. patent application Ser. No. 10/426,776 is also a continuation-in-part of U.S. patent application Ser. No. 10/105,992, filed Mar. 25, 2002 (abandoned), which is a continuation of U.S. patent application Ser. No. 09/406,045, filed Sep. 27, 1999, now U.S. Pat. No. 6,451,994. U.S. patent application Ser. No. 10/426,776 is also a continuation-in-part of U.S. patent application Ser. No. 10/314,881, filed Dec. 9, 2002, now U.S. Pat. No. 6,767,727, which is a continuation of U.S. patent application Ser. No. 09/773,426, filed Jan. 31, 2001, now U.S. Pat. No. 6,534,302, which is a continuation-in-part of U.S. patent application Ser. No. 09/495,823, filed Jan. 31, 2000, now U.S. Pat. No. 6,780,627. U.S. patent application Ser. No. 10/426,776 is also a continuation-in-part of U.S. patent application Ser. No. 09/692,785, filed Oct. 20, 2000 (abandoned), which claims the benefit of U.S. Provisional Application Ser. No. 60/161,188, filed Oct. 22, 1999 (abandoned). U.S. patent application Ser. No. 10/426,776 is also a continuation-in-part of U.S. patent application Ser. No. 10/284,014, filed Oct. 30, 2002 (abandoned), which claims the benefit of U.S. Provisional Application Ser. No. 60/335,003, filed Oct. 31, 2001 (abandoned). U.S. patent application Ser. No. 10/426,776 is also a continuation-in-part of U.S. patent application Ser. No. 10/284,059, filed Oct. 30, 2002 (abandoned), which claims the benefit of U.S. Provisional Application Ser. No. 60/335,037, filed Oct. 31, 2001 (abandoned). The entire contents of each of the above-referenced patent applications are incorporated herein by this reference.

INDEX

| Chapter | Page | Title |
|---|---|---|
| I. | 2 | 27411, A NOVEL HUMAN PGP SYNTHASE |
| II. | 88 | 23413, A NOVEL HUMAN UBIQUITIN PROTEASE |
| III. | 155 | 22438, 23553, 25278, AND 26212 NOVEL HUMAN SULFATASES |
| IV. | 239 | NUCLEIC ACID MOLECULES DERIVED FROM RAT BRAIN AND PROGRAMMED CELL DEATH MODELS |
| V. | 339 | METHODS AND COMPOSITIONS FOR THE DIAGNOSIS AND TREATMENT OF CELLULAR PROLIFERATION DISORDERS USING 86604 |
| VII. | 414 | METHODS AND COMPOSITIONS FOR THE TREATMENT AND DIAGNOSIS OF CELLULAR PROLIFERATIVE DISORDERS USING 32222 |

I. 27411, A NOVEL HUMAN PGP SYNTHASE

Background of the Invention

Cardiolipin is a dimeric phospholipid which plays an important role in mitochondrial biogenesis and function. It is required for activity of several mitochondrial enzymes and possibly for the transport of proteins into the mitochondria in eukaryotes (Minskoff, S. et al. (1997) Biochimica et Biophysica Acta 1348: 187-191). Cardiolipin appears to be involved either directly or indirectly, in the modulation of a number of cellular processes including the activation of mitochondrial enzymes and the production of energy by oxidative phosphorylation (Hatch, G. (1998) International J. of Mol. Medicine. 1: 33-41).

Cardiolipin is found in animals, plants, and fungi. In mammals it is found exclusively in mitochondria. Cardiolipin is the principal polyglycerophospholipid found in the heart and most mammalian tissues (Hatch, G. (1998) International J. of Molec. Medicine 1:33-41). The biosynthetic pathway of cardiolipin has been well studied in yeasts. The first enzyme in the cardiolipin biosynthetic pathway is phosphatidylglycerolphosphate synthase (PGP synthase). PGP synthase is a key enzyme in the pathway as it catalyzes the committed first step in the pathway.

The biosynthesis of cardiolipin occurs in 3 enzymatic steps. In the first step, PGP synthase catalyzes the formation of phosphatidylglycerolphosphate (PGP) from phosphatidyl-CMP (CDP-diacylglycerol, CDP-DG) and glycerol 3-phosphate. PGP is then dephosphorylated to phosphatidylglycerol (PG) by PGP phosphatase. Finally, in eukaryotes cardiolipin is synthesized from PG and another molecule of CDP-DG in a reaction catalyzed by cardiolipin synthase.

Cardiolipin appears to be essential for the function of several enzymes of oxidative phosphorylation. (Hatch, G. (1996) Molecular and Cellular Biochemistry 159:139-148). Also, cardiolipin has been implicated in the role of many enzymatic activities, including but not limited to: (1) cytochrome c oxidase, (2) carnitine acylcarnitine translocase, (3) mitochondrial protein import, and (4) binding of matrix Ca+2 (Kawasaki, K. (1999) J. of Biological Chemistry, Vol. 274, No. 3, 1828-1834). There must be stringent levels of control of the enzymes involved in cardiolipin metabolism in the heart in order to maintain the appropriate content and molecular species composition of the phospholipid. The maintenance of cardiolipin content and molecular composition in cardiac mitochondria is essential for proper cardiac function (Hatch, G. (1998) International J. of Mol. Medicine. 1:33-41).

Phosphatidylglycerol (PG) and cardiolipin (CL) are the most widely distributed glycerophosphatides in the membrane lipids of animals, plants and microbes (Hostletler, K. Y. (1982) in Phospholipids (Hawthorne and Ansell, eds) pp. 215-261, Elsevier/North Holland Biomedical Press, Amsterdam).

PG is localized in many intracellular locations as a component of phospholipids, representing less than 1% of total lipid phosphorous, except in the lung where it represents about 10% of the total phospholipids (Mason, R. J. et al., (1980) Biochim. Biophys. Acta 617: 36-50). PG serves as an important component of the pulmonary surfactant in the lung (Ohtsuka et al., (1993) J. Biol. Chem. Vol. 268:22908-22913). CL is localized primarily in the mitochondria and appears to be essential for the function of several enzymes of oxidative phosphorylation. CL is essential for production of energy for the heart to beat (Hatch, G. M. (1996) Molecular and Cellular Biochemistry, 159: 139-148).

PGP synthase has been extensively studied and characterized in two evolutionarily divergent yeasts, *Saccharomyces cerevisiae* and *Schizosaccharomyces pombe*. PGP synthase has been purified to homogeneity from *S. pombe* (Minskoff, S. et al. (1997) Biochimica et Biophysica Acta 1348: 187-191). In contrast to the second and third enzymes of the cardiolipin biosynthetic pathway, PGP synthase activity is highly regulated both by cross-pathway control and by factors affecting mitochondrial development.

PGP synthase has been shown to be controlled by two sets of factors: cross-pathway control and factors affecting mitochondrial development. Cross-pathway control of phosphatidylinositol and phosphatidylcholine control is characterized by three parameters. First, the availability of the water-soluble phospholipid precursor inositol controls expression of phospholipid biosynthetic enzymes. Second, inositol repression of phospholipid biosynthesis occurs only if cells can synthesize phosphatidyl-choline. Third, inositol repression is mediated by the INO2-INO4-OPI1 regulatory genes. PGP synthase is regulated by inositol. However, it is not subject to control by the INO2-INO4-OPI1 regulatory genes. PGP synthase activity is decreased 3-5 fold in *Saccharomyces cerevisiae* cells grown in the presence of inositol (Greenberg, M. L. et al., (1988) Mol. Cell. Biol. 8: 4773-4779).

PGP synthase is commonly referred to as glycerophosphate phosphatidyl-transferase (E.C. 2.7.8.5). It catalyzes a substituted phospho group transfer. The natural substrate of the enzyme is CDP-1,2-diacyl-sn-glycerol and glycerol 3-phosphate (involved in the synthesis of phosphatidylglycerol). Different cofactors and prosthetic groups which have been shown to be important for maximal PGP synthase activity include, but are not limited to: Triton X-100, phosphatidylethanolamine and phosphatidylinositol. Different metal/salts which have been shown to be important for PGP synthase activity include, but are not limited to: Mn+2, Mg+2, Ca+2, Co+2, and Ba+2.

PGP synthases in two different yeasts (*S. cerevisiae* and *S. pombe*) were found to be sensitive to thioreactive compounds and have a requirement for divalent cations (Minskoff, S. et al. (1997) Biochimica et Biophysica Acta 1348:187-191).

Inhibitors of PGP synthase have been shown to include, but are not limited to: liponucleotide, CDPdiacylglycerol, glycerol 3-phosphate, thioreactive agents, calcium, inositol, Triton X-100, magnesium, cadmium, zinc, copper, and mercury. As one example, PGP synthase activity was shown to decrease 3 to 5 fold in *S. cerevisiae* cells grown in the presence of inositol.

PGP synthase activity can be assayed by determining the conversion of [14C(U)]glycerol 3-phosphate to phosphatidyl [14C(U)]glycerol 3-phosphate as described by Cao et al. (Cao et al. (1994) LIPIDS, Vol. 29, no. 7, pp.475-480).

Chinese hamster ovary (CHO) cells defective in PGP synthase production have been studied to better elucidate the role of the enzyme in the biosynthesis of PG and CL (Ohtsuka, T. et al., (1993) J. Biol. Chem. Vol. 268, No. 30, pp. 22908-22913). Ohtsuka et al. developed a rapid autoradiographic screening assay for detecting PGP synthase activity in the lysates of Chinese hamster ovary cell colonies immobilized on polyester, as described by Raetz et al. (Raetz et al., (1982) Proc. Natl. Acad. Sci. U.S.A. 79: 3223-3227). The Ohtsuka study confirmed the role of PGP synthase in the biosynthesis of PG and its essential role in the growth of CHO cells. The results provided direct evidence for the formation of PG in vivo and that PG is a major metabolic precursor for the biosynthesis of cellular CL.

Recent research has focused on the generation of a PGP-synthase defective mutant in CHO-K1 cells (Kawasaki, K. et al. (1999) J. Biol. Chem. Vol. 274:1828-1834). Kawasaki et al. isolated a Chinese hamster ovary (CHO) cDNA encoding a putative protein similar in sequence to the yeast PGS1 gene product, PGP synthase. The CHO PGS1 cDNA encoded a protein having high amino acid homology with the yeast PGS1. Transfection of CHO-K1 cells with CHO PGS1 cDNA in *E. coli* resulted in a highly elevated PGP synthase activity level. Moreover, when the CHO PGS1 was introduced into a mutant PGS-S (a temperature-sensitive mutant defective in PGP synthase), the mutant recovered normal biosynthesis and cellular content of PG and CL. The results demonstrated the CHO PGS1 cDNA encodes a PGP synthase. (Kawasaki, K. et al. (1999) J. Biol. Chem. Vol. 274, No. 3, pp. 1828-1834). The cloned CHO PGS1 cDNA was able to complement the mitochondrial defect as well as the biosynthetic defects in CL and PG biosynthesis.

Moreover, there is an apparent difference in the molecular mechanisms of the PGP synthases between eukaryotic and prokaryotic organisms. The eukaryotic PGP synthases most likely utilize a ping-pong reaction mechanism, in contrast to the prokaryotic PGP synthases that employ a bi-bi reaction mechanism (Dryden, S. (1996) J. Bacteriol. 178: 1030-1038). PGP synthase is an essential enzyme in bacteria (Heacock, P. N. et al., (1987) J. Biol. Chem. 262:13044-13049). Presumably, this difference in reaction mechanism between eukaryotic and prokaryotic PGP synthases might represent a target for antibacterial agents (Kawasaki, K. et al. (1999) J. Biol. Chem. Vol. 274, No. 3, pp. 1828-1$^{834}$).

PGP synthases are important as relates to cardiolipin metabolism in aging and thyroid dysfunction. Aging and hypothyroidism are two conditions associated with mitochondrial dysfunction and cardiolipin deficiency. (Schlame, M. et al., (1997) Biochimica et Biophysica Acta, 1348:207-213). In both cases, mitochondrial cardiolipin deficiency could be correlated with a decrease in metabolite transport activity across mitochondrial membrane. As relates to the aging process, it has been suggested that cardiolipin deficiency is the cause of reduced metabolite transport due to changes in the membrane environment of the carrier proteins (Paradies et al. (1992) Biochim. Biophys. Acta 1103: 324-326).

Conversely, hyperthyroidism is characterized by mitochondria with increased cardiolipin content and increased metabolite transport activities (Paradies (1990) Biochim. Biophys. Acta 1019:133-136). Thyroxine is a well-known stimulator of mitochondrial biogenesis; it is known to increase the number of mitochondria as well as enhance their performance.

Accordingly, PGP synthases are a major target for drug action and development. Accordingly, it is valuable to the field of pharmaceutical development to identify and characterize novel PGP synthases and tissues and disorders in which PGP synthases are differentially expressed. The present invention advances the state of the art by providing a novel human PGP synthase and tissues and disorders in which expression of the human PGP synthase is relevant. Accordingly, the invention provides methods directed to expression of the PGP synthase.

SUMMARY OF INVENTION

It is an object of the invention to identify a novel PGP synthase.

It is a further object of the invention to provide novel PGP synthase polypeptides that are useful as reagents or targets in assays applicable to treatment and diagnosis of PGP synthase-mediated or -related disorders.

It is a further object of the invention to provide polynucleotides corresponding to the novel PGP synthase polypeptides that are useful as targets and reagents in PGP synthase assays applicable to treatment and diagnosis of PGP synthase-mediated or -related disorders and useful for producing novel PGP synthase polypeptides by recombinant methods.

A specific object of the invention is to identify compounds that act as agonists and antagonists and modulate the expression of the novel PGP synthase.

A further specific object of the invention is to provide compounds that modulate expression of the PGP synthase for treatment and diagnosis of PGP synthase-related disorders.

The invention is thus based on the identification of a novel human PGP synthase. The amino acid sequence for PGP synthase is shown in SEQ ID NO:2. The nucleotide sequence for PGP synthase is shown in SEQ ID NO:1.

The invention provides isolated PGP synthase polypeptides, including a polypeptide having the amino acid sequence shown in SEQ ID NO:2, or the amino acid sequences encoded by the cDNAs deposited as Patent Deposit Nos. PTA-2011 and PTA-2340.

The invention also provides isolated PGP synthase nucleic acid molecules having the sequence shown in SEQ ID NO:1, SEQ ID NO:3, or in the deposited cDNAs.

The invention also provides variant polypeptides having an amino acid sequence that is substantially homologous to the amino acid sequence shown in SEQ ID NO:2 or encoded by the deposited cDNAs.

The invention also provides variant nucleic acid sequences that are substantially homologous to the nucleotide sequence shown in SEQ ID NO:1 or in the deposited cDNAs.

The invention also provides fragments of the polypeptides shown in SEQ ID NO:2 and nucleotide sequence shown in SEQ ID NO:1 as well as substantially homologous fragments of the polypeptides or nucleic acids.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the PGP synthase nucleic acid molecules and polypeptides, and particularly recombinant vectors and host cells.

The invention also provides methods of making the vectors and host cells and methods for using them to produce the PGP synthase nucleic acid molecules and polypeptides.

The invention also provides antibodies or antigen-binding fragments thereof that selectively bind the PGP synthase polypeptides and fragments.

The invention also provides methods of screening for compounds that modulate expression or activity of the PGP synthase polypeptides or nucleic acid (RNA or DNA).

The invention also provides a process for modulating PGP synthase polypeptide or nucleic acid expression or activity, especially using the screened compounds. Modulation may be used to treat conditions related to aberrant activity or expression of the PGP synthase polypeptides or nucleic acids.

The invention also provides assays for determining the activity of or the presence or absence of the PGP synthase polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DETAILED DESCRIPTION OF THE INVENTION

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods and materials are now described. All publications mentioned herein are incorporated by reference for the purpose of describing and disclosing cell lines, vectors, and methodologies which are reported in the publications which might be used in connection with the invention. Nothing is to be construed as an admission that the invention is not entitled to antedate such disclosure by virtue of prior invention.

"Nucleic acid sequence" as used herein, refers to an oligonucleotide, nucleotide, or polynucleotide, and fragments and portions thereof, and to DNA or RNA of genomic or synthetic origin which may be single- or double-stranded, and represents the sense or antisense strand. Similarly, "amino acid sequence" as used herein refers to an oligopeptide, peptide, polypeptide, or protein sequence, and fragments or portions thereof, and to naturally occurring, recombinant or synthetic molecules.

Where "amino acid sequence" is recited herein to refer to an amino acid sequence of a naturally occurring protein molecule, amino acid sequence and like terms, such as "polypeptide" or "protein" are not meant to limit the amino acid sequence to the complete, native amino acid sequence associated with the recited protein.

PGP synthase as used herein, refers to the amino acid sequences of substantially purified PGP synthase obtained from any species, particularly mammalian, including bovine, ovine, porcine, murine, equine, and preferably human, from any source whether natural, synthetic, semi-synthetic, or recombinant.

A "deletion" as used herein, refers to a change in either amino acid or nucleotide sequence in which one or more amino acids or nucleotide residues, are absent.

An "insertion" or "addition", as used herein, refers to a change in an amino acid or nucleotide sequence resulting in the addition of one or more amino acid or nucleotide residues.

A "substitution" as used herein, refers to the replacement of one or more amino acids or nucleotides by different amino acids or nucleotides, respectively.

The term "biologically active" as used herein, refers to a protein having structural, regulatory, or biochemical functions of the PGP synthase. Also "immunologically" active refers to the capability of the natural, recombinant, or synthetic PGP synthase, or any oligopeptide thereof, to induce a specific immune response in appropriate animals or cells and to bind with specific antibodies.

The term "agonist" as used herein, refers to a molecule which, when bound to the synthase causes a change in PGP synthase which modulates activity of PGP synthase. Agonists may include proteins, nucleic acids, carbohydrates or any other molecules.

The terms "antagonist" or "inhibitor", as used herein, refer to a molecule which blocks or modulates the biological activity of PGP synthase. Antagonists may include proteins, nucleic acids, carbohydrates, or any other molecules.

The term "modulate" as used herein, refers to a change in the biological level or activity of PGP synthase. Modulation may be an increase or a decrease in protein activity, a change in binding characteristics of PGP synthase to its substrate or effector molecule, or any other change in the biological, functional, or immunological properties of PGP synthase.

The term "derivative" as used herein, refers to the chemical modifications of a nucleic acid encoding PGP synthase or the encoded PGP synthase. Illustrations of such modifications would be replacement of hydrogen by an alkyl, acyl, or amino group. A nucleic acid derivative would encode a polypeptide which retains essential biological characteristics of the natural molecule.

Polypeptides

The invention is based on the identification of a novel PGP synthase and the polynucleotide sequence encoding the PGP synthase.

The invention thus relates to a novel PGP synthase having the amino acid sequence shown in SEQ ID NO:2, or the amino acid sequences encoded by the deposited cDNAs as Patent Deposit Nos. PTA-2011 or PTA-2340.

Plasmids containing the nucleotide sequences of the invention were deposited with the Patent Depository of the American Type Culture Collection (ATCC), Manassas, Va., on Jun. 9, 2000 and Aug. 10, 2000 and assigned Patent Deposit Nos. PTA-2011 and PTA-2340, respectively. The deposits will be maintained under the terms of the Budapest Treaty on the International Recognition of the Deposit of Microorganisms. The deposit is provided as a convenience to those of skill in the art and is not an admission that a deposit is required under 35 U.S.C. §112. The deposited sequences, as well as the polypeptides encoded by the sequence, are incorporated herein by reference and controls in the event of any conflict, such as a sequencing error, with description in this application.

"PGP synthase polypeptide" or "PGP synthase protein" refers to the polypeptide in SEQ ID NO:2, or the polypeptide encoded by the deposited cDNA. The term "PGP synthase protein" or "PGP synthase polypeptide", however, further includes the numerous variants described herein, as well as fragments derived from the full-length PGP synthase and variants. By "variants" is intended proteins or polypeptides having an amino acid sequence that is at least about 60%, 65%, or 70%, preferably about 75%, 85%, 90%, 91%, 92%, 93%, 94%, 95%, 96%, 97%, 98%, or 99% identical to the amino acid sequence of SEQ ID NO:2. Variants also include polypeptides encoded by the cDNA inserts of the plasmids deposited with the ATCC as Patent Deposit Number PTA-2011 or PTA-2340, or polypeptides encoded by a nucleic acid molecule that hybridizes to the nucleic acid molecule of SEQ ID NO:1, SEQ ID NO:3, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:2. If alignment is needed for this comparison the sequences should be aligned for maximum identity. "Looped" out sequences from deletions or insertions, or mismatches, are considered differences. Such variants retain the functional activity of the PGP synthase like proteins of the invention. Variants include polypeptides that differ in amino acid sequence due to natural allelic variation or mutagenesis.

PGP synthases are found in most mammalian tissues with the highest concentrations in the heart, lung, and liver.

The present invention thus provides isolated or purified polypeptides of the PGP synthase and variants and fragments thereof.

Based on a Blast search, highest homology to the PGP synthase of the invention was shown to phosphatidylglycerophosphate synthase from *Cricetulus griseus* (Genbank Acc. No. AB016930). The polypeptide of the invention is 93% identical to the *C. griseus* phosphatidylglycerophosphate synthase in the region from amino acids 4 to 556 of SEQ ID NO:2. The nucleotide sequence of the invention is 87% identical to the *C. griseus* phosphatidylglycerophosphate synthase nucleotide sequence in the region from nucleotides 326-1991 of SEQ ID NO:1.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The PGP synthase polypeptides can be purified from mammalian tissues (McMurray, W. C. et al., (1978) Can J. Biochem. 56, 414-419). It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the PGP synthase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A PGP synthase polypeptide is also considered to be isolated when it is part of a membrane preparation or is purified and then reconstituted with membrane vesicles or liposomes.

The language "substantially free of chemical precursors or other chemicals" includes preparations of the PGP synthase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the PGP synthase polypeptides comprise the amino acid sequences shown in SEQ ID NO:2. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the PGP synthase of SEQ ID NO:2. Variants also include proteins substantially homologous to the PGP synthase but derived from another organism, i.e., an ortholog. Variants also include proteins that are substantially homologous to the PGP synthase that are produced by chemical synthesis. Variants also include proteins that are substantially homologous to the PGP synthase that are produced by recombinant methods. Variants retain the functional activity of the PGP synthase like polypeptides set forth in SEQ ID NO:2. It is understood, however, that variants exclude any amino acid sequences disclosed prior to the invention.

As used herein, two proteins (or a region of the proteins) are substantially homologous when the amino acid sequences have at least about 60%, 65%, 70%, 75%, 80%, 85%, 90%, 91%, 92%, 93%, 94%, 95%, 96%, 97%, 98%, or 99% identity. A substantially homologous amino acid sequence, according to the present invention, will be encoded by a nucleic acid sequence hybridizing to the nucleic acid sequence, or portion thereof, of the sequence shown in SEQ ID NO:1 or SEQ ID NO:3 under stringent conditions as more fully described below. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) J. Mol. Biol. 48:444-453 algorithm which has been incorporated into the GAP program in the GCG software package using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) CABIOS 4:11-17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to the 27411 nucleic acid molecules of the invention. BLAST protein searches can be performed with the XBLAST program, score=50, wordlength=3 to obtain amino acid sequences homologous to the 27411 protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., XBLAST and NBLAST) can be used.

The invention also encompasses polypeptides having a lower degree of identity but having sufficient similarity so as to perform one or more of the same functions performed by the PGP synthase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Iie; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306-1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

A variant polypeptide can differ in amino acid sequence by one or more substitutions, deletions, insertions, inversions, fusions, and truncations or a combination of any of these. Variant polypeptides can be fully functional or can lack function in one or more activities. Variants include those having alterations that affect interaction with any of the substrates or effector molecules, including but not limited to those disclosed herein or that affect the function of the PGP synthase that normally results from such interaction. For example, variants of the PGP synthase can have an altered binding affinity for the substrates, CDP-diacylglycerol and glycerol 3-phosphate.

Another useful variation provides a fusion protein in which one or more domains or subregions are operationally fused to one or more domains or subregions from another PGP synthase. Specifically, a domain or subregion can be introduced that alters the substrate specificities or the rate of the enzymatic reaction.

Fully functional variants typically contain only conservative variations or variations in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally occurring or can be made by recombinant means or chemical synthesis to provide useful and novel characteristics for the PGP synthase polypeptide. This includes preventing immunogenicity from pharmaceutical formulations by preventing protein aggregation.

Amino acids that are essential for function can be identified by methods known in the art, such as site-directed mutagenesis or alanine-scanning mutagenesis (Cunningham et al. (1985) Science 244:1081-1085). The latter procedure introduces single alanine mutations at every residue in the molecule. The resulting mutant molecules are then tested for PGP synthase activity, such as the binding affinity for the substrates or determining the catalytic constants for substituted phospho group transfer between CDP-diacylglycerol and glycerol 3-phosphate. Sites that are critical for substrate binding can also be determined by structural analysis such as crystallization, nuclear magnetic resonance or photoaffinity labeling (Smith et al. (1992) J. Mol. Biol. 224:899-904; de Vos et al. (1992) Science 255:306-312).

The assays for PGP synthase enzyme activity are well known in the art and can be found for example, in Ohtsuka et al. (1993) J. Biol. Chem. Vol. 268, No.30, 22908-22913). Substantial homology can be to the entire nucleic acid or amino acid sequence or to fragments of these sequences.

The invention thus also includes polypeptide fragments of the PGP synthase. Fragments can be derived from the amino acid sequences shown in SEQ ID NO:2. However, the invention also encompasses fragments of the variants of the PGP synthase as described herein.

The fragments to which the invention pertains, however, are not to be construed as encompassing fragments that may be disclosed prior to the present invention. Accordingly, a fragment of the PGP synthase can comprise at least about 20, 25, 30, 40, 50, 100, 150, 200, 250, 300, 350, 400, 450, 500, 550, or 556 contiguous amino acids. Fragments can retain one or more of the biological activities of the protein, for example the ability to bind the substrate or the ability to catalyze the substituted phospho group transfer. Alternatively, fragments can be used as an immunogen to generate PGP synthase antibodies.

Biologically active fragments (peptides which are, for example, 5, 10, 15, 20, 30, 40, 50, 100, 150, 200, 250, 300, 350, 400, 450, 500, 550, or 556 amino acids in length) can comprise a domain or motif including a substrate binding site, catalytic binding site and sites for glycosylation, protein kinase C phosphorylation, Casein kinase II phosphorylation, cyclic AMP and cGMP-dependent phosphorylation, tyrosine kinase phosphorylation and N-myristoylation. Further possible fragments may include sites important for cellular and subeellular targeting.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the PGP synthase or PGP syntilase variants. These epitope-bearing peptides are useful to raise antibodies that bind specifically to an PGP synthase polypeptide or region or fragment. These peptides can contain at least 5, 10, at least 15, or between at least about 15 to about 30 amino acids.

Non-limiting examples of antigenic polypeptides that can be used to generate antibodies include but are not limited to peptides derived from an extracellular site. However, intracellularly-made antibodies ("intrabodies") are also encompassed, which would recognize intracellular peptide regions.

The epitope-bearing PGP synthase polypeptides may be produced by any conventional means (Houghten, R. A. (1985) Proc. Natl. Acad. Sci. USA 82:5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the PGP synthase fragment and an additional region fused to the carboxyl terminus of the fragment.

The invention thus provides chimeric or fusion proteins. These comprise a PGP synthase peptide sequence operatively linked to a heterologous peptide having an amino acid sequence not substantially homologous to the PGP synthase. "Operatively linked" indicates that the PGP synthase peptide and the heterologous peptide are fused in-frame. The heterologous peptide can be fused to the N-terminus or C-terminus of the PGP synthase or can be internally located. In the case where an expression cassette contains two protein-coding regions joined in a contiguous manner in the same reading frame, the encoded polypeptide is herein defined as a "heterologous polypeptide" or a "chimeric polypeptide" or a "fusion polypeptide". As used herein, a PGP synthase "heterologous protein" or "chimeric protein" or "fusion protein" comprises a PGP synthase polypeptide operatively linked to a non-PGP synthase polypeptide.

In one embodiment the fusion protein does not affect PGP synthase function per se. For example, the fusion protein can be a GST-fusion protein in which the PGP synthase sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant PGP synthase. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) J. Mol. Recog. 8:52-58 (1995) and Johanson et al. J. Biol. Chem. 270:9459-9471). Thus, this invention also encompasses soluble fusion proteins containing an PGP synthase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) Current Protocols in Molecular Biology). Moreover, many expression vectors are commercially available that already encode a fusion moiety (e.g., a GST protein). An PGP synthase-encoding nucleic acid can be cloned into such an expression vector such that the fusion moiety is linked in-frame to the PGP synthase.

Another form of fusion protein is one that directly affects PGP synthase functions. Accordingly, a PGP synthase polypeptide is encompassed by the present invention in which one or more of the PGP synthase domains (or parts thereof) has been replaced by homologous domains (or parts thereof) from another PGP synthase. Accordingly, various permutations are possible. For example, the binding or catalytic domain, or subregion thereof, can be replaced with the domain or subregion from another PGP synthase or another phosphatidyl transferase. Thus, chimeric PGP synthases can be formed in which one or more of the native domains or subregions has been replaced by another.

Additionally, chimeric PGP synthase proteins can be produced in which one or more functional sites is derived from a different PGP synthase or isoform. It is understood however that sites could be derived from other PGP synthases that occur in the mammalian genome but which have not yet been discovered or characterized. Such sites include but are not limited to the catalytic site and substrate binding sites, and other functional sites disclosed herein.

It is further recognized that the nucleic acid sequences of the invention can be altered to contain codons, which are preferred, or non-preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

The isolated PGP synthase can be purified from cells that naturally express it, including but not limited to heart, lung and liver as well as the tissues. The PGP synthase of the present invention can also be purified from cells that have been altered to express it (recombinant), or synthesized using known protein synthesis methods.

In one embodiment, the protein is produced by recombinant DNA techniques. For example, a nucleic acid molecule encoding the PGP synthase polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (1990) Meth. Enzymol. 182: 626-646) and Rattan et al. (1992) Ann. N.Y. Acad. Sci. 663:48-62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The PGP synthase polypeptides are useful for producing antibodies specific for the PGP synthase, regions, or fragments.

The PGP synthase polypeptides are useful for biological assays related to PGP synthase. Such assays involve any of the known PGP synthase functions or activities or properties useful for diagnosis and treatment of PGP synthase-related conditions, including CL and PG biosynthesis.

The PGP synthase polypeptides are also useful in drug screening assays, in cell-based or cell-free systems. Cell-based systems can be native, i.e., cells that normally express the PGP synthase, as a biopsy or expanded in cell culture. In one embodiment, however, cell-based assays involve recombinant host cells expressing the PGP synthase, such as those disclosed in the background above.

Determining the ability of the test compound to interact with the PGP synthase can also comprise determining the ability of the test compound to preferentially bind to the polypeptide as compared to the ability of a known binding molecule (e.g. CDP-diacylglycerol and glycerol 3-phosphate) to bind to the polypeptide.

The polypeptides can be used to identify compounds that modulate PGP synthase activity. Such compounds, for example, can increase or decrease the affinity or rate of binding to the substrates CDP-diacylglycerol and glycerol 3-phosphate, compete with the substrates for binding to the PGP synthase, or displace substrates bound to the PGP synthase. Such compounds can also increase or decrease the enzymatic activity of the PGP synthase. Compounds that modulate PGP synthase activity include, but are not limited to, liponucleotides, CDP diacylglycerol, glycerol 3-phosphate (Hirabayashi et al. (1976) Biochemistry 15: 5205-5211), thioreactive agents (Carman et al. (1984) J. Food Biochem 8:321-333), inositol (Bleasdale et al. (1982) Biochim. Biophys. Acta 710:377-390), and Ca2+ (Dowhan et al. (1992) Methods Enzymol 71:313-321).

The PGP synthase of the present invention and appropriate variants and fragments can be used in high-throughput screens to assay candidate compounds for the ability to bind to the PGP synthase. These compounds can be further screened against a functional PGP synthase to determine the effect of the compound on the PGP synthase activity. Compounds can be identified that activate (agonist) or inactivate (antagonist) the PGP synthase to a desired degree. Modulatory methods can be performed in vitro (e.g., by culturing the cell with the agent) or, alternatively, in vivo (e.g., by administering the agent to a subject).

The PGP synthase polypeptides can be used to screen a compound for the ability to stimulate or inhibit interaction between the PGP synthase protein and a target molecule that normally interacts with the PGP synthase protein. The target can be a cofactor, metal ion, or PGA synthase substrate. Different cofactors and prosthetic groups which have been shown to be important for maximal PGP synthase activity include, but are not limited to Triton X-100, phosphatidylethanolamine and phosphatidylinositol.

Different metal/salts which have been shown to be important for PGP synthase activity include, but are not limited to Mn+2, Mg+2, Ca+2, Co+2, and Ba+2. The assay includes the steps of combining the PGP synthase protein with a candidate compound under conditions that allow the PGP synthase protein or fragment to interact with the target molecule, and to detect the formation of a complex between the PGP synthase protein and the target or to detect the biochemical consequence of the interaction with the PGP synthase and the target.

Determining the ability of the PGP synthase to bind to a target molecule can also be accomplished using a technology such as real-time Bimolecular Interaction Analysis (BIA). Sjolander et al. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) Anticancer Drug Des. 12:145).

Examples of methods for the synthesis of molecular libraries can be found in the art, for example in DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233. Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. 97:6378-6382); (Felici (1991) J. Mol. Biol. 222:301-310); (Ladner supra).

Candidate compounds include, for example, 1) peptides such as soluble peptides, including Ig-tailed fusion peptides and members of random peptide libraries (see, e.g., Lam et al. (1991) Nature 354:82-84; Houghten et al. (1991) Nature 354: 84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) Cell 72:767-778); 3) antibodies (e.g., polyclonal, monoclonal, humanized, anti-idiotypic, chimeric, and single chain antibodies as well as Fab, F(ab')2, Fab expression library fragments, and epitope-binding fragments of antibodies); and 4) small organic and inorganic molecules (e.g., molecules obtained from combinatorial and natural product libraries).

One candidate compound is a soluble full-length PGP synthase or fragment that competes for substrate binding, including but not limited to those disclosed herein. Other candidate compounds include mutant PGP synthases or appropriate fragments containing mutations that affect PGP synthase function and thus compete for substrates, e.g., CDP-diacylglcerol and glycerol 3-phosphate. Accordingly, a fragment that competes for substrate binding, for example with a higher affinity, or a fragment that binds substrate(s) but does not catalyze the phospho group transfer is encompassed by the invention.

The invention provides other end points to identify compounds that modulate (stimulate or inhibit) PGP synthase activity. The assays typically involve an assay of events that result from a substituted phospho group transfer that indicate PGP synthase activity. Thus, the expression of genes that are up- or down-regulated in response to the PGP synthase enzyme can be assayed. In one embodiment, the regulatory region of such genes can be operably linked to a marker that is easily detectable, such as luciferase. Additionally, measurements of metabolite transport across mitochondrial membranes and mitochondrial cardiolipin content can serve as parameters to quantify PGP synthase activity.

Any of the biological or biochemical functions mediated by the PGP synthase can be used as an endpoint assay. These include all of the biochemical or biological events described herein, in the references cited herein and incorporated by reference for these events, and other PGP synthase functions known to those of ordinary skill in the art.

Binding and/or activating compounds can also be screened by using chimeric PGP synthase proteins in which one or more domains, sites, and the like, as disclosed herein, or parts thereof, can be replaced by their heterologous counterparts derived from other PGP synthases. For example, a substrate binding region or cofactor binding region can be used that interacts with a different substrate or cofactor specificity and/or affinity than the native PGP synthase. Alternatively, a heterologous targeting sequence can replace the native targeting sequence. This will result in different subcellular or cellular localization. As a further alternative, sites that are responsible for developmental, temporal, or tissue specificity can be replaced by heterologous sites such that the PGP synthase can be detected under conditions of specific developmental, temporal, or tissue-specific expression.

The PGP synthase polypeptides are also useful in competition binding assays in methods designed to discover compounds that interact with the PGP synthase. Thus, a compound is exposed to a PGP synthase polypeptide under conditions that allow the compound to bind or to otherwise interact with the polypeptide. Soluble PGP synthase polypeptide is also added to the mixture. If the test compound interacts with the soluble PGP synthase polypeptide, it decreases the amount of complex formed or activity from the PGP synthase target. This type of assay is particularly useful in cases in which compounds are sought that interact with specific regions of the PGP synthase. Thus, the soluble polypeptide that competes with the target PGP synthase region is designed to contain peptide sequences corresponding to the region of interest.

Another type of competition-binding assay can be used to discover compounds that interact with specific functional sites and inhibit PGP synthase. As an example, the substrates (CDP-diacylglycerol and glycerol 3-phosphate) and a candidate compound can be added to a sample of PGP synthase. Compounds that interact with PGP synthase at the same site as the substrates will reduce the amount of complex formed between the PGP synthase and the substrates. One example of a group of compounds that affect PGP synthase activity are thioreactive agents. Additional inhibitors of PGP synthase include: liponucleotide, inositol, Triton X-100, and the divalent cations of magnesium, calcium, cadmium, zinc, mercury, and copper at certain critical millimolar concentrations.

To perform cell free drug screening assays, it is desirable to immobilize either the PGP synthase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/PGP synthase fusion proteins can be adsorbed onto glutathione sepharose beads (Sigma Chemical, St. Louis, Mo.) or glutathione derivatized microtitre plates, which are then combined with the cell lysates (e.g., 35S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of PGP synthase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a PGP synthase-binding target component and a candidate compound are incubated in the PGP synthase-presenting wells and the amount of complex trapped in the well can be quantitated. Methods for detecting such complexes, in addition to those described above for the GST-immobilized complexes, include immunodetection of complexes using antibodies reactive with the PGP synthase target molecule, or which are reactive with PGP synthase and compete with the target molecule; as well as enzyme-linked assays which rely on detecting an enzymatic activity associated with the target molecule.

Modulators of PGP synthase activity identified according to these drug screening assays can be used to treat a subject with a disorder mediated by PGP synthase, by treating cells that express the PGP synthase. These methods of treatment include the steps of administering the modulators of PGP synthase activity in a pharmaceutical composition as described herein, to a subject in need of such treatment. Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. "Subject", as used herein, can refer to a mammal, e.g. a human, or to an experimental or animal or disease model. The subject can also be a non-human animal, e.g. a horse, cow, goat, or other domestic animal. A therapeutic agent includes, but is not limited to, small molecules, peptides, antibodies, ribozymes and antisense oligonucleotides.

The PGP synthases are expressed in tissues including, but not limited to heart, lung, liver, and the tissues. Hence the PGP synthase of the present invention is relevant to treating disorders involving these tissues.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconiosis, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorragic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, a1-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lympliangitis and lymphedema; tumors, including benign tumors and tumor-like conditions, such as hemangioma, lymphangioma, gloinus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the skeletal muscle include tumors such as rhabdomyosarcoma.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomeruloscierosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matrix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telangectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B1) deficiency and vitamin B12 deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders of the breast include, but are not limited to, disorders of development; inflammations, including but not limited to, acute mastitis, periductal mastitis, periductal inastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the ovary include, for example, polycystic ovarian disease, Stein-Leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Disorders involving the prostate include, but are not limited to, inflammations, benign enlargement, for example, nodular hyperplasia (benign prostatic hypertrophy or hyperplasia), and tumors such as carcinoma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

In normal bone marrow, the myelocytic series (polymorphoneuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 of Immunology, Immunopathology and Immunity, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dennatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Disorders involving the tonsils include, but are not limited to, tonsillitis, Peritonsillar abscess, squamous cell carcinoma, dyspnea, hyperplasia, follicular hyperplasia, reactive lymphoid hyperplasia, non-Hodgkin's lymphoma and B-cell lymphoma.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast, and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 27411 nucleic acid and protein of the invention can be used to treat and/or diagnose a variety of proliferative disorders. e.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof.

Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

PGP synthases are important as relates to cardiolipin metabolism in the aging process and thyroid dysfunction. Aging and hypothyroidism are two conditions associated with mitochondrial dysfunction and cardiolipin deficiency. (Schlame, M. et al., (1997) Biochimica et Biophysica Acta, 1348:207-213). Also, hyperthyroidism is characterized by mitochondria with increased cardiolipin content and increased metabolite transport activities. (Paradies, G. et al., (1992) Biochim. Biophys. Acta, 1019:133-136). Therefore, PGP synthases may prove to be useful clinical tools for treating any of these processes and conditions.

The PGP synthase polypeptides are thus useful for treating a PGP synthase-associated disorder characterized by aberrant expression or activity of an PGP synthase. In one embodiment, the method involves administering an agent (e.g., an agent identified by a screening assay described or cited herein), or combination of agents that modulates (e.g., upregulates or downregulates) expression or activity of the protein. In another embodiment, the method involves administering the PGP synthase as therapy to compensate for reduced or aberrant expression or activity of the protein.

Methods for treatment include but are not limited to the use of soluble PGP synthase or fragments of the PGP synthase protein that compete for substrate binding, or interfere with the reaction mediated by the PGP synthase polypeptide. These PGP synthase or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer).

In yet another aspect of the invention, the proteins of the invention can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO 94/10300), to identify other proteins (captured proteins) which bind to or interact with the proteins of the invention and modulate their activity.

The PGP synthase polypeptides also are useful to provide a target for diagnosing a disease or predisposition to disease mediated by the PGP synthase, including, but not limited to, diseases involving tissues in which the PGP synthase is expressed, as described herein. Accordingly, methods are provided for detecting the presence, or levels of, the PGP synthase in a cell, tissue, or organism. The method involves contacting a biological sample with a compound capable of interacting with the PGP synthase such that the interaction can be detected.

One agent for detecting PGP synthase is an antibody capable of selectively binding to PGP synthase. A biological sample includes tissues, cells and biological fluids isolated from a subject, as well as tissues, cells and fluids present within a subject.

The PGP synthase also provides a target for diagnosing active disease, or predisposition to disease, in a patient having a variant PGP synthase. Thus, PGP synthase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered PGP synthase activity in cell-based or cell-free assay, alteration in substrate binding, altered substituted phospho group transfer, altered antibody-binding pattern, altered isoelectric point, direct amino acid sequencing, and any other of the known assay techniques useful for detecting mutations in a protein in general or in an PGP synthase specifically.

In vitro techniques for detection of PGP synthase include enzyme linked immunosorbent assays (ELISAs), Western blots, immunoprecipitations and immunofluorescence. Alternatively, the protein can be detected in vivo in a subject by introducing into the subject a labeled anti-PGP synthase antibody. For example, the antibody can be labeled with a radioactive marker whose presence and location in a subject can be detected by standard imaging techniques. Particularly useful are methods, which detect the allelic variant of the PGP synthase expressed in a subject, and methods, which detect fragments of the PGP synthase in a sample.

The PGP synthase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) Clin. Exp. Pharmacol. Physiol. 23(10-11):983-985, and Linder, M. W. (1997) Clin. Chem. 43(2):254-266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the PGP synthase in which one or more of the PGP synthase functions in one population is different from those in another population. The polypeptides thus allow a target to ascertain a genetic predisposition that can affect treatment modality. Thus, in an PGP synthase-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The PGP synthase polypeptides are also useful for monitoring therapeutic effects during clinical trials and other treatment. Thus, the therapeutic effectiveness of an agent that is designed to increase or decrease gene expression, protein levels or PGP synthase activity can be monitored over the course of treatment using the PGP synthase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the PGP synthase and its variants and fragments. An antibody is considered to selectively bind, even if it also binds to other proteins that are not substantially homologous with the PGP synthase. These other proteins share homology with a fragment or domain of the PGP synthase. This conservation in specific regions gives rise to antibodies that bind to both proteins by virtue of the homologous sequence. In this case, it would be understood that antibody binding to the PGP synthase is still selective.

To generate antibodies, an isolated PGP synthase polypeptide is used as an immunogen to generate antibodies using standard techniques for polyclonal and monoclonal antibody preparation. Either the full-length protein or antigenic peptide fragment can be used.

Antibodies are preferably prepared from these regions or from discrete fragments in these regions. However, antibodies can be prepared from any region of the peptide as described herein. A preferred fragment produces an antibody that diminishes or completely prevents substrate or cofactor binding or prevents the transfer of the phospho group. Antibodies can be developed against the entire PGP synthase or domains of the PGP synthase as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')2) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

An appropriate immunogenic preparation can be derived from native, recombinantly expressed, or chemically synthesized peptides.

Antibody Uses

The antibodies can be used to isolate a PGP synthase by standard techniques, such as affinity chromatography or immunoprecipitation. The antibodies can facilitate the purification of the natural PGP synthase from cells and recombinantly produced PGP synthase expressed in host cells.

The antibodies are useful to detect the presence of PGP synthase in cells or tissues to determine the pattern of expression of the PGP synthase among various tissues in an organism and over the course of normal development.

The antibodies can be used to detect PGP synthase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length PGP synthase can be used to identify PGP synthase turnover.

Further, the antibodies can be used to assess PGP synthase expression in disease states such as in active stages of the disease or in an individual with a predisposition toward disease related to PGP synthase function. When a disorder is caused by an inappropriate tissue distribution, developmental expression, or level of expression of the PGP synthase protein, the antibody can be prepared against the normal PGP synthase protein. If a disorder is characterized by a specific mutation in the PGP synthase, antibodies specific for this mutant protein can be used to assay for the presence of the specific mutant PGP synthase. However, intracellularly-made antibodies ("intrabodies") are also encompassed, which would recognize intracellular PGP synthase peptide regions.

The antibodies can also be used to assess normal and aberrant subcellular localization of cells in the various tissues in an organism. Antibodies can be developed against the whole PGP synthase or portions of the PGP synthase.

The diagnostic uses can be applied, not only in genetic testing, but also in monitoring a treatment modality. Accordingly, where treatment is ultimately aimed at correcting PGP synthase expression level or the presence of aberrant PGP synthase and aberrant tissue distribution or developmental expression, antibodies directed against the PGP synthase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic PGP synthase can be used to identify individuals that require modified treatment modalities.

The antibodies are also useful as diagnostic tools as an immunological marker for aberrant PGP synthase analyzed by electrophoretic mobility, isoelectric point, tryptic peptide digest, and other physical assays known to those in the art.

The antibodies are also useful for tissue typing. Thus, where a specific PGP synthase has been correlated with expression in a specific tissue, antibodies that are specific for this PGP synthase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting PGP synthase function, for example, blocking substrate binding or disrupting transfer of the phospho group between CDP-diacylglycerol and glycerol 3-phosphate.

These uses can also be applied in a therapeutic context in which treatment involves inhibiting PGP synthase function. An antibody can be used, for example, to block substrate binding. Antibodies can be prepared against specific fragments containing sites required for function or against intact PGP synthase associated with a cell.

Completely human antibodies are particularly desirable for therapeutic treatment of human patients. For an overview of this technology for producing human antibodies, see Lonberg et al. (1995) Int. Rev. Immunol. 13:65-93. For a detailed discussion of this technology for producing human antibodies and human monoclonal antibodies and protocols for producing such antibodies, e.g., U.S. Pat. Nos. 5,625,126; 5,633,425; 5,569,825; 5,661,016; and 5,545,806.

The invention also encompasses kits for using antibodies to detect the presence of an PGP synthase protein in a biological sample. The kit can comprise antibodies such as a labeled or labelable antibody and a compound or agent for detecting PGP synthase in a biological sample; means for determining the amount of PGP synthase in the sample; and means for comparing the amount of PGP synthase in the sample with a standard. The compound or agent can be packaged in a suitable container. The kit can further comprise instructions for using the kit to detect PGP synthase.

Polynucleotides

The nucleotide sequence in SEQ ID NO:1 was obtained by sequencing the deposited human cDNA. Accordingly, the sequence of the deposited clones are controlling as to any discrepancies between the two and any reference to the sequences of SEQ ID NO:1, includes reference to the sequences of the deposited cDNA.

The specifically disclosed cDNAs comprise the coding region and 5' and 3' untranslated sequences in SEQ ID NO:1.

The invention provides isolated polynucleotides encoding the novel PGP synthase. The term "PGP synthase polynucleotide" or "PGP synthase nucleic acid" refers to the sequences shown in SEQ ID NO:1, SEQ ID NO:3, or in the deposited cDNAs. The term "PGP synthase polynucleotide" or "PGP synthase nucleic acid" further includes variants and fragments of the PGP synthase polynucleotides. Generally, nucleic acid molecules that are fragments of the 27411 nucleic acid comprise at least 15, 20, 38, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1400, 1500, 1600, 1700, 1800, 1900, 2000, 2100, 2200, 2300, 2400, 2500, 2600, 2686 nucleotides or up to the number of nucleotides present in a full-length human PGP synthase-like nucleotide sequence disclosed herein (for example, 2686 nucleotides for SEQ ID NO:1) depending upon the intended use. Alternatively, a nucleic acid molecule that is a fragment of a 27411-like nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2686 of SEQ ID NO:1.

An "isolated" PGP synthase nucleic acid is one that is separated from other nucleic acid present in the natural source of the PGP synthase nucleic acid. Preferably, an "isolated" nucleic acid is free of sequences which naturally flank the PGP synthase nucleic acid (i.e., sequences located at the 5' and 3' ends of the nucleic acid) in the genomic DNA of the organism from which the nucleic acid is derived. However, there can be some flanking nucleotide sequences, for example up to about 5 kb. The important point is that the PGP synthase nucleic acid is isolated from flanking sequences such that it can be subjected to the specific manipulations described herein, such as recombinant expression, preparation of probes and primers, and other uses specific to the PGP synthase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The PGP synthase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The PGP synthase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

PGP synthase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

PGP synthase nucleic acid can comprise the nucleotide sequences shown in SEQ ID NO:1 and SEQ ID NO:3 corresponding to human PGP synthase cDNA.

In one embodiment, the PGP synthase nucleic acid comprises only the coding region.

The invention further provides variant PGP synthase polynucleotides, and fragments thereof, that differ from the nucleotide sequences shown in SEQ ID NO:1 due to degeneracy of the genetic code and thus encode the same protein as that encoded by the nucleotide sequences shown in SEQ ID NO:1 or SEQ ID NO:3.

The invention also provides PGP synthase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Generally, nucleotide sequences variants of the invention will have at least 60%, 65%, 70%, 75%, 80%, 85%, 90%, 91%, 92%, 93%, 94%, 95%, 96%, 97%, 98%, or 99% identity to the nucleotide sequence disclosed herein. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a PGP synthase that is at least about 60-65%, 65-70%, typically at least about 70-75%, more typically at least about 80-85%, and most typically at least about 90-95% or more homologous to the nucleotide sequence shown in SEQ ID NO:1, SEQ ID NO:3 or a fragment of these sequences. Such nucleic acid molecules can readily be identified as being able to hybridize under stringent conditions, to the nucleotide sequence shown in SEQ ID NO:1, SEQ ID NO:3, or a fragment of these sequences. It is understood that stringent hybridization does not indicate substantial homology where it is due to general homology, such as poly A sequences, or sequences common to all or most proteins, all PGP synthase, all phospho group transferases. Moreover, it is understood that variants do not include any of the nucleic acid sequences that may have been disclosed prior to the invention.

As used herein, the term "hybridizes under stringent conditions" describes conditions for hybridization and washing. Stringent conditions are known to those skilled in the art and can be found in Current Protocols in Molecular Biology John Wiley & Sons, N.Y. (1989), 6.3.1-6.3.6. Aqueous and non-aqueous methods are described in that reference and either can be used. A preferred, example of stringent hybridization conditions are hybridization in 6× sodium chloride/sodium citrate (SSC) at about 45□C, followed by one or more washes in 0.2×SSC, 0.1% SDS at 50° C. Another example of stringent hybridization conditions are hybridization in 6× sodium chloride/sodium citrate (SSC) at about 45□C, followed by one or more washes in 0.2×SSC, 0.1% SDS at 55° C. A further example of stringent hybridization conditions are hybridization in 6× sodium chloride/sodium citrate (SSC) at about 45□C, followed by one or more washes in 0.2×SSC, 0.1% SDS at 60° C. Preferably, stringent hybridization conditions are hybridization in 6× sodium chloride/sodium citrate (SSC) at about 45□C, followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, or SEQ ID NO:3, corresponds to a naturally occurring nucleic acid molecule.

As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:1, SEQ ID NO:3 or the complement thereof. In one embodiment, the nucleic acid consists of a portion of the nucleotide sequence of SEQ ID NO:1, SEQ ID NO:3 or the complement thereof.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, preferably at least about 15, 18, 20, 23 or 25 nucleotides, and can be 30, 40, 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600 or more nucleotides in length. Longer fragments, for example, 30 or more nucleotides in length, which encode antigenic proteins or polypeptides described herein are useful.

For PGP synthase, for example, nucleotide sequences from about 1 to about 285, from about 1992 to about 2041 and from about 2562 to about 2643 are especially relevant and encompass fragments of 5-10, 10-15, 15-20, 20-25, etc., as disclosed herein. The nucleotide sequence from about 1 to about 1991 encompasses fragments greater than about 315, 325, 345, 355 or 365 nucleotides; the nucleotide sequence from about 1074 to about 2689 encompasses fragments greater than 167, 175, 185, 195, or 205 nucleotides; and the nucleotide sequence from about 2507 to about 2689 encompasses fragments greater than 28, 35, 40, 45, 50, or 55 nucleotides.

The fragment can be single or double-stranded and can comprise DNA or RNA. The fragment can be derived from either the coding or the non-coding sequence.

In another embodiment an isolated PGP synthase nucleic acid encodes the entire coding region. In another embodiment the isolated PGP synthase nucleic acid encodes a sequence corresponding to the mature protein. For example, the mature form of the PGP synthase is from about amino acid 68 to the last amino acid. Other fragments include nucleotide sequences encoding the amino acid fragments described herein.

Thus, PGP synthase nucleic acid fragments further include sequences corresponding to the domains described herein, subregions also described, and specific functional sites. PGP synthase nucleic acid fragments also include combinations of the domains, segments, and other functional sites described above. A person of ordinary skill in the art would be aware of the many permutations that are possible.

Where the location of the domains or sites have been predicted by computer analysis, one of ordinary skill would appreciate that the amino acid residues constituting these domains can vary depending on the criteria used to define the domains.

However, it is understood that a PGP synthase fragment includes any nucleic acid sequence that does not include the entire gene.

The invention also provides PGP synthase nucleic acid fragments that encode epitope bearing regions of the PGP synthase proteins described herein.

Nucleic acid fragments, according to the present invention, are not to be construed as encompassing those fragments that may have been disclosed prior to the invention.

Polynucleotide Uses

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) Science 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NO:1 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The PGP synthase polynucleotides are thus useful for probes, primers, and in biological assays.

Where the polynucleotides are used to assess PGP synthase properties or functions, such as in the assays described herein, all or less than all of the entire cDNA can be useful. Assays specifically directed to PGP synthase functions, such as assessing agonist or antagonist activity, encompass the use of known fragments. Further, diagnostic methods for assessing PGP synthase function can also be practiced with any fragment, including those fragments that may have been known prior to the invention. Similarly, in methods involving treatment of PGP synthase dysfunction, all fragments are encompassed including those, which may have been known in the art.

The PGP synthase polynucleotides are useful as a hybridization probe for cDNA and genomic DNA to isolate a full-length cDNA and genomic clones encoding the polypeptides described in SEQ ID NO:2 and to isolate cDNA and genomic clones that correspond to variants producing the same polypeptides shown in SEQ ID NO:2 or the other variants described herein. Variants can be isolated from the same tissue and organism from which the polypeptides shown in SEQ ID NO:2 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the PGP synthase. Accordingly, it could be derived from 5' noncoding regions, the coding region, and 3' noncoding regions.

The nucleic acid probe can be, for example, the full-length cDNA of SEQ ID NO:1 or a fragment thereof, such as an oligonucleotide of at least 10-15, 15-20, 20-25, 25-30, 100, 250, or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NO:1 or SEQ ID NO:3 and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) Nucleic Acids Res. 24(17):3357-63, Mag et al. (1989) Nucleic Acids Res. 17:5973, and Peterser et al. (1975) Bioorganic Med. Chem. Lett. 5:1119.

The nucleic acid molecules and fragments of the invention can also include other appended groups such as peptides (e.g., for targeting host cell PGP synthase in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood brain barrier (see, e.g., PCT Publication No. WO 89/10134). In addition, oligonucleotides can be modified with hybridization-triggered cleavage agents (see, e.g., Krol et al. (1988) Bio-Techniques 6:958-976) or intercalating agents (see, e.g., Zon (1988) Pharm Res. 5:539-549).

The PGP synthase polynucleotides are also useful as primers for PCR to amplify any given region of a PGP synthase polynucleotide.

The PGP synthase polynucleotides are also useful for constructing recombinant vectors. Such vectors include expression vectors that express a portion of, or all of, the PGP synthase polypeptides. Vectors also include insertion vectors, used to integrate into another polynucleotide sequence, such as into the cellular genome, to alter in situ expression of PGP synthase genes and gene products. For example, an endogenous PGP synthase coding sequence can be replaced via homologous recombination with all or part of the coding region containing one or more specifically introduced mutations.

The PGP synthase polynucleotides are also useful for expressing antigenic portions of the PGP synthase proteins.

The PGP synthase polynucleotides are also useful as probes for determining the chromosomal positions of the PGP synthase polynucleotides by means of in situ hybridization methods, such as FISH. (For a review of this technique, see Verma et al. (1988) Human Chromosomes: A Manual of Basic Techniques (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) Nature 325:783-787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The PGP synthase polynucleotide probes are also useful to determine patterns of the presence of the gene encoding the PGP synthase and their variants with respect to tissue distribution, for example, whether gene duplication has occurred and whether the duplication occurs in all or only a subset of tissues. The genes can be naturally occurring or can have been introduced into a cell, tissue, or organism exogenously.

The PGP synthase polynucleotides are also useful for designing ribozymes corresponding to all, or a part, of the mRNA produced from genes encoding the polynucleotides described herein.

The PGP synthase polynucleotides are also useful for constructing host cells expressing a part, or all, of the PGP synthase polynucleotides and polypeptides.

The PGP synthase polynucleotides are also useful for constructing transgenic animals expressing all, or a part, of the PGP synthase polynucleotides and polypeptides.

The PGP synthase polynucleotides are also useful for making vectors that express part, or all, of the PGP synthase polypeptides.

The PGP synthase polynucleotides are also useful as hybridization probes for determining the level of PGP synthase nucleic acid expression. Accordingly, the probes can be used to detect the presence of, or to determine levels of, PGP synthase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the PGP synthase genes.

Alternatively, the probe can be used in an in situ hybridization context to assess the position of extra copies of the PGP synthase genes, as on extrachromosomal elements or as integrated into chromosomes in which the PGP synthase gene is not normally found, for example as a homogeneously staining region.

These uses are relevant for diagnosis of disorders involving an increase or decrease in PGP synthase expression relative to normal, such as a proliferative disorder or a differentiative or developmental disorder.

Disorders in which PGP synthase expression is relevant include, but are not limited to disease conditions associated with defective cardiolipin (CL) and phosphatidylglycerol (PG) biosynthesis and metabolism.

Tissues and/or cells in which 27411 is expressed are described above herein. As such, the gene is particularly relevant for the treatment of disorders involving these tissues.

Furthermore, disorders in which 27411 expression is relevant are disclosed herein above.

Thus, the present invention provides a method for identifying a disease or disorder associated with aberrant expression or activity of PGP synthase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the PGP synthase, such as by measuring the level of a PGP synthase-encoding nucleic acid in a sample of cells from a subject e.g., mRNA or genomic DNA, or determining if the PGP synthase gene has been mutated.

Nucleic acid expression assays are useful for drug screening to identify compounds that modulate PGP synthase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the PGP synthase gene. The method typically includes assaying the ability of the compound to modulate the expression of the PGP synthase nucleic acid and thus identifying a compound that can be used to treat a disorder characterized by undesired PGP synthase nucleic acid expression.

The assays can be performed in cell-based and cell-free systems. Cell-based assays include cells naturally expressing the PGP synthase nucleic acid or recombinant cells genetically engineered to express specific nucleic acid sequences, for example those cited above and in the background.

Alternatively, candidate compounds can be assayed in vivo in patients or in transgenic animals.

The assay for PGP synthase nucleic acid expression can involve direct assay of nucleic acid levels, such as mRNA levels, or on collateral compounds involved in the PGP synthase catalyzed reaction. Further, the expression of genes that are up- or down-regulated in response to the PGP synthase signal pathway can also be assayed. In this embodiment the regulatory regions of these genes can be operably linked to a reporter gene such as luciferase.

Thus, modulators of PGP synthase gene expression can be identified in a method wherein a cell is contacted with a candidate compound and the expression of mRNA determined. The level of expression of PGP synthase mRNA in the presence of the candidate compound is compared to the level of expression of PGP synthase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate PGP synthase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid. Disorders that the gene is particularly relevant for treating have been disclosed herein above.

Alternatively, a modulator for PGP synthase nucleic acid expression can be a small molecule or drug identified using the screening assays described herein as long as the drug or small molecule inhibits the PGP synthase nucleic acid expression.

The PGP synthase polynucleotides are also useful for monitoring the effectiveness of modulating compounds on the expression or activity of the PGP synthase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The PGP synthase polynucleotides are also useful in diagnostic assays for qualitative changes in PGP synthase nucleic acid, and particularly in qualitative changes that lead to pathology. The polynucleotides can be used to detect mutations in PGP synthase genes and gene expression products such as mRNA. The polynucleotides can be used as hybridization probes to detect naturally-occurring genetic mutations in the PGP synthase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the PGP synthase gene associated with a dysfunction provides a diagnostic tool for an active disease or susceptibility to disease when the disease results from overexpression, underexpression, or altered expression of a PGP synthase.

Mutations in the PGP synthase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) PNAS 91:360-364), the latter of which can be particularly useful for detecting point mutations in the gene (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in an PGP synthase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant PGP synthase gene and a wild-type gene can be determined by direct DNA sequencing. A variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the gene include methods in which protection from cleavage agents is used to detect mismatched bases in RNA/RNA or RNA/DNA duplexes (Myers et al. (1985) Science 230:1242); Cotton et al. (1988) PNAS 85:4397; Saleeba et al. (1992) Meth. Enzymol. 217:286-295), electrophoretic mobility of mutant and wild type nucleic acid is compared (Orita et al. (1989) PNAS 86:2766; Cotton et al. (1993) Mutat. Res. 285:125-144; and Hayashi et al. (1992) Genet. Anal. Tech. Appl. 9:73-79), and movement of mutant or wild-type fragments in polyacrylamide gels containing a gradient of denaturant is assayed using denaturing gradient gel electrophoresis (Myers et al. (1985) Nature 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) Trends Genet. 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) Human Mutation 7:244-255; Kozal et al. (1996) Nature Medicine 2:753-759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The PGP synthase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the PGP synthase gene that results in altered affinity for a coenzyme could result in an excessive or decreased drug effect with standard concentrations of the coenzyme that activate the PGP synthase. Accordingly, the PGP synthase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The PGP synthase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The PGP synthase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the PGP synthase sequence can be used to provide an alternative technique, which determines the actual DNA sequence of selected fragments in the genome of an individual. Thus, the PGP synthase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The PGP synthase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The PGP synthase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The PGP synthase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The PGP synthase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of PGP synthase probes can be used to identify tissue by species and/or by organ type.

In a similar fashion, these primers and probes can be used to screen tissue culture for contamination (i.e. screen for the presence of a mixture of different types of cells in a culture).

Alternatively, the PGP synthase polynucleotides can be used directly to block transcription or translation of PGP synthase gene sequences by means of antisense or ribozyme constructs. Thus, in a disorder characterized by abnormally high or undesirable PGP synthase gene expression, nucleic acids can be directly used for treatment.

The PGP synthase polynucleotides are thus useful as antisense constructs to control PGP synthase gene expression in cells, tissues, and organisms. A DNA antisense polynucleotide is designed to be complementary to a region of the gene involved in transcription, preventing transcription and hence production of PGP synthase protein. An antisense RNA or DNA polynucleotide would hybridize to the mRNA and thus block translation of mRNA into PGP synthase protein.

Examples of antisense molecules useful to inhibit nucleic acid expression include antisense molecules complementary to a fragment of the 5' untranslated region of SEQ ID NO:1, which also includes the start codon and antisense molecules which are complementary to a fragment of the 3' untranslated region of SEQ ID NO:1.

Alternatively, a class of antisense molecules can be used to inactivate mRNA in order to decrease expression of a PGP synthase nucleic acid. Accordingly, these molecules can treat a disorder characterized by abnormal or undesired PGP synthase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the PGP synthase protein.

The PGP synthase polynucleotides also provide vectors for gene therapy in patients containing cells that are aberrant in PGP synthase gene expression. Thus, recombinant cells, which include the patient's cells that have been engineered ex vivo and returned to the patient, are introduced into an individual where the cells produce the desired PGP synthase protein to treat the individual.

The invention also encompasses kits for detecting the presence of an PGP synthase nucleic acid in a biological sample. For example, the kit can comprise reagents such as a labeled or labelable nucleic acid or agent capable of detecting PGP synthase nucleic acid in a biological sample; means for determining the amount of PGP synthase nucleic acid in the sample; and means for comparing the amount of PGP synthase nucleic acid in the sample with a standard. The compound or agent can be packaged in a suitable container. The kit can further comprise instructions for using the kit to detect PGP synthase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) J. Mol. Biol. 215:403-410) and BLAZE (Brutlag et al. (1993) Comp. Chem. 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the PGP synthase polynucleotides. The term "vector" refers to a vehicle, preferably a nucleic acid molecule that can transport the PGP synthase polynucleotides. When the vector is a nucleic acid molecule, the PGP synthase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the PGP synthase polynucleotides. Alternatively, the vector may integrate into the host cell genome and produce additional copies of the PGP synthase polynucleotides when the host cell replicates.

The invention provides vectors for the maintenance (cloning vectors) or vectors for expression (expression vectors) of the PGP synthase polynucleotides. The vectors can function in procaryotic or eukaryotic cells or in both (shuttle vectors).

Expression vectors contain cis-acting regulatory regions that are operably linked in the vector to the PGP synthase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the PGP synthase polynucleotides from the vector. Alternatively, a trans-acting factor may be supplied by the host cell. Finally, a trans-acting factor can be produced from the vector itself.

It is understood, however, that in some embodiments, transcription and/or translation of the PGP synthase polynucleotides can occur in a cell-free system.

The regulatory sequence to which the polynucleotides described herein can be operably linked include promoters for directing mRNA transcription. These include, but are not limited to, the left promoter from bacteriophage A, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) Molecular Cloning: A Laboratory Manual 2nd. ed., Cold Spring Harbor Laboratory Press, Cold Spring Harbor, N.Y.).

A variety of expression vectors can be used to express a PGP synthase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) Molecular Cloning: A Laboratory Manual 2nd. ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The PGP synthase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the PGP synthase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) Gene 69:301-315) and pET 11d (Studier et al. (1990) Gene Expression Technology: Methods in Enzymology 185:60-89).

Recombinant protein expression can be maximized in a host bacteria by providing a genetic background wherein the host cell has an impaired capacity to proteolytically cleave the recombinant protein. (Gottesman, S. (1990) Gene Expression Technology: Methods in Enzymology 185, Academic Press, San Diego, Calif. 119-128). Alternatively, the sequence of the polynucleotide of interest can be altered to provide preferential codon usage for a specific host cell, for example *E. coli*. (Wada et al. (1992) Nucleic Acids Res. 20:2111-2118).

The PGP synthase polynucleotides can also be expressed by expression vectors that are operative in yeast. Examples of vectors for expression in yeast e.g., *S. cerevisiae* include pYepSec1 (Baldari et al. (1987) EMBO J. 6:229-234), pMFa (Kurjan et al. (1982) Cell 30:933-943), pJRY88 (Schultz et al. (1987) Gene 54:113-123), and pYES2 (Invitrogen Corporation, San Diego, Calif.).

The PGP synthase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow et al. (1989) Virology 170:31-39).

In certain embodiments of the invention, the polynucleotides described herein are expressed in mammalian cells using mammalian expression vectors. Examples of mammalian expression vectors include pCDM8 (Seed, B. (1987) Nature 329:840) and pMT2PC (Kaufman et al. (1987) EMBO J. 6:187-195).

The expression vectors listed herein are provided by way of example only of the well-known vectors available to those of ordinary skill in the art that would be useful to express the PGP synthase polynucleotides. The person of ordinary skill in the art would be aware of other vectors suitable for maintenance propagation or expression of the polynucleotides described herein. These are found for example in Sambrook et al. (1989) Molecular Cloning: A Laboratory Manual 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (Molecular Cloning: A Laboratory Manual, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the PGP synthase polynucleotides can be introduced either alone or with other polynucleotides that are not related to the PGP synthase polynucleotides such as those providing trans-acting factors for expression vectors. When more than one vector is introduced into a cell, the vectors can be introduced independently, co-introduced or joined to the PGP synthase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the PGP synthase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

The host cells expressing the polypeptides described herein, and particularly recombinant host cells, have a variety of uses. First, the cells are useful for producing PGP synthase proteins or polypeptides that can be further purified to produce desired amounts of PGP synthase protein or fragments. Thus, host cells containing expression vectors are useful for polypeptide production.

Host cells are also useful for conducting cell-based assays involving the PGP synthase or PGP synthase fragments. Thus, a recombinant host cell expressing a native PGP synthase is useful to assay for compounds that stimulate or inhibit PGP synthase function. These include, but are not limited to those disclosed herein and above in the background.

Host cells are also useful for identifying PGP synthase mutants in which these functions are affected. If the mutants naturally occur and give rise to a pathology, host cells containing the mutations are useful to assay compounds that have a desired effect on the mutant PGP synthase (for example, stimulating or inhibiting function) which may not be indicated by their effect on the native PGP synthase.

Recombinant host cells are also useful for expressing the chimeric polypeptides described herein to assess compounds that activate or suppress activation by means of a heterologous domain, segment, site, and the like, as disclosed herein.

Further, mutant PGP synthase can be designed in which one or more of the various functions is engineered to be increased or decreased and used to augment or replace PGP synthase proteins in an individual. Thus, host cells can provide a therapeutic benefit by replacing an aberrant PGP synthase or providing an aberrant PGP synthase that provides a therapeutic result. In one embodiment, the cells provide PGP synthase that are abnormally active.

In another embodiment, the cells provide PGP synthase that are abnormally inactive. These PGP synthase can compete with endogenous PGP synthase in the individual.

In another embodiment, cells expressing PGP synthase that are not catalytically active, are introduced into an individual in order to compete with endogenous PGP synthase. For example, in the case in which excessive amounts of a PGP synthase substrate or effector is part of a treatment modality, it may be necessary to inactivate this molecule at a specific point in treatment. Providing cells that compete for the molecule, but which cannot be affected by PGP synthase activation would be beneficial.

Homologously recombinant host cells can also be produced that allow the in situ alteration of endogenous PGP synthase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. Nos. 5,272,071, and 5,641,670. Briefly, specific polynucleotide sequences corresponding to the PGP synthase polynucleotides or sequences proximal or distal to an PGP synthase gene are allowed to integrate into a host cell genome by homologous recombination where expression of the gene can be affected. In one embodiment, regulatory sequences are introduced that either increase or decrease expression of an endogenous sequence. Accordingly, a PGP synthase protein can be produced in a cell not normally producing it. Alternatively, increased expression of PGP synthase protein can be effected in a cell normally producing the protein at a specific level. Further, expression can be decreased or eliminated by introducing a specific regulatory sequence. The regulatory sequence can be heterologous to the PGP synthase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant PGP synthase proteins. Such mutations could be introduced, for example, into the specific functional regions such as the ligand-binding site.

In one embodiment, the host cell can be a fertilized oocyte or embryonic stem cell that can be used to produce a transgenic animal containing the altered PGP synthase gene. Alternatively, the host cell can be a stem cell or other early tissue precursor that gives rise to a specific subset of cells and can be used to produce transgenic tissues in an animal. See also Thomas et al., Cell 51:503 (1987) for a description of homologous recombination vectors. The vector is introduced into an embryonic stem cell line (e.g., by electroporation) and cells in which the introduced gene has homologously recombined with the endogenous PGP synthase gene is selected (see e.g., Li, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by gemmline transmission of the transgene. Methods for constructing homologous recombination vectors and homologous recombinant animals are described further in Bradley, A. (1991) Current Opinion in Biotechnology 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a PGP synthase protein and identifying and evaluating modulators of PGP synthase protein activity.

Other examples of transgenic animals include non-human primates, sheep, dogs, cows, goats, chickens, and amphibians.

In one embodiment, a host cell is a fertilized oocyte or an embryonic stem cell into which PGP synthase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the PGP synthase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the PGP synthase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) PNAS 89:6232-6236. Another example of a recombinase system is the FLP recombinase system of *S. cerevisiae* (O'Gorman et al. (1991) Science 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect substrate binding may not be evident from in vitro cell-free or cell-based assays. Accordingly, it is useful to provide non-human transgenic animals to assay in vivo PGP synthase function, including substrate, cofactor and substituted phospho group transfer interactions. Similar methods could be used to determine the effect of specific mutant PGP synthase and the effect of chimeric PGP synthase on such enzyme functions. It is also possible to assess the effect of null mutations, that is mutations that substantially or completely eliminate one or more PGP synthase functions.

In general, methods for producing transgenic animals include introducing a nucleic acid sequence according to the present invention, the nucleic acid sequence capable of expressing the PGP synthase protein in a transgenic animal, into a cell in culture or in vivo. When introduced in vivo, the nucleic acid is introduced into an intact organism such that one or more cell types and, accordingly, one or more tissue types, express the nucleic acid encoding the PGP synthase protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The PGP synthase nucleic acid molecules, polypeptides and modulators of the polypeptide and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PGP synthase protein or anti-PGP synthase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 27411 preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 27411 nucleic acid, polypeptide, or antibody.

The capture probes can be a set of nucleic acids from a selected sample, e.g., a sample of nucleic acids derived from a control or non-stimulated tissue or cell.

The method can include contacting the 27411 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes with an allele of 27411. Such methods can be used to diagnose a subject, e.g., to evaluate risk for a disease or disorder, to evaluate suitability of a selected treatment for a subject, to evaluate whether a subject has a disease or disorder. 27411 is associated with PGP synthase activity, thus it is useful for disorders associated with abnormal PGP synthase activity, cardiolipin biosynthesis, and PG biosynthesis.

The method can be used to detect SNPs.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or mis express 27411 or from a cell or subject in which a 27411 mediated response has been elicited, e.g., by contact of the cell with 27411 nucleic acid or protein, or administration to the cell or subject 27411 nucleic acid or protein; contacting the array with one or more inquiry probe, wherein an inquiry probe can be a nucleic acid, polypeptide, or antibody (which is preferably other than 27411 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 27411 (or does not express as highly as in the case of the 27411 positive plurality of capture probes) or from a cell or subject which in which a 27411 mediated response has not been elicited (or has been elicited to a lesser extent than in the first sample); contacting the array with one or more inquiry probes (which is preferably other than a 27411 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 27411, e.g., analyzing structure, function, or relatedness to other nucleic acid or amino acid sequences. The method includes: providing a 27411 nucleic acid or amino acid sequence; comparing the 27411 sequence with one or more preferably a plurality of sequences from a collection of sequences, e.g., a nucleic acid or protein sequence database; to thereby analyze 27411.

Preferred databases include GenBank™. The method can include evaluating the sequence identity between a 27411 sequence and a database sequence. The method can be performed by accessing the database at a second site, e.g., over the internet.

In another aspect, the invention features, a set of oligonucleotides, useful, e.g., for identifying SNP's, or identifying specific alleles of 27411. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with different labels, such that an oligonucleotide that hybridizes to one allele provides a signal that is distinguishable from an oligonucleotide that hybridizes to a second allele.

This invention is further illustrated by the following examples that should not be construed as limiting. The contents of all references, patents and published patent applications cited throughout this application are incorporated herein by reference.

EXAMPLES

Example 1

Identification and Characterization of 27411, Human PGP Synthase

The human 27411 sequence (SEQ ID NO:1), that is approximately 2686 nucleotides long including untranslated regions, contains a predicted methionine-initiated coding sequence of about 1671 nucleotides (nucleotides 315-1985 of SEQ ID NO:1; SEQ ID NO:3). The coding sequence encodes a 556 amino acid protein (SEQ ID NO:2).

The human 27411 sequence (SEQ ID NO:1) contains the following functional sites: three N-glycosylation sites are found from about amino acid 213 to about amino acid 216, from about amino acid 236 to about amino acid 239, and from about amino acid 390 to about amino acid 393 of SEQ ID NO:2; two cyclic AMP and cGMP-dependent protein kinase phosphorylation sites are found from about amino acid 46 to about amino acid 49 and from about amino acid 172 to about 175 of SEQ ID NO:2; three protein kinase C phosphorylation sites are found from about amino acid 35 to about amino acid 37, from about amino acid 243 to about amino acid 245, and from about amino acid 313 to about amino acid 315 of SEQ ID NO:2; five casein kinase II phosphorylation sites are found from about amino acid 102 to about amino acid 105, from about amino 143 to about amino acid 146, from about amino acid 333 to about amino acid 336, from about amino acid 374 to about amino acid 377, and from about amino acid 402 to about amino acid 405 of SEQ ID NO:2; one tyrosine kinase phosphorylation site is found from about amino acid 344 to about amino acid 352 of SEQ ID NO:2; five N-myristoylation sites are found from about amino acid 19 to about amino acid 24, from about amino acid 91 to about amino acid 96, from about amino acid 234 to about amino acid 239, from about amino acid 423 to about amino acid 428, and from about amino acid 527 to about amino acid 532 of SEQ ID NO:2; and an amidation site is found from about amino acid 170 to about amino acid 173 of SEQ ID NO:2.

PFAM analysis indicates that the 27411 polypeptide shares a high degree of sequence similarity with phospholipase D domains from amino acids 215-241 and 460-493 of SEQ ID NO:2. The phospholipase D domain (HMM) has been assigned the PFAM Accession PF00614. For general information regarding PFAM identifiers, PS prefix and PF prefix domain identification numbers, refer to Sonnhammer et al. (1997) Protein 28:405-420.

In one embodiment, a 27411-like protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 26, or 27 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in Zagotta W. N. et al. (1996) Annual Rev. Neuronsci. 19:235-63, the contents of which are incorporated herein by reference.

In a preferred embodiment, a 27411-like polypeptide or protein has at least one transmembrane domain or a region which includes at least 18, 20, 22, 24, 25, 26, or 27 amino acid residues and has at least about 60%, 70% 80% 90% 95%, 99%, or 100% sequence identity with a "transmembrane domain," e.g., at least one transmembrane domain of human 27411-like (e.g., amino acid residues 51 to 73 or 469 to 485 of SEQ ID NO:2).

In another embodiment, a 27411-like protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring 27411-like, or 27411-like protein.

In a preferred embodiment, a 27411-like polypeptide or protein has a "non-transmembrane domain" or a region which includes at least about 1-396, preferably about 100-396, more preferably about 200-350, and even more preferably about 240-280 amino acid residues, and has at least about 60%, 70% 80% 90% 95%, 99% or 100% sequence identity with a "non-transmembrane domain", e.g., a non-transmembrane domain of human 27411-like (e.g., residues 1 to 51, 74 to 468, and 486 to 556 of SEQ ID NO:2). Preferably, a non-transmembrane domain is capable of catalytic activity (e.g., PGP synthase).

A non-transmembrane domain located at the N-terminus of a 27411-like protein or polypeptide is referred to herein as an "N-terminal non-transmembrane domain." As used herein, an "N-terminal non-transmembrane domain" includes an amino acid sequence having about 1-51, preferably about 10-45, more preferably about 20-40, or even more preferably about 20-35 amino acid residues in length and is located outside the boundaries of a membrane. For example, an N-terminal non-transmembrane domain is located at about amino acid residues 1 to 50 of SEQ ID NO:2.

Similarly, a non-transmembrane domain located at the C-terminus of 27411-like protein or polypeptide is referred to herein as a "C-terminal non-transmembrane domain." As used herein, an "C-terminal non-transmembrane domain" includes an amino acid sequence having about 1-71, preferably about 10-75, preferably about 20-60, more preferably about 25-45 amino acid residues in length and is located outside the boundaries of a membrane. For example, an C-terminal non-transmembrane domain is located at about amino acid residues 486 to 556 of SEQ ID NO:2.

A 27411-like molecule can further include a signal sequence. As used herein, a "signal sequence" refers to a peptide of about 20-80 amino acid residues in length which occurs at the N-terminus of secretory and integral membrane proteins and which contains a majority of hydrophobic amino acid residues. For example, a signal sequence contains at least about 12-25 amino acid residues, preferably about 30-70 amino acid residues, more preferably about 68 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 27411-like protein contains a signal sequence of about amino acids 1 to 68 of SEQ ID NO:2. The "signal sequence" may be cleaved during processing of the mature protein. The mature 27411-like protein corresponds to amino acids 69 to 556 of SEQ ID NO:2.

The 27411 protein displays approximately 26% identity from aa 85-522 to a ProDom consensus sequence found in O-phosphatidyltransferase CDP-diacylglycerol serine phosphatidylserine synthase transferase phospholipid biosynthesis; approximately 31% identity from aa 476-554 to a ProDom consensus sequence found in receptor nuclear co-repressor N-cor retinoid X interacting protein; approximately 31% identity from aa 260-324 to a ProDom consensus sequence found in SIPI protein phosphorylation; and, approximately 38% identity from aa 210-247 to a ProDom consensus sequence found in protein transferase HP019 transmembrane CSGC-MDOG intergenic region. These sequences were identified by the ProDom program, which is available from INRA, GREG (107/94), MESR (ACC-SV13), the CNRS "Genome Initiative" and the European Union. A detailed description of ProDom analysis can be found in Corpet et al. (1999) Nuc. Acids Res. 27:263-267.

Example 2

Tissue Distribution of 27411 mRNA

Expression levels of 27411 in various tissue and cell types were determined by quantitative RT-PCR (Reverse Transcriptase Polymerase Chain Reaction; Taqman® brand PCR kit, Applied Biosystems). The quantitative RT-PCR reactions were performed according to the kit manufacturer's instructions. The results of the Taqman® analysis are described herein.

TaqMan analysis of 27411 revealed expression in a number of tissues, including the following: artery, diseased artery, vein, coronary smooth muscle cells, HUVEC (umbilical vein endothelial cells), hemangioma, heart, congestive heart failure heart, kidney, skeletal muscle, adipose, pancreas, primary osteoblasts, differentiated osteoclasts, skin, spinal cord, brain cortex, brain hypothalamus, nerve, dorsal root ganglion, breast, breast tumor, ovary, ovarian tumor, prostate, prostate tumor, salivary glands, colon, colon tumor, lung, lung tumor, chronic obstructive pulmonary disease lung, inflammatory bowel disease colon, liver, liver fibrosis, spleen, tonsil, lymph node, small intestine, macrophages, synovium, mononuclear bone marrow cells, activated peripheral blood mononuclear cells, neutrophils, megakaryocytes, and erythroid tissue.

Northern blot hybridizations with various RNA samples are performed under standard conditions and washed under stringent conditions, i.e., 0.2×SSC at 65° C. A DNA probe corresponding to all or a portion of the 27411 cDNA (SEQ ID NO:1) can be used. The DNA is radioactively labeled with 32P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb hybridization solution (Clontech) and washed at high stringency according to manufacturer's recommendations.

Example 3

Recombinant Expression of 27411 in Bacterial Cells

In this example, 27411 is expressed as a recombinant glutathione-S-transferase (GST) fusion polypeptide in *E. coli* and the fusion polypeptide is isolated and characterized. Specifically, 27411 is fused to GST and this fusion polypeptide is expressed in *E. coli*, e.g., strain PEB 199. Expression of the GST-27411 fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 27411 Protein in COS Cells

To express the 27411 gene in COS cells, the pcDNA/Amp vector by Invitrogen Corporation (San Diego, Calif.) is used.

This vector contains an SV40 origin of replication, an ampicillin resistance gene, an *E. coli* replication origin, a CMV promoter followed by a polylinker region, and an SV40 intron and polyadenylation site. A DNA fragment encoding the entire 27411 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 27411 DNA sequence is amplified by PCR using two primers. The 5' primer contains the restriction site of interest followed by approximately twenty nucleotides of the 27411 coding sequence starting from the initiation codon; the 3' end sequence contains complementary sequences to the other restriction site of interest, a translation stop codon, the HA tag or FLAG tag and the last 20 nucleotides of the 27411 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 27411 gene is inserted in the correct orientation. The ligation mixture is transformed into *E. coli* cells (strains HB101, DH5□, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 27411-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 27411 polypeptide is detected by radiolabelling (35S-methionine or 35S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with 35S-methionine (or 35S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 27411 coding sequence is cloned directly into the polylinker of the pcDNA/Amp vector using the appropriate restriction sites. The resulting plasmid is transfected into COS cells in the manner described above, and the expression of the 27411 polypeptide is detected by radiolabelling and immunoprecipitation using a 27411 specific monoclonal antibody.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

II. 23413, A NOVEL HUMAN UBIQUITIN PROTEASE

Background of the Invention

Polypeptides

The invention is based on the identification of a novel human ubiquitin protease. Specifically, an expressed sequence tag (EST) was selected based on homology to ubiquitin protease sequences. This EST was used to design primers based on sequences that it contains and used to identify a cDNA from an endothelial cell cDNA library. Positive clones were sequenced and the overlapping fragments were assembled. Analysis of the assembled sequence revealed that the cloned cDNA molecule encodes a ubiquitin protease containing the conserved HIS and CYS boxes of the UBP family of deubiquitinating enzymes.

The invention thus relates to a novel ubiquitin protease having the deduced amino acid sequence shown (SEQ ID NO:4). The 23413 seqeunce (SEQ ID NO:4) contains the following functional sites: two glycosylation sites are found from about amino acid 188 to about amino acid 191 and from about amino acid 335 to about amino acid 338 of SEQ ID NO:4, with the actual modified residue being the first amino acid; two cyclic AMP and cyclic GMP-dependent protein kinase phosphorylation sites are found from about amino acid 84 to about amino acid 87 and from about amino acid 288 to about amino acid 291 of SEQ ID NO:4, with the actual modified residue being the last amino acid; five protein kinase C phosphorylation sites are found from about amino acid 169 to about amino acid 171, from about amino acid 185 to about amino acid 187, from about amino acid 223 to about amino acid 225, from about amino acid 260 to about amino acid 262, and from about amino acid 266 to about amino acid 268 of SEQ ID NO:4, with the actual modified residue being the first amino acid; four casein kinase II phosphorylation sites are found from about amino acid 22 to about amino acid 25, from about amino 197 to about amino acid 200, from about amino acid 208 to about amino acid 211, and from about amino acid 343 to about amino acid 346 of SEQ ID NO:4, with the actual modified residue being the first amino acid; one tyrosine kinase phosphorylation site is found from about amino acid 119 to about amino acid 125 of SEQ ID NO:4, with the actual modified residue being the last amino acid; two N-myristoylation sites are found from about amino acid 61 to about amino acid 66, and from about amino acid 312 to about amino acid 317 of SEQ ID NO:4, with the actual modified residue being the first amino acid; and one amidation site is found from about amino acid 233 to about amino acid 236 of SEQ ID NO:4. In addition, amino acids corresponding to the UCH signature are found at amino acids 302-319 of SEQ ID NO:4.

"Ubiquitin protease polypeptide" or "ubiquitin protease protein" refers to the polypeptide in SEQ ID NO:4 or encoded by the deposited cDNA. The term "ubiquitin protease protein" or "ubiquitin protease polypeptide", however, further includes the numerous variants described herein, as well as fragments derived from the full-length ubiquitin proteases and variants.

Tissues and/or cells in which the ubiquitin protease nucleic acid is found are described herein. Tissues in which the gene is highly expressed include breast, testes, liver, and fetal liver. The gene is also significantly expressed in thymus, brain, skeletal muscle, prostate, thyroid, fetal kidney, fetal heart, and ovary. The ubiquitin protease is particularly expressed in tissues involved in breast and lung cancer. The gene is also particularly expressed in liver metastases. These liver metastases are derived from malignant colonic tissue. Expression has been confirmed by Northern blot analysis.

The present invention thus provides an isolated or purified ubiquitin protease polypeptide and variants and fragments thereof.

Based on a BLAST search, highest homology was shown to murine UBP43 (Liu et al. (1999) *Molecular and Cellular Biology* 19:3029-3038).

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The ubiquitin protease polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the ubiquitin protease having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A ubiquitin protease polypeptide is also considered to be isolated when it is part of a membrane preparation or is purified and then reconstituted with membrane vesicles or liposomes.

The language "substantially free of chemical precursors or other chemicals" includes preparations of the ubiquitin protease polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the ubiquitin protease polypeptide comprises the amino acid sequence shown in SEQ ID NO:4. However, the invention also encompasses sequence variants. Variants include a substantially homologous protein encoded by the same genetic locus in an organism, i.e., an allelic variant.

Variants also encompass proteins derived from other genetic loci in an organism, but having substantial homology to the ubiquitin protease of SEQ ID NO:4. Variants also include proteins substantially homologous to the ubiquitin protease but derived from another organism, i.e., an ortholog. Variants also include proteins that are substantially homologous to the ubiquitin protease that are produced by chemical synthesis. Variants also include proteins that are substantially homologous to the ubiquitin protease that are produced by recombinant methods. It is understood, however, that variants exclude any amino acid sequences disclosed prior to the invention.

As used herein, two proteins (or a region of the proteins) are substantially homologous when the amino acid sequences are at least about 70-75%, typically at least about 80-85%, and most typically at least about 90-95% or more homologous. A substantially homologous amino acid sequence, according to the present invention, will be encoded by a nucleic acid sequence hybridizing to the nucleic acid sequence, or portion thereof, of the sequence shown in SEQ ID NO:4 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequence herein having 372 amino acid residues, at least 111, preferably at least 149, more preferably at least 186, even more preferably at least 223, and even more preferably at least 260, 297, 335, and 372 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the ubiquitin protease. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and GIn, exchange of the basic residues Lys and Arg and replacements among the aromatic residues Phe, Tyr. Guidance concenling which amino acid changes are likely to be phenotypically silent are found in Bowie et al., *Science* 247:1306-1310 (1990).

TABLE 2

| Conservative Amino Acid Substitutions. | |
|---|---|
| Aromatic | Phenylalanine<br>Tryptophan<br>Tyrosine |

TABLE 2-continued

| Conservative Amino Acid Substitutions. | |
| --- | --- |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988*; Biocomputing: Informatics and Genome Projects*, Smith, D. W., ed., Academic Press, New York, 1993*; Computer Analysis of Sequence Data, Part* 1, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci*. USA 90:5873-5877. Such an algorithm is incorporated into the NBLAST and XBLAST programs (version 2.0) as described in Altschul et al. (1997) *Nucleic Acids Res.* 25:3389-3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444-453) algorithm which has been incorporated into the GAP program in the GCG software package using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387) using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3-5; and FASTA described in Pearson et al. (1988) *PNAS* 85:2444-8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of ubiquitin binding, ubiquitin recognition, interaction with ubiquitinated substrate protein, such as binding or proteolysis, subunit interaction, particularly within the proteasome, activation or binding by ATP, developmental expression, temporal expression, tissue-specific expression, interacting with cellular components, such as transcriptional regulatory factors, and particularly trans-acting transcriptional regulatory factors, proteolytic cleavage of peptide bonds in polyubiquitin and peptide bonds between ubiquitin or polyubiquitin and substrate protein, and proteolytic cleavage of peptide bonds between ubiquitin or polyubiquitin and a peptide or amino acid.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the ubiquitin protease polypeptide. This includes preventing immunogenicity from pharmaceutical formulations by preventing protein aggregation.

Useful variations further include alteration of catalytic activity. For example, one embodiment involves a variation at the binding site that results in binding but not hydrolysis, or slower hydrolysis, of the peptide bond. A further useful variation results in an increased rate of hydrolysis of the peptide bond. A further useful variation at the same site can result in higher or lower affinity for substrate. Useful variations also include changes that provide for affinity for a different ubiquitinated substrate protein than that normally recognized. Other useful variations involving altered recognition affect recognition of the type of substrate normally recognized. For example, one variation could result in recognition of ubiquitinated intact substrate but not of substrate remnants, such as ubiquitinated amino acid or peptide that are proteolysis products that result from the hydrolysis of the intact ubiquitinated substrate. Alternatively, the protease could be varied so that one or more of the remnant products is recognized but not the intact protein substrate. Another variation would affect the ability of the protease to rescue a ubiquitinated protein. Thus, protein substrates that are normally rescued from proteolysis would be subject to degradation. Further useful variations affect the ability of the protease to be induced by activators, such as cytokines, including but not limited to, those disclosed herein. Another useful variation would affect the recognition of ubiquitin substrate so that the enzyme could not recognize one or more of a linear polyubiquitin, branched chain polyubiquitin, linear polyubiquitinated substrate, or branched chain polyubiquitin substrate. Specific variations include truncation in which, for example, a HIS domain is deleted, the variation resulting in decrease or loss of deubiquitination activity. Another useful variation includes one that prevents activation by ATP. Another useful variation provides a fusion protein in which one or more domains or subregions are operationally fused to one or more domains or subregions from another UBP or from a UCH. Specifically, a domain or subregion can be introduced that provides a rescue function to an enzyme not normally having this function or for recognition of a specific substrate wherein recognition is not available to the original enzyme. Other variations include those that affect ubiquitin recognition or recognition of a ubiquitinated substrate protein. Further variations could affect specific subunit interaction, particularly in the proteasome. Other variations would affect developmental, temporal, or tissue-specific expression. Other variations would affect the interaction with cellular components, such as transcriptional regulatory factors.

Amino acids that are essential for function can be identified by methods known in the art, such as site-directed mutagenesis or alanine-scanning mutagenesis (Cunningham et al. (1985) *Science* 244:1081-1085). The latter procedure introduces single alanine mutations at every residue in the molecule. The resulting mutant molecules are then tested for biological activity, such as peptide hydrolysis in vitro or ubiquitin-dependent in vitro activity, such as proliferative activity, receptor-mediated signal transduction, and other cellular processes including, but not limited, those disclosed herein that are a function of the ubiquitin system. Sites that are critical for binding or recognition can also be determined by structural analysis such as crystallization, nuclear magnetic resonance or photoaffinity labeling (Smith et al. (1992) *J. Mol. Biol.* 224:899-904; de Vos et al. (1992) *Science* 255:306-312).

The assays for deubiquitinating enzyme activity are well known in the art and can be found, for example, in Zhu et al. (1997) *Journal of Biological Chemistry* 272:51-57, Mitch et al. (1999) *American Journal of Physiology* 276:C1132-C1138, Liu et al. (1999) *Molecular and Cell Biology* 19:3029-3038, and such as those cited in various reviews, for example, Ciechanover et al. (1994) *The FASEB Journal* 8:182-192, Chiechanover (1994) *Biol. Chem. Hoppe-Seyler* 375:565-581, Hershko et al. (1998) *Annual Review of Biochemistry* 67:425-479, Swartz (1999) *Annual Review of Medicine* 50:57-74, Ciechanover (1998) *EMBO Journal* 17:7151-7160, and D'Andrea et al. (1998) *Critical Reviews in Biochemistry and Molecular Biology* 33:337-352. These assays include, but are not limited to, the disappearance of substrate, including decrease in the amount of polyubiquitin or ubiquitinated substrate protein or protein remnant, appearance of intermediate and end products, such as appearance of free ubiquitin monomers, general protein turnover, specific protein turnover, ubiquitin binding, binding to ubiquitinated substrate protein, subunit interaction, interaction with ATP, interaction with cellular components such as trans-acting regulatory factors, stabilization of specific proteins, and the like.

Substantial homology can be to the entire nucleic acid or amino acid sequence or to fragments of these sequences.

The invention thus also includes polypeptide fragments of the ubiquitin protease. Fragments can be derived from the amino acid sequence shown in SEQ ID NO:4. However, the invention also encompasses fragments of the variants of the ubiquitin proteases as described herein.

The fragments to which the invention pertains, however, are not to be construed as encompassing fragments that may be disclosed prior to the present invention.

Accordingly, a fragment can comprise at least about 10, 15, 20, 25, 30, 35, 40, 45, 50 or more contiguous amino acids. Fragments can retain one or more of the biological activities of the protein, for example the ability to bind to ubiquitin or hydrolyze peptide bonds, as well as fragments that can be used as an immunogen to generate ubiquitin protease antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic site, UBP or UCH signature, membrane-associated regions and sites for glycosylation, cAMP and cGMP-dependent protein kinase phosphorylation, protein kinase C phosphorylation, casein kinase II phosphorylation, tyrosine kinase phosphorylation, N-myristoylation, and amidation. Further possible fragments include the catalytic site or domain including the cysteine or histidine boxes, ubiquitin recognition sites, ubiquitin binding sites, sites important for subunit interaction, and sites important for carrying out the other functions of the protease as described herein.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the ubiquitin protease and variants. These epitope-bearing peptides are useful to raise antibodies that bind specifically to a ubiquitin protease polypeptide or region or fragment. These peptides can contain at least 10, 12, at least 14, or between at least about 15 to about 30 amino acids.

Non-limiting examples of antigenic polypeptides that can be used to generate antibodies include but are not limited to peptides derived from an extracellular site. However, intracellularly-made antibodies ("intrabodies") are also encompassed, which would recognize intracellular peptide regions.

The epitope-bearing ubiquitin protease polypeptides may be produced by any conventional means (Houghten, R. A. (1985) *Proc. Natl. Acad. Sci. USA* 82:5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the ubiquitin protease fragment and an additional region fused to the carboxyl terminus of the fragment.

The invention thus provides chimeric or fusion proteins. These comprise a ubiquitin protease peptide sequence operatively linked to a heterologous peptide having an amino acid sequence not substantially homologous to the ubiquitin protease. "Operatively linked" indicates that the ubiquitin protease peptide and the heterologous peptide are fused in-frame. The heterologous peptide can be fused to the N-terminus or C-terminus of the ubiquitin protease or can be internally located.

In one embodiment the fusion protein does not affect ubiquitin protease function per se. For example, the fusion protein can be a GST-fusion protein in which the ubiquitin protease sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant ubiquitin protease. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52-58 (1995) and Johanson et al. *J. Biol. Chem.* 270:9459-9471). Thus, this invention also encompasses soluble fusion proteins containing a ubiquitin protease polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A ubiquitin protease-encoding nucleic acid can be cloned into such an expression vector such that the fusion moiety is linked in-frame to the ubiquitin protease.

Another form of fusion protein is one that directly affects ubiquitin protease functions. Accordingly, a ubiquitin protease polypeptide is encompassed by the present invention in which one or more of the ubiquitin protease domains (or parts thereof) has been replaced by homologous domains (or parts thereof) from another UBP or UCH species. Accordingly, various permutations are possible. One or more functional sites as disclosed herein from the specifically disclosed protease can be replaced by one or more functional sites from a corresponding UBP family member or from a UCH family member. Thus, chimeric ubiquitin proteases can be formed in which one or more of the native domains or subregions has been replaced by another.

Additionally, chimeric ubiquitin protease proteins can be produced in which one or more functional sites is derived from a different ubiquitin protease family. It is understood however that sites could be derived from ubiquitin protease families that occur in the mammalian genome but which have not yet been discovered or characterized. Such sites include but are not limited to any of the functional sites disclosed herein.

The isolated ubiquitin proteases can be purified from cells that naturally express it, such as from thymus, testes, brain, breast, skeletal muscle, liver, prostate, thyroid, ovary, fetal kidney, fetal heart, fetal liver, liver metastases derived from colon, and malignant lung and breast tissue, especially purified from cells that have been altered to express it (recombinant), or synthesized using known protein synthesis methods.

In one embodiment, the protein is produced by recombinant DNA techniques. For example, a nucleic acid molecule encoding the ubiquitin protease polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1-12 (1983); Seifter et al. (1990) *Meth. Enzymol.* 182: 626-646) and Rattan et al. (1992) *Ann. N.Y. Acad. Sci.* 663:48-62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The ubiquitin protease polypeptides are useful for producing antibodies specific for the ubiquitin protease, regions, or fragments.

The ubiquitin protease polypeptides are useful for biological assays related to ubiquitin protease function. Such assays involve any of the known functions or activities or properties useful for diagnosis and treatment of ubiquitin- or ubiquitin protease-related conditions. Potential assays have been disclosed herein and generically include disappearance of substrate, appearance of end product, and general or specific protein turnover.

The ubiquitin protease polypeptides are also useful in drug screening assays, in cell-based or cell-free systems. Cell-based systems can be native, i.e., cells that normally express the ubiquitin protease, as a biopsy or expanded in cell culture. In one embodiment, however, cell-based assays involve recombinant host cells expressing the ubiquitin protease.

Determining the ability of the test compound to interact with the ubiquitin protease can also comprise determining the ability of the test compound to preferentially bind to the polypeptide as compared to the ability of a known binding molecule (e.g., ubiquitin) to bind to the polypeptide.

The polypeptides can be used to identify compounds that modulate ubiquitin protease activity. Such compounds, for example, can increase or decrease affinity for polyubiquitin, either linear or branched chain, ubiquitinated protein substrate, or ubiquitinated protein substrate remnants. Such compounds could also, for example, increase or decrease the rate of binding to these components. Such compounds could also compete with these components for binding to the ubiquitin protease or displace these components bound to the ubiquitin protease. Such compounds could also affect interaction with other components, such as ATP, other subunits, for example, in the 19S complex, and transcriptional regulatory factors. It is understood, therefore, that such compounds can be identified not only by means of ubiquitin, but by means of any of the components that functionally interact with the disclosed protease. This includes, but is not limited to, any of those components disclosed herein.

Both ubiquitin protease and appropriate variants and fragments can be used in high-throughput screens to assay candidate compounds for the ability to bind to the ubiquitin protease. These compounds can be further screened against a functional ubiquitin protease to determine the effect of the compound on the ubiquitin protease activity. Compounds can be identified that activate (agonist) or inactivate (antagonist) the ubiquitin protease to a desired degree. Modulatory methods can be performed in vitro (e.g., by culturing the cell with the agent) or, alternatively, in vivo (e.g., by administering the agent to a subject.

The ubiquitin protease polypeptides can be used to screen a compound for the ability to stimulate or inhibit interaction between the ubiquitin protease protein and a target molecule that normally interacts with the ubiquitin protease protein. The target can be ubiquitin, ubiquitinated substrate, or polyubiquitin or another component of the pathway with which the ubiquitin protease protein normally interacts (for example, ATP). The assay includes the steps of combining the ubiquitin protease protein with a candidate compound under conditions that allow the ubiquitin protease protein or fragment to interact with the target molecule, and to detect the formation of a complex between the ubiquitin protease protein and the target or to detect the biochemical consequence of the interaction with the ubiquitin protease and the target. Any of the associated effects of protease function can be assayed. This includes the production of hydrolysis products, such as free terminal peptide substrate, free terminal amino acid from the hydrolyzed substrate, free ubiquitin, lower molecular weight species of hydrolyzed polyubiquitin, released intact substrate protein resulting from rescue from proteolysis, free polyubiquitin formed from hydrolysis of the polyubiquitin from intact substrate, and substrate remnants, such as amino acids and peptides produced from proteolysis of the substrate protein, and biological endpoints of the pathway.

Determining the ability of the ubiquitin protease to bind to a target molecule can also be accomplished using a technology such as real-time Bimolecular Interaction Analysis (BIA). Sjolander et al. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 97:6378-6382); (Felici (1991) *J. Mol. Biol.* 222:301-310); (Ladner supra).

Candidate compounds include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354: 84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767-778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble full-length ubiquitin protease or fragment that competes for substrate binding. Other candidate compounds include mutant ubiquitin proteases or appropriate fragments containing mutations that affect ubiquitin protease function and compete for substrate. Accordingly, a fragment that competes for substrate, for example with a higher affinity, or a fragment that binds substrate but does not hydrolyze the peptide bond, is encompassed by the invention.

Other candidate compounds include ubiquitinated protein or protein analog that binds to the protease but is not released or released slowly. Other candidate compounds include analogs of the other natural substrates, such as substrate remnants that bind to but are not released or released more slowly. Further candidate compounds include activators of the proteases such as cytokines, including but not limited to, those disclosed herein.

The invention provides other end points to identify compounds that modulate (stimulate or inhibit) ubiquitin protease activity. The assays typically involve an assay of events in the pathway that indicate ubiquitin protease activity. This can include cellular events that result from deubiquitination, such as cell cycle progression, programmed cell death, growth factor-mediated signal transduction, or any of the cellular processes including, but not limited to, those disclosed herein as resulting from deubiquitination. Specific phenotypes include changes in stress response, DNA replication, receptor internalization, cellular transformation or reversal of transformation, and transcriptional silencing.

Assays are based on the multiple cellular functions of deubiquitinating enzymes. These enzymes act at various different levels in the regulation of protein ubiquitination. A deubiquitinating enzyme can degrade a linear polyubiquitin chain into monomeric ubiquitin molecules. Deubiquitinating enzymes, such as isopeptidase-T, can degrade a branched multiubiquitin chain into monomeric ubiquitin molecules. Deubiquitinating enzymes can remove ubiquitin from a ubiquitin-conjugated target protein. The deubiquitinating enzyme, such as FAF or PA700 isopeptidase, can remove polyubiquitin from a ubiquitinated target protein, and thereby rescue the target from degradation by the 26S proteasome. Deubiquitinating enzymes such as Doa-4 can remove polyubiquitin from proteasome degradation products. The result of all of these is to regulate the cellular pool of free monomeric ubiquitin. Accordingly, assays can be based on detection of any of the products produced by hydrolysis/deubiquitination.

Further, the expression of genes that are up- or down-regulated by action of the ubiquitin protease can be assayed. In one embodiment, the regulatory region of such genes can be operably linked to a marker that is easily detectable, such as luciferase.

Accordingly, any of the biological or biochemical functions mediated by the ubiquitin protease can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric ubiquitin protease proteins in which one or more domains, sites, and the like, as disclosed herein, or parts thereof, can be replaced by their heterologous counterparts derived from other ubiquitin proteases. For example, a recognition or binding region can be used that interacts with different substrate specificity and/or affinity than the native ubiquitin protease. Accordingly, a different set of pathway components is available as an end-point assay for activation. Further, sites that are responsible for developmental, temporal, or tissue specificity can be replaced by heterologous sites such that the protease can be detected under conditions of specific developmental, temporal, or tissue-specific expression.

The ubiquitin protease polypeptides are also useful in competition binding assays in methods designed to discover compounds that interact with the ubiquitin protease. Thus, a compound is exposed to a ubiquitin protease polypeptide under conditions that allow the compound to bind to or to otherwise interact with the polypeptide. Soluble ubiquitin protease polypeptide is also added to the mixture. If the test compound interacts with the soluble ubiquitin protease polypeptide, it decreases the amount of complex formed or activity from the ubiquitin protease target. This type of assay is particularly useful in cases in which compounds are sought that interact with specific regions of the ubiquitin protease. Thus, the soluble polypeptide that competes with the target ubiquitin protease region is designed to contain peptide sequences corresponding to the region of interest.

Another type of competition-binding assay can be used to discover compounds that interact with specific functional sites. As an example, ubiquitin and a candidate compound can be added to a sample of the ubiquitin protease. Compounds that interact with the ubiquitin protease at the same site as ubiquitin will reduce the amount of complex formed between the ubiquitin protease and ubiquitin. Accordingly, it is possible to discover a compound that specifically prevents interaction between the ubiquitin protease and ubiquitin. Another example involves adding a candidate compound to a sample of ubiquitin protease and polyubiquitin. A compound that competes with polyubiquitin will reduce the amount of hydrolysis or binding of the polyubiquitin to the ubiquitin protease. Accordingly, compounds can be discovered that directly interact with the ubiquitin protease and compete with polyubiquitin. Such assays can involve any other component that interacts with the ubiquitin protease, such as ubiquitinated substrate protein, ubiquitinated substrate remnants, and cellular components with which the protease interacts such as transcriptional regulatory factors.

To perform cell free drug screening assays, it is desirable to immobilize either the ubiquitin protease, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/ubiquitin protease fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of ubiquitin protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a ubiquitin protease-binding target component, such as ubiquitin, polyubiquitin, ubiquitinated substrate protein, ubiquitinated substrate protein remnant, or ubiquitinated remnant amino acid, and a candidate compound are incubated in the ubiquitin protease-presenting wells and the amount of complex trapped in the well can be quantitated. Methods for detecting such complexes, in addition to those described above for the GST-immobilized complexes, include immunodetection of complexes using antibodies reactive with the ubiquitin protease target molecule, or which are reactive with ubiquitin protease and compete with the target molecule; as well as enzyme-linked assays which rely on detecting an enzymatic activity associated with the target molecule.

Modulators of ubiquitin protease activity identified according to these drug screening assays can be used to treat a subject with a disorder mediated by the ubiquitin protease pathway, by treating cells that express the ubiquitin protease, including but not limited to tissues of the liver, breast, brain, and testes. Our data indicates that 23413 mRNA expression was increased in normal breast, lung, liver, and colon. 23413 mRNA wxpression was enhanced in maglignant breast, lung, liver, and colon metastases. In one embodiment, the cells treated are lung or breast cancer cells. In another embodiment of the invention the cells that are treated are colon metastases to the liver. These methods of treatment include the steps of administering the modulators of ubiquitin protease activity in a pharmaceutical composition as described herein, to a subject in need of such treatment.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the brain include, but are limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney and nephronophthisis-uremic medullary cystic disease complex, acquired (dialysis-associated) cystic disease and simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomeruloscierosis, amyloidosis, fibrillary and immunotactoid glomerulonephritis, and other systemic disorders; diseases affecting tubules and interstitium, including, but not limited to, acute tubular necrosis and tubulointerstitial nephritis, including but not limited to, pyelonephritis and urinary tract infection, acute pyelonephritis, chronic pyelonephritis and reflux nephropathy, tubulointerstitial nephritis induced by drugs and toxins, including but not limited to, acute drug-induced interstitial nephritis, analgesic abuse nephropathy, and nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including, including but not limited to, benign nephrosclerosis, malignant hypertension and accelerated nephrosclerosis, renal artery stenosis, and thrombotic microangiopathies, including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors, such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor, choriocarcinoma, teratoma, and mixed tumors, tumors of sex cord-gonadal stroma including, but not limited to, Leydig (interstitial) cell tumors and Sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors, such as rhabdomyosarcoma.

The ubiquitin protease polypeptides are thus useful for treating a ubiquitin protease-associated disorder characterized by aberrant expression or activity of a ubiquitin protease. The polypeptides can also be useful for treating a disorder characterized by excessive amounts of polyubiquitin or ubiquitinated substrate/remnant/amino acid. In one embodiment, the method involves administering an agent (e.g., an agent identified by a screening assay described herein), or combination of agents that modulates (e.g., upregulates or downregulates) expression or activity of the protein. In another embodiment, the method involves administering the ubiquitin protease as therapy to compensate for reduced or aberrant expression or activity of the protein.

Methods for treatment include but are not limited to the use of soluble ubiquitin protease or fragments of the ubiquitin protease protein that compete for substrates including those disclosed herein. These ubiquitin proteases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO 94/10300), to identify other proteins (captured proteins) which bind to or interact with the proteins of the invention and modulate their activity.

The ubiquitin protease polypeptides also are useful to provide a target for diagnosing a disease or predisposition to disease mediated by the ubiquitin protease, including, but not limited to, diseases involving tissues in which the ubiquitin proteases are expressed as disclosed herein, such as in breast cancer. Accordingly, methods are provided for detecting the presence, or levels of, the ubiquitin protease in a cell, tissue, or organism. The method involves contacting a biological sample with a compound capable of interacting with the ubiquitin protease such that the interaction can be detected.

The polypeptides are also useful for treating a disorder characterized by reduced amounts of these components. Thus, increasing or decreasing the activity of the protease is beneficial to treatment. The polypeptides are also useful to provide a target for diagnosing a disease characterized by excessive substrate or reduced levels of substrate. Accordingly, where substrate is excessive, use of the protease polypeptides can provide a diagnostic assay. Furthermore, for example, proteases having reduced activity can be used to diagnose conditions in which reduced substrate is responsible for the disorder.

One agent for detecting ubiquitin protease is an antibody capable of selectively binding to ubiquitin protease. A biological sample includes tissues, cells and biological fluids isolated from a subject, as well as tissues, cells and fluids present within a subject.

The ubiquitin protease also provides a target for diagnosing active disease, or predisposition to disease, in a patient having a variant ubiquitin protease. Thus, ubiquitin protease can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered ubiquitin protease activity in cell-based or cell-free assay, alteration in binding to or hydrolysis of polyubiquitin, binding to ubiquitinated substrate protein or hydrolysis of the ubiquitin from the protein, binding to ubiquitinated protein remnant, including peptide or amino acid, and hydrolysis of the ubiquitin from the remnant, general protein turnover, specific protein turnover, antibody-binding pattern, altered isoelectric point, direct amino acid sequencing, and any other of the known assay techniques useful for detecting mutations in a protein in general or in a ubiquitin protease specifically, including assays discussed herein.

In vitro techniques for detection of ubiquitin protease include enzyme linked immunosorbent assays (ELISAs), Western blots, immunoprecipitations and immunofluorescence. Alternatively, the protein can be detected in vivo in a subject by introducing into the subject a labeled anti-ubiquitin protease antibody. For example, the antibody can be labeled with a radioactive marker whose presence and location in a subject can be detected by standard imaging techniques. Particularly useful are methods, which detect the allelic variant of the ubiquitin protease expressed in a subject, and methods, which detect fragments of the ubiquitin protease in a sample.

The ubiquitin protease polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10-11):983-985, and Linder, M. W. (1997) *Clin. Chem.* 43(2):254-266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the ubiquitin protease in which one or more of the ubiquitin protease functions in one population is different from those in another population. The polypeptides thus allow a target to ascertain a genetic predisposition that can affect treatment modality. Thus, in a ubiquitin-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The ubiquitin protease polypeptides are also useful for monitoring therapeutic effects during clinical trials and other treatment. Thus, the therapeutic effectiveness of an agent that is designed to increase or decrease gene expression, protein levels or ubiquitin protease activity can be monitored over the course of treatment using the ubiquitin protease polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the ubiquitin protease and its variants and fragments. An antibody is considered to selectively bind, even if it also binds to other proteins that are not substantially homologous with the ubiquitin protease. These other proteins share homology with a fragment or domain of the ubiquitin protease. This conservation in specific regions gives rise to antibodies that bind to both proteins by virtue of the homologous sequence. In this case, it would be understood that antibody binding to the ubiquitin protease is still selective.

To generate antibodies, an isolated ubiquitin protease polypeptide is used as an immunogen to generate antibodies using standard techniques for polyclonal and monoclonal antibody preparation. Either the full-length protein or antigenic peptide fragment can be used. Antibodies are preferably prepared from these regions or from discrete fragments in these regions. However, antibodies can be prepared from any region of the peptide as described herein. A preferred fragment produces an antibody that diminishes or completely prevents substrate hydrolysis or binding. Antibodies can be developed against the entire ubiquitin protease or domains of the ubiquitin protease as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or $F(ab')_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

An appropriate immunogenic preparation can be derived from native, recombinantly expressed, or chemically synthesized peptides.

Antibody Uses

The antibodies can be used to isolate a ubiquitin protease by standard techniques, such as affinity chromatography or immunoprecipitation. The antibodies can facilitate the purification of the natural ubiquitin protease from cells and recombinantly produced ubiquitin protease expressed in host cells.

The antibodies are useful to detect the presence of ubiquitin protease in cells or tissues to determine the pattern of expression of the ubiquitin protease among various tissues in an organism and over the course of normal development.

The antibodies can be used to detect ubiquitin protease in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length ubiquitin protease can be used to identify ubiquitin protease turnover.

Further, the antibodies can be used to assess ubiquitin protease expression in disease states such as in active stages of the disease or in an individual with a predisposition toward disease related to ubiquitin or ubiquitin protease function. When a disorder is caused by an inappropriate tissue distribution, developmental expression, or level of expression of the ubiquitin protease protein, the antibody can be prepared against the normal ubiquitin protease protein. If a disorder is characterized by a specific mutation in the ubiquitin protease, antibodies specific for this mutant protein can be used to assay for the presence of the specific mutant ubiquitin protease. However, intracellularly-made antibodies ("intrabodies") are also encompassed, which would recognize intracellular ubiquitin protease peptide regions.

The antibodies can also be used to assess normal and aberrant subcellular localization of cells in the various tissues in an organism. Antibodies can be developed against the whole ubiquitin protease or portions of the ubiquitin protease.

The diagnostic uses can be applied, not only in genetic testing, but also in monitoring a treatment modality. Accordingly, where treatment is ultimately aimed at correcting ubiquitin protease expression level or the presence of aberrant ubiquitin proteases and aberrant tissue distribution or developmental expression, antibodies directed against the ubiquitin protease or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic ubiquitin protease can be used to identify individuals that require modified treatment modalities.

The antibodies are also useful as diagnostic tools as an immunological marker for aberrant ubiquitin protease analyzed by electrophoretic mobility, isoelectric point, tryptic peptide digest, and other physical assays known to those in the art.

The antibodies are also useful for tissue typing. Thus, where a specific ubiquitin protease has been correlated with expression in a specific tissue, antibodies that are specific for this ubiquitin protease can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting ubiquitin protease function, for example, blocking ubiquitin or polyubiquitin binding, or binding to ubiquitinated substrate or substrate remnants.

These uses can also be applied in a therapeutic context in which treatment involves inhibiting ubiquitin protease function. An antibody can be used, for example, to block ubiquitin binding. Antibodies can be prepared against specific fragments containing sites required for function or against intact ubiquitin protease associated with a cell.

Completely human antibodies are particularly desirable for therapeutic treatment of human patients. For an overview of this technology for producing human antibodies, see Lonberg et al. (1995) *Int. Rev. Immunol.* 13:65-93. For a detailed discussion of this technology for producing human antibodies and human monoclonal antibodies and protocols for producing such antibodies, e.g., U.S. Pat. Nos. 5,625,126; 5,633,425; 5,569,825; 5,661,016; and 5,545,806.

The invention also encompasses kits for using antibodies to detect the presence of a ubiquitin protease protein in a biological sample. The kit can comprise antibodies such as a labeled or labelable antibody and a compound or agent for detecting ubiquitin protease in a biological sample; means for determining the amount of ubiquitin protease in the sample; and means for comparing the amount of ubiquitin protease in the sample with a standard. The compound or agent can be packaged in a suitable container. The kit can further comprise instructions for using the kit to detect ubiquitin protease.

Polynucleotides

The nucleotide sequence in SEQ ID NO:5 was obtained by sequencing the deposited human cDNA. Accordingly, the sequence of the deposited clone is controlling as to any discrepancies between the two and any reference to the sequence of SEQ ID NO:5 includes reference to the sequence of the deposited cDNA.

The specifically disclosed cDNA comprises the coding region and 5' and 3' untranslated sequences in SEQ ID NO:5.

The invention provides isolated polynucleotides encoding the novel ubiquitin protease. The term "ubiquitin protease polynucleotide" or "ubiquitin protease nucleic acid" refers to the sequence shown in SEQ ID NO:5 or in the deposited cDNA. The term "ubiquitin protease polynucleotide" or "ubiquitin protease nucleic acid" further includes variants and fragments of the ubiquitin protease polynucleotide.

An "isolated" ubiquitin protease nucleic acid is one that is separated from other nucleic acid present in the natural source of the ubiquitin protease nucleic acid. Preferably, an "isolated" nucleic acid is free of sequences which naturally flank the ubiquitin protease nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the ubiquitin protease nucleic acid is isolated from flanking sequences such that it can be subjected to the specific manipulations described herein, such as recombinant expression, preparation of probes and primers, and other uses specific to the ubiquitin protease nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The ubiquitin protease polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The ubiquitin protease polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Ubiquitin protease polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

Ubiquitin protease nucleic acid can comprise the nucleotide sequence shown in SEQ ID NO:5, corresponding to human cDNA.

In one embodiment, the ubiquitin protease nucleic acid comprises only the coding region.

The invention further provides variant ubiquitin protease polynucleotides, and fragments thereof, that differ from the nucleotide sequence shown in SEQ ID NO:5 due to degeneracy of the genetic code and thus encode the same protein as that encoded by the nucleotide sequence shown in SEQ ID NO:5.

The invention also provides ubiquitin protease nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO:5 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a ubiquitin protease that is at least about 60-65%, 65-70%, typically at least about 70-75%, more typically at least about 80-85%, and most typically at least about 90-95% or more homologous to the nucleotide sequence shown in SEQ ID NO:5. Such nucleic acid molecules can readily be identified as being able to hybridize under stringent conditions, to the nucleotide sequence shown in SEQ ID NO:5 or a fragment of the sequence. It is understood that stringent hybridization does not indicate substantial homology where it is due to general homology, such as poly A sequences, or sequences common to all or most proteins or all deubiquitinating enzymes. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60-65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1-6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50-65° C. In another non-limiting example, nucleic acid molecules are allowed to hybridize in 6× sodium chloride/sodium citrate (SSC) at about 45° C., followed by one or more low stringency washes in 0.2×SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:5 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:5 or the complement of SEQ ID NO:5. In one embodiment, the nucleic acid consists of a portion of the nucleotide sequence of SEQ ID NO:5 or the complement of SEQ ID NO:5. The nucleic acid fragments of the invention are at least about 15, preferably at least about 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length ubiquitin protease polynucleotides. The fragment can be single or double-stranded and can comprise DNA or RNA. The fragment can be derived from either the coding or the non-coding sequence.

In another embodiment an isolated ubiquitin protease nucleic acid encodes the entire coding region. In another embodiment the isolated ubiquitin protease nucleic acid encodes a sequence corresponding to the mature protein that may be from about amino acid 6 to the last amino acid. Other fragments include nucleotide sequences encoding the amino acid fragments described herein.

Thus, ubiquitin protease nucleic acid fragments further include sequences corresponding to the domains described herein, subregions also described, and specific functional sites. Ubiquitin protease nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that a ubiquitin protease fragment includes any nucleic acid sequence that does not include the entire gene.

The invention also provides ubiquitin protease nucleic acid fragments that encode epitope bearing regions of the ubiquitin protease proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17): 3389-3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NO:5 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The ubiquitin protease polynucleotides are thus useful for probes, primers, and in biological assays.

Where the polynucleotides are used to assess ubiquitin protease properties or functions, such as in the assays described herein, all or less than all of the entire cDNA can be useful. Assays specifically directed to ubiquitin protease functions, such as assessing agonist or antagonist activity, encompass the use of known fragments. Further, diagnostic methods for assessing ubiquitin protease function can also be practiced with any fragment, including those fragments that may have been known prior to the invention. Similarly, in methods involving treatment of ubiquitin protease dysfunction, all fragments are encompassed including those, which may have been known in the art.

The ubiquitin protease polynucleotides are useful as a hybridization probe for cDNA and genomic DNA to isolate a full-length cDNA and genomic clones encoding the polypeptide described in SEQ ID NO:4 and to isolate cDNA and genomic clones that correspond to variants producing the same polypeptide shown in SEQ ID NO:4 or the other variants described herein. Variants can be isolated from the same tissue and organism from which the polypeptides shown in SEQ ID NO:4 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the ubiquitin protease. Accordingly, it could be derived from 5' noncoding regions, the coding region, and 3' noncoding regions.

The nucleic acid probe can be, for example, the full-length cDNA of SEQ ID NO:5 or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequence of SEQ ID NO:5, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357-63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell ubiquitin proteases in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958-976) or intercalating agents (see, e.g., Zon (1988) *Pharm Res.* 5:539-549).

The ubiquitin protease polynucleotides are also useful as primers for PCR to amplify any given region of a ubiquitin protease polynucleotide.

The ubiquitin protease polynucleotides are also useful for constructing recombinant vectors. Such vectors include expression vectors that express a portion of, or all of, the ubiquitin protease polypeptides. Vectors also include insertion vectors, used to integrate into another polynucleotide sequence, such as into the cellular genome, to alter in situ expression of ubiquitin protease genes and gene products. For example, an endogenous ubiquitin protease coding sequence can be replaced via homologous recombination with all or part of the coding region containing one or more specifically introduced mutations.

The ubiquitin protease polynucleotides are also useful for expressing antigenic portions of the ubiquitin protease proteins.

The ubiquitin protease polynucleotides are also useful as probes for determining the chromosomal positions of the ubiquitin protease polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783-787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The ubiquitin protease polynucleotide probes are also useful to determine patterns of the presence of the gene encoding the ubiquitin proteases and their variants with respect to tissue distribution, for example, whether gene duplication has occurred and whether the duplication occurs in all or only a subset of tissues. The genes can be naturally occurring or can have been introduced into a cell, tissue, or organism exogenously.

The ubiquitin protease polynucleotides are also useful for designing ribozymes corresponding to all, or a part, of the mRNA produced from genes encoding the polynucleotides described herein.

The ubiquitin protease polynucleotides are also useful for constructing host cells expressing a part, or all, of the ubiquitin protease polynucleotides and polypeptides.

The ubiquitin protease polynucleotides are also useful for constructing transgenic animals expressing all, or a part, of the ubiquitin protease polynucleotides and polypeptides.

The ubiquitin protease polynucleotides are also useful for making vectors that express part, or all, of the ubiquitin protease polypeptides.

The ubiquitin protease polynucleotides are also useful as hybridization probes for determining the level of ubiquitin protease nucleic acid expression. Accordingly, the probes can be used to detect the presence of, or to determine levels of, ubiquitin protease nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the ubiquitin protease genes.

Alternatively, the probe can be used in an in situ hybridization context to assess the position of extra copies of the ubiquitin protease genes, as on extrachromosomal elements or as integrated into chromosomes in which the ubiquitin protease gene is not normally found, for example as a homogeneously staining region.

These uses are relevant for diagnosis of disorders involving an increase or decrease in ubiquitin protease expression relative to normal, such as a proliferative disorder, a differentiative or developmental disorder, or a hematopoietic disorder.

The ubiquitin protease is expressed in tissues including, but not limited to normal human thymus, testes, brain, breast, ovary, skeletal muscle, liver, prostate, and thyroid. As such, the gene is particularly relevant for the treatment of disorders involving these tissues. The gene is also expressed in fetal kidney, fetal heart, and fetal liver. The gene is also expressed in liver metastases derived from colon, and malignant lung and breast and therefore, treatment is relevant to these disorders.

Disorders involving the above tissues are discussed herein above.

Thus, the present invention provides a method for identifying a disease or disorder associated with aberrant expression or activity of ubiquitin protease nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the ubiquitin protease, such as by measuring the level of a ubiquitin protease-encoding nucleic acid in a sample of cells from a subject e.g., mRNA or genomic DNA, or determining if the ubiquitin protease gene has been mutated.

Nucleic acid expression assays are useful for drug screening to identify compounds that modulate ubiquitin protease nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the ubiquitin protease gene. The method typically includes assaying the ability of the compound to modulate the expression of the ubiquitin protease nucleic acid and thus identifying a compound that can be used to treat a disorder characterized by undesired ubiquitin protease nucleic acid expression.

The assays can be performed in cell-based and cell-free systems. Cell-based assays include cells naturally expressing the ubiquitin protease nucleic acid or recombinant cells genetically engineered to express specific nucleic acid sequences.

Alternatively, candidate compounds can be assayed in vivo in patients or in transgenic animals.

The assay for ubiquitin protease nucleic acid expression can involve direct assay of nucleic acid levels, such as mRNA levels, or on collateral compounds involved in the pathway (such as free ubiquitin pool or protein turnover). Further, the expression of genes that are up- or down-regulated in response to the ubiquitin protease activity can also be assayed. In this embodiment the regulatory regions of these genes can be operably linked to a reporter gene such as luciferase.

Thus, modulators of ubiquitin protease gene expression can be identified in a method wherein a cell is contacted with a candidate compound and the expression of mRNA determined. The level of expression of ubiquitin protease mRNA in the presence of the candidate compound is compared to the level of expression of ubiquitin protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate ubiquitin protease nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid, including the disorders described herein.

Alternatively, a modulator for ubiquitin protease nucleic acid expression can be a small molecule or drug identified using the screening assays described herein as long as the drug or small molecule inhibits the ubiquitin protease nucleic acid expression.

The ubiquitin protease polynucleotides are also useful for monitoring the effectiveness of modulating compounds on the expression or activity of the ubiquitin protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The ubiquitin protease polynucleotides are also useful in diagnostic assays for qualitative changes in ubiquitin protease nucleic acid, and particularly in qualitative changes that lead to pathology. The polynucleotides can be used to detect mutations in ubiquitin protease genes and gene expression products such as mRNA. The polynucleotides can be used as hybridization probes to detect naturally-occurring genetic mutations in the ubiquitin protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the ubiquitin protease gene associated with a dysfunction provides a diagnostic tool for an active disease or susceptibility to disease when the disease results from overexpression, underexpression, or altered expression of a ubiquitin protease.

Mutations in the ubiquitin protease gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241: 1077-1080; and Nakazawa et al. (1994) *PNAS* 91:360-364), the latter of which can be particularly useful for detecting point mutations in the gene (see Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the nommal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a ubiquitin protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant ubiquitin protease gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286-295), electrophoretic mobility of mutant and wild type nucleic acid is compared (Orita et al. (1989) *PNAS* 86:2766; Cotton et al. (1993) *Mutat. Res.* 285:125-144; and Hayashi et al. (1992) *Genet. Anal. Tech. Appl.* 9:73-79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244-255; Kozal et al. (1996) *Nature Medicine* 2:753-759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The ubiquitin protease polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the ubiquitin protease gene that results in altered affinity for ubiquitin could result in an excessive or decreased drug effect with standard concentrations of ubiquitin or analog. Accordingly, the ubiquitin protease polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The ubiquitin protease polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The ubiquitin protease polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the ubiquitin protease sequence can be used to provide an alternative technique, which determines the actual DNA sequence of selected fragments in the genome of an individual. Thus, the ubiquitin protease sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The ubiquitin protease sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The ubiquitin protease polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The ubiquitin protease polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The ubiquitin protease polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of ubiquitin protease probes can be used to identify tissue by species and/or by organ type.

In a similar fashion, these primers and probes can be used to screen tissue culture for contamination (i.e. screen for the presence of a mixture of different types of cells in a culture).

Alternatively, the ubiquitin protease polynucleotides can be used directly to block transcription or translation of ubiquitin protease gene sequences by means of antisense or ribozyme constructs. Thus, in a disorder characterized by abnormally high or undesirable ubiquitin protease gene expression, nucleic acids can be directly used for treatment.

The ubiquitin protease polynucleotides are thus useful as antisense constructs to control ubiquitin protease gene expression in cells, tissues, and organisms. A DNA antisense polynucleotide is designed to be complementary to a region of the gene involved in transcription, preventing transcription and hence production of ubiquitin protease protein. An antisense RNA or DNA polynucleotide would hybridize to the mRNA and thus block translation of mRNA into ubiquitin protease protein.

Examples of antisense molecules useful to inhibit nucleic acid expression include antisense molecules complementary to a fragment of the 5' untranslated region of SEQ ID NO:5 which also includes the start codon and antisense molecules which are complementary to a fragment of the 3' untranslated region of SEQ ID NO:5.

Alternatively, a class of antisense molecules can be used to inactivate mRNA in order to decrease expression of ubiquitin protease nucleic acid. Accordingly, these molecules can treat a disorder characterized by abnormal or undesired ubiquitin protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the ubiquitin protease protein.

The ubiquitin protease polynucleotides also provide vectors for gene therapy in patients containing cells that are aberrant in ubiquitin protease gene expression. Thus, recombinant cells, which include the patient's cells that have been engineered ex vivo and returned to the patient, are introduced into an individual where the cells produce the desired ubiquitin protease protein to treat the individual.

The invention also encompasses kits for detecting the presence of a ubiquitin protease nucleic acid in a biological sample. For example, the kit can comprise reagents such as a labeled or labelable nucleic acid or agent capable of detecting ubiquitin protease nucleic acid in a biological sample; means for determining the amount of ubiquitin protease nucleic acid in the sample; and means for comparing the amount of ubiquitin protease nucleic acid in the sample with a standard. The compound or agent can be packaged in a suitable container. The kit can further comprise instructions for using the kit to detect ubiquitin protease mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the ubiquitin protease polynucleotides. The term "vector" refers to a vehicle, preferably a nucleic acid molecule that can transport the ubiquitin protease polynucleotides. When the vector is a nucleic acid molecule, the ubiquitin protease polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the ubiquitin protease polynucleotides. Alternatively, the vector may integrate into the host cell genome and produce additional copies of the ubiquitin protease polynucleotides when the host cell replicates.

The invention provides vectors for the maintenance (cloning vectors) or vectors for expression (expression vectors) of the ubiquitin protease polynucleotides. The vectors can function in procaryotic or eukaryotic cells or in both (shuttle vectors). Expression vectors contain cis-acting regulatory regions that are operably linked in the vector to the ubiquitin protease polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the ubiquitin protease polynucleotides from the vector. Alternatively, a trans-acting factor may be supplied by the host cell. Finally, a trans-acting factor can be produced from the vector itself.

It is understood, however, that in some embodiments, transcription and/or translation of the ubiquitin protease polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd. ed.*, Cold Spring Harbor Laboratory Press, Cold Spring Harbor, N.Y.).

A variety of expression vectors can be used to express a ubiquitin protease polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual 2nd. ed.*, Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The ubiquitin protease polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the ubiquitin protease polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301-315) and pET 11d (Studier et al. (1990) *Gene Expression Technology: Methods in Enzymology* 185:60-89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119-128). Alternatively, the sequence of the polynucleotide of interest can be altered to provide preferential codon usage for a specific host cell, for example *E. coli*. (Wada et al. (1992) *Nucleic Acids Res.* 20:2111-2118).

The ubiquitin protease polynucleotides can also be expressed by expression vectors that are operative in yeast. Examples of vectors for expression in yeast e.g., *S. cerevisiae* include pYepSec1 (Baldari et al. (1987) *EMBO J.* 6:229-234), pMFa (Kurjan et al. (1982) *Cell* 30:933-943), pJRY88 (Schultz et al. (1987) *Gene* 54:113-123), and pYES2 (Invitrogen Corporation, San Diego, Calif.).

The ubiquitin protease polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow et al. (1989) *Virology* 170:31-39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187-195).

The expression vectors listed herein are provided by way of example only of the well-known vectors available to those of ordinary skill in the art that would be useful to express the ubiquitin protease polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual 2nd, ed.*, Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the ubiquitin protease polynucleotides can be introduced either alone or with other polynucleotides that are not related to the ubiquitin protease polynucleotides such as those providing trans-acting factors for expression vectors. When more than one vector is introduced into a cell, the vectors can be introduced independently, co-introduced or joined to the ubiquitin protease polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the ubiquitin protease polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing ubiquitin protease proteins or polypeptides that can be further purified to produce desired amounts of ubiquitin protease protein or fragments. Thus, host cells containing expression vectors are useful for polypeptide production.

Host cells are also useful for conducting cell-based assays involving the ubiquitin protease or ubiquitin protease fragments. Thus, a recombinant host cell expressing a native ubiquitin protease is useful to assay for compounds that stimulate or inhibit ubiquitin protease function. This includes disappearance of substrate (polyubiquitin, ubiquitinated substrate protein, ubiquitinated substrate remnants), appearance of end product (ubiquitin monomers, polyubiquitin hydrolyzed from substrate or substrate remnant, free substrate that has been rescued by hydrolysis of ubiquitin), general or specific protein turnover, and the various other molecular functions described herein that include, but are not limited to, substrate; recognition, substrate binding, subunit association, and interaction with other cellular components. Modulation of gene expression can occur at the level of transcription or translation.

Host cells are also useful for identifying ubiquitin protease mutants in which these functions are affected. If the mutants naturally occur and give rise to a pathology, host cells containing the mutations are useful to assay compounds that have a desired effect on the mutant ubiquitin protease (for example, stimulating or inhibiting function) which may not be indicated by their effect on the native ubiquitin protease.

Recombinant host cells are also useful for expressing the chimeric polypeptides described herein to assess compounds that activate or suppress activation or alter specific function by means of a heterologous domain, segment, site, and the like, as disclosed herein.

Further, mutant ubiquitin proteases can be designed in which one or more of the various functions is engineered to be increased or decreased (e.g., binding to ubiquitin, polyubiquitin, or ubiquitinated protein substrate) and used to augment or replace ubiquitin protease proteins in an individual. Thus, host cells can provide a therapeutic benefit by replacing an aberrant ubiquitin protease or providing an aberrant ubiquitin protease that provides a therapeutic result. In one embodiment, the cells provide ubiquitin proteases that are abnormally active.

In another embodiment, the cells provide ubiquitin proteases that are abnormally inactive. These ubiquitin proteases can compete with endogenous ubiquitin proteases in the individual.

In another embodiment, cells expressing ubiquitin proteases that cannot be activated, are introduced into an individual in order to compete with endogenous ubiquitin proteases for ubiquitin substrates. For example, in the case in which excessive ubiquitin substrate or analog is part of a treatment modality, it may be necessary to inactivate this molecule at a specific point in treatment. Providing cells that compete for the molecule, but which cannot be affected by ubiquitin protease activation would be beneficial.

Homologously recombinant host cells can also be produced that allow the in situ alteration of endogenous 23413 polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. Nos. 5,272,071, and 5,641,670. Briefly, specific polynucleotide sequences corresponding to the 23413 polynucleotides or sequences proximal or distal to a 23413 gene are allowed to integrate into a host cell genome by homologous recombination where expression of the gene can be affected. In one embodiment, regulatory sequences are introduced that either increase or decrease expression of an endogenous sequence. Accordingly, a 23413 protein can be produced in a cell not normally producing it. Alternatively, increased expression of 23413 protein can be effected in a cell normally producing the protein at a specific level. Further, expression can be decreased or eliminated by introducing a specific regulatory sequence. The regulatory sequence can be heterologous to the 23413 protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant 23413 proteins. Such mutations could be introduced, for example, into the specific functional regions such as the ligand-binding site.

In one embodiment, the host cell can be a fertilized oocyte or embryonic stem cell that can be used to produce a transgenic animal containing the altered ubiquitin protease gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous ubiquitin protease gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a ubiquitin protease protein and identifying and evaluating modulators of ubiquitin protease protein activity.

Other examples of transgenic animals include non-human primates, sheep, dogs, cows, goats, chickens, and amphibians.

In one embodiment, a host cell is a fertilized oocyte or an embryonic stem cell into which ubiquitin protease polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the ubiquitin protease nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the ubiquitin protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect, for example, binding, activation, and protein turnover, may not be evident from in vitro cell-free or cell-based assays. Accordingly, it is useful to provide non-human transgenic animals to assay in vivo ubiquitin protease function, including substrate interaction, the effect of specific mutant ubiquitin proteases on ubiquitin protease function and substrate interaction, and the effect of chimeric ubiquitin proteases. It is also possible to assess the effect of null mutations, that is mutations that substantially or completely eliminate one or more ubiquitin protease functions.

In general, methods for producing transgenic animals include introducing a nucleic acid sequence according to the present invention, the nucleic acid sequence capable of expressing the receptor protein in a transgenic animal, into a cell in culture or in vivo. When introduced in vivo, the nucleic acid is introduced into an intact organism such that one or more cell types and, accordingly, one or more tissue types, express the nucleic acid encoding the receptor protein. Alternatively, the nucleic acid can be introduced into virtually all cells in an organism by transfecting a cell in culture, such as an embryonic stem cell, as described herein for the production of transgenic animals, and this cell can be used to: produce an entire transgenic organism. As described, in a further embodiment, the host cell can be a fertilized oocyte. Such cells are then allowed to develop in a female foster animal to produce the transgenic organism.

Pharmaceutical Compositions

The ubiquitin protease nucleic acid molecules, protein modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a ubiquitin protease protein or anti-ubiquitin protease antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

III. 22438, 23553, 25278, AND 26212 NOVEL HUMAN SULFATASES

Background of the Invention

The biology and functions of the reversible sulfation pathway catalyzed by human sulfotransferases and sulfatases has been reviewed by Coughtrie et al. (Chemico-Biological Interactions 109: 3-27 (1998)). This review, summarized below, focuses on the sulfation of small molecules carried out by cytosolic sulfotransferases rather than the sulfation of macromolecules and lipids catalyzed by membrane-associated sulfotransferases.

Sulfation functions in the metabolism of xenobiotic compounds, steroid biosynthesis, and modulating the biological activity and inactivation and elimination of potent endogenous chemicals such as thyroid hormones, steroids and catechols. This pathway is reversible, comprising the sulfotransferase enzymes that cause the sulfation and the sulfatases that hydrolyze the sulfate esters formed by the action of the sulfotransferases. Accordingly, the interplay between these families regulates the availability and biological activity of xenobiotic and endogenous chemicals. The sulfatases, including the arylsulfatases (ARS), are located in lysosomes or endoplasmic reticulum. The presence of sulfated components depends upon the availability of key members of the sulfate pathway, i.e., substrate and activated sulfate donor molecule (co-substrate) and the balance between sulfation and sulfate conjugate hydrolysis that depends upon the activity and localization of the sulfotransferases and the sulfatases. Essentially, divalent sulfate is converted to adenosine 5' phosphosulfate (PAPS) by hydrolysis of ATP. This compound is in turn converted to 3' phosphoadenosine 5' phosphosulfate by hydrolysis of ATP to ADP. This compound is then converted to adenosine 3' 5' biphosphate concurrently with the formation of 4-nitrophenolsulfate from 4-nitrophenol. An ARS would then cleave the monovalent sulfate from the 4-nitrophenolsulfate to produce the original 4-nitrophenol. This forms the basis for the sulfation system in humans. Over- or under-production of any of these key molecules can result in sulfate-related disorders. For example, the brachymorphic mouse has a connective tissue disorder that results from a defect in PAPS formation that causes undersulfated cartilage proteoglycans.

ARS enzymes and their genes have been associated with specific genetic diseases. ARSA is located in the lysosomes and removes sulfate from sulfated glycolipids. A deficiency of ARSA has been associated with metachromatic leukodystrophy and multiple sulfatase deficiency (MSD). ARSB is located in lysosomes and has, as an endogenous substrate, dermatan sulfate and chondrotin sulfate. A deficiency of ARSB is associated with Maroteaux-Lamy syndrome and MSD. ARSC is located in the endoplasmic reticulum and has, as its endogenous substrate, cholesterol sulfate and steroid sulfates. A deficiency of ARSC is associated with X-linked ichthyosis and MSD. ARSD may be associated with MSD. ARSE has been associated with chondrodysplasia punctata and MSD. ARSF may be associated with MSD. ARSC hydrolyses sulfate esters on a wide range of steroids and cholesterol. ARSs also hydrolyse sulfate conjugates of xenobiotics.

MSD results from an inability to perform a co- or post-translational modification of a cysteine residue to serine semialdehyde (2-oxo-3-propionic acid). This residue is conserved in all eukaryotic sulfatases described by Coughtrie et al. ARSC may have a very broad specificity, extending to iodothyronine sulfates and a number of sulfate conjugates of xenobiotic phenols.

The kinetic and catalytic properties of ARS enzymes in isolation, important for understanding substrate specificity and the physical and chemical properties of enzymes, and substrates that allow substrate preference, have been characterized recently based on recombinant enzyme systems. For the expression of the human sulfotransferases, COS and V79 cells have been used. Coughtrie et al. have constructed and characterized V79 cell lines stably expressing ARSA, ARSB, and ARSC. These cell lines exhibited the expected substrate preferences of the three enzymes among the substrates 4-nitrocatechol sulfate, estrone sulfate, and dehydroepiandrosterone sulfate (DHEAS).

The sulfation of small molecules can be broadly divided into the areas of chemical defense, hormone biosynthesis, and bioactivation. It was originally viewed that sulfation protected against the toxic effects of xenobiotics in that sulfate conjugates are more readily excreted in urine or bile and generally exhibit reduced pharmacological/biological activity relative to the parent compound. Many drugs and other xenobiotics are conjugated with sulfate. Many phenolic metabolites of the cytochrome P450 mono-oxygenase system are excreted as sulfate conjugates.

Further, potent endogenous chemicals, such as steroids and catecholamines are found at high levels as circulating sulfate conjugates. For example, greater than 90% of circulating dopamine exists as the sulfated form. Sulfation is also suggested to play a role in the inactivation of potent steroids such as estrogens and androgens. Accordingly, sulfation is important in metabolism and homeostasis of such compounds in humans. DHEAS is the major circulating steroid in humans and estrone sulfate is the major estrogen. These chemicals act as precursors of estrogens and androgens. Extremely large quantities of such steroids or estrogens may occur during various stages of development, such as pregnancy. Estrone sulfate is a precursor for β-estradiol synthesis. In breast cancer cells it is hydrolysed by steroid sulfatase (ARSC) to estrone which is then converted to P-estradiol by action of another enzyme. Accordingly, ARSC is important for maintaining active estrogen. It is thus an important therapeutic target for the treatment of breast cancer.

Cholesterol sulfate, synthesized in the skin epidermis, may have a role in keratinocyte differentiation. Accordingly, hydrolysis of cholesterol sulfate by steroid sulfatase may be important in skin formation and differentiation. This is the major organ affected in X-linked ichthyosis caused by mutations in ARSC.

Although sulfation may widely serve to detoxify potent compounds, some sulfate conjugates are more biologically active than the corresponding parent compound. Minoxidil and cicletanine are activated upon sulfation. Further, an inhibitor of ARSC was shown to potentiate the memory enhancing effect of DHEAS. This suggests a role for sulfates and sulfation in the central nervous system.

An important example of bioactivation by means of sulfation, however, occurs with dietary and environmental mutagens and carcinogens. For a large number of these, sulfation is the terminal step in the pathway to metabolic activation. Examples of such chemicals include aromatic amines (including heterocyclic amines) and benzylic alchohols of chemicals such as polycyclic aromatic hydrocarbons, safrole, and estragole.

The sulfatase gene family has been reviewed in Parenti et al. (Current Opinion in Genetics and Development 7:386-391 (1997)), summarized below.

The sulfatase family of enzymes is functionally and structurally similar. Nevertheless, these enzymes catalyze the hydrolysis of sulfate ester bonds from a wide variety of substrates ranging from complex molecules such as glycosaminoglycans and sulfolipids to steroid sulfates (see also Coughtrie et al., above). Several human genetic disorders result from the accumulation of intermediate sulfate compounds that result from a deficiency of single or multiple sulfatase activities. A subset of sulfatase, ARS, is characterized by the ability to hydrolyze sulfate esters of chromogenic or fluorogenic aromatic compounds such as p-nitrocatechol sulfate and 4-methylumbelliferyl sulfate. Desulfation is required to degrade glycosaminoglycans, heparan sulfate, chondroitin sulfate and dermatan sulfate and sulfolipids. Steroid sulfatase differs from other members of the family with respect to subcellular localization. It is localized in the microsomes rather than in lysosomes. Further, ARSD, ARSE, and ARSF are also non-lysosomal, being localized in the endoplasmic reticulum or Golgi compartment.

The natural substrate of ARSA is cerebroside sulfate. Associated diseases are MLD and MSD. The natural substrate of ARSB is dermatan sulfate. The disease associated with this enzyme is MPSVI and MSD. The natural substrate of ARSC/STS is sulfated steroids. Diseases associated with this enzyme are XLI and MSD. The natural substrates of ARSD-F are unknown. The natural substrates of iduronate-2-sulfate sulfatase (IDS) are dermatan sulfate and herparan sulfate. Diseases associated with this enzyme are MPSII and MSD. The natural substrate of galactose 6-sulfatase is keratan sulfate and chondroitin 6-sulfate. Diseases associated with this enzyme include MPSIVA and MSD. The natural substrate of glucosamine-6-sulfatase is heparan sulfate and keratan sulfate. A disease associated with this enzyme is MPSIIID and MSD. The natural substrate of glucuronate-2-sulfatase is heparan sulfate. The natural substrate of glucosamine-3-sulfatase is heparan sulfate.

Sulfatases are activated through conversion of a cysteine residue as described above. The conversion is required for catalytic activity and is defective in MSD. It is likely that all sulfatases undergo the same modification. The substitution of this cysteine was shown to destroy the enzymatic activity of N-acetyl galactosamine-4-sulfatase (ARSB). It has been shown that the modified residue and a metal ion are located at the base of a substrate binding pocket.

Nine human sulfatase genes are known and murine rat, goat, or avian orthologs for some of these have been identified. A high degree of similarity occurs particularly in the amino terminal region which contains accordingly a potential consensus sulfatase signature.

Sulfatases, as discussed above, are associated with human disease. Most sulfatase deficiencies cause lysosomal storage disorders. The mucopolysaccharidoses contain various associations of mental retardation, facial dysmorphisms, skeletal deformities, hepatosplenomegaly, and deformities of soft tissues caused by deficiencies of sulfatases acting on glycosaminoglycans. In metachromatic leukodystrophy, a deficiency of ARSA causes the storage of sulfolipids in the central and peripheral nervous systems, leading to neurologic deterioration. X-linked icythyosis is caused by STS deficiency leading to increased cholesterol sulfate levels. MSD, a disorder in which all sulfatase activities are simultaneously defective, was shown to result from a defect in the co- or post-translational processing of sulfatases.

Accordingly, sulfatases are a major target for drug action and development. Therefore, it is valuable to the field of pharmaceutical development to identify and characterize previously unknown sulfatases. The present invention advances the state of the art by providing previously unidentified human sulfatases.

SUMMARY OF THE INVENTION

Novel sulfatase nucleotide sequences, and the deduced sulfatase polypeptides are described herein. Accordingly, the invention provides isolated sulfatase nucleic acid molecules having the sequences shown in SEQ ID NOS:6, 7, 8 and 9.

It is also an object of the invention to provide nucleic acid molecules encoding the sulfatase polypeptides, and variants and fragments thereof. Such nucleic acid molecules are useful as targets and reagents in sulfatase expression assays, are applicable to treatment and diagnosis of sulfatase-related disorders and are useful for producing novel sulfatase polypeptides by recombinant methods.

The invention thus further provides nucleic acid constructs comprising the nucleic acid molecules described herein. In a preferred embodiment, the nucleic acid molecules of the invention are operatively linked to a regulatory sequence. The invention also provides vectors and host cells for expressing the sulfatase nucleic acid molecules and polypeptides, and particularly recombinant vectors and host cells.

In another aspect, it is an object of the invention to provide isolated sulfatase polypeptides and fragments and variants thereof, including a polypeptide having the amino acid sequence shown in SEQ ID NOS:10, 11, 12 or 13 or the amino acid sequences encoded by the deposited cDNAs. The disclosed sulfatase polypeptides are useful as reagents or targets in sulfatase assays and are applicable to treatment and diagnosis of sulfatase-related disorders.

The invention also provides assays for determining the activity of or the presence or absence of the sulfatase polypeptides or nucleic acid molecules in a biological sample, including for disease diagnosis. In addition, the invention provides assays for determining the presence of a mutation in the polypeptides or nucleic acid molecules, including for disease diagnosis.

A further object of the invention is to provide compounds that modulate expression of the sulfatase for treatment and diagnosis of sulfatase-related disorders. Such compounds may be used to treat conditions related to aberrant activity or expression of the sulfatase polypeptides or nucleic acids.

The disclosed invention further relates to methods and compositions for the study, modulation, diagnosis and treatment of sulfatase related disorders. The compositions include sulfatase polypeptides, nucleic acids, vectors, transformed cells and related variants thereof. In particular, the invention relates to the diagnosis and treatment of sulfatase-related disorders including, but not limited to disorders as described in the background above, further herein, or involving a tissue described herein.

In yet another aspect, the invention provides antibodies or antigen-binding fragments thereof that selectively bind the sulfatase polypeptides and fragments. Such antibodies and antigen binding fragments have use in the detection of the sulfatase polypeptide, and in the prevention, diagnosis and treatment of sulfatase related disorders.

The sulfatases disclosed herein are designated as follows: 22438, 23553, 25278, and 26212.

DETAILED DESCRIPTION OF THE INVENTION

Sulfatase Polypeptides

The invention is based on the identification of the novel human 22438 sulfatase. In situ hybridization experiments showed that this sulfatase is expressed in the following monkey tissues: sub-populations of DRG neurons (mainly in small and medium sized neurons), in spinal cord (interneurons and motor neurons), and in the brain. The sulfatase is also expressed in human brain. The sulfatase cDNA was identified based on consensus motifs or protein domains characteristic of sulfatases and, in particular, arylsulfatase. BLAST analysis has shown homology with human arylsulfatase E, a human iduronate-2-sulfatase, human N-acetylgalactosamine-6-sulfatase, murine arylsulfatase A, and human arylsulfatase A. However, some homology has also been found with other arylsulfatases from various mammalian species, including, but not limited to, human arylsulfatase D, E, F, and B.

The invention is also based on the identification of the novel human 23553 sulfatase. Taqman analysis has shown positive differential expression in breast and colon cancer and in colonic metastases to the liver. This sulfatase has been identified as a glucosamine-6-sulfatase based on ProDom matches and BLAST analysis. Some homology has also been found to human arylsulfatase A, human N-acetylglucosamine-6-sulfatase, and human iduronate-2-sulfatase.

The invention is also based on the identification of the novel human 25278 sulfatase. The sulfatase is differentially expressed in human colon cancer and in colonic metastases to the liver, as determined by Taqman analysis. This sulfatase has been identified as a N-acetylgalactosamine-4-sulfatase by ProDom matching and BLAST homology alignment. Further, based on BLAST analysis, some homology has also been shown to arylsulfatase B and arylsulfatase A.

The invention is also based on the identification of the novel human 26212 sulfatase. This sulfatase has been identified as an arylsulfatase by ProDom matching and BLAST sequence alignment. Homology has been shown to arylsulfatase B. Some homology has also been found with arylsulfatase F, E, D, and A, as well as with iduronate 2 sulfatase. Arylsulfatase B is also known as N-acetylgalactosamine-4-sulfatase.

Specifically, newly-identified human genes, termed 22438, 23553, 25278, and 26212 sulfatases are provided. These sequences, and other nucleotide sequences encoding the sulfatase proteins or fragments and variants thereof, are referred to as "22438, 23553, 25278, and 26212 sulfatase sequences."

The sulfatase cDNA was identified in human cDNA libraries. Specifically, expressed sequence tags (EST) found in human cDNA libraries, were selected based on homology to known sulfatase sequences. Based on such EST sequences, primers were designed to identify a full length clone from a human cDNA library. Positive clones were sequenced and the overlapping fragments were assembled. The 22438, 23553, 25278, and 26212 sulfatase amino acid sequences are shown in SEQ ID NOS:10, 11, 12, and 13. The 22438, 23553, 25278, and 26212 sulfatase cDNA sequences are shown in SEQ ID NOS:6, 7, 8 and 9. The corresponding open reading frames for the 22438, 23553, 25278, and 26212 sulfatase cDNA sequences are shown in SEQ ID NOS:14, 15, 16 and 17.

Analysis of the assembled sequences revealed that the cloned cDNA molecules encoded sulfatase-like polypeptides. BLAST analysis indicated that the 23553 sulfatase is a glucosamine-6-sulfatase, that the 25278 sulfatase is an N-acetylgalactosamine-4-sulfatase, that the 22438 is an arylsulfatase with highest homology to arylsulfatase A and E genes and that the 26212 sulfatase is an arylsulfatase with highest homology to the arylsulfatase B gene (N-acetylgalactosamine-4-sulfatase).

The sulfatase sequences of the invention belong to the sulfatase family of molecules having conserved functional features. The term "family" when referring to the proteins and nucleic acid molecules of the invention is intended to mean two or more proteins or nucleic acid molecules having sufficient amino acid or nucleotide sequence identity as defined herein to provide a specific function. Such family members can be naturally-occurring and can be from either the same or different species. For example, a family can contain a first protein of murine origin and an ortholog of that protein of human origin, as well as a second, distinct protein of human origin and a murine ortholog of that protein.

The 22438 sulfatase gene encodes an approximately 2175 nucleotide mRNA transcript having the corresponding cDNA set forth in SEQ ID NO:6. This transcript has an open reading frame which encodes a 525 amino acid protein (SEQ ID NO:10).

The 23553 sulfatase gene encodes an approximately 4321 nucleotide mRNA transcript having the corresponding cDNA set forth in SEQ ID NO:7. This transcript has an open reading frame which encodes an 871 amino acid protein (SEQ ID NO:11).

The 25278 sulfatase gene encodes an approximately 2877 nucleotide mRNA transcript having the corresponding cDNA set forth in SEQ ID NO:8. This transcript has an open reading frame which encodes a 569 amino acid protein (SEQ ID NO:12).

The 26212 sulfatase gene encodes an approximately 2253 nucleotide mRNA transcript having the corresponding cDNA set forth in SEQ ID NO:9. This transcript has an open reading frame which encodes a 599 amino acid protein (SEQ ID NO:13).

Prosite program analysis was used to predict various sites including but not limited to N-Glycosylation, Protein Kinase C phosphorlyation, Casein Kinase II phosphorylation, N-myristolation, Amidation and Sulfatase Signature 2 sites within the 22438 sulfatase protein. The human 22438 sequence (SEQ ID NO:10) contains the following functional sites: four N-glycosylation sites from about amino acid 117 to 120, 215 to 218, 356 to 359, and 497 to 500 of SEQ ID NO:10; five protein kinase C phosphorylation sites from about amino acid 28 to 30, 93 to 95, 237 to 239, 290 to 292, and 422 to 424 of SEQ ID NO:10; six casein kinase II phosphorylation sites from about amino acid 120 to 123, 290 to 292, 335 to 338, 364 to 367, 444 to 447, and 499 to 502 of SEQ ID NO:10; ten N-myristoylation sites from about amino acid 12 to 17, 33 to 38, 52 to 57, 97 to 102, 113 to 118, 158 to 163, 328 to 333, 388 to 393, 418 to 423, and 435 to 440 of SEQ ID NO:10; and one amidation site from about amino acid 382 to 385 of SEQ ID NO:10. The 22438 sequence additionally contains a Sulfatases signature 2 consensus sequence at about amino acids 129 to 138 of SEQ ID NO:10.

Prosite program analysis was used to predict various sites including but not limited to N-Glycosylation, Protein Kinase C phosphorlyation, Casein Kinase II phosphorylation, Tyrosine Kinase Phosphorylation, N-myristolation and Sulfatase Signature 1 sites within the 23553 sulfatase protein. The human 23553 sequence (SEQ ID NO:11) contains the following functional sites: ten N-glycosylation sites from about amino acid 64 to 67, 111 to 114, 131 to 134, 148 to 151, 170 to 173, 197 to 200, 240 to 243, 623 to 626, 773 to 776 and 783 to 786 of SEQ ID NO:11; seventeen protein kinase C phosphorylation sites from about amino acid 24 to 26, 27 to 29, 66 to 68, 96 to 98, 206 to 208, 400 to 402, 425 to 427, 468 to 470, 484 to 486, 488 to 490, 505 to 507, 516 to 518, 520 to 522, 530 to 532, 611 to 613, 615 to 617 and 635 to 637 of SEQ ID NO:11; seven casein kinase II phosphorylation sites from about amino acid 107 to 110, 288 to 291, 367 to 370, 376 to 379, 452 to 455, 505 to 508 and 781 to 784 of SEQ ID NO:11; six N-myristoylation sites from about amino acid 19 to 24, 161 to 166, 325 to 330, 592 to 597, 763 to 768 and 851 of SEQ ID NO:11; and one tyrosine kinase phosphorylation site from about amino acid 637 to 645 of SEQ ID NO:11. The 23553 sequence additionally contains a Sulfatases signature 1 consensus sequence at about amino acids 85 to 97 of SEQ ID NO:11.

Prosite program analysis was used to predict various sites including but not limited to N-Glycosylation, Protein Kinase C phosphorlyation, Casein Kinase II phosphorylation, N-myristolation, Amidation, Tyrosine Kinase Phosphorylation, Sulfatase Signature 1 and Sulfatase Signature 2 sites within the 25278 sulfatase protein. The human 25278 sequence (SEQ ID NO:12) contains the following functional sites: four N-glycosylation sites from about amino acid 276 to 279, 288 to 291, 466 to 469, and 496 to 499 of SEQ ID NO:12; seven protein kinase C phosphorylation sites from about amino acid 102 to 104, 160 to 162, 244 to 246, 340 to 342, 383 to 385, 457 to 459 and 566 to 568 of SEQ ID NO:12; six casein kinase II phosphorylation sites from about amino acid 67 to 70, 244 to 247, 268 to 271, 317 to 320, 363 to 366, and 525 to 528 of SEQ ID NO:12; nine N-myristoylation sites from about amino acid 110 to 115, 169 to 174, 205 to 210, 300 to 305, 321 to 326, 356 to 361, 402 to 407, 409 to 414 and 447 to 452 of SEQ ID NO:12; and two amidation site from about amino acid 312 to 315 and 541 to 544 of SEQ ID NO:12. The 25278 sequence additionally contains a Sulfatases signature 2 consensus sequence at about amino acids 139 to 148 of SEQ ID NO:12 and a Sulfatases signature 1 consensus sequence at about amino acid 91 to 103 of SEQ ID NO:12.

Prosite program analysis was used to predict various sites including but not limited to N-Glycosylation, Protein Kinase C phosphorlyation, Casein Kinase II phosphorylation, N-myristolation, Amidation, Tyrosine Kinase Phosphorylation, Sulfatase Signature 1 and Sulfatase Signature 2 sites within the 26212 sulfatase protein. The human 26212 sequence (SEQ ID NO:13) contains the following functional sites: six N-glycosylation sites from about amino acid 157 to 160, 306 to 309, 318 to 321, 431 to 434, 497 to 500 and 527 to 530 of SEQ ID NO:13; two cAMP and cGMP dependant protein kinase phosphorylation sites from about amino acid 521 to 524 and 562 to 565 of SEQ ID NO:13; eight protein kinase C phosphorylation sites from about amino acid 131 to 133, 189 to 191, 243 to 245, 413 to 415, 489 to 491, 509 to 511, 559 to 561 and 576 to 578 of SEQ ID NO:13; four casein kinase II phosphorylation sites from about amino acid 298 to 301, 347 to 350, 386 to 389 and 406 to 409 SEQ ID NO:13; ten N-myristoylation sites from about amino acid 28 to 33, 56 to 61, 139 to 144, 198 to 203, 235 to 240, 329 to 334, 343 to 348, 351 to 356, 432 to 437 and 439 to 444 of SEQ ID NO:13; and one tyrosine kinase phosphorylation site from about amino acid 163 to 169 of SEQ ID NO:13. The 26212 sequence additionally contains a Sulfatases signature 2 consensus sequence at about amino acids 168 to 177 of SEQ ID NO:13 and a Sulfatases signature 1 consensus sequence at about amino acid 120 to 132 of SEQ ID NO:13.

In situ hybridization experiments showed that 22438 is expressed in subpopulations of DRG neurons, spinal cord, and brain, as disclosed hereinabove.

Expression of the 22438 sulfatase mRNA in the above cells and tissues indicates that the sulfatase is likely to be involved in the proper function of and in disorders involving these tissues. Accordingly, the disclosed invention further relates to methods and compositions for the study, modulation, diagnosis and treatment of sulfatase related disorders, especially disorders of these tissues that include, but are not limited to those disclosed herein.

The 23553 sulfatase is differentially expressed in breast and colon cancer and in colonic metastases to the liver. Accordingly, the disclosed invention further relates to methods and compositions for the study, modulation, diagnosis and treatment in these tissues (normal and tumor).

The 25278 sulfatase is differentially expressed in colon tumors and colonic metastases to the liver. Accordingly, the disclosed invention further relates to methods and compositions for the study, modulation, diagnosis and treatment in these normal and tumor tissues.

The 26212 sulfatase is differentially expressed in colon metastases and lung tumors. Accordingly, the disclosed invention further relates to methods and compositions for the study, modulation, diagnosis and treatment in these normal and tumor tissues.

The compositions include sulfatase polypeptides, nucleic acids, vectors, transformed cells and related variants and fragments thereof, as well as agents that modulate expression of the polypeptides and polynucleotides. In particular, the invention relates to the modulation, diagnosis and treatment of sulfatase related disorders as described herein.

Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease "Subject, as used herein, can refer to a mammal, e.g. a human, or to an experimental or animal or disease model. The subject can also be a non-human animal, e.g. a horse, cow, goat, or other domestic animal. A therapeutic agent includes, but is not limited to, small molecules, peptides, antibodies, ribozymes and antisense oligonucleotides.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B1) deficiency and vitamin B12 deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Furthermore, as disclosed in the background hereinabove, specific disorders have been associated with function of the various sulfatases. Accordingly, the sulfatases disclosed herein, having homology to specific sulfatases as disclosed herein, are useful for diagnosis and treatment of the disorders associated with sulfatase dysfunction as disclosed herein and to modulation of gene expression in the affected tissues.

The sequences of the invention find use in diagnosis of disorders involving an increase or decrease in sulfatase expression relative to normal expression, such as a proliferative disorder, a differentiative disorder, or a developmental disorder. The sequences also find use in modulating sulfatase-related responses. By "modulating" is intended the upregulating or downregulating of a response. That is, the compositions of the invention affect the targeted activity in either a positive or negative fashion.

The invention relates to novel sulfatases, having the deduced amino acid sequence shown in (SEQ ID NOS:10, 11, 12 and 13). The deposited sequences, as well as the polypeptides encoded by the sequences, are incorporated herein by reference and control in the event of any conflict, such as a sequencing error, with description in this application.

Thus, the present invention provides an isolated or purified sulfatase polypeptides and variants and fragments thereof. "Sulfatase polypeptide" or "sulfatase protein" refers to the polypeptide in SEQ ID NOS:10, 11, 12 or 13 or encoded by the deposited cDNAs. The term "sulfatase protein" or "sulfatase polypeptide," however, further includes the numerous variants described herein, as well as fragments derived from the full-length sulfatase and variants.

Sulfatase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

In one embodiment, the language "substantially free of cellular material" includes preparations of sulfatase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

The sulfatase polypeptide is also considered to be isolated when it is part of a membrane preparation or is purified and then reconstituted with membrane vesicles or liposomes.

The language "substantially free of chemical precursors or other chemicals" includes preparations of the sulfatase polypeptide in which it is separated from chemical precursors or other chemicals that are involved in its synthesis. The language "substantially free of chemical precursors or other chemicals" includes, but is not limited to, preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the sulfatase polypeptide comprises the amino acid sequence shown in SEQ ID NOS: 10, 11, 12 or 13. However, the invention also encompasses sequence variants. By "variants" is intended proteins or polypeptides having an amino acid sequence that is at least about 45%, 55%, 65%, preferably about 75%, 85%, 95%, or 98% identical to the amino acid sequence of SEQ ID NOS: 10, 11, 12 or 13. Variants also include polypeptides encoded by the cDNA insert of the plasmid or polypeptides encoded by a nucleic acid molecule that hybridizes to the nucleic acid molecule of SEQ ID NOS:6, 7, 8, 9, 14, 15, 16 or 17, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:10, 11, 12 or 13. If alignment is needed for this comparison the sequences should be aligned for maximum identity. "Looped" out sequences from deletions or insertions, or mismatches, are considered differences. Such variants generally retain the functional activity of the 22438-like, 23553-like, 25278-like, or 26212-like proteins of the invention. Variants include polypeptides that differ in amino acid sequence due to natural allelic variation or mutagenesis.

Variants include a substantially homologous protein encoded by the same genetic locus in an organism, i.e., an allelic variant. Variants also encompass proteins derived from other genetic loci in an organism, but having substantial homology to the sulfatase of SEQ ID NOS:10, 11, 12 or 13. Variants also include proteins substantially homologous to the sulfatase but derived from another organism, i.e., an ortholog. Variants also include proteins that are substantially homologous to the sulfatase that are produced by chemical synthesis. Variants also include proteins that are substantially homologous to the sulfatase that are produced by recombinant methods. Variants retain the biological activity (for example, sulfatase activity) of the polypeptide set forth by the reference sequence (SEQ ID NOS:10, 11, 12 or 13). It is understood, however, that variants exclude any amino acid sequences disclosed prior to the invention.

Preferred sulfatase polypeptides of the present invention have an amino acid sequence sufficiently identical to the amino acid sequence of SEQ ID NOS:10, 11, 12 or 13. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 60%, 65%, 70%, 75%, 80%, 85%, 90%, 95%, 96%, 97%, 98% or 99% identity are defined herein as sufficiently identical.

In one embodiment, a variant of the 23553 sulfatase is greater than 92% homologous. In another embodiment, a variant of the 25278 sulfatase is greater than 50% identical. In another embodiment, the 26212 sulfatase is greater than 50% identical.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444-453 algorithm which has been incorporated into the GAP program in the GCG software package using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) CABIOS 4:11-17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al. (1997) Nucleic Acids Res. 25(17):3389-3402. When utilizing BLAST and Gapped BLAST programs, the default parameters of the respective programs (e.g., XBLAST and NBLAST) can be used.

The invention also encompasses polypeptides having a lower degree of identity but having sufficient similarity so as to perform one or more of the same functions performed by the sulfatase. Similarity is determined by conservative amino acid substitution, as shown in Table 4. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306-1310 (1990).

TABLE 3

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

A variant polypeptide can differ in amino acid sequence by one or more substitutions, deletions, insertions, inversions, fusions, and truncations or a combination of any of these. Variant polypeptides can be fully functional or can lack function in one or more activities. Thus, in the present case, variations can affect the function, for example, of one or more of regions including a metal (e.g., Ca++)-binding domain, activation domain, sulfatase catalytic domain, the region containing a propeptide, regulatory regions, substrate binding regions, regions involved in membrane association or subcellular localization, regions involved in post-translational modification, for example, by phosphorylation, and regions that are important for effector function (i.e., agents that act upon the protein, such as in the conversion of cysteine to 2-amino-3-oxoproprionic acid or serine semi-aldehyde).

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the sulfatase polypeptide. This includes preventing immunogenicity from pharmaceutical formulations by preventing protein aggregation.

Useful variations further include alteration of functional activity. For example, one embodiment involves a variation at the substrate binding site that results in binding but not hydrolysis or more or less hydrolysis of the substrate than wild type. A further useful variation at the same site can result in altered affinity for the substrate. Useful variations also include changes that provide for affinity for another substrate. Useful variations further include the ability to bind an effector molecule with greater or lesser affinity, such as not to bind or to bind but not release it. Further useful variations include alteration in the ability of the propeptide to be cleaved by a cleavage protein, including alteration in the binding or recognition site. Further, the cleavage site can also be modified so that recognition and cleavage are by a different protease. A specific useful variation involves a variation in the ability to be bound or activated by the enzyme that activates the sulfatase by the conversion of cysteine to 2-3-oxoproprionic acid or serine semi-aldehyde. Further variation could include a variation in the specificity of metal binding.

Another useful variation provides a fusion protein in which one or more domains or subregions are operationally fused to one or more domains, subregions, or motifs from another sulfatase. For example, a transmembrane domain from a protein can be introduced into the sulfatase such that the protein is anchored in the cell surface. Other permutations include changing the number of sulfatase domains, and mixing of sulfatase domains from different sulfatase families, so that substrate specificity is altered. Mixing these various domains can allow the formation of novel sulfatase molecules with different host cell, subcellular localization, substrate, and effector molecule (one that acts on the sulfatase) specificity.

The term "substrate" is intended to refer not only to the sulfated substrate that is cleaved by the sulfatase domain, but to refer to any component with which the polypeptide interacts in order to produce an effect on that component or a subsequent biological effect that is a result of interacting with that component. This can include, but is not limited to, for example, interaction with the sulfatase activation enzyme and components involved in the conversion of 3' phosphoadenosine 5' phosphosulfate to adenosine 3' 5' biphosphate.

Amino acids that are essential for function can be identified by methods known in the art, such as site-directed mutagenesis or alanine-scanning mutagenesis (Cunningham et al. (1985) Science 244:1081-1085). The latter procedure introduces single alanine mutations at every residue in the molecule. The resulting mutant molecules are then tested for biological activity, such as peptide bond hydrolysis in vitro or related biological activity, such as proliferative activity. Sites that are critical for binding can also be determined by structural analysis such as crystallization, nuclear magnetic resonance or photoaffinity labeling (Smith et al. (1992) J. Mol. Biol. 224:899-904; de Vos et al. (1992) Science 255:306-312).

The invention thus also includes polypeptide fragments of the sulfatases. Fragments can be derived from the amino acid sequence shown in SEQ ID NOS:10, 11, 12 or 13. However, the invention also encompasses fragments of the variants of the sulfatase polypeptides as described herein. The fragments to which the invention pertains, however, are not to be construed as encompassing fragments that may be disclosed prior to the present invention.

A fragment can comprise at least about 10, 11, 12, 13, 14, 15, 16, 17, 18, 19, 20, 21, 22, 23, 24, 25, 30, 35, 40, 45, 50 or more contiguous amino acids. Fragments can retain one or more of the biological activities of the protein, for example as discussed above, as well as fragments that can be used as an immunogen to generate sulfatase antibodies.

For example, for the 25278 sulfatase, the invention encompasses amino acid fragments greater than 5 amino acids, particularly from regions up to around nucleotide 450 and beyond around nucleotide 1520. However, even in regions between around nucleotide 450 to around nucleotide 1520, fragments include those that are five or greater excluding those which may have been disclosed prior to the present invention.

For the 23553 sulfatase, fragments particularly include fragments of 5 amino acids or more up to around nucleotide 670.

For the 26212 sulfatase, for example, fragments containing 5 or more amino acids up to about nucleotide 572 are particularly encompassed by the invention. However, fragments of 5 amino acids or more encoded by around nucleotide 572 to around nucleotide 1985 are also encompassed by the invention with the understanding that such fragments do not encompass those which may have been disclosed prior to the invention.

Biologically active fragments (peptides which are, for example, about 5, 10, 15, 20, 25, 30, 35, 40, 50, 100 or more amino acids in length) can comprise a functional site. Such sites include but are not limited to those discussed above, such as a catalytic site, regulatory site, site important for substrate recognition or binding, regions containing a sulfatase domain or motif, phosphorylation sites, glycosylation sites, and other functional sites disclosed herein.

Fragments, for example, can extend in one or both directions from the functional site to encompass 5, 10, 15, 20, 30, 40, 50, or up to 100 amino acids. Further, fragments can include sub-fragments of the specific sites or regions disclosed herein, which sub-fragments retain the function of the site or region from which they are derived.

The invention also provides fragments with immunogenic properties. These contain an epitope-bearing portion of the sulfatase polypeptide and variants. These epitope-bearing peptides are useful to raise antibodies that bind specifically to a sulfatase polypeptide or region or fragment. These peptides can contain at least 10, 12, at least 14, or between at least about 15 to about 30 amino acids. The epitope-bearing sulfatase polypeptides may be produced by any conventional means (Houghten, R. A. (1985) Proc. Natl. Acad. Sci. USA 82:5131-5135). Simultaneous multiple peptide synthesis is described in U.S. Pat. No. 4,631,211.

Non-limiting examples of antigenic polypeptides that can be used to generate antibodies include but are not limited to peptides derived from extracellular regions. However, intracellularly-made antibodies ("intrabodies") are also encompassed, which would recognize intracellular peptide regions.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the sulfatase polypeptide fragment and an additional region fused to the carboxyl terminus of the fragment.

The invention thus provides chimeric or fusion proteins. These comprise a sulfatase peptide sequence operatively linked to a heterologous peptide having an amino acid sequence not substantially homologous to the sulfatase polypeptide. "Operatively linked" indicates that the sulfatase polypeptide and the heterologous peptide are fused in-frame. The heterologous peptide can be fused to the N-terminus or C-terminus of the sulfatase polypeptide or can be internally located.

In one embodiment the fusion protein does not affect sulfatase function per se. For example, the fusion protein can be a GST-fusion protein in which sulfatase sequences are fused to the N- or C-terminus of the GST sequences. Other types of fusion proteins include, but are not limited to, enzymatic fusion proteins, for example beta-galactosidase fusions, yeast two-hybrid GAL4 fusions, poly-His fusions and Ig fusions. Such fusion proteins, particularly poly-His fusions, can facilitate the purification of recombinant sulfatase polypeptide. In certain host cells (e.g., mammalian host cells), expression and/or secretion of a protein can be increased by using a heterologous signal sequence. Therefore, in another embodiment, the fusion protein contains a heterologous signal sequence at its C- or N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) J. Mol. Recog. 8:52-58 (1995) and Johanson et al. J. Biol. Chem. 270:9459-9471). Thus, this invention also encompasses soluble fusion proteins containing a sulfatase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) Current Protocols in Molecular Biology). Moreover, many expression vectors are commercially available that already encode a fusion moiety (e.g., a GST protein). A sulfatase-encoding nucleic acid can be cloned into such an expression vector such that the fusion moiety is linked in-frame to sulfatase.

Another form of fusion protein is one that directly affects sulfatase functions. Accordingly, a sulfatase polypeptide is encompassed by the present invention in which one or more of the sulfatase regions (or parts thereof) has been replaced by heterologous or homologous regions (or parts thereof) from another sulfatase. Accordingly, various permutations are possible, for example, as discussed above. Thus, chimeric sulfatases can be formed in which one or more of the native domains or subregions has been duplicated, removed, or replaced by another. This includes but is not limited to catalytic sulfatase or substrate binding domains, and regions involved in activation.

It is understood however that such regions could be derived from a sulfatase that has not yet been characterized. Moreover, sulfatase function can be derived from peptides that contain these functions but are not in a sulfatase family.

The isolated 22438 sulfatase protein can be purified from cells that naturally express it, such as DRG neurons, including small and medium sized neurons, spinal cord, including interneurons and motor neurons, and brain, especially purified from cells that have been altered to express it (recombinant), or synthesized using known protein synthesis methods.

The isolated 23553 sulfatase protein can be purified from cells that naturally express it, such as cells from any of the tissues including normal versus cancerous colon, liver, lung, adenocarcinoma, and sqamous cell carcinoma tissues, especially purified from cells that have been altered to express it (recombinant), or synthesized using known protein synthesis methods.

The isolated 25278 sulfatase protein can be purified from cells that naturally express it, such as cells from any of the tissues normal versus cancerous colon, liver, lung, adenocarcinoma, and sqamous cell carcinoma tissues, especially purified from cells that have been altered to express it (recombinant), or synthesized using known protein synthesis methods.

The isolated 26212 sulfatase protein can be purified from cells that naturally express it, such as cells from any of the tissues normal versus cancerous colon, liver, lung, adenocarcinoma, and sqamous cell carcinoma tissues, especially purified from cells that have been altered to express it (recombinant), or synthesized using known protein synthesis methods.

In one embodiment, the protein is produced by recombinant DNA techniques. For example, a nucleic acid molecule encoding the sulfatase polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (1990) Meth. Enzymol. 182: 626-646) and Rattan et al. (1992) Ann. N.Y. Acad. Sci. 663:48-62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Sulfatase polypeptides are useful for producing antibodies specific for sulfatase, regions, or fragments.

Sulfatase polypeptides are useful for biological assays related to sulfatases. Such assays involve any of the known sulfatase functions or activities or properties useful for diagnosis and treatment of sulfatase-related conditions, including those in the references cited herein, which are incorporated by reference for these assays, functions, and disorders.

These assays include, but are not limited to, binding to and/or cleaving specific substrates to produce fragments, steady state levels of sulfated compounds, cysteine modification, and biological assays related to the functions produced by sulfated compounds. Specific substrates useful for assays related to sulfate conjugate hydrolysis include but are not limited to xenobiotics, thyroid hormones, steroids, and catechols. Specific sulfate conjugates include, but are not limited to, 3$\alpha$-sulfatolithocholyltaurine, sulfate conjugates of estrone, 4-methylumbelliferone, and harmol, sulfated cartilage and proteoglycans, 4-nitrophenol, simple phenols, hydroxyarylamines, iodothyronines, catecholamines, 1-naphthyl, salbutamol, estrogens, ethinylestradiol, equilenin, diethylstilbestrol, androgens, cholesterol bile salts, pregnenolone, benzylic alcohols, glycolipidsulfates, complex carbohydrates such as dermatan and chondrotin sulfate, steroid sulfate, sulfate conjugates of xenobiotics, cholesterol sulfate, xenobiotic phenyls, o-cresol, vanillan, eugenol, m-cresol, thymol, ethyl-4,4-dihydroxybenzoate, p-cresol, sesamol, methyl-2,6-dihydroxy-4-methylbenzyloate, methyl-2,4-dihydroxybenzoate, methyl-3,5-dihydroxybenzoate, tyramine, dopamine, 5 hydroxytryptamine, pyrogallol, 4-nitrocatecholsulfate, estrone sulfate, metabolites of the cytochrome P450 mono-oxygenase system, dihydroepiandrosterone sulfate (DHEAS), minoxidil, cicletanine, sulfated mutagens and carcinogens, such as aromatic amines (including heterocyclic amines), and benzylic alcohols of chemicals such as polycyclic aromatic hydrocarbons, saffrole and estragole, glycosaminoglycans, sulfolipids, betahydroxysteroids, sulfate esters of chromogenic or fluorogenic aromatic compounds, cerebroside sulfate, keritan sulfate, and heparan sulfate. Substrates also include any in the references cited herein, which are incorporated herein by reference for these substrates. Accordingly the assays include, but are not limited to, these sulfated substrates and biological effects of sulfation or desulfation of these substrates and associated biochemical, cellular, or phenotypic effects of sulfation of desulfation, and any of the other biological or functional properties of these proteins, including, but not limited to, those disclosed herein, and in any reference cited herein which is incorporated herein by reference for the disclosure of these properties and for the assays based on these properties. Further, assays may relate to changes in the protein, per se, and on the effects of these changes, for example, activation of the sulfatase by modification of a cysteine residue as disclosed herein, cleavage of the propeptide by a proteinase, induction of expression of the protein in vivo, inhibition of function, as well as any other effects on the protein mentioned herein or cited in any reference herein, which are incorporated herein by reference for these effects and for the subsequent biological consequences of these effects.

Sulfatase polypeptides are also useful in drug screening assays, in cell-based or cell-free systems. Cell-based systems can be native, i.e., cells that normally express sulfatase, such as those discussed above, especially tumor cells, as a biopsy, or expanded in cell culture. In one embodiment, however, cell-based assays involve recombinant host cells expressing sulfatase. Accordingly, these drug-screening assays can be based on effects on protein function as described above for biological assays useful for diagnosis and treatment.

Determining the ability of the test compound to interact with a sulfatase can also comprise determining the ability of the test compound to preferentially bind to the polypeptide as compared to the ability of a known binding molecule to bind to the polypeptide.

The polypeptides can be used to identify compounds that modulate sulfatase activity. Such compounds, for example, can increase or decrease affinity or rate of binding to substrate, compete with substrate for binding to sulfatase, or displace substrate bound to sulfatase. Both sulfatase and appropriate variants and fragments can be used in high-throughput screens to assay candidate compounds for the ability to bind to sulfatase. These compounds can be further screened against a functional sulfatase to determine the effect of the compound on sulfatase activity. Compounds can be identified that activate (agonist) or inactivate (antagonist) sulfatase to a desired degree. Modulatory methods can be performed in vitro (e.g., by culturing the cell with the agent) or, alternatively, in vivo (e.g., by administering the agent to a subject).

Sulfatase polypeptides can be used to screen a compound for the ability to stimulate or inhibit interaction between sulfatase protein and a target molecule that normally interacts with the sulfatase, for example, substrate of the sulfatase domain. The assay includes the steps of combining sulfatase protein with a candidate compound under conditions that allow the sulfatase protein or fragment to interact with the target molecule, and to detect the formation of a complex between the sulfatase protein and the target or to detect the biochemical consequence of the interaction with the sulfatase and the target.

Determining the ability of the sulfatase to bind to a target molecule can also be accomplished using a technology such as real-time Bimolecular Interaction Analysis (BIA). Sjolander et al. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) Anticancer Drug Des. 12:145).

Examples of methods for the synthesis of molecular libraries can be found in the art, for example in DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carell et al. (1994) Angew. Chem. Int. Ed. Engl. 33:2059; Carell et al. (1994) Angew. Chem. Int. Ed. EngI. 33:2061; and in Gallop et al. (1994) J. Med. Chem. 37:1233. Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. 97:6378-6382); (Felici (1991) J. Mol. Biol. 222:301-310); (Ladner supra).

Candidate compounds include, for example, 1) peptides such as soluble peptides, including Ig-tailed fusion peptides and members of random peptide libraries (see, e.g., Lam et al. (1991) Nature 354:82-84; Houghten et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) Cell 72:767-778); 3) antibodies (e.g., polyclonal, monoclonal, humanized, anti-idiotypic, chimeric, and single chain antibodies as well as Fab, F(ab')2, Fab expression library fragments, and epitope-binding fragments of antibodies); 4) small organic and inorganic molecules (e.g., molecules obtained from combinatorial and natural product libraries); substrate analogs including, but not limited to, substrates disclosed herein.

One candidate compound is a soluble full-length sulfatase or fragment that competes for substrate. Other candidate compounds include mutant sulfatases or appropriate fragments containing mutations that affect sulfatase function and compete for substrate. Accordingly, a fragment that competes for substrate, for example with a higher affinity, or a fragment that binds substrate but does not process or otherwise affect it, is encompassed by the invention.

The invention provides other end points to identify compounds that modulate (stimulate or inhibit) sulfatase activity. The assays typically involve an assay of cellular events that indicate sulfatase activity. Thus, the expression of genes that are up- or down-regulated in response to sulfatase activity can be assayed. In one embodiment, the regulatory region of such genes can be operably linked to a marker that is easily detectable, such as luciferase. Alternatively, modification of the sulfatase could also be measured.

Any of the biological or biochemical functions mediated by the sulfatase can be used as an endpoint assay. These include any of the biochemical or biochemical/biological events described herein, in any reference cited herein, incorporated by reference for these endpoint assay targets, and other functions known to those of ordinary skill in the art. Specific end points can include, but are not limited to, the events resulting from expression (or lack thereof) of sulfatase activity. With respect to disorders, this would include, but not be limited to, effects on function, differentiation, and proliferation, which can be assayed, as well as the biological effects of function, such as disorders discussed hereinabove and in the references cited hereinabove which are incorporated herein by reference for the disorders disclosed in those references and other disorders and pathology. In the case of the 22438 sulfatase, models of pain can be used as an end point. In the case of the 23553 and 25278 sulfatases, tumor progression can be used as an end point. In the case of the 26212 sulfatase, tumor angiogenesis and/or tumor progression can be used as an end point.

Binding and/or activating compounds can also be screened by using chimeric sulfatase proteins in which one or more regions, segments, sites, and the like, as disclosed herein, or parts thereof, can be replaced by heterologous and homologous counterparts derived from other sulfatases. For example, a catalytic region can be used that interacts with a different substrate specificity and/or affinity than the native sulfatase. Accordingly, a different set of components is available as an end-point assay for activation. As a further alternative, the site of modification by an effector protein, for example, activation or phosphorylation, can be replaced with the site for a different effector protein. Activation can also be detected by a reporter gene containing an easily detectable coding region operably linked to a transcriptional regulatory sequence that is part of the native pathway in which sulfatase is involved.

Sulfatase polypeptides are also useful in competition binding assays in methods designed to discover compounds that interact with the sulfatase. Thus, a compound is exposed to a sulfatase polypeptide under conditions that allow the compound to bind or to otherwise interact with the polypeptide. Soluble sulfatase polypeptide is also added to the mixture. If the test compound interacts with the soluble sulfatase polypeptide, it decreases the amount of complex formed or activity from the sulfatase target. This type of assay is particularly useful in cases in which compounds are sought that interact with specific regions of the sulfatase. Thus, the soluble polypeptide that competes with the target sulfatase region is designed to contain peptide sequences corresponding to the region of interest.

Another type of competition-binding assay can be used to discover compounds that interact with specific functional sites. As an example, bindable substrate analog and a candidate compound can be added to a sample of the sulfatase. Compounds that interact with the sulfatase at the same site as the substrate or analog will reduce the amount of complex formed between the sulfatase and the substrate or analog. Accordingly, it is possible to discover a compound that specifically prevents interaction between the sulfatase and the component. Another example involves adding a candidate compound to a sample of sulfatase and cleavable substrate. A compound that competes with the substrate will reduce the amount of hydrolysis or binding of the substrate to the sulfatase. Accordingly, compounds can be discovered that directly interact with the sulfatase and compete with the substrate. Such assays can involve any other component that interacts with the sulfatase.

To perform cell free drug screening assays, it is desirable to immobilize either sulfatase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/sulfatase fusion proteins can be adsorbed onto glutathione sepharose beads (Sigma Chemical, St. Louis, Mo.) or glutathione derivatized microtitre plates, which are then combined with the cell lysates (e.g., 35S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of sulfatase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a sulfatase-binding target component, such as substrate or activating enzyme, and a candidate compound are incubated in sulfatase-presenting wells and the amount of complex trapped in the well can be quantitated. Methods for detecting such complexes, in addition to those described above for the GST-immobilized complexes, include immunodetection of complexes using antibodies reactive with the sulfatase target molecule, or which are reactive with the sulfatase and compete with the target molecule; as well as enzyme-linked assays which rely on detecting an enzymatic activity associated with the target molecule.

Modulators of sulfatase activity identified according to these drug screening assays can be used to treat a subject with a disorder related to the sulfatase, by treating cells that express the sulfatase. These methods of treatment include the steps of administering the modulators of sulfatase activity in a pharmaceutical composition as described herein, to a subject in need of such treatment.

The 23553, 25278, and 26212 sulfatases are differentially expressed in tumor cells as disclosed herein. Accordingly, these sulfatases are relevant to these disorders and relevant as well to differentiation, function, and growth of the tissues giving rise to the tumors. The 22438 sulfatase is expressed as described above, and accordingly is relevant for disorders involving these tissues. Disorders include, but are not limited to, those discussed hereinabove. Moreover, since the gene is expressed in the central nervous system, this sulfatase is relevant for the treatment of pain.

Sulfatase polypeptides are thus useful for treating a sulfatase-associated disorder characterized by aberrant expression or activity of a sulfatase. "Aberrant expression" or "misexpression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

In one embodiment, the method involves administering an agent (e.g., an agent identified by a screening assay described herein), or combination of agents that modulates (e.g., upregulates or downregulates) expression or activity of the protein. In another embodiment, the method involves administering sulfatase as therapy to compensate for reduced or aberrant expression or activity of the protein.

Methods for treatment include but are not limited to the use of soluble sulfatase or fragments of sulfatase protein that compete for substrate or any other component that directly interacts with sulfatase, or any of the enzymes that modify the sulfatase. These sulfatases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a disorder characterized by an aberrant hematopoietic response. In another example, it is desirable to achieve tissue regeneration in a subject.

In yet another aspect of the invention, the proteins of the invention can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO 94/10300), to identify other proteins (captured proteins) which bind to or interact with the proteins of the invention and modulate their activity.

Sulfatase polypeptides also are useful to provide a target for diagnosing a disease or predisposition to disease mediated by the sulfatase, including, but not limited to, those diseases disclosed herein, in the references cited herein, and as disclosed above in the background. Accordingly, methods are provided for detecting the presence, or levels of the sulfatase in a cell, tissue, or organism. The method involves contacting a biological sample with a compound capable of interacting with the sulfatase such that the interaction can be detected. One agent for detecting a sulfatase is an antibody capable of selectively binding to the sulfatase. A biological sample includes tissues, cells and biological fluids isolated from a subject, as well as tissues, cells and fluids present within a subject.

The sulfatase also provides a target for diagnosing active disease, or predisposition to disease, in a patient having a variant sulfatase. Thus, sulfatase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered sulfatase activity in cell-based or cell-free assays, such as by alteration in substrate binding or degradation, or ability to be activated by the activation enzyme, or antibody-binding pattern, altered isoelectric point, direct amino acid sequencing, and any other of the known assay techniques useful for detecting mutations in a protein in general or in a sulfatase specifically, such as are disclosed herein.

In vitro techniques for detection of sulfatase include enzyme linked immunosorbent assays (ELISAs), Western blots, immunoprecipitations and immunofluorescence. Alternatively, the protein can be detected in vivo in a subject by introducing into the subject a labeled anti-sulfatase antibody. For example, the antibody can be labeled with a radioactive marker whose presence and location in a subject can be detected by standard imaging techniques. Particularly useful are methods, which detect the alletic variant of sulfatase expressed in a subject, and methods, which detect fragments of sulfatase in a sample.

Sulfatase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) Clin. Exp. Pharmacol. Physiol. 23(10-11):983-985, and Linder, M. W. (1997) Clin. Chem. 43(2):254-266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of sulfatase in which one or more of sulfatase functions in one population is different from those in another population. The polypeptides thus allow a target to ascertain a genetic predisposition that can affect treatment modality. Thus, in a peptide-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

Sulfatase polypeptides are also useful for monitoring therapeutic effects during clinical trials and other treatment. Thus, the therapeutic effectiveness of an agent that is designed to increase or decrease gene expression, protein levels or sulfatase activity can be monitored over the course of treatment using sulfatase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the sulfatase and its variants and fragments. An antibody is considered to selectively bind, even if it also binds to other proteins that are not substantially homologous with the sulfatase. These other proteins share homology with a fragment or domain of sulfatase. This conservation in specific regions gives rise to antibodies that bind to both proteins by virtue of the homologous sequence. In this case, it would be understood that antibody binding to the sulfatase is still selective.

Antibodies can be polyclonal or monoclonal. An intact antibody, or a fragment thereof (e.g. Fab or F(ab')2) can be used. An appropriate immunogenic preparation can be derived from native, recombinantly expressed, or chemically synthesized peptides.

To generate antibodies, an isolated sulfatase polypeptide is used as an immunogen to generate antibodies using standard techniques for polyclonal and monoclonal antibody preparation. Either the full-length protein or antigenic peptide fragment can be used. Regions having a high antigenicity index are disclosed hereinabove.

Antibodies are preferably prepared from these regions or from discrete fragments in these regions. However, antibodies can be prepared from any region of the peptide as described herein. A preferred fragment produces an antibody that diminishes or completely prevents substrate hydrolysis or binding. Antibodies can be developed against the entire sulfatase or domains of the sulfatase as described herein, for example, the substrate binding region, sulfatase motif, or subregions thereof. Antibodies can also be developed against other specific functional sites as disclosed herein.

The antigenic peptide can comprise a contiguous sequence of at least 12, 14, 15-20, 20-25, or 25-30 or more amino acid residues. In one embodiment, fragments correspond to regions that are located on the surface of the protein, e.g., hydrophilic regions. These fragments are not to be construed, however, as encompassing any fragments, which may be disclosed prior to the invention.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

Antibody Uses

The antibodies can be used to isolate a sulfatase by standard techniques, such as affinity chromatography or immunoprecipitation. The antibodies can facilitate the purification of the natural sulfatase from cells and recombinantly produced sulfatase expressed in host cells.

The antibodies are useful to detect the presence of a sulfatase in cells or tissues to determine the pattern of expression of the sulfatase among various tissues in an organism and over the course of normal development. The antibodies can be used to detect a sulfatase in situ, in vitro, or in a cell lysate or supernatant in order to evaluate the abundance and pattern of expression. Antibody detection of circulating fragments of the full length sulfatase can be used to identify sulfatase turnover. In addition, the antibodies can be used to assess abnormal tissue distribution or abnormal expression during development.

Further, the antibodies can be used to assess sulfatase expression in disease states such as in active stages of the disease or in an individual with a predisposition toward disease related to sulfatase function. When a disorder is caused by an inappropriate tissue distribution, developmental expression, or level of expression of sulfatase protein, the antibody can be prepared against the normal sulfatase protein. If a disorder is characterized by a specific mutation in sulfatase, antibodies specific for this mutant protein can be used to assay for the presence of the specific mutant sulfatase. However, intracellularly-made antibodies ("intrabodies") are also encompassed, which would recognize intracellular sulfatase peptide regions.

The antibodies can also be used to assess normal and aberrant subcellular localization of cells in the various tissues in an organism. Antibodies can be developed against the whole sulfatase or portions of the sulfatase.

The diagnostic uses can be applied, not only in genetic testing, but also in monitoring a treatment modality. Accordingly, where treatment is ultimately aimed at correcting sulfatase expression level or the presence of aberrant sulfatases and aberrant tissue distribution or developmental expression, antibodies directed against the sulfatase or relevant fragments can be used to monitor therapeutic efficacy.

Additionally, antibodies are useful in pharmacogenomic analysis. Thus, antibodies prepared against polymorphic sulfatase can be used to identify individuals that require modified treatment modalities.

The antibodies are also useful as diagnostic tools as an immunological marker for aberrant sulfatase analyzed by electrophoretic mobility, isoelectric point, tryptic peptide digest, and other physical assays known to those in the art.

The antibodies are also useful for tissue typing. Thus, where a specific sulfatase has been correlated with expression in a specific tissue, antibodies that are specific for this sulfatase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting sulfatase function, for example, substrate binding, or sulfatase activity. For example, sulfatase activity may be measured by the ability to form a binding complex with a sulfated conjugate, such as disclosed herein.

These uses can also be applied in a therapeutic context in which treatment involves inhibiting sulfatase function. An antibody can be used, for example, to block substrate binding. Antibodies can be prepared against specific fragments containing sites required for function or against intact sulfatase associated with a cell.

Completely human antibodies are particularly desirable for therapeutic treatment of human patients. For an overview of this technology for producing human antibodies, see Lonberg et al. (1995) Int. Rev. Immunol. 13:65-93. For a detailed discussion of this technology for producing human antibodies and human monoclonal antibodies and protocols for producing such antibodies, e.g., U.S. Pat. Nos. 5,625,126; 5,633,425; 5,569,825; 5,661,016; and 5,545,806.

The invention also encompasses kits for using antibodies to detect the presence of a sulfatase protein in a biological sample. The kit can comprise antibodies such as a labeled or labelable antibody and a compound or agent for detecting the sulfatase in a biological sample; means for determining the amount of sulfatase in the sample; and means for comparing the amount of sulfatase in the sample with a standard. The compound or agent can be packaged in a suitable container. The kit can further comprise instructions for using the kit to detect the sulfatase.

Polynucleotides

The nucleotide sequences in SEQ ID NOS:6, 7, 8 and 9 were obtained by sequencing the deposited human cDNAs. Accordingly, the sequences of the deposited clones are controlling as to any discrepancies between the two and any reference to a sequence of SEQ ID NOS:6, 7, 8 and 9, includes reference to the sequence of the deposited cDNA.

The specifically disclosed cDNA comprises the coding region and 5' and 3' untranslated sequences in SEQ ID NOS:6, 7, 8 and 9. The coding sequences of the cDNA's are set forth in SEQ ID NOS:14, 15, 16 and 17.

The invention provides isolated polynucleotides encoding the novel sulfatases. The term "sulfatase polynucleotide" or "sulfatase nucleic acid" refers to the sequences shown in SEQ ID NOS:6, 7, 8, 9, 14, 15, 16 or 17, or in the deposited cDNAs. The term "sulfatase polynucleotide" or "sulfatase nucleic acid" further includes variants and fragments of sulfatase polynucleotides.

Generally, nucleotide sequence variants of the invention will have at least 60%, 65%, 70%, 75%, 80%, 85%, 90%, 91%, 92%, 93%, 94%, 95%, 96%, 97%, 98%, or 99% identity to one of the nucleotide sequences disclosed herein.

An "isolated" sulfatase nucleic acid is one that is separated from other nucleic acid present in the natural source of sulfatase nucleic acid. Preferably, an "isolated" nucleic acid is free of sequences which naturally flank sulfatase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the sulfatase nucleic acid is isolated from flanking sequences such that it can be subjected to the specific manipulations described herein, such as recombinant expression, preparation of probes and primers, and other uses specific to the sulfatase nucleic acid sequences. In one embodiment, the sulfatase nucleic acid comprises only the coding region.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

Sulfatase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

Sulfatase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Sulfatase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides variant sulfatase polynucleotides, and fragments thereof, that differ from the nucleotide sequence shown in SEQ ID NOS:6, 7, 8, 9, 14, 15, 16 or 17 due to degeneracy of the genetic code and thus encode the same protein as that encoded by a nucleotide sequence shown in SEQ ID NOS:6, 7, 8, 9, 14, 15, 16 or 17.

Alternatively, a nucleic acid molecule that is a fragment of a 22438-like nucleotide sequence of the present invention comprises a nucleotide sequence consisting of nucleotides 1-100, 100-200, 200-300, 300-400, 400-500, 500-600, 600-700, 700-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2175 of SEQ ID NO:6.

A nucleic acid molecule that is a fragment of a 23553-like nucleotide sequence of the present invention comprises a nucleotide sequence consisting of nucleotides 1-100, 100-200, 200-300, 300-400, 400-500, 500-600, 600-700, 700-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2700, 2700-2800, 2800-2900, 2900-3000, 3000-3100, 3100-3200, 3200-3300, 3300-3400, 3400-3500, 3500-3600, 3600-3700, 3700-3800, 3800-3900, 3900-4000, 4000-4100, 4100-4200, 4200-4300, 4300-4321 of SEQ ID NO:7.

A nucleic acid molecule that is a fragment of a 25278-like nucleotide sequence of the present invention comprises a nucleotide sequence consisting of nucleotides 1-100, 100-200, 200-300, 300-400, 400-500, 500-600, 600-700, 700-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2700, 2700-2800, 2800-2900, 2900-2940 of SEQ ID NO:8.

A nucleic acid molecule that is a fragment of a 26212-like nucleotide sequence of the present invention comprises a nucleotide sequence consisting of nucleotides 1-100, 100-200, 200-300, 300-400, 400-500, 500-600, 600-700, 700-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2253 of SEQ ID NO:9.

The invention also provides sulfatase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NOS:6, 7, 8, 9, 14, 15, 16 or 17, and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a sulfatase that is typically at least about 40-45%, 45-50%, 50-55%, 55-60%, 60-65%, 65-70%, 70-75%, more typically at least about 75-80% or 80-85%, and most typically at least about 85-90% or 90-95% or more homologous to the nucleotide sequence shown in SEQ ID NOS:6, 7, 8 or 9, or a fragment of this sequence. Such nucleic acid molecules can readily be identified as being able to hybridize under stringent conditions, to the nucleotide sequence shown in SEQ ID NOS:6, 7, 8, 9, 14, 15, 16 or 17, or a fragment of the sequence.

In the case of the 23553 sulfatase, in one embodiment, a variant is greater than 65% homologous with respect to nucleotide sequence. For the 25278 sulfatase, in one embodiment, a variant is greater than 50-60% homologous with respect to nucleotide sequence. With respect to the 26212 sulfatase, in one embodiment, a variant is greater than about 65-75% homologous with respect to nucleotide sequence.

It is understood that stringent hybridization does not indicate substantial homology where it is due to general homology, such as polyA+ sequences, or sequences common to all or most proteins, sulfatases, arylsulfatases, glucosamine-6-sulfatases, N-acetylgalactosamine-4-sulfatases, or any of the sulfatases to which the sulfatases of the present invention have shown homology by BLAST analysis, for example, regions to arylsulfatases A, B, C, D, E, F, IDS, and the like. Moreover, it is understood that variants do not include any of the nucleic acid sequences that may have been disclosed prior to the invention.

As used herein, the term "hybridizes under stringent conditions" describes conditions for hybridization and washing. Stringent conditions are known to those skilled in the art and can be found in Current Protocols in Molecular Biology John Wiley & Sons, N.Y. (1989), 6.3.1-6.3.6. Aqueous and non-aqueous methods are described in that reference and either can be used. A preferred, example of stringent hybridization conditions are hybridization in 6× sodium chloride/sodium citrate (SSC) at about 45□C, followed by one or more washes in 0.2×SSC, 0.1% SDS at 50° C. Another example of stringent hybridization conditions are hybridization in 6× sodium chloride/sodium citrate (SSC) at about 45□C, followed by one or more washes in 0.2×SSC, 0.1% SDS at 55° C. A further example of stringent hybridization conditions are hybridization in 6× sodium chloride/sodium citrate (SSC) at about 45□C, followed by one or more washes in 0.2×SSC, 0.1% SDS at 60° C. Preferably, stringent hybridization conditions are hybridization in 6× sodium chloride/sodium citrate (SSC) at about 45□C, followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NOS:6, 7, 8, 9, 14, 15, 16 or 17 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

The present invention also provides isolated nucleic acids that contain a single or double stranded fragment or portion that hybridizes under stringent conditions to the nucleotide sequence of SEQ ID NOS:6, 7, 8, 9, 14, 15, 16 or 17, or the complements of SEQ ID NOS:6, 7, 8, 9, 14, 15, 16 or 17. In one embodiment, the nucleic acid consists of a portion of a nucleotide sequence of SEQ ID NOS:6, 7, 8, 9, 14, 15, 16 or 17 and the complements. The nucleic acid fragments of the invention are at least about 10-15, preferably at least about 15-20 or 20-25 contiguous nucleotides, and can be 30, 33, 35, 40, 50, 60, 70, 75, 80, 90, 100, 200, 500 or more nucleotides in length. Longer fragments, for example, 600 or more nucleotides in length, which encode antigenic proteins or polypeptides described herein are also useful.

In the case of the 23553 sulfatase, in one embodiment, fragments are derived from nucleotide 1 to about nucleotide 670 and comprise 5-10 and 10-20 contiguous base pairs, and particularly greater than 18. For this sulfatase, in another embodiment, a fragment is derived from around nucleotide 3008 to 3514 and comprises around 5-10 and 10-20 contiguous nucleotides. In other embodiments for this sulfatase, a fragment is derived from around nucleotide 3994 to 4321 and is about 5-10 or 10-20 contiguous nucleotides. For the 25278, in one embodiment, a fragment is derived from around nucleotide 130 to around nucleotide 454 and comprises a contiguous sequence of about 5-10 or 10-20 nucleotides. In another embodiment, the fragment is derived from around nucleotide 454 to around nucleotide 1400 and comprises around 5-10 or 10-20 contiguous nucleotides, especially a fragment greater than 17 nucleotides. In another embodiment the fragment is derived from around nucleotide 1400 to around nucleotide 1850 and comprises a continuous sequence of around 5-10, 10-20, or 20-25 nucleotides, especially a fragment greater than 23 nucleotides. In another embodiment, a fragment is derived from about nucleotide 1933 to about nucleotide 2421. Such a fragment comprises around 5-10 or 10-20 contiguous nucleotides. For the 26212 sulfatase, in one embodiment, a fragment is derived from around nucleotide 272 to around nucleotide 538 and comprises a contiguous sequence of around 5-10 or 10-20 nucleotides, especially a fragment greater than 17 nucleotides. In another embodiment, the fragment is derived from around nucleotide 538 to around nucleotide 751 and comprises a contiguous sequence of at least 5-10 or 10-20 nucleotides, especially greater than 12 nucleotides. In another embodiment, the fragment is derived from around nucleotide 1074 to around 1551 and comprises a contiguous nucleotide sequence of around 5-10, 10-20, or 20-30, especially greater than 20 nucleotides. In a further embodiment, the fragment is derived from around nucleotide 2052 to 2251 and comprises a contiguous sequence of 5-10 and 10-20 nucleotides, especially fragments greater than 18 nucleotides.

The fragment can comprise DNA or RNA and can be derived from either the coding or the non-coding sequence.

In another embodiment an isolated sulfatase nucleic acid encodes the entire coding region. In another embodiment the isolated sulfatase nucleic acid encodes a sequence corresponding to the mature protein. Other fragments include nucleotide sequences encoding the amino acid fragments described herein.

Thus, sulfatase nucleic acid fragments further include sequences corresponding to the regions described herein, subregions also described, and specific functional sites. Sulfatase nucleic acid fragments also include combinations of the regions, segments, motifs, and other functional sites described above. It is understood that a sulfatase fragment includes any nucleic acid sequence that does not include the entire gene. A person of ordinary skill in the art would be aware of the many permutations that are possible. Nucleic acid fragments, according to the present invention, are not to be construed as encompassing those fragments that may have been disclosed prior to the invention.

Where the location of the regions or sites have been predicted by computer analysis, one of ordinary skill would appreciate that the amino acid residues constituting these regions can vary depending on the criteria used to define the regions.

Polynucleotide Uses

The nucleotide sequences of the present invention can be used as a "query sequence" to perform a search against public databases, for example, to identify other family members or related sequences.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) Science 254:1497-1500. Typically, a probe comprises a region of nucleotide sequence that hybridizes under highly stringent conditions to at least about 15, typically about 20-25, and more typically about 30, 40, 50 or 75 consecutive nucleotides of the nucleic acid sequence shown in SEQ ID NOS:6, 7, 8, 9, 14, 15, 16 or 17, and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

Sulfatase polynucleotides are thus useful for probes, primers, and in biological assays. Where the polynucleotides are used to assess sulfatase properties or functions, such as in the assays described herein, all or less than all of the entire cDNA can be useful. Assays specifically directed to sulfatase functions, such as assessing agonist or antagonist activity, encompass the use of known fragments. Further, diagnostic methods for assessing sulfatase function can also be practiced with any fragment, including those fragments that may have been known prior to the invention. Similarly, in methods involving treatment of sulfatase dysfunction, all fragments are encompassed including those, which may have been known in the art.

Sulfatase polynucleotides are useful as a hybridization probe for cDNA and genomic DNA to isolate a full-length cDNA and genomic clones encoding the polypeptides described in SEQ ID NOS:10, 11, 12, or 13, and to isolate cDNA and genomic clones that correspond to variants producing the same polypeptides shown in SEQ ID NOS:10, 11, 12, or 13, or the other variants described herein. Variants can be isolated from the same tissue and organism from which a polypeptide shown in SEQ ID NOS:10, 11, 12, or 13 was isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the sulfatase polypeptide. Accordingly, it could be derived from 5' noncoding regions, the coding region, and 3' noncoding regions.

The nucleic acid probe can be, for example, the full-length cDNA of SEQ ID NOS:6, 7, 8, 9, 14, 15, 16 or 17 or a fragment thereof, such as an oligonucleotide of at least 5, 10, 15, 20, 25, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein, ribozymes or antisense molecules. For example, a fragment can be hybridized to any portion of an mRNA and a larger or full-length cDNA can be produced.

Antisense nucleic acids of the invention can be designed using the nucleotide sequences of SEQ ID NOS:6, 7, 8, 9, 14, 15, 16 or 17 and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosyl queosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) Nucleic Acids Res. 24(17):3357-63, Mag et al. (1989) Nucleic Acids Res. 17:5973, and Peterser et al. (1975) Bioorganic Med. Chem. Lett. 5:1119.

The nucleic acid molecules and fragments of the invention can also include other appended groups such as peptides (e.g., for targeting host cell sulfatases in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) Bio-Techniques 6:958-976) or intercalating agents (see, e.g., Zon (1988) Pharm Res. 5:539-549).

Sulfatase polynucleotides are also useful as primers for PCR to amplify any given region of a sulfatase polynucleotide.

Sulfatase polynucleotides are also useful for constructing recombinant vectors. Such vectors include expression vectors that express a portion of, or all of, the sulfatase polypeptides. Vectors also include insertion vectors, used to integrate into another polynucleotide sequence, such as into the cellular genome, to alter in situ expression of sulfatase genes and gene products. For example, an endogenous sulfatase coding sequence can be replaced via homologous recombination with all or part of the coding region containing one or more specifically introduced mutations.

Sulfatase polynucleotides are also useful for expressing antigenic portions of sulfatase proteins.

Sulfatase polynucleotides are also useful as probes for determining the chromosomal positions of sulfatase polynucleotides by means of in situ hybridization methods, such as FISH. (For a review of this technique, see Verma et al. (1988) Human Chromosomes: A Manual of Basic Techniques (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) Nature 325:783-787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

Sulfatase polynucleotide probes are also useful to determine patterns of the presence of the gene encoding sulfatases and their variants with respect to tissue distribution, for example, whether gene duplication has occurred and whether the duplication occurs in all or only a subset of tissues. The genes can be naturally occurring or can have been introduced into a cell, tissue, or organism exogenously.

Sulfatase polynucleotides are also useful for designing ribozymes corresponding to all, or a part, of the mRNA produced from genes encoding the polynucleotides described herein.

Sulfatase polynucleotides are also useful for constructing host cells expressing a part, or all, of a sulfatase polynucleotide or polypeptide.

Sulfatase polynucleotides are also useful for constructing transgenic animals expressing all, or a part, of a sulfatase polynucleotide or polypeptide.

Sulfatase polynucleotides are also useful for making vectors that express part, or all, of a sulfatase polypeptide.

Sulfatase polynucleotides are also useful as hybridization probes for determining the level of sulfatase nucleic acid expression. Accordingly, the probes can be used to detect the presence of, or to determine levels of, sulfatase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of a sulfatase gene.

Alternatively, the probe can be used in an in situ hybridization context to assess the position of extra copies of a sulfatase gene, as on extrachromosomal elements or as integrated into chromosomes in which the sulfatase gene is not normally found, for example, as a homogeneously staining region.

These uses are relevant for diagnosis of disorders involving an increase or decrease in sulfatase expression relative to normal, such as a proliferative disorder, a differentiative or developmental disorder, or a hematopoietic disorder. Disorders in which sulfatase expression is relevant include, but are not limited to, those disclosed herein above.

Disorders in which 22438 sulfatase expression is relevant include, but are not limited to, those involving the tissues as disclosed herein and those associated with pain.

Disorders in which 23553 sulfatase expression is relevant include, but are not limited to, breast and colon carcinoma.

Disorders in which 25278 sulfatase expression is relevant include, but are not limited to, colon carcinoma.

Disorders in which 26212 sulfatase expression is relevant include, but are not limited to, hemangioma and uterine adenocarcinoma.

Thus, the present invention provides a method for identifying a disease or disorder associated with aberrant expression or activity of a sulfatase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a sulfatase, such as by measuring the level of a sulfatase-encoding nucleic acid in a sample of cells from a subject e.g., mRNA or genomic DNA, or determining if the sulfatase gene has been mutated.

Nucleic acid expression assays are useful for drug screening to identify compounds that modulate sulfatase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals. The invention thus provides a method for identifying a compound that can be used to treat a disorder associated with nucleic acid expression of a sulfatase gene. The method typically includes assaying the ability of the compound to modulate the expression of the sulfatase nucleic acid and thus identifying a compound that can be used to treat a disorder characterized by undesired sulfatase nucleic acid expression.

The assays can be performed in cell-based and cell-free systems. Cell-based assays include cells naturally expressing the sulfatase nucleic acid or recombinant cells genetically engineered to express specific nucleic acid sequences. Alternatively, candidate compounds can be assayed in vivo in patients or in transgenic animals.

The assay for sulfatase nucleic acid expression can involve direct assay of nucleic acid levels, such as mRNA levels, or on collateral compounds (such as substrate hydrolysis). Further, the expression of genes that are up- or down-regulated in response to sulfatase activity can also be assayed. In this embodiment the regulatory regions of these genes can be operably linked to a reporter gene such as luciferase.

Thus, modulators of sulfatase gene expression can be identified in a method wherein a cell is contacted with a candidate compound and the expression of mRNA determined. The level of expression of sulfatase mRNA in the presence of the candidate compound is compared to the level of expression of sulfatase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate sulfatase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

Alternatively, a modulator for sulfatase nucleic acid expression can be a small molecule or drug identified using the screening assays described herein as long as the drug or small molecule inhibits sulfatase nucleic acid expression.

Sulfatase polynucleotides are also useful for monitoring the effectiveness of modulating compounds on the expression or activity of a sulfatase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

Sulfatase polynucleotides are also useful in diagnostic assays for qualitative changes in sulfatase nucleic acid, and particularly in qualitative changes that lead to pathology. The polynucleotides can be used to detect mutations in sulfatase genes and gene expression products such as mRNA. The polynucleotides can be used as hybridization probes to detect naturally-occurring genetic mutations in a sulfatase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of a sulfatase gene associated with a dysfunction provides a diagnostic tool for an active disease or susceptibility to disease when the disease results from overexpression, underexpression, or altered expression of a sulfatase.

Mutations in a sulfatase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) PNAS 91:360-364), the latter of which can be particularly useful for detecting point mutations in the gene (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a sulfatase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant sulfatase gene and a wild-type gene can be determined by direct DNA sequencing. A variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the gene include methods in which protection from cleavage agents is used to detect mismatched bases in RNA/RNA or RNA/DNA duplexes (Myers et al. (1985) Science 230:1242); Cotton et al. (1988) PNAS 85:4397; Saleeba et al. (1992) Meth. Enzymol. 217:286-295), electrophoretic mobility of mutant and wild type nucleic acid is compared (Orita et al. (1989) PNAS 86:2766; Cotton et al. (1993) Mutat. Res. 285:125-144; and Hayashi et al. (1992) Genet. Anal. Tech. Appl. 9:73-79), and movement of mutant or wild-type fragments in polyacrylamide gels containing a gradient of denaturant is assayed using denaturing gradient gel electrophoresis (Myers et al. (1985) Nature 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) Trends Genet. 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) Human Mutation 7:244-255; Kozal et al. (1996) Nature Medicine 2:753-759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

Sulfatase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the sulfatase gene that results in altered affinity for a substrate-related compound could result in an excessive or decreased drug effect with standard concentrations of the compound. Accordingly, the sulfatase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

Sulfatase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Sulfatase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the sulfatase sequences can be used to provide an alternative technique, which determines the actual DNA sequence of selected fragments in the genome of an individual. Thus, the sulfatase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. Sulfatase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

Sulfatase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

Sulfatase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

Sulfatase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of sulfatase probes can be used to identify tissue by species and/or by organ type.

In a similar fashion, these primers and probes can be used to screen tissue culture for contamination (i.e. screen for the presence of a mixture of different types of cells in a culture).

Alternatively, sulfatase polynucleotides can be used directly to block transcription or translation of sulfatase gene sequences by means of antisense or ribozyme constructs. Thus, in a disorder characterized by abnormally high or undesirable sulfatase gene expression, nucleic acids can be directly used for treatment.

Sulfatase polynucleotides are thus useful as antisense constructs to control sulfatase gene expression in cells, tissues, and organisms. A DNA antisense polynucleotide is designed to be complementary to a region of the gene involved in transcription, preventing transcription and hence production of sulfatase protein. An antisense RNA or DNA polynucleotide would hybridize to the mRNA and thus block translation of mRNA into sulfatase protein.

Examples of antisense molecules useful to inhibit nucleic acid expression include antisense molecules complementary to a fragment of the 5' untranslated region of SEQ ID NOS:6, 7, 8 or 9, which also includes the start codon and antisense molecules which are complementary to a fragment of the 3' untranslated region of SEQ ID NOS:6, 7, 8 or 9.

Alternatively, a class of antisense molecules can be used to inactivate mRNA in order to decrease expression of sulfatase nucleic acid. Accordingly, these molecules can treat a disorder characterized by abnormal or undesired sulfatase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the sulfatase protein.

Sulfatase polynucleotides also provide vectors for gene therapy in patients containing cells that are aberrant in sulfatase gene expression. Thus, recombinant cells, which include the patient's cells that have been engineered ex vivo and returned to the patient, are introduced into an individual where the cells produce the desired sulfatase protein to treat the individual.

The invention also encompasses kits for detecting the presence of a sulfatase nucleic acid in a biological sample. For example, the kit can comprise reagents such as a labeled or labelable nucleic acid or agent capable of detecting sulfatase nucleic acid in a biological sample; means for determining the amount of sulfatase nucleic acid in the sample; and means for comparing the amount of sulfatase nucleic acid in the sample with a standard.

The compound or agent can be packaged in a suitable container. The kit can further comprise instructions for using the kit to detect sulfatase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) J. Mol. Biol. 215:403-410) and BLAZE (Brutlag et al. (1993) Comp. Chem. 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing sulfatase polynucleotides. The term "vector" refers to a vehicle, preferably a nucleic acid molecule that can transport sulfatase polynucleotides. When the vector is a nucleic acid molecule, the sulfatase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of sulfatase polynucleotides. Alternatively, the vector may integrate into the host cell genome and produce additional copies of sulfatase polynucleotides when the host cell replicates.

The invention provides vectors for the maintenance (cloning vectors) or vectors for expression (expression vectors) of sulfatase-polynucleotides. The vectors can function in prokaryotic or eukaryotic cells or in both (shuttle vectors).

Expression vectors contain cis-acting regulatory regions that are operably linked in the vector to sulfatase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of sulfatase polynucleotides from the vector. Alternatively, a trans-acting factor may be supplied by the host cell. Finally, a trans-acting factor can be produced from the vector itself.

It is understood, however, that in some embodiments, transcription and/or translation of sulfatase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) Molecular Cloning: A Laboratory Manual 2nd. ed., Cold Spring Harbor Laboratory Press, Cold Spring Harbor, N.Y.).

A variety of expression vectors can be used to express a sulfatase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) Molecular Cloning: A Laboratory Manual 2nd. ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

Sulfatase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of sulfatase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) Gene 69:301-315) and pET 11d (Studier et al. (1990) Gene Expression Technology: Methods in Enzymology 185:60-89).

Recombinant protein expression can be maximized in a host bacteria by providing a genetic background wherein the host cell has an impaired capacity to proteolytically cleave the recombinant protein. (Gottesman, S. (1990) Gene Expression Technology: Methods in Enzymology 185, Academic Press, San Diego, Calif. 119-128).

It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

Sulfatase polynucleotides can also be expressed by expression vectors that are operative in yeast. Examples of vectors for expression in yeast e.g., *S. cerevisiae* include pYepSec1 (Baldari et al. (1987) EMBO J. 6:229-234), pMFa (Kurjan et al. (1982) Cell 30:933-943), pJRY88 (Schultz et al. (1987) Gene 54:113-123), and pYES2 (Invitrogen Corporation, San Diego, Calif.).

Sulfatase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow et al. (1989) Virology 170:31-39).

In certain embodiments of the invention, the polynucleotides described herein are expressed in mammalian cells using mammalian expression vectors. Examples of mammalian expression vectors include pCDM8 (Seed, B. (1987) Nature 329:840) and pMT2PC (Kaufman et al. (1987) EMBO J. 6:187-195).

The expression vectors listed herein are provided by way of example only of the well-known vectors available to those of ordinary skill in the art that would be useful to express sulfatase polynucleotides. The person of ordinary skill in the art would be aware of other vectors suitable for maintenance propagation or expression of the polynucleotides described herein. These are found for example in Sambrook et al. (1989) Molecular Cloning: A Laboratory Manual 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (Molecular Cloning: A Laboratory Manual, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, sulfatase polynucleotides can be introduced either alone or with other polynucleotides that are not related to sulfatase polynucleotides such as those providing trans-acting factors for expression vectors. When more than one vector is introduced into a cell, the vectors can be introduced independently, co-introduced or joined to the sulfatase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the sulfatase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

The host cells expressing the polypeptides described herein, and particularly recombinant host cells, have a variety of uses. First, the cells are useful for producing sulfatase proteins or polypeptides that can be further purified to produce desired amounts of sulfatase protein or fragments. Thus, host cells containing expression vectors are useful for polypeptide production.

Host cells are also useful for conducting cell-based assays involving sulfatase or sulfatase fragments. Thus, a recombinant host cell expressing a native sulfatase is useful to assay for compounds that stimulate or inhibit sulfatase function, gene expression at the level of transcription or translation, and interaction with other cellular components.

Host cells are also useful for identifying sulfatase mutants in which these functions are affected. If the mutants naturally occur and give rise to a pathology, host cells containing the mutations are useful to assay compounds that have a desired effect on the mutant sulfatase (for example, stimulating or inhibiting function) which may not be indicated by their effect on the native sulfatase.

Recombinant host cells are also useful for expressing the chimeric polypeptides described herein to assess compounds that activate or suppress activation by means of a heterologous domain, segment, site, and the like, as disclosed herein.

Further, mutant sulfatases can be designed in which one or more of the various functions is engineered to be increased or decreased and used to augment or replace sulfatase proteins in an individual. Thus, host cells can provide a therapeutic benefit by replacing an aberrant sulfatase or providing an aberrant sulfatase that provides a therapeutic result. In one embodiment, the cells provide sulfatases that are abnormally active.

In another embodiment, the cells provide sulfatases that are abnormally inactive. These sulfatases can compete with endogenous sulfatases in the individual.

In another embodiment, cells expressing sulfatases that cannot be activated, are introduced into an individual in order to compete with endogenous sulfatases for substrate. For example, in the case in which excessive substrate or substrate analog is part of a treatment modality, it may be necessary to effectively inactivate the substrate or substrate analog at a specific point in treatment. Providing cells that compete for the molecule, but which cannot be affected by sulfatase activation would be beneficial.

Homologously recombinant host cells can also be produced that allow the in situ alteration of endogenous sulfatase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. Nos. 5,272,071, and 5,641,670. Briefly, specific polynucleotide sequences corresponding to the sulfatase polynucleotides or sequences proximal or distal to a sulfatase gene are allowed to integrate into a host cell genome by homologous recombination where expression of the gene can be affected. In one embodiment, regulatory sequences are introduced that either increase or decrease expression of an endogenous sequence. Accordingly, a sulfatase protein can be produced in a cell not normally producing it. Alternatively, increased expression of sulfatase protein can be effected in a cell normally producing the protein at a specific level. Further, expression can be decreased or eliminated by introducing a specific regulatory sequence. The regulatory sequence can be heterologous to the sulfatase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant sulfatase proteins. Such mutations could be introduced, for example, into the specific functional regions such as the peptide substrate-binding site.

In one embodiment, the host cell can be a fertilized oocyte or embryonic stem cell that can be used to produce a transgenic animal containing the altered sulfatase gene. Alternatively, the host cell can be a stem cell or other early tissue precursor that gives rise to a specific subset of cells and can be used to produce transgenic tissues in an animal. See also Thomas et al., Cell 51:503 (1987) for a description of homologous recombination vectors. The vector is introduced into an embryonic stem cell line (e.g., by electroporation) and cells in which the introduced gene has homologously recombined with the endogenous sulfatase gene is selected (see e.g., LI, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinions in Biotechnology 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a sulfatase protein and identifying and evaluating modulators of sulfatase protein activity.

Other examples of transgenic animals include non-human primates, sheep, dogs, cows, goats, chickens, and amphibians.

In one embodiment, a host cell is a fertilized oocyte or an embryonic stem cell into which sulfatase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the sulfatase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the sulfatase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) PNAS 89:6232-6236. Another example of a recombinase system is the FLP recombinase system of *S. cerevisiae* (O'Gorman et al. (1991) Science 251:1351-1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect binding or activation, may not be evident from in vitro cell-free or cell-based assays. Accordingly, it is useful to provide non-human transgenic animals to assay in vivo sulfatase function, including peptide interaction, the effect of specific mutant sulfatases on sulfatase function and peptide interaction, and the effect of chimeric sulfatases. It is also possible to assess the effect of null mutations, that is mutations that substantially or completely eliminate one or more sulfatase functions.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

Sulfatase nucleic acid molecules, proteins, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo by in vivo transcription or translation of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a sulfatase protein or anti-sulfatase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 22438, 23553, 25278, or 26212 nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 22438, 23553, 25278, or 26212 nucleic acid, polypeptide, or antibody.

The capture probes can be a set of nucleic acids from a selected sample, e.g., a sample of nucleic acids derived from a control or non-stimulated tissue or cell.

The method can include contacting the 22438, 23553, 25278, or 26212 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes with an allele of 22438, 23553, 25278, or 26212. Such methods can be used to diagnose a subject, e.g., to evaluate risk for a disease or disorder, to evaluate suitability of a selected treatment for a subject, to evaluate whether a subject has a disease or disorder. 22438, 23553, 25278, or 26212 are associated with sulfatase activity, thus it is useful for disorders associated with abnormal sulfatase activity.

The method can be used to detect SNPs, as described below.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or misexpress 22438, 23553, 25278, or 26212, or from a cell or subject in which a 22438, 23553, 25278, or 26212 mediated response has been elicited, e.g., by contact of the cell with 22438, 23553, 25278, or 26212 nucleic acid or protein, or administration to the cell or subject 22438, 23553, 25278, or 26212 nucleic acid or protein; contacting the array with one or more inquiry probe, wherein an inquiry probe can be a nucleic acid, polypeptide, or antibody (which is preferably other than 22438, 23553, 25278, or 26212 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 22438, 23553, 25278, or 26212 (or does not express as highly as in the case of the 22438, 23553, 25278, or 26212 positive plurality of capture probes) or from a cell or subject which in which a 22438, 23553, 25278, or 26212 mediated response has not been elicited (or has been elicited to a lesser extent than in the first sample); contacting the array with one or more inquiry probes (which is preferably other than a 22438, 23553, 25278, or 26212 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing 22438, 23553, 25278, or 26212, e.g., analyzing structure, function, or relatedness to other nucleic acid or amino acid sequences. The method includes: providing a 22438, 23553, 25278, or 26212 nucleic acid or amino acid sequence; comparing the 22438, 23553, 25278, or 26212 sequence with one or more preferably a plurality of sequences from a collection of sequences, e.g., a nucleic acid or protein sequence database; to thereby analyze 22438, 23553, 25278, or 26212.

Preferred databases include GenBank™. The method can include evaluating the sequence identity between a 22438, 23553, 25278, or 26212 sequence and a database sequence. The method can be performed by accessing the database at a second site, e.g., over the internet.

In another aspect, the invention features, a set of oligonucleotides, useful, e.g., for identifying SNP's, or identifying specific alleles of 22438, 23553, 25278, or 26212. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with different labels, such that an oligonucleotides which hybridizes to one allele provides a signal that is distinguishable from an oligonucleotides which hybridizes to a second allele.

This invention is further illustrated by the following examples which should not be construed as limiting. The contents of all references, patents and published patent applications cited throughout this application are incorporated herein by reference.

EXAMPLES

Example 1

Identification and Characterization of Human 22438 cDNAs

The human 22438 sequence (SEQ ID NO:6), which is approximately 2175 nucleotides long including untranslated regions, contains a predicted methionine-initiated coding sequence of about 1578 nucleotides (nucleotides 248-1825 of SEQ ID NO:6; SEQ ID NO:14). The coding sequence encodes a 525 amino acid protein (SEQ ID NO:10).

PFAM analysis indicates that 22438 contains a sulfatase domain. For general information regarding PFAM identifiers, PS prefix and PF prefix domain identification numbers, refer to Sonnhammer et al. (1997) Protein 28:405-420.

As used herein, the term "sulfatase domain" includes an amino acid sequence of about 80-420 amino acid residues in length and having a bit score for the alignment of the sequence to the sulfatase domain (HMM) of at least 8. Preferably, a sulfatase domain includes at least about 100-250 amino acids, more preferably about 130-200 amino acid residues, or about 160-200 amino acids and has a bit score for the alignment of the sequence to the sulfatase domain (HMM) of at least 16 or greater. The sulfatase domain (HMM) has been assigned the PFAM Accession PF00884. An alignment of the sulfatase domain (amino acids 36 to 462 of SEQ ID NO:10) of human 22438 with a consensus amino acid sequence derived from a hidden Markov model derived from Pfam has a bit score of 323 and E-value of 3.5e-93.

In a preferred embodiment 22438-like polypeptide or protein has a "sulfatase domain" or a region which includes at least about 100-250, more preferably about 130-200 or 160-200, amino acid residues and has at least about 60%, 70%, 80%, 90%, 95%, 99%, or 100% sequence identity with a "sulfatase domain," e.g., the sulfatase domain of human 22438-like polypeptide or protein (e.g., amino acid residues 36-462 of SEQ ID NO:10).

To identify the presence of an "sulfatase" domain in a 22438-like protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al. (1993) Protein Sci. 2:305-314, the contents of which are incorporated herein by reference.

Example 2

Tissue Distribution of 22348 mRNA

Northern blot hybridizations with various RNA samples are performed under standard conditions and washed under stringent conditions, i.e., 0.2×SSC at 65° C. A DNA probe corresponding to all or a portion of the 22348 cDNA (SEQ ID NO:6) can be used. The DNA is radioactively labeled with 32P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb hybridization solution (Clontech) and washed at high stringency according to manufacturer's recommendations.

Example 3

Identification and Characterization of Human 23553 cDNAs

The human 23553 sequence (SEQ ID NO:7), which is approximately 4321 nucleotides long including untranslated regions, contains a predicted methionine-initiated coding sequence of about 2616 nucleotides (nucleotides 510-3125 of SEQ ID NO:7; SEQ ID NO:15). The coding sequence encodes a 871 amino acid protein (SEQ ID NO:11).

PFAM analysis indicates that 23553 contains a sulfatase domain. For general information regarding PFAM identifiers, PS prefix and PF prefix domain identification numbers, refer to Sonnhammer et al. (1997) Protein 28:405-420. An alignment of the sulfatase domain (amino acids 43 to 467 of SEQ ID NO:11) of human 23553 with a consensus amino acid sequence derived from a hidden Markov model derived from Pfam has a bit score of 268.9 and E-value of 6.5e-77. For further information on sulfatase domains, see Example 1.

In one embodiment, a 23553-like protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, or 24 amino acid residues and spans a phospholipid membrane. Transmembrane domains are rich in hydrophobic residues, and typically have an $\alpha$-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in Zagotta W. N. et al. (1996) Annual Rev. Neuronsci. 19:235-63, the contents of which are incorporated herein by reference.

In a preferred embodiment, a 23553-like polypeptide or protein has at least one transmembrane domain or a region which includes at least 18, 20, 22, or 24 amino acid residues and has at least about 60%, 70% 80% 90% 95%, 99%, or 100% sequence identity with a "transmembrane domain," e.g., at least one transmembrane domain of human 23553 (e.g., amino acid residues 7 to 25 of SEQ ID NO:11).

In another embodiment, a 23553 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring 23553-like protein.

In a preferred embodiment, a 23553-like polypeptide or protein has a "non-transmembrane domain" or a region which includes at least about 1-350, preferably about 200-320, more preferably about 230-300, and even more preferably about 240-280 amino acid residues, and has at least about 60%, 70% 80% 90% 95%, 99% or 100% sequence identity with a "non-transmembrane domain", e.g., a non-transmembrane domain of human 23553-like protein.

A non-transmembrane domain located at the N-terminus of a 23553-like protein or polypeptide is referred to herein as an "N-terminal non-transmembrane domain." As used herein, an "N-terminal non-transmembrane domain" includes an amino acid sequence having about 1-100. For example, an N-terminal non-transmembrane domain is located at about amino acid residues 1 to 6 of SEQ ID NO:11.

Similarly, a non-transmembrane domain located at the C-terminus of a 23553-like protein or polypeptide is referred to herein as a "C-terminal non-transmembrane domain." As used herein, a "C-terminal non-transmembrane domain" includes an amino acid sequence having about 1-800, preferably about 15-500, preferably about 20-270, more preferably about 25-255 amino acid residues in length and is located outside the boundaries of a membrane. For example, a C-terminal non-transmembrane domain is located at about amino acid residues 26-871 of SEQ ID NO:11.

The ORF analyzer predicts that 23553 has a signal peptide. Therefore, a 23553-like molecule can further include a signal sequence. As used herein, a "signal sequence" refers to a peptide of about 20-80 amino acid residues in length which occurs at the N-terminus of secretory and integral membrane proteins and which contains a majority of hydrophobic amino acid residues. For example, a signal sequence contains at least about 12-25 amino acid residues, preferably about 30-70 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 23553-like protein contains a signal sequence of about amino acids 1-22 of SEQ ID NO:11. The "signal sequence" is cleaved during processing of the mature protein. The mature 23553-like protein corresponds to amino acids 23-871 of SEQ ID NO:11.

CLUSTAL multiple sequence alignment analysis shows homology between 23553 and the following sequences (identified by GenBank accession number): P14217, *Chiamydomonas reinhardtii* arylsulfatase; Q10723, *Volvox carteri* arylsulfatase; CAB40661, human N-acetylglucosamine-6-sulfatase homolog; P15586, human N-acetylglucosamine-6-sulfatase; P50426, goat N-acetylglucosamine-6-sulfatase; AAA83618, *C. elegans* putative sulfatase; AAC02716, *Neurospora crassa* arylsulfatase; P31447, *E. coli* hypothetical sulfatase.

Example 4

Tissue Distribution of 23553 mRNA

In normal human tissues tested, TaqMan analyses revealed high expression of 23553 was in trachea, vein, osteoblast, kidney, and testes. Significant expression of 23553 was found in adipose, colon, skeletal muscle, thyroid, prostate, and other tissues. In comparisons of normal and tumor tissue, 23553 expression was detected in all samples tested, with increased expression in breast, colon, and lung tumors. Further, elevated expression of 23553 was found in glioblastoma samples, as compared to normal brain tissue samples. Expression levels were determined by quantitative PCR (Taqman® brand quantitative PCR kit, Applied Biosystems). The quantitative PCR reactions were performed according to the kit manufacturer's instructions.

cDNA library array analysis of 23553 revealed expression in adipose, adrenal gland, bone, brain, colon, colon metastases to liver, endothelial, heart, liver, lung, muscle, osteoblast, skin, testes, thyroid, and other tissue. Reverse transcriptase polymerase chain reaction (RT-PCR) revealed 23553 expression in clinical samples of normal and tumor colon tissue, normal and metastatic liver tissue, and in lung squamous cell carcinoma tissue. In situ hybridization showed expression of 23553 in the following tissues: 3 of 3 breast tumor; 0 of 2 normal breast; 4 of 4 lung tumor; 0 of 2 normal lung; 4 of 4 colon tumor; and 2 of 2 liver metasteses. In all cases, expression of 23553 was confined to the stromal component of tissue; no expression was detected in normal or tumor epithelium.

Angiogenic growth factors (e.g., bFGF) are present in the extracellular matrix (ECM), and can be released from the ECM by heparinase-like enzymes. This includes the glycosyl-sulfatases. The released growth factors in turn stimulate blood vessel formation. See Baird A, Ling N., "Fibroblast growth factors are present in the extracellular matrix produced by endothelial cells in vitro: implications for a role of heparinase-like enzymes in the neovascular response," Biochem Biophys Res Commun. (1987) 142(2):428-35.

As noted, 23553 has amino acid sequence features that place it in the class of glycosyl sulfate cleaving enzymes. Taqman results (above) show that its expression is elevated in clinical tumor samples. In situ hybridization shows specific, localized 23553 expression in the tumor stromal component of all tumor samples tested, whereas its expression is low or absent in normal tissues. This suggests that, through catalytic activity, 23553 promotes tumor growth or is involved in tumor maintenance by degrading the ECM and releasing growth factors.

Example 5

Identification and Characterization of Human 25278 cDNAs

The human 25278 sequence (SEQ ID NO:8), which is approximately 2877 nucleotides long including untranslated regions, contains a predicted methionine-initiated coding sequence of about 1710 nucleotides (nucleotides 334-2043 of SEQ ID NO:8; SEQ ID NO:16). The coding sequence encodes a 569 amino acid protein (SEQ ID NO:12).

PFAM analysis indicates that 25278 has a sulfatase domain. For general information regarding PFAM identifiers, PS prefix and PF prefix domain identification numbers, refer to Sonnhammer et al. (1997) Protein 28:405-420. An alignment of the sulfatase domain (amino acids 47 to 471 of SEQ ID NO:12) of human 25278 with a consensus amino acid sequence derived from a hidden Markov model derived from Pfam has a bit score of 289.7 and E-value of 3.6e-83. For further information on sulfatase domains, see Example 1. TaqMan analysis on human 25278 revealed expression in colon tumor samples as compared to normal colon samples as well as in liver metastases as compared to normal liver samples.

Example 6

Identification and Characterization of Human 26212 cDNAs

The human 26212 sequence (SEQ ID NO:9), which is approximately 2253 nucleotides long including untranslated regions, contains a predicted methionine-initiated coding sequence of about 1800 nucleotides (nucleotides 324-2123 of SEQ ID NO:9; SEQ ID NO:17). The coding sequence encodes a 599 amino acid protein (SEQ ID NO:13).

PFAM analysis indicates that 26212 has a sulfatase domain. For general information regarding PFAM identifiers, PS prefix and PF prefix domain identification numbers, refer to Sonnhammer et al. (1997) Protein 28:405-420. An alignment of the sulfatase domain (amino acids 76 to 502 of SEQ ID NO:13) of human 26212 with a consensus amino acid sequence derived from a hidden Markov model derived from Pfam has a bit score of 324.5 and E-value of 1.3e-93. For further information on sulfatase domains, see Example 1.

In one embodiment, 26212-like protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, or 24 amino acid residues and spans a phospholipid membrane. For more information on transmembrane domains, see example 3.

In a preferred embodiment, a 26212-like polypeptide or protein has at least one transmembrane domain or a region which includes at least 18, 20, 22, 24, 25, or 30 amino acid residues and has at least about 60%, 70% 80% 90% 95%, 99%, or 100% sequence identity with a "transmembrane domain," e.g., at least one transmembrane domain of human 26212-like polypeptide or protein (e.g., amino acid residues 24 to 44 of SEQ ID NO:13).

In another embodiment, a 26212-like protein includes at least one "non-transmembrane domain." The C-terminal amino acid residue of a non-transmembrane domain is adjacent to an N-terminal amino acid residue of a transmembrane domain in a naturally occurring 26212-like protein. For more information on non-transmembrane domains, see Example 3.

In a preferred embodiment, a 26212-like polypeptide or protein has a "non-transmembrane domain" or a region which includes at least about 1-350, preferably about 200-320, more preferably about 230-300, and even more preferably about 240-280 amino acid residues, and has at least about 60%, 70% 80% 90% 95%, 99% or 100% sequence identity with a "non-transmembrane domain", e.g., a non-transmembrane domain of human 26212-like polypeptide or protein. An N-terminal non-transmembrane domain is located at about amino acid residues 1 to 23 of SEQ ID NO:13. A C-terminal non-transmembrane domain is located at about amino acid residues 45 to 599 of SEQ ID NO:13. A 26212-like molecule can further include a signal sequence. For more information on signal sequences, see Example 3.

Example 7

Tissue Distribution of 26212 mRNA

In six independent experiments, 26212 showed higher levels of expression in proliferating endothelial cells as compared to arrested endothelial cells. 26212 expression was also higher in proliferating endothelial cells than in non-endothelial cells. 26212 expression levels were upregulated in breast tissue cell lines treated with epidermal growth factor, as well.

26212 is expressed in hemangiomas and other angiogenic tissues, including fetal heart, uterine adenocarcinoma, and endometrial polyps. Endothelial and glial cells showed higher levels of 26212 expression as compared to other tissues and cells. 26212 also showed higher levels of expressing in some lung, breast and brain tumors as compared to normal tissues. Expression levels of 26212 were found to be higher in proliferating endothelial cells than in tumors, too. Expression levels were determined by quantitative PCR (Taqman® brand quantitative PCR kit, Applied Biosystems). The quantitative PCR reactions were performed according to the kit manufacturer's instructions.

In situ hybridization analysis was also carried out. 26212 showed weak expression in ovarian tumor, and no expression in normal ovary. Similarly, colon metastases showed weak expression of 26212, and normal colon tissue and primary tumors showed no expression. A subset of lung tumors tested showed expression of 26212, while no expression was revealed in normal lung.

Angiogenic growth factors (e.g., bFGF) are present in the extracellular matrix (ECM), and can be released from the ECM by heparinase-like enzymes. This includes the glycosyl-sulfatases. The released growth factors in turn stimulate blood vessel formation by, e.g., attracting endothelial cells to form new vessels. See Baird A, Ling N., "Fibroblast growth factors are present in the extracellular matrix produced by endothelial cells in vitro: implications for a role of heparinase-like enzymes in the neovascular response," Biochem Biophys Res Commun. (1987) 142(2):428-35.

As noted, 26212 has amino acid sequence features that place it in the class of glycosyl sulfate cleaving enzymes. Taqman results (above) show that its expression is elevated in proliferating endothelial cells, suggesting that 26212 is specifically involved in active angiogenic sites.

Example 8

Recombinant Expression of 22348, 23553, 25278, or 26212 in Bacterial Cells

In this example, 22348, 23553, 25278, or 26212 is expressed as a recombinant glutathione-S-transferase (GST) fusion polypeptide in *E. coli* and the fusion polypeptide is isolated and characterized. Specifically, 22348, 23553, 25278, or 26212 is fused to GST and this fusion polypeptide is expressed in *E. coli*, e.g., strain PEB199. Expression of the GST-26212 fusion protein in PEB 199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 9

Expression of Recombinant 22348, 23553, 25278, or 26212 Protein in COS Cells To express the 22348, 23553, 25278, or 26212 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 22348, 23553, 25278, or 26212 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 22348, 23553, 25278, or 26212 DNA sequence is amplified by PCR using two primers. The 5' primer contains the restriction site of interest followed by approximately twenty nucleotides of the 22348, 23553, 25278, or 26212 coding sequence starting from the initiation codon; the 3' end sequence contains complementary sequences to the other restriction site of interest, a translation stop codon, the HA tag or FLAG tag and the last 20 nucleotides of the 22348, 23553, 25278, or 26212 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 22348, 23553, 25278, or 26212 gene is inserted in the correct orientation. The ligation mixture is transformed into *E. coli* cells (strains HB101, DH5□, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 22348, 23553, 25278, or 26212-pcDNA/Amp plasmid DNA using the calcium phosphate or calcium chloride co-precipitation methods, DEAE-dextran-mediated transfecti on, lipofection, or electroporati on. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 22348, 23553, 25278, or 26212 polypeptide is detected by radiolabelling (35S-methionine or 35S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with 35S-methionine (or 35S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 22348, 23553, 25278, or 26212 coding sequence is cloned directly into the polylinker of the pcDNA/Amp vector using the appropriate restriction sites. The resulting plasmid is transfected into COS cells in the manner described above, and the expression of the 22348, 23553, 25278, or 26212 polypeptide is detected by radiolabelling and immunoprecipitation using a 22348, 23553, 25278, or 26212 specific monoclonal antibody.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

IV. NUCLEIC ACID MOLECULES DERIVED FROM RAT BRAIN AND PROGRAMMED CELL DEATH MODELS

Background of the Invention

A great deal of effort has been expended by the modern scientific research community to identify and sequence genes, particularly human genes. The identification of genes and knowledge of their nucleic acid sequences pave the way for many scientific and commercial advancements, both in research applications and in diagnostic and therapeutic applications. For example, advances in gene identification and sequencing allow the production of the products encoded by these genes, such as by recombinant and synthetic means. Furthermore, identification of genes and the products they encode provide important information about the mechanism of disease and can provide new diagnostic tests and therapeutic treatments for the diagnosis and treatment of disease. Thus, identification and sequencing of genes provide valuable information and compositions for use in the biotechnology and pharmaceutical industries.

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. Dying cells are eliminated by phagocytes, without an inflammatory response.

Programmed cell death (PCD) is a highly regulated process (Wilson (1998) Biochem. Cell. Biol. 76:573-582). The death signal is then transduced through various signaling pathways that converge on caspase-mediated degradative cascades resulting in the activation of late effectors of morphological and physiological aspects of apoptosis, including DNA fragmentation and cytoplasmic condensation. In addition, regulation of programmed cell death may be integrated with regulation of energy, redox- and ion homeostasis in the mitochondria (reviewed by Kroemer (1998) Cell Death and Differentiation 5:547), and/or cell-cycle control in the nucleus and cytoplasm (reviewed by Choisy-Rossi and Yonish-Rouach (1998) Cell Death and Differentiation 5:129-131; Dang (1999) Molecular and Cellular Biology 19:1-11; and Kasten and Giordano (1998) Cell Death and Differentiation 5:132-140). Many mammalian genes regulating apoptosis have been identified as homologs of genes originally identified genetically in *Caenorhabditis elegans* or *Drosophila melanogaster*, or as human oncogenes. Other programmed cell death genes have been found by domain homology to known motifs, such as death domains, that mediate protein-protein interactions within the programmed cell death pathway.

The mechanisms that mediate apoptosis include, but are not limited to, the activation of endogenous proteases, loss of mitochondrial function, and structural changes such as disruption of the cytoskeleton, cell shrinkage, membrane blebbing, and nuclear condensation due to degradation of DNA. The various signals that trigger apoptosis may bring about these events by converging on a common cell death pathway that is regulated by the expression of genes that are highly conserved. Caspases (cysteine proteases having specificity for aspartate at the substrate cleavage site) are central to the apoptotic program, are. These proteases are responsible for degradation of cellular proteins that lead to the morphological changes seen in cells undergoing apoptosis. One of the human caspases was previously known as the interleukin-IB (IL-1β) converting enzyme (ICE), a cysteine protease responsible for the processing of pro-IL-1β to the active cytokine. Overexpression of ICE in Rat-1 fibroblasts induces apoptosis (Miura et al. (1993) Cell 75:653).

Many caspases and proteins that interact with caspases possess domains of about 60 amino acids called a caspase recruitment domain (CARD). Apoptotic proteins may bind to each other via their CARDs. Different subtypes of CARDs may confer binding specificity, regulating the activity of various caspases. (Hofmann et al. (1997) TIBS 22:155).

The functional significance of CARDs have been demonstrated in two recent publications. Duan et al. (1997) Nature 385:86 showed that deleting the CARD at the N-terminus of RAIDD, a newly identified protein involved in apoptosis, abolished the ability of RAIDD to bind to caspases. In addition, Li et al. (1997) Cell 91:479 showed that the N-terminal 97 amino acids of apoptotic protease activating factor-1 (Apaf-1) was sufficient to confer caspase-9-binding ability.

Thus, programmed cell death (apoptosis) is a normal physiological activity necessary to proper and differentiation in all vertebrates. Defects in apoptosis programs result in disorders including, but not limited to, neurodegenerative disorders, cancer, immunodeficiency, heart disease and autoimmune diseases (Thompson et al. (1995) Science 267: 1456).

In vertebrate species, neuronal programmed cell death mechanisms have been associated with a variety of developmental roles, including the removal of neuronal precursors which fail to establish appropriate synaptic connections (Oppenheim et al. (1991) Annual Rev. Neuroscience 14:453-501), the quantiative matching of pre- and post-synaptic population sizes (Herrup et al. (1987) J. Neurosci. 7:829-836), and sculpting of neuronal circuits, both during development and in the adult (Bottjer et al. (1992) J. Neurobiol. 23:1172-1191).

Inappropriate apoptosis has been suggested to be involved in neuronal loss in various neurodegenerative diseases such as Alzheimer's disease (Loo et al. (1993) Proc. Natl. Acad. Sci. 90:7951-7955), Huntington's disease (Portera-Cailliau et al. (1995) J. Neurosc. 15:3775-3787), amyotrophic lateral sclerosis (Rabizadeh et al. (1995) Proc. Natl. Acad. Sci. 92:3024-3028), and spinal muscular atrophy (Roy et al. (1995) Cell 80:167-178).

In addition, improper expression of genes involved in apoptosis has been implicated in carcinogenesis. Thus, it has been shown that several "oncogenes" are in fact involved in apoptosis, such as in the Bcl family.

Accordingly, genes involved in apoptosis are important targets for therapeutic intervention. It is important, therefore, to identify novel genes involved in apoptosis or to discover whether known genes function in this process.

Nucleic acid probes have long been used to detect complementary nucleic acid sequences in a nucleic acid of interest (the "target" nucleic acid). In some assay formats, the nucleic acid is tethered, i.e., by covalent attachment, to a solid support. Arrays of nucleic acid sequences immobilized on solid supports have been used to detect specific nucleic acid sequences in a target nucleic acid. See, e.g., PCT patent publication Nos. WO 89/10977 and 89/11548. Others have proposed the use of large numbers of nucleic acid sequences to provide the complete nucleic acid sequence of a target nucleic with methods for using arrays of immobilized nucleic acid sequences for this purpose. See U.S. Pat. Nos. 5,202,231 and 5,002,867 and PCT patent publication No. WO 93/17126.

The development of specific microarray technology has provided methods for making very large arrays of nucleic acid sequences in very small physical arrays. See U.S. Pat. No. 5,143,854 and PCT patent publication Nos. WO 90/15070 and 92/10092, each of which is incorporated herein by reference. U.S. patent application Ser. No. 082,937, filed Jun. 25, 1993, describes methods for making arrays of sequences that can be used to provide the complete sequence of a target nucleic acid and to detect the presence of a nucleic acid containing a specific nucleotide sequence. Thus, microfabricated arrays of large numbers of nucleic acid sequences, called "DNA chips" offer great promise for a wide variety of applications.

SUMMARY OF THE INVENTION

The present invention is based on the identification of novel nucleic acid molecules derived from rat brain and programmed cell death cDNA libraries.

Thus, in one aspect, the invention provides an isolated nucleic acid molecule that comprises a nucleotide sequence selected from the group consisting of the sequences shown in SEQ ID NOS:18-51 and the complements of the sequences shown in SEQ ID NOS:18-51.

The invention also provides an isolated fragment or portion of any of the sequences shown in SEQ ID NOS:18-51 and the complement of the sequences shown in SEQ ID NOS:18-51. In some embodiments, the fragment is useful as a probe or primer, and/or is at least 15, more preferably at least 18, even more preferably 20-25, 30, 50, 100, 200 or more nucleotides in length.

In another embodiment, the invention provides an isolated nucleic acid molecule that comprises a nucleotide sequence that is at least about 60% identical, about 65% identical, about 70% identical, about 80% identical, about 90% identical, about 95% identical, about 96% identical, about 97% identical, about 98% identical, or about 99% or more identical to a nucleotide sequence selected from the group consisting of the sequences shown in SEQ ID NOS:18-51 and the complements of the sequences shown in SEQ ID NOS:18-51.

In another embodiment, the invention provides an isolated nucleic acid molecule that hybridizes under highly stringent conditions to a nucleotide sequence selected from the group consisting of the sequences shown in SEQ ID NOS:18-51 and the complements of the sequences shown in SEQ ID NOS: 18-51.

The invention further provides nucleic acid vectors comprising the nucleic acid molecules described above. In one embodiment, the nucleic acid molecules of the invention are operatively linked to at least one expression control element.

The invention further includes host cells, such as bacterial cells, fungal cells, plant cells, insect cells and mammalian cells, comprising the nucleic acid vectors described above.

In another aspect, the invention provides isolated gene products, proteins and polypeptides encoded by nucleic acid molecules of the invention.

The invention further provides antibodies, including monoclonal antibodies, or antigen-binding fragments thereof, which selectively bind to the isolated proteins and polypeptides of the invention.

The invention also provides methods for preparing proteins and polypeptides encoded by isolated nucleic acid molecules described herein by culturing a host cell containing a vector molecule of the invention.

Additionally, the invention provides a method for assaying for the presence of a nucleic acid sequence, protein or polypeptide of the present invention, in a biological sample, e.g., in a tissue sample, by contacting said sample with an agent (e.g., an antibody or a nucleic acid molecule) suitable for specific detection of the nucleic acid sequence, protein or polypeptide.

A general object of the invention is to provide a microarray of unique nucleic acid sequences useful for analyzing gene expression in various biological contexts including, but not limited to, development, differentiation, and pathological states, in vitro and in vivo.

More specific objects include, but are not limited to, use of the microarray to discover specific patterns of gene expression in those biological contexts.

More specific objects of the invention include the discovery of genes associated with development, differentiation, and pathological states, both in vitro and in vivo.

More specific objects of the invention include, but are not limited to, functional gene discovery, in other words, assigning a function to a previously uncharacterized gene sequence.

More specific objects of the invention include, but are not limited to, use of the microarray to obtain candidate target genes for diagnosis and treatment.

More specific objects of the invention include, but are not limited to, use of the microarray to discover compounds that are useful for diagnosis or treatment based on one or more sequences in the array.

Accordingly, the invention provides a unique microarray of nucleic acid sequences useful for analyzing gene expression in various biological contexts including, but not limited to, development, differentiation, and pathological states in vivo and in vitro.

The invention is also directed to one or more variants or fragments of one or more of the nucleic acid sequences that constitute the microarray.

The invention is also directed to the use of the microarray to discover specific patterns of gene expression in those biological contexts.

The invention also provides a method to discover genes associated with development, differentiation, and pathological states in vivo and in vitro.

The invention also provides a method for functional gene discovery, that is, a method to assign a function to an uncharacterized gene sequence.

The invention also provides the use of the microarray to obtain candidate-target genes for diagnosis and treatment.

The invention also provides use of the microarray to discover compounds that are useful for diagnosis or treatment based on one or more sequences in the microarray.

In a specific disclosed embodiment, the invention provides a microarray of genes associated with programmed cell death (PCD) (apoptosis). Specifically, genes whose expression is associated with programmed cell death in rat cerebellar granule neurons (CGN) were identified.

The invention also provides a kit comprising a nucleic acid probe which hybridizes to a nucleotide sequence of claim 1 and instructions for use, and a kit comprising an agent which binds to a polypeptide of claim 10 and instructions for use.

The inventors sequenced the 5' ends of an extensive group of partial and full length cDNA clones and grouped these sequences into clusters based on nucleic acid sequence homology, assembled each cluster into a cDNA consensus sequence based on contiguous 5' cDNA sequences, and placed a unique cDNA from each cluster into a microarray. The microarray was constructed with approximately 7296 cloned cDNA sequences. The microarray was then used for transcriptional profiling in various tissues and in two programmed cell death model systems. Expression data were analyzed with an expression pattern clustering algorithm. cDNAs with similar expression patterns were grouped together. Approximately 500 cDNAs were discovered to be regulated in programmed cell death models. These cDNAs are useful for diagnosis and treatment of programmed cell death-related conditions and for the discovery of compounds useful for treatment and diagnosis of programmed cell death related conditions. The cDNAs are further useful to discover other nucleic acid sequences whose expression is related to programmed cell death.

The invention is thus also directed to subarrays, in various biological groupings, such as a programmed cell death microarray.

The invention is thus also directed to one or more variants or fragments of one or more nucleic acid sequences in a subarray.

DETAILED DESCRIPTION OF THE INVENTION

I. Isolated Nucleic Acid Molecules

The invention encompasses the discovery and isolation of nucleic acid molecules that are expressed in rat brain and in programmed cell death in vitro models.

Accordingly, the invention provides isolated nucleic acid molecules comprising a nucleotide sequence and the complements thereof. In one embodiment, the isolated nucleic acid molecule has the formula: 5' (R1)n-(R2)-R3)m 3' wherein, at the 5' end of the molecule R1 is either hydrogen or any nucleotide residue when n=1, and is any nucleotide residue when n>1; at the 3' end of the molecule R3 is either hydrogen, a metal or any nucleotide residue when m=1, and is any nucleotide residue when m>1; n and m are integers between about 1 and 5000; and R2 is a nucleic acid having a nucleotide sequence selected from the group consisting of the sequences disclosed herein and the complements of the sequences disclosed herein. The R2 nucleic acid is oriented so that its 5' residue is bound to the 3' molecule of R1, and its 3' residue is bound to the 5' molecule of R3. Any stretch of nucleic acid residues denoted by either R1 or R3, which is greater than 1, is preferably a heteropolymer, but can also be a homopolymer. In certain embodiments, n and m are integers between about 1 and 2000, preferably between about 1 and 1000, and preferably between about 1 and 500. In other embodiments, the isolated nucleic acid molecule is at least about 15 nucleotides, preferably at least about 100 nucleotides, more preferably at least about 150 nucleotides, and even more preferably at least about 200 or more nucleotides in length. In still another embodiment, R1 and R3 are both hydrogen.

As appropriate, the isolated nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. The nucleic acid molecule can include all or a portion of the coding sequence of the genes of the invention. Additionally, the nucleic acid molecule can be fused to a marker sequence, for example, a sequence that encodes a polypeptide to assist in isolation or purification of the polypeptide. Such sequences include, but are not limited to, those which encode a glutathione-S-transferase (GST) fusion protein and those which encode a hemaglutin A (HA) polypeptide marker from influenza.

An “isolated” nucleic acid molecule, as used herein, is one that is separated from nucleic acid which normally flanks the nucleic acid molecule in nature. With regard to genomic DNA, the term “isolated” refers to nucleic acid molecules which are separated from the chromosome with which the genomic DNA is naturally associated. For example, the isolated nucleic acid molecule can contain less than about 5 kb, 4 kb, 3 kb, 2 kb, 1 kb, 0.5 kb or 0.1 kb of nucleotides which flank the nucleic acid molecule in the genomic DNA of the cell from which the nucleic acid is derived.

Moreover, an isolated nucleic acid of the invention, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated. In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

Further, recombinant DNA contained in a vector is included in the definition of “isolated” as used herein. Also, isolated nucleic acid molecules include recombinant DNA molecules in heterologous host cells, as well as partially or substantially purified DNA molecules in solution. “Isolated” nucleic acid molecules also encompass in vivo and in vitro RNA transcripts of the DNA molecules of the present invention.

The invention further provides variants of the isolated nucleic acid molecules of the invention. Such variants can be naturally occurring, such as allelic variants (same locus), homologs (different locus), and orthologs (different organism), or may be constructed by recombinant DNA methods or by chemical synthesis. Such non-naturally occurring variants can be made using well-known mutagenesis techniques, including those applied to polynucleotides, cells, or organisms. Accordingly, variants can contain nucleotide substitutions, deletions, inversions and/or insertions in either or both the coding and non-coding region of the nucleic acid molecule. Further, the variations can produce both conservative and non-conservative amino acid substitutions.

Typically, variants have a substantial identity with a nucleic acid molecule selected from the group consisting of the sequences disclosed herein and the complements thereof. Particularly preferred are nucleic acid molecules and fragments which have at least about 60%, at least about 70, at least about 80, at least about 85%, at least about 90%, at least about 95%, at least about 96%, at least about 97%, at least about 98%, or at least about 99% or more identity with nucleic acid molecules described herein.

Such nucleic acid molecules can be readily identified as being able to hybridize under stringent conditions to a nucleotide sequence and the complements thereof. In one embodiment, the variants hybridize under high stringency hybridization conditions (e.g., for selective hybridization) to a nucleotide sequence.

As used herein, the term “hybridizes under stringent conditions” describes conditions for hybridization and washing. Stringent conditions are known to those skilled in the art and can be found in Current Protocols in Molecular Biology, John Wiley & Sons, N.Y. (1989), 6.3.1-6.3.6. Aqueous and non-aqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45□C, followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences. In certain embodiments, the length of a sequence aligned for comparison purposes is at least 30%, preferably at least 40%, more preferably at least 60%, and even more preferably at least 70%, 80% or 90% of the length of the reference sequence. The actual comparison of the two sequences can be accomplished by well-known methods, for example, using a mathematical algorithm. A preferred, non-limiting example of such a mathematical algorithm is described in Karlin et al. (1993) Proc. Natl. Acad. Sci. USA, 90:5873-5877. Such an algorithm is incorporated into the NBLAST and XBLAST programs (version 2.0) as described in Altschul et al. (1997) Nucleic Acids Res., 25:389-3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) Comput. Appl. Biosci. 10:3-5; and FASTA described in Pearson and Lipman (1988) PNAS, 85:2444-8.

In another embodiment, the percent identity between two amino acid sequences can be accomplished using the GAP program in the CGC software package using either a BLOSUM 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the CGC software package, using a gap weight of 50 and a length weight of 3.

The present invention also provides isolated nucleic acids that contain a fragment or portion that hybridizes under highly stringent conditions to a nucleotide sequence and the complements thereof. In one embodiment, the nucleic acid consists of a portion of a nucleotide sequence and the complements thereof. The nucleic acid fragments of the invention are at least about 15, preferably at least about 18, 20, 23 or 25 nucleotides, and can be 30, 40, 50, 100, 200 or more nucleotides in length. Longer fragments, for example, 30 or more nucleotides in length, which encode antigenic proteins or polypeptides described herein are useful. Additionally, nucleotide sequences described herein can also be contigged (e.g., overlapped or joined) to produce longer sequences.

In a related aspect, the nucleic acid fragments of the invention are used as probes or primers in assays such as those described herein. "Probes" are oligonucleotides that hybridize in a base-specific manner to a complementary strand of nucleic acid. Such probes include polypeptide nucleic acids, as described in Nielsen et al. (1991) Science, 254, 1497-1500. Typically, a probe comprises a region of nucleotide sequence that hybridizes under highly stringent conditions to at least about 15, typically about 20-25, and more typically about 40, 50 or 75 consecutive nucleotides of a nucleic acid selected from the group consisting of the sequences disclosed herein and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The nucleic acid molecules of the invention such as those described above can be identified and isolated using standard molecular biology techniques and the sequence information provided in the sequences. For example, nucleic acid molecules can be amplified and isolated by the polymerase chain reaction using synthetic oligonucleotide primers designed based on one or more of the sequences provided in the sequences disclosed herein and the complements thereof. See generally PCR Technology: Principles and Applications for DNA Amplification (ed. H. A. Erlich, Freeman Press, NY, N.Y., 1992); PCR Protocols: A Guide to Methods and Applications (Eds. Innis, et al. Academic Press, San Diego, Calif., 1990); Mattila et al. (1991) Nucleic Acids Res. 19:4967; Eckert et al. (1991) PCR Methods and Applications, 1:17; PCR (eds. McPherson et al. IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace (1989) Genomics, 4:560, Landegren et al. (1988) Science, 241:1077, transcription amplification (Kwoh et al. (1989) Proc. Natl. Acad. Sci. USA, 86:1173), and self-sustained sequence replication (Guatelli et al. (1990) Proc. Nat. Acad. Sci. USA, 87:1874)

and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a cDNA library, mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a protein of the appropriate molecular weight. For example, the direct analysis of the nucleotide sequence of nucleic acid molecules of the present invention can be accomplished using well-known methods that are commercially available. See, for example, Sambrook et al. Molecular Cloning, A Laboratory Manual (2nd Ed., CSHP, New York 1989); Zyskind et al. Recombinant DNA Laboratory Manual, (Acad. Press, 1988)). Using these or similar methods, the protein(s) and the DNA encoding the protein can be isolated, sequenced and further characterized.

Antisense nucleic acids of the invention can be designed using the nucleotide sequences of the sequences described herein, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyl uracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry, 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA, 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) Nucleic Acids Res. 24(17):3357-63, Mag et al. (1989) Nucleic Acids Res. 17:5973, and Peterser et al. (1975) Bioorganic Med. Chem. Lett. 5:1119.

The nucleic acid molecules and fragments of the invention can also include other appended groups such as peptides (e.g., for targeting host cell receptors in vivo), or agents facilitating transport across the cell membrane (see, e.g., Letsinger et al. (1989) Proc. Natl. Acad. Sci. USA, 86:6553-6556; Lemaitre et al. (1987) Proc. Natl. Acad. Sci. USA, 84:648-652; PCT Publication No. WO88/0918) or the blood brain barrier (see, e.g., PCT Publication No. WO89/10134). In addition, oligonucleotides can be modified with hybridization-triggered cleavage agents (see, e.g., Krol et al. (1988) Bio-Techniques, 6:958-976) or intercalating agents (see, e.g., Zon (1988) Pharm Res. 5:539-549).

Uses of the nucleic acids of the invention are described in detail in below. In general, the isolated nucleic acid sequences can be used as molecular weight markers on Southern gels, and as chromosome markers which are labeled to map related gene positions. The nucleic acid sequences can also be used to compare with endogenous DNA sequences in patients to identify genetic disorders, and as probes, such as to hybridize and discover related DNA sequences or to subtract out known sequences from a sample. The nucleic acid sequences can further be used to derive primers for genetic fingerprinting, to raise anti-protein antibodies using DNA immunization techniques, and as an antigen to raise anti-DNA antibodies or elicit immune responses. Additionally, the nucleotide sequences of the invention can be used identify and express recombinant proteins for analysis, characterization or therapeutic use, or as markers for tissues in which the corresponding protein is expressed, either constitutively, during tissue differentiation, or in disease states.

Vectors and Host Cells

Another aspect of the invention pertains to nucleic acid vectors containing a nucleic acid selected from the group consisting of the sequences disclosed herein. These vectors comprise a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene, 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) Gene, 69:301-315) and pET 11d (Studier et al. Gene Expression Technology: Methods in Enzymology, 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, Gene Expression Technology: Methods in Enzymology, 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) EMBO J. 6:229-234), pMFa (Kurjan and Herskowitz (1982) Cell 3.0:933-943), pJRY88 (Schultz et al. (1987) Gene, 54:113-123), pYES2 (Invitrogen Corporation, San Diego, Calif.), and pPicZ (InVitrogen Corp, San Diego, Calif.).

Alternatively, a nucleic acid of the invention can be expressed in insect cells using baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology, 170:31-39).

In yet another embodiment, a nucleic acid of the invention is expressed in mammalian cells using a mammalian expression vector. Examples of mammalian expression vectors include pCDM8 (Seed (1987) Nature, 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell, 33:729-740; Queen and Baltimore (1983) Cell, 33:741-748), neuron-specific promoters (e.g., the neurofilament promoter; Byrne and Ruddle (1989) Proc. Natl. Acad. Sci. USA, 86:5473-5477), pancreas-specific promoters (Edlund et al. (1985) Science, 230:912-916), and mammary gland-specific promoters (e.g., milk whey promoter; U.S. Pat. No. 4,873,316 and European Application Publication No. 264,166). Developmentally regulated promoters are also encompassed, for example the murine hox promoters (Kessel and Gruss (1990) Science, 249:374-379) and the alpha-fetoprotein promoter (Campes and Tilghman (1989) Genes Dev. 3:537-546).

The invention further provides a recombinant expression vector comprising a DNA molecule of the invention cloned into the expression vector in an antisense orientation. That is, the DNA molecule is operably linked to at least one expression control element in a manner which allows for expression (by transcription of the DNA molecule) of an RNA molecule which is antisense to an mRNA of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid of the invention can be expressed in bacterial cells (e.g., *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Nucleic acid encoding a selectable marker can be introduced into a host cell on the same vector as that nucleic acid of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid of the invention have been introduced. Such host cells can then be used to create non-human transgenic animals in which exogenous nucleotide sequences have been introduced into their genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid of the invention into the male pronuclei of a fertilized oocyte, e.g., by microinjection, retroviral infection, and allowing the oocyte to develop in a pseudopregnant female foster animal. The sequence can be introduced as a transgene into the genome of a non-human animal. Intronic sequences and polyadenylation signals can also be included in the transgene to increase the efficiency of expression of the transgene. A tissue-specific regulatory sequence(s) can be operably linked to the transgene to direct expression of a polypeptide in particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA in tissues or cells of the animals. A transgenic founder animal can then be used to breed additional animals carrying the transgene. Moreover, transgenic animals carrying a transgene encoding the transgene can further be bred to other transgenic animals carrying other transgenes.

Homologously recombinant host cells can also be produced that allow the in situ alteration of endogenous polynucleotide sequences of the invention in a host cell genome. The host cell includes, but is not limited to, a stable cell line, cell in vivo, or cloned microorganism. This technology is more fully described in WO 93/09222, WO 91/12650, WO 91/06667, U.S. Pat. Nos. 5,272,071, and 5,641,670. Briefly, specific polynucleotide sequences corresponding to the polynucleotides or sequences proximal or distal to a gene are allowed to integrate into a host cell genome by homologous recombination where expression of the gene can be affected. In one embodiment, regulatory sequences are introduced that either increase or decrease expression of an endogenous sequence. Accordingly, a protein can be produced in a cell not normally producing it. Alternatively, increased expression of a protein can be effected in a cell normally producing the protein at a specific level. Further, expression can be decreased or eliminated by introducing a specific regulatory sequence. The regulatory sequence can be heterologous to the protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant proteins of the invention. Such mutations could be introduced, for example, into the specific functional regions.

To create an homologous recombinant animal, a vector is prepared which contains at least a portion of a nucleic acid of the invention into which a deletion, addition or substitution has been introduced to thereby alter, e.g., functionally disrupt, the endogenous gene. In one embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced nucleic acid has homologously recombined with the endogenous gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823-829 and in PCT Publication Nos. WO 90/11354, WO 91/01140, WO 92/0968, and WO 93/04169.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of *Saccharomyces cerevisiae* (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT Publication Nos. WO 97/07668 and WO 97/07669.

Polypeptides

The present invention also provides isolated polypeptides and variants and fragments thereof that are encoded by the nucleic acid molecules of the invention, especially as shown in SEQ ID NOS:18-51. For example, as described above, the nucleotide sequences can be used to design primers to clone and express cDNAs encoding the polypeptides of the invention. Further, the nucleotide sequences of the invention, e.g., the sequences disclosed herein, can be analyzed using routine search algorithms (e.g., BLAST, Altschul et al. (1990) J. Mol. Biol. 215:403-410; BLAZE, Brutlag et al. (1993) Comp. Chem. 17:203-207) to identify open reading frames (ORFs).

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be "isolated" or "purified."

The polypeptides of the invention can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the protein preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide comprises an amino acid sequence encoded by a nucleic acid comprising a nucleotide sequence selected from the group consisting of the sequences disclosed herein and the complements thereof. However, the invention also encompasses sequence variants. Variants include a substantially homologous protein encoded by the same genetic locus in an organism, i.e., an allelic variant. Variants also encompass proteins derived from other genetic loci in an organism, but having substantial homology to a polypeptide encoded by a nucleic acid comprising a nucleotide sequence and the complements thereof. Variants also include proteins substantially homologous to these polypeptides but derived from another organism, i.e., an ortholog. Variants also include proteins that are substantially homologous to these polypeptides that are produced by chemical synthesis. Variants also include proteins that are substantially homologous or identical to these polypeptides that are produced by recombinant methods.

As used herein, two proteins (or a region of the proteins) are substantially homologous or identical when the amino acid sequences are at least about 45-55%, typically at least about 70-75%, more typically at least about 80-85%, and most typically at least about 90-95% or more homologous or identical. A substantially homologous amino acid sequence, according to the present invention, will be encoded by a nucleic acid hybridizing to a nucleic acid sequence selected from the group consisting of the sequences, or portion thereof under stringent conditions as more described above.

To determine the percent homology or identity of two amino acid sequences, or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The invention also encompasses polypeptides having a lower degree of identity but having sufficient similarity so as to perform one or more of the same functions performed by a polypeptide encoded by a nucleic acid of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al. (1990) Science 247:1306-1310.

TABLE 4

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Preferred computer program methods to determine identify and similarity between two sequences include, but are not limited to, GCG program package (Devereux, J., et al. (1984) Nucleic Acids Res. 12(1):387), BLASTP, BLASTN, FASTA (Atschul, S. F. et al. (1990) J. Molec. Biol. 215:403).

A variant polypeptide can differ in amino acid sequence by one or more substitutions, deletions, insertions, inversions, fusions, and truncations or a combination of any of these. Further, variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the polypeptide. This includes preventing immunogenicity from pharmaceutical formulations by preventing protein aggregation.

Amino acids that are essential for function can be identified by methods known in the art, such as site-directed mutagenesis or alanine-scanning mutagenesis (Cunningham et al. (1989) Science 244:1081-1085). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al. (1992) J. Mol. Biol. 224:899-904; de Vos et al. (1992) Science 255:306-312).

The invention also includes polypeptide fragments of the polypeptides of the invention. Fragments can be derived from a polypeptide encoded by a nucleic acid comprising a nucleotide sequence selected from the group consisting of the sequences disclosed herein and the complements thereof. However, the invention also encompasses fragments of the variants of the polypeptides described herein.

As used herein, a fragment comprises at least 6 contiguous amino acids. Useful fragments include those that retain one or more of the biological activities of the polypeptide as well as fragments that can be used as an immunogen to generate polypeptide specific antibodies.

Biologically active fragments (peptides which are, for example, 6, 9, 12, 15, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites.

The invention also provides fragments with immunogenic properties. These contain an epitope-bearing portion of the polypeptides and variants of the invention. These epitope-bearing peptides are useful to raise antibodies that bind specifically to a polypeptide or region or fragment. These peptides can contain at least 6, 7, 8, 9, 12, at least 14, or between at least about 15 to about 30 amino acids. The epitope-bearing peptide and polypeptides may be produced by any conventional means (Houghten (1985) Proc. Natl. Acad. Sci. USA 82:5131-5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion proteins. These comprise a polypeptide of the invention operatively linked to a heterologous protein having an amino acid sequence not substantially homologous to the polypeptide. "Operatively linked" indicates that the polypeptide protein and the heterologous protein are fused in-frame. The heterologous protein can be fused to the N-terminus or C-terminus of the polypeptide. In one embodiment the fusion protein does not affect function of the polypeptide per se. For example, the fusion protein can be a GST-fusion protein in which the polypeptide sequences are fused to the C-terminus of the GST sequences. Other types of fusion proteins include, but are not limited to, enzymatic fusion proteins, for example beta-galactosidase fusions, yeast two-hybrid GAL fusions, poly-His fusions and Ig fusions. Such fusion proteins, particularly poly-His fusions, can facilitate the purification of recombinant polypeptide. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al. (1995) Journal of Molecular Recognition 8:52-58 and Johanson et al. (1995) The Journal of Biological Chemistry 270, 16:9459-9471. Thus, this invention also encompasses soluble fusion proteins containing a polypeptide of the invention and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence that is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed and re-amplified to generate a chimeric nucleic acid sequence (see Ausubel et al., Current Protocols in Molecular Biology, 1992). Moreover, many expression vectors are commercially available that already encode a fusion moiety (e.g., a GST protein). A nucleic acid encoding a polypeptide of the invention can be cloned into such an expression vector such that the fusion moiety is linked in-frame to the polypeptide protein.

The isolated polypeptide can be purified from cells that naturally express it, purified from cells that have been altered to express it (recombinant), or synthesized using known protein synthesis methods.

In one embodiment, the protein is produced by recombinant DNA techniques. For example, a nucleic acid molecule encoding the polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a proprotein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al., Meth. Enzymol. 182: 626-646 (1990) and Rattan et al. (1992) Ann. N.Y. Acad. Sci. 663:48-62.

As is also well known, polypeptides are not always entirely linear. For instance, polypeptides may be branched as a result of ubiquitination, and they may be circular, with or without branching, generally as a result of post-translation events, including natural processing event and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino terminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Uses of the polypeptides of the invention are described in detail below. In general, polypeptides or proteins of the present invention can be used as a molecular weight marker on SDS-PAGE gels or on molecular sieve gel filtration columns using art-recognized methods. The polypeptides of the present invention can be used to raise antibodies or to elicit an immune response. The polypeptides can also be used as a reagent, e.g., a labeled reagent, in assays to quantitatively determine levels of the protein or a molecule to which it binds (e.g., a receptor or a ligand) in biological fluids. The polypeptides can also be used as markers for tissues in which the corresponding protein is preferentially expressed, either constitutively, during tissue differentiation, or in a diseased state. The polypeptides can be used to isolate a corresponding binding partner, e.g., receptor or ligand, such as, for example, in an interaction trap assay, and to screen for peptide or small molecule antagonists or agonists of the binding interaction.

Antibodies

In another aspect, the invention provides antibodies to the polypeptides and polypeptide fragments of the invention, e.g., having an amino acid encoded by a nucleic acid comprising all or a portion of a nucleotide sequence selected from the group consisting of the sequences disclosed herein. The term "antibody" as used herein refers to immunoglobulin molecules and immunologically active portions of immunoglobulin molecules, i.e., molecules that contain an antigen binding site that specifically binds an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')2 fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol. Today 4:72), the EBV-hybridoma technique (Cole et al. (1985), Monoclonal Antibodies and Cancer Therapy, Alan R. Liss, Inc., pp. 77-96) or trioma techniques. The technology for producing hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med. 54:387-402. Moreover, the ordinarily skilled worker will appreciate that there are many variations of such methods that also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a polypeptide of the invention, e.g., using a standard ELISA assay.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison (1985) Science 229:1202-1207; Oi et al. (1986) Bio/fechniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) Int. Rev. Immunol. 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." This technology is described, for example, in Jespers et al. (1994) Bio/technology 12:899-903).

Uses of the antibodies of the invention are described in detail below. In general, antibodies of the invention (e.g., a monoclonal antibody) can be used to isolate a polypeptide of the invention by standard techniques, such as affinity chromatography or immunoprecipitation. A polypeptide specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, (-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) J. Mol. Biol. 215:403-410) and BLAZE (Brutlag et al. (1993) Comp. Chem. 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Detection Assays

Portions or fragments of the nucleotide sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the nucleic acid (or a portion of the sequence) has been isolated, it can be used to map the location of the gene on a chromosome. The mapping of the sequences to chromosomes is an important first step in correlating these sequences with genes associated with disease. Briefly, genes can be mapped to chromosomes by preparing PCR primers (preferably 15-25 bp in length) from the nucleic acid molecules described herein. Computer analysis of the sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the appropriate nucleotide sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycle. Using the nucleic acid molecules of the invention to design oligonucleotide primers, sublocalization can be achieved with panels of fragments from specific chromosomes. Other mapping strategies which can similarly be used to map a specified sequence to its chromosome include in situ hybridization (described in Fan et al. (1990) PNAS 97:6223-27), pre-screening with labeled flow-sorted chromosomes, and pre-selection by hybridization to chromosome specific cDNA libraries.

Fluorescence in situ hybridization (FISH) of a nucleotide sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a nucleotide sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. for a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Medelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) Nature 325:783-787.

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible form chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The nucleotide sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique that determines the actual base-by-base DNA sequence of selected portions of an individual's genome. Thus, the nucleic acid molecules described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid molecules of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of these sequences can comfortably provide positive individual identification with a panel of perhaps 10 to 1,000 primers which each yield a noncoding amplified sequence of 100 bases. If predicted coding sequences are used, a more appropriate number of primers for positive individual identification would be 500-2,000.

If a panel of reagents from nucleic acid molecules described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means of positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of sequences described herein are particularly appropriate for this use, as greater numbers of polymorphisms occur in the noncoding regions, making it easier to differentiate individuals using this technique. Examples of polynucleotide reagents include the nucleic acid molecules or the invention, or portions thereof, e.g., fragments having a length of at least 20 bases, preferably at least 30 bases.

The nucleic acid molecules described herein can further be used to provide polynucleotide reagents, e.g., labeled or labelable probes which can be used in, or example, an in situ hybridization technique, to identify a specific tissue. This can be very useful in cases where a forensic pathologist is presented with a tissue of unknown origin. Panels of such probes can be used to identify tissue by species and/or by organ type.

In a similar fashion, these reagents, primers or probes can be used to screen tissue culture for contamination (i.e., screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining protein and/or nucleic acid expression as well as activity of proteins of the invention, in the context of a biological sample (e.g., blood, serum, cells, tissue) to thereby determine whether an individual is afflicted with a disease or disorder, or is at risk of developing a disorder, associated with aberrant expression or activity. The invention also provides for prognostic (or predictive) assays for determining whether an individual is at risk of developing a disorder associated with activity or expression of proteins or nucleic acids of the invention.

Disorders relating to programmed cell death are particularly relevant as discussed in detail herein below.

For example, mutations in a specified gene can be assayed in a biological sample. Such assays can be used for prognostic or predictive purpose to thereby prophylactically treat an individual prior to the onset of a disorder characterized by or associated with expression or activity of nucleic acid molecules or proteins of the invention.

Another aspect of the invention pertains to monitoring the influence of agents (e.g., drugs, compounds) on the expression or activity of proteins of the invention in clinical trials.

These and other agents are described in further detail in the following sections.

1. Diagnostic Assays

An exemplary method for detecting the presence or absence of proteins or nucleic acids of the invention in a biological sample involves obtaining a biological sample from a test subject and contacting the biological sample with a compound or an agent capable of detecting the protein, or nucleic acid (e.g., mRNA, genomic DNA) that encodes the protein, such that the presence of the protein or nucleic acid is detected in the biological sample. A preferred agent for detecting mRNA or genomic DNA is a labeled nucleic acid probe capable of hybridizing to mRNA or genomic DNA sequences described herein. The nucleic acid probe can be, for example, a full-length nucleic acid, or a portion thereof, such as an oligonucleotide of at least 15, 30, 50, 100, 250 or 500 nucleotides in length and sufficient to specifically hybridize under stringent conditions to appropriate mRNA or genomic DNA. For example, the nucleic acid probe can be all or a portion of the sequences disclosed herein, or the complement of the sequences disclosed herein, or a portion thereof. Other suitable probes for use in the diagnostic assays of the invention are described herein.

In one embodiment, the agent for detecting proteins of the invention is an antibody capable of binding to the protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, calls and biological fluids isolated from a subject, as well as tissues, cells and fluids present within a subject. That is, the detection method of the invention can be used to detect mRNA, protein, or genomic DNA of the invention in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled anti-protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample or biopsy isolated by conventional means from a subject.

In another embodiment, the methods further involve obtaining a control biological sample from a control subject, contacting the control sample with a compound or agent capable of detecting protein, mRNA, or genomic DNA of the invention, such that the presence of protein, mRNA or genomic DNA is detected in the biological sample, and comparing the presence of protein, mRNA or genomic DNA in the control sample with the presence of protein, mRNA or genomic DNA in the test sample.

The invention also encompasses kits for detecting the presence of proteins or nucleic acid molecules of the invention in a biological sample. For example, the kit can comprise a labeled compound or agent capable of detecting protein or mRNA in a biological sample; means for determining the amount of in the sample; and means for comparing the amount of in the sample with a standard. The compound or agent can be packaged in a suitable container. The kit can further comprise instructions for using the kit to detect protein or nucleic acid.

2. Prognostic Assays

The diagnostic methods described herein can furthermore be utilized to identify subjects having or at risk of developing a disease or disorder associated with aberrant expression or activity of proteins and nucleic acid molecules of the invention. Accordingly, the term "diagnostic" refers not only to ascertaining whether a subject has an active disease but also relates to ascertaining whether a subject is predisposed to developing active disease as well as ascertaining the probability that treatment of active disease will be effective. For example, the assays described herein, such as the preceding diagnostic assays or the following assays can be utilized to identify a subject having or at risk of developing a disorder associated with protein or nucleic acid expression or activity such as a proliferative disorder, a differentiative or developmental disorder, or a hematopoietic disorder. Alternatively, the prognostic assays can be utilized to identify a subject having or at risk for developing a differentiative or proliferative disease (e.g., cancer). Thus, the present invention provides a method for identifying a disease or disorder associated with aberrant expression or activity of proteins or nucleic acid molecules of the invention, in which a test sample is obtained from a subject and protein or nucleic acid (e.g., mRNA, genomic DNA) is detected, wherein the presence of protein or nucleic acid is diagnostic for a subject having or at risk of developing a disease or disorder associated with aberrant expression or activity of the protein or nucleic acid sequence of the invention. As used herein, a "test sample" refers to a biological sample obtained from a subject of interest. For example, a test sample can be a biological fluid (e.g., serum), cell or tissue sample.

Disorders relating to programmed cell death are particularly relevant as discussed in detail herein below.

Furthermore, the prognostic assays described herein can be used to determine whether a subject can be administered an agent (e.g., an agonist, antagonist, peptidomimetic, protein, polypeptide, nucleic acid, small molecule, or other drug candidate) to treat a disease or disorder associated with aberrant expression or activity of a protein or nucleic acid molecule of the invention. For example, such methods can be used to determine whether a subject can be effectively treated with an agent for a disorder, such as a proliferative disorder, a differentiative or a developmental disorder. Alternatively, such methods can be used to determine whether a subject can be effectively treated with an agent for a differentiative or proliferative disease (e.g., cancer). Thus, the present invention provides methods for determining whether a subject can be effectively treated with an agent for a disorder associated with aberrant expression or activity of a protein or nucleic acid of the present invention, in which a test sample is obtained and protein or nucleic acid expression or activity is detected (e.g., wherein the abundance of particular protein or nucleic acid expression or activity is diagnostic for a subject that can be administered the agent to treat a disorder associated with aberrant expression or activity.)

Disorders relating to programmed cell death are particularly relevant as discussed in detail herein below.

The methods of the invention can also be used to detect genetic alterations in genes or nucleic acid molecules of the present invention, thereby determining if a subject with the altered gene is at risk for a disorder characterized by aberrant development, aberrant cellular differentiation, aberrant cellular proliferation or an aberrant hematopoietic response. In certain embodiments, the methods include detecting, in a sample of cells from the subject, the presence or absence of a genetic alteration characterized by at least one of an alteration affecting the integrity of a gene encoding a particular protein, or the mis-expression of the gene. For example, such genetic alterations can be detected by ascertaining the existence of at least one of (1) a deletion of one or more nucleotides; (2) an addition of one or more nucleotides; (3) a substitution of one or more nucleotides, (4) a chromosomal rearrangement; (5) an alteration in the level of a messenger RNA transcript; (6) aberrant modification, such as of the methylation pattern of the genomic DNA; (7) the presence of a non-wild type splicing pattern of a messenger RNA transcript; (8) a non-wild type level; (9) allelic loss; and (10) inappropriate post-translational modification. As described herein, there are a large number of assay techniques known in the art that can be used for detecting alterations in a particular gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such an anchor PCR or RACE PCR, or, alternatively, in a ligation chain reaction (LCR) (see, e.g., Landegran et al. (1988) Science 241:1077-1080; and Nakazawa et al. (1994) PNAS 91:360-364), the latter of which can be particularly useful for detecting point mutations (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to the gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh et al., (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a given gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicate mutations in the sample DNA. Moreover, the use of sequence specific ribozymes (see, for sample, U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotide probes (Cronin et al. (1996) Human Mutation 7:244-255; Kozal et al. (1996) Nature Medicine 2:753-759). For example, genetic mutations can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the gene and detect mutations by comparing the sequence of the gene from the sample with the corresponding wild-type (control) gene sequence. Examples of sequencing reactions include those based on techniques developed by Maxim and Gilbert ((1997) PNAS 74:560) or Sanger ((1977) PNAS 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type sequence with potentially mutant RNA or DNA obtained from a tissue sample. The double-standard duplexes are treated with an agent that cleaves single-stranded regions of the duplex such as which will exist due to base pair mismatches between the control and sample strands. For instance, RNA/DNA duplexes can be treated with Rnase and DNA/DNA hybrids treated with S1 nuclease to enzymatically digest the mismatched regions. After digestion of the mismatched regions, the resulting material is then separated by size on denaturing polyacrylamide gels to determine the site of mutation. See, for example Cotton et al. (1988) Proc. Natl. Acad. Sci. USA 85:4397; Saleeba et al. (1992) Methods Enzymol. 217:286-295. In certain embodiments, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on an nucleotide sequence of the invention is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) Proc. Natl. Acad. Sci. USA 86:2766, see also Cotton (1993) Mutat Res 285:125-144; and Hayashi (1992) Genet Anal. Tech. Appl. 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6320). Such allele-specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene of the present invention. Any cell type or tissue in which the gene is expressed may be utilized in the prognostic assays described herein.

3. Monitoring of Effects During Clinical Trials

Monitoring the influence of agents (e.g., drugs, compounds) on the expression or activity of nucleic acid molecules or proteins of the present invention (e.g., modulation of cellular signal transduction, regulation of gene transcription in a cell involved in development or differentiation, regulation of cellular proliferation) can be applied not only in basic drug screening, but also in clinical trials. For example, the effectiveness of an agent determined by a screening assay as described herein to increase gene expression, protein levels, or upregulate protein activity, can be monitored in clinical trials of subjects exhibiting decreased gene expression, protein levels, or downregulated protein activity. Alternatively, the effectiveness of an agent determined by a screening assay to decrease gene expression, protein levels, or downregulate protein activity, can be monitored in clinical trials of subjects exhibiting increased gene expression, protein levels, or upregulated protein activity. In such clinical trials, the expression or activity of the specified gene and, preferably, other genes that have been implicated in, for example, a proliferative disorder can be used as a "read out" or markers of the phenotype of a particular cell.

For example, and not by way of limitation, genes that are modulated in cells by treatment with an agent (e.g., compound, drug or small molecule) which modulates protein activity (e.g., identified in a screening assay as described herein) can be identified. Thus, to study the effect of agents on proliferative disorders, developmental or differentiative disorder, or hematopoietic disorder, for example, in a clinical trial, cells can be isolated and RNA prepared and analyzed for the levels of expression of the specified gene and other genes implicated in the proliferative disorder, developmental or differentiative disorder, or hematopoietic disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of the specified gene or other genes. In this way, the gene expression pattern can serve as a marker, indicative of the physiological response of the cells to the agent. Accordingly, this response state may be determined before, and at various points during, treatment of the individual with the agent.

Disorders relating to programmed cell death are particularly relevant as discussed in detail herein below.

In one embodiment, the present invention provides a method for monitoring the effectiveness of treatment of a subject with an agent (e.g., an agonist, antagonist, peptidomimetic, protein, polypeptide, nucleic acid, small molecule, or other drug candidate identified by the screening assays described herein) comprising the steps of (i) obtaining a pre-administration sample from a subject prior to administration of the agent; (ii) detecting the level of expression of a specified protein, mRNA, or genomic DNA of the invention in the pre-administration sample; (iii) obtaining one or more post-administration samples from the subject; (iv) detecting the level of expression or activity of the protein, mRNA, or genomic DNA in the post-administration samples; (v) comparing the level of expression or activity of the protein, mRNA, or genomic DNA in the pre-administration sample with the protein, mRNA, or genomic DNA in the post-administration sample or samples; and (vi) altering the administration of the agent to the subject accordingly. For example, increased administration of the agent may be desirable to increase the expression or activity of the protein or nucleic acid molecule to higher levels than detected, i.e., to increase effectiveness of the agent. Alternatively, decreased administration of the agent may be desirable to decrease effectiveness of the agent. According to such an embodiment, protein or nucleic acid expression or activity may be used as an indicator of the effectiveness of an agent, even in the absence of an observable phenotypic response.

Screening Assays

The invention provides a method (also referred to herein as a "screening assay") for identifying modulators, i.e., candidate or test compounds or agents (e.g., antisense, polypeptides, peptidomimetics, small molecules or other drugs) which bind to nucleic acid molecules, polypeptides or proteins described herein or have a stimulatory or inhibitory effect on, for example, expression or activity of the nucleic acid molecules, polypeptides or proteins of the invention.

As an example, apoptosis-specific assays may be used to identify modulators of any of the target nucleic acids or proteins of the present invention, which proteins and/or nucleic acids are related to apoptosis. Accordingly, an agent that modulates the level or activity of any of these nucleic acids or proteins can be identified by means of apoptosis-specific assays. For example, high throughput screens exist to identify apoptotic cells by the use of chromatin or cytoplasmic-specific dyes. Thus, hallmarks of apoptosis, cytoplasmic condensation and chromosome fragmentation, can be used as a marker to identify modulators of any of the genes related to programmed-cell death described herein. Other assays include, but are not limited to, the activation of specific endogenous proteases, loss of mitochondrial function, cytoskeletal disruption, cell shrinkage, membrane blebbing, and nuclear condensation due to degradation of DNA.

In one embodiment, the invention provides assays for screening candidate or test compounds that bind to or modulate the activity of protein or polypeptide described herein or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) Anticancer Drug Des. 12:145).

Examples of methods for the synthesis of molecular libraries can be found in the art, for example in DeWitt et al. (1993) Proc. Natl. Acad. Sci. U.S.A. 90:6909; Erb et al. (1994) Proc. Natl. Acad. Sci. U.S.A. 91:11422; Zuckermann et al. (1994). J. Med. Chem. 37:2678; Cho et al. (1993) Science 261:1303; Carell et al. (1994) Angew. Chem. Int. Ed. Engl. 33:2059;

Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. U.S.A. 89:1865-1869) or on phage (Scott and Smith (1990) Science 249:386-390); (Devlin (1990) Science 249:404-406); (Cwirla et al. (1990) Proc. Natl. Acad. Sci. 97:6378-6382); (Felici (1991) J. Mol. Biol. 222:301-310); (Ladner supra).

In one embodiment, an assay is a cell-based assay in which a cell that expresses an encoded polypeptide (e.g., cell surface protein such as a receptor) is contacted with a test compound and the ability of the test compound to bind to the polypeptide is determined. The cell, for example, can be of mammalian origin, such as a keratinocyte. Determining the ability of the test compound to bind to the polypeptide can be accomplished, for example, by coupling the test compound with a radioisotope or enzymatic label such that binding of the test compound to the polypeptide can be determined by detecting the labeled with 125I, 35S, 14C, or 3H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a test compound to interact with the polypeptide without the labeling of any of the interactants. For example, a microphysiometer can be used to detect the interaction of a test compound with the polypeptide without the labeling of either the test compound or the polypeptide. McConnell et al. (1992) Science 257:1906-1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and polypeptide.

In one embodiment, the assay comprises contacting a cell which expresses an encoded protein described herein on the cell surface (e.g., a receptor) with a polypeptide ligand or biologically-active portion thereof, to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide as compared to the ability of the ligand, or a biologically active portion thereof, to bind to the polypeptide.

In another embodiment, an assay is a cell-based assay comprising contacting a cell expressing a particular target molecule described herein with a test compound and determining the ability of the test compound to modulate or alter (e.g. stimulate or inhibit) the activity of the target molecule. Determining the ability of the test compound to modulate the activity of the target molecule can be accomplished, for example, by determining the ability of a known ligand to bind to or interact with the target molecule. Determining the ability of the known ligand to bind to or interact with the target molecule can be accomplished by one of the methods described above for determining direct binding. In one embodiment, determining the ability of the known ligand to bind to or interact with the target molecule can be accomplished by determining the activity of the target molecule. For example, the activity of the target molecule can be determined by detecting induction of a cellular second messenger of the target (e.g., intracellular Ca2+, diacylglycerol, IP3, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a cellular response, for example, development, differentiation or rate of proliferation.

In yet another embodiment, an assay of the present invention is a cell-free assay in which protein of the invention or biologically active portion thereof is contacted with a test compound and the ability of the test compound to bind to the protein or biologically active portion thereof is determined. Binding of the test compound to the protein can be determined either directly or indirectly as described above. In one embodiment, the assay includes contacting the protein or biologically active portion thereof with a known compound which binds the protein to form an assay mixture, contacting the assay mixture with a test compound, and determining the ability of the test compound to interact with the protein. Determining the ability of the test compound to interact with the protein comprises determining the ability of the test compound to preferentially bind to the protein or biologically active portion thereof as compared to the known compound.

In another embodiment, the assay is a cell-free assay in which a protein of the invention or biologically active portion thereof is contacted with a test compound and the ability of the test compound to modulate or alter (e.g., stimulate or inhibit) the activity of the protein or biologically active portion thereof is determined. Determining the ability of the test compound to modulate the activity of the protein can be accomplished, for example, by determining the ability of the protein to bind to a known target molecule by one of the methods described above for determining direct binding. Determining the ability of the protein to bind to a target molecule can also be accomplished using a technology such as real-time Bimolecular Interaction Analysis (BIA). Sjolander and Urbaniczky (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

In an alternative embodiment, determining the ability of the test compound to modulate the activity of a protein of the invention can be accomplished by determining the ability of the protein to further modulate the activity of a target molecule. For example, the catalytic/enzymatic activity of the target molecule on an appropriate substrate can be determined as previously described.

In yet another embodiment, the cell-free assay involves contacting a protein of the invention or biologically active portion thereof with a known compound which binds the protein to form an assay mixture, contacting the assay mixture with a test compound, and determining the ability of the test compound to interact with the protein, wherein determining the ability of the test compound to interact with the protein comprises determining the ability of the protein to preferentially bind to or modulate the activity of a target molecule.

The cell-free assays of the present invention are amenable to use of both soluble and/or membrane-bound forms of isolated proteins. In the case of cell-free assays in which a membrane-bound form an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton®X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

In more than one embodiment of the above assay methods of the present invention, it may be desirable to immobilize either the protein or its target molecule to facilitate separation of complexed from uncomplexed forms of one or both of the proteins, as well as to accommodate automation of the assay. Binding of a test compound to the protein, or interaction of the protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or protein of the invention, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either a protein of the invention or a target molecule can be immobilized utilizing conjugation of biotin and streptavidin. Biotinylated protein of the invention or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a protein of the invention or target molecules, but which do not interfere with binding of the protein to its target molecule, can be derivatized to the wells of the plate, and unbound target or protein trapped in the wells by antibody conjugation. Methods for detecting such complexes, in addition to those described above for the GST-immobilized complexes, include immunodetection of complexes using antibodies reactive with the protein or target molecule, as well as enzyme-linked assays which rely on detecting an enzymatic activity associated with the protein or target molecule.

In another embodiment, modulators of expression of nucleic acid molecules of the invention are identified in a method wherein a cell is contacted with a candidate compound and the expression of appropriate mRNA or protein in the cell is determined. The level of expression of appropriate mRNA or protein in the presence of the candidate compound is compared to the level of expression of mRNA or protein in the absence of the candidate compound. The candidate compound can then be identified as a modulator of expression based on this comparison. For example, when expression of mRNA or protein is greater (statistically significantly greater) in the presence of the candidate compound than in its absence, the candidate compound is identified as a stimulator or enhancer of the mRNA or protein expression. Alternatively, when expression of the mRNA or protein is less (statistically significantly less) in the presence of the candidate compound than in its absence, the candidate compound is identified as an inhibitor of the mRNA or protein expression. The level of mRNA or protein expression in the cells can be determined by methods described herein for detecting mRNA or protein.

In yet another aspect of the invention, the proteins of the invention can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins (captured proteins) which bind to or interact with the proteins of the invention and modulate their activity. Such captured proteins are also likely to be involved in the propagation of signals by the proteins of the invention as, for example, downstream elements of a protein-mediated signaling pathway. Alternatively, such captured proteins are likely to be cell-surface molecules associated with non-protein-expressing cells, wherein such captured proteins are involved in signal transduction.

This invention further pertains to novel agents identified by the above-described screening assays. Accordingly, it is within the scope of this invention to further use an agent identified as described herein in an appropriate animal model. For example, an agent identified as described herein (e.g., a modulating agent, an antisense nucleic acid molecule, a specific antibody, or a protein-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Methods of Treatment

The present invention provides for both prophylactic and therapeutic methods of treating a subject at risk of (or susceptible to) a disorder or having a disorder associated with aberrant expression or activity of or related to proteins or nucleic acids of the invention. Methods of treatment involve modulating nucleic acid or polypeptide level or activity in a subject having a disorder that can be treated by such modulation. Accordingly, modulation can cause up regulation or down regulation of the levels of expression or up regulation or down regulation of the activity of the nucleic acid or protein. Disorders relating to programmed cell death are particularly relevant as discussed in detail herein below.

Expression of the nucleic acids of the invention has been shown for the following tissues: testes, brain, heart, kidney, skeletal muscle, spleen, lung, smooth muscle, pancreas, and liver. Accordingly, disorders to which the methods disclosed herein are particularly relevant include those involving these tissues.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, a1-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver metastatic tumors, and liver fibrosis.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B1) deficiency and vitamin B12 deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Preferred disorders include those involving the central nervous system and particularly the brain.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with the molecules of the present invention or modulators according to that individual's drug response genotype. Pharmacogenomics allows a clinician or physician to target prophylactic or therapeutic treatments to patients who will most benefit from the treatment and to avoid treatment of patients who will experience toxic drug related side effects.

1. Prophylactic Methods

In one aspect, the invention provides a method for preventing in a subject, a disease or condition associated with aberrant expression or activity of genes or proteins of the present invention, by administering to the subject an agent which modulates expression or at least one activity of a gene or protein of the invention. Subjects at risk for a disease that is caused or contributed to by aberrant gene expression or protein activity can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The appropriate agent can be determined based on screening assays described herein.

2. Therapeutic Methods

Another aspect of the invention pertains to methods of modulating expression or activity of genes or proteins of the invention for therapeutic purposes. The modulatory method of the invention involves contacting a cell with an agent that modulates one or more of the activities of the specified protein associated with the cell. An agent that modulates protein activity can be an agent as described herein, such as a nucleic acid or a protein, a naturally-occurring target molecule of a protein described herein, a polypeptide, a peptidomimetic, or other small molecule. In one embodiment, the agent stimulates one or more protein activities. Examples of such stimulatory agents include active protein as well as a nucleic acid molecule encoding the protein that has been introduced into the cell. In another embodiment, the agent inhibits one or more protein activities. Examples of such inhibitory agents include antisense nucleic acid molecules and anti-protein antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a protein or nucleic acid molecule of the invention. In one embodiment, the method involves administering an agent (e.g., an agent identified by a screening assay described herein), or combination of agents that modulates (e.g., upregulates or downregulates) expression or activity of a gene or protein of the invention. In another embodiment, the method involves administering a protein or nucleic acid molecule of the invention as therapy to compensate for reduced or aberrant expression or activity of the protein or nucleic acid molecule.

Stimulation of protein activity is desirable in situations in which the protein is abnormally downregulated and/or in which increased protein activity is likely to have a beneficial effect. Likewise, inhibition of protein activity is desirable in situations in which the protein is abnormally upregulated and/or in which decreased protein activity is likely to have a beneficial effect. One example of such a situation is where a subject has a disorder characterized by aberrant development or cellular differentiation. Another example of such a situation is where the subject has a proliferative disease (e.g., cancer) or a disorder characterized by an aberrant hematopoietic response. Yet another example of such a situation is where it is desirable to achieve tissue regeneration in a subject (e.g., where a subject has undergone brain or spinal cord injury and it is desirable to regenerate neuronal tissue in a regulated manner).

Pharmaceutical Compositions

The nucleic acid molecules, protein modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a ubiquitin protease protein or anti-ubiquitin protease antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

3. Pharmacogenomics

The molecules of the present invention, as well as agents, or modulators which have a stimulatory or inhibitory effect on the protein activity (e.g., gene expression) as identified by a screening assay described herein can be administered to individuals to treat (prophylactically or therapeutically) disorders (e.g., proliferative or developmental disorders) associated with aberrant protein activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a molecule of the invention or modulator thereof, as well as tailoring the dosage and/or therapeutic regimen of treatment with such a molecule or modulator.

Pharmacogenomics deals with clinically significant hereditary variations in the response to drugs due to altered drug disposition and abnormal action in affected persons. See e.g., Eichelbaum (1996) Clin Exp. Pharmacol. Physiol. 23(10-11):983-985 and Linder (1997) Clin. Chem. 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1,000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a protein or a polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2Cl9) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme is the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a molecule or modulator of the present invention) can given an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a molecule or modulator of the invention, such as a modulator identified by one of the exemplary screening assays described herein.

Disorders which may be treated or diagnosed by methods described herein include, but are not limited to disorders involving apoptosis. Certain disorders are associated with an increased number of surviving cells, which are produced and continue to survive or proliferate when apoptosis is inhibited.

As used herein, "programmed cell death" refers to a genetically regulated process involved in the normal development of multicellular organisms. This process occurs in cells destined for removal in a variety of normal situations, including larval development of the nematode *C. elegans*, insect metamorphosis, development in mammalian embryos, including the nephrogenic zone in the developing kidney, and regression or atrophy (e.g., in the prostate after castration). Programmed cell death can occur following the withdrawal of growth and trophic factors in many cells, nutritional deprivation, hormone treatment, ultraviolet irradiation, and exposure to toxic and infectious agents including reactive oxygen species and phosphatase inhibitors, e.g., okadaic acid, calcium ionophores, and a number of cancer chemotherapeutic agents. See Wilson (1998) Biochem. Cell Biol. 76:573-582 and Hetts (1998) JAMA 279:300-307, the contents of which are incorporated herein by reference. Thus, the proteins of the invention, by being differentially expressed during programmed cell death, e.g., neuronal programmed cell death, can modulate a programmed cell death pathway activity and provide novel diagnostic targets and therapeutic agents for disorders characterized by deregulated programmed cell death, particularly in cells that express the protein.

As used herein, a "disorder characterized by deregulated programmed cell death" refers to a disorder, disease or condition which is characterized by a deregulation, e.g., an upregulation or a downregulation, of programmed cell death. Programmed cell death deregulation can lead to deregulation of cellular proliferation and/or cell cycle progression. Examples of disorders characterized by deregulated programmed cell death include, but are not limited to, neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, Jakob-Creutzfieldt disease, or AIDS related dementias; myelodysplastic syndromes, e.g., aplastic anemia; ischemic injury, e.g., myocardial infarction, stroke, or reperfusion injury; autoimmune disorders, e.g., systemic lupus erythematosus, or immune-mediated glomerulonephritis; or profilerative disorders, e.g., cancer, such as follicular lymphomas, carcinomas with p53 mutations, or hormone-dependent tumors, e.g., breast cancer, prostate cancer, or ovarian cancer). Clinical manifestations of faulty apoptosis are also seen in stroke and in rheumatoid arthritis. Wilson (1998) Biochem. Cell. Biol. 76:573-582.

Failure to remove autoimmune cells that arise during development or that develop as a result of somatic mutation during an immune response can result in autoimmune disease. One of the molecules that plays a critical role in regulating cell death in lymphocytes is the cell surface receptor for Fas.

Viral infections, such as those caused by herpesviruses, poxviruses, and adenoviruses, may result in aberrant apoptosis. Populations of cells are often depleted in the event of viral infection, with perhaps the most dramatic example being the cell depletion caused by the human immunodeficiency virus (HIV). Most T cells that die during HIV infections do not appear to be infected with HIV. Stimulation of the CD4 receptor may result in the enhanced susceptibility of uninfected T cells to undergo apoptosis.

Many disorders can be classified based on whether they are associated with abnormally high or abnormally low apoptosis. Thompson (1995) Science 267:1456-1462. Apoptosis may be involved in acute trauma, myocardial infarction, stroke, and infectious diseases, such as viral hepatitis and acquired immunodeficiency syndrome.

Primary apoptosis deficiencies include graft rejection. Accordingly, the invention is relevant to the identification of genes useful in inhibiting graft rejection.

Primary apoptosis deficiencies also include autoimmune diabetes. Accordingly, the invention is relevant to the identification of genes involved in autoimmune diabetes and accordingly, to the identification of agents that act on these targets to modulate the expression of these genes and hence, to treat or diagnose this disorder. Further, it has been suggested that all autoimmune disorders can be viewed as primary deficiencies of apoptosis (Hetts, above). Accordingly, the invention is relevant for screening for gene expression and transcriptional profiling in any autoimmune disorder and for screening for agents that affect the expression or transcriptional profile of these genes.

Primary apoptosis deficiencies also include local self reactive disorder. This includes Hashimoto thyroiditis.

Primary apoptosis deficiencies also include lymphoproliferation and autoimmunity. This includes, but is not limited to, Canale-Smith syndrome.

Primary apoptosis deficiencies also include cancer. For example, p53 induces apoptosis by acting as a transcription factor that activates expression of various apoptosis-mediating genes or by upregulating apoptosis-mediating genes such as Bax.

Primary apoptosis excesses are associated with neurodegenerative disorders including Alzheimer's disease, Parkinson's disease, spinal muscular atrophy, and amyotrophic lateral sclerosis.

Primary apoptosis excesses are also associated with heart disease including idiopathic dilated cardiomyopathy, ischemic cardiomyopathy, and valvular heart disease. Evidence has also been shown of apoptosis in heart failure resulting from arrhythmogenic right ventricular dysplasia. For all these disorders, see Hetts, above.

Death receptors also include the TNF receptor-1 and hence, TNF acts as a death ligand.

A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow.

These disorders could result from the activation of genes that promote apoptosis, acquired deficiencies in stromal cells or hematopoietic survival factors, or the direct effects of toxins and mediators of immune responses.

Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

The invention also pertains to disorders of the central nervous system (CNS). These disorders include, but are not limited to cognitive and neurodegenerative disorders such as Alzheimer's disease, senile dementia, Huntington's disease, amyotrophic lateral sclerosis, and Parkinson's disease, as well as Gilles de la Tourette's syndrome, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as bipolar affective disorder, e.g., severe bipolar affective (mood) disorder (BP-I), bipolar affective (mood) disorder with hypomania and major depression (BP-II). Further CNS-related disorders include, for example, those listed in the American Psychiatric Association's Diagnostic and Statistical manual of Mental Disorders (DSM), the most current version of which is incorporated herein by reference in its entirety.

As used herein, "differential expression" or differentially expressed" includes both quantative and qualitative differences in the temporal and/or cellular expression pattern of a gene, e.g., the programmed cell death genes disclosed herein, among, for example, normal cells and cells undergoing programmed cell death. Genes which are differentially expressed can be used as part of a prognostic or diagnostic marker for the evaluation of subjects at risk for developing a disorder characterized by deregulated programmed cell death. Depending on the expression level of the gene, the progression state of the disorder can also be evaluated.

Arrays and Microarrays

The term "array" refers to a set of nucleic acid sequences disclosed herein. Preferred arrays contain numerous genes. The term can refer to all of the sequences disclosed herein but could also include sequences not disclosed, for example, sequences included as controls for specific biological processes. A "subarray" is also an array but is obtained by creating an array of less than all of the sequences in a starting array. For example, an array of programmed cell death cDNAs, such as those disclosed herein.

In one embodiment of the invention, an array comprising the nucleic acid sequences disclosed herein.

The array can include the maximum number of disclosed sequences or can be based on increments of sequences to form a subarray of the maximum number of sequences.

Thus, in one embodiment of the invention, the invention is directed to an array comprising the sequences disclosed (the maximum number of sequences) in increments of about 10, i.e., 10, 20, 30, 40, 50, 60, 70, 80, 90, 100, 110, etc. In another embodiment, the sequences are found in increments of about 50, i.e., 50, 100, 150, 200, 250, 300, etc., up to the maximum number in the array. In a further embodiment, the sequences are found in increments of about 100, i.e., 100, 200, 300, 400, etc., up to the maximum number of sequences. In one embodiment, each of these subarrays contains at least one novel gene. In one embodiment of the invention, there is the proviso that the novel gene is not rlrxl015 f and h, rlrx018 a and b, rlrx020 a, b, c, d, e, f, and g (NARC1), and rlrx022 f and h (NARC2). In a preferred embodiment, the subarray of the complete array of nucleic acid sequences disclosed herein is in increments of about 100 sequences. In a more preferred embodiment, the subarray is in increments of about 500 sequences. In a still more preferred embodiment, the subarray is in increments of about 1000 sequences.

In another embodiment of the invention, the invention is directed to a subarray comprising the nucleic acid sequences disclosed herein. The same types of ranges accordingly applies to this subarray. Thus in one embodiment of the invention, the invention is directed to nucleic acids in this subarray in increments of about 10, i.e., 10, 20, 30, 40, 50, 60, 70, 80, 90, 100, 110, etc. up to the maximum number of sequences in the subarray. In another embodiment, the sequences are found in increments of about 50, i.e., 50, 100, 150, 200, 250, 300, 350, etc., up to the maximum number in the subarray. In a further embodiment, the sequences are found in increments of about 100, i.e., 100, 200, 300, 400, etc., up to the maximum number of sequences in the subarray.

The same types of ranges apply to subarrays, such as that described herein, and to functional subarrays, including but not limited to, those disclosed herein, including but not limited to, apoptosis, cell proliferation, cytoskeletal reorganization, secretion, synapse formation, hormone response, synaptic vesicle release, and calcium signal transduction. In one embodiment of the invention, the invention is directed to a function-biased array comprising sequences having a specific function in increments of about 10, i.e., 10, 20, 30, 40, 50, 60, 70, 80, 90, 100, 110, etc. In another embodiment, the sequences are found in increments of about 50, i.e., 50, 100, 150, 200, 250, 300, etc., up to the maximum number of such sequences in the subarray. In a further embodiment, the sequences are found in increments of about 100, i.e., 100, 200, 300, 400, etc., up to the maximum number of such sequences. In one embodiment, each of these subarrays contains at least one novel gene, as described herein. In one embodiment of the invention, there is the proviso that the novel gene is not rlrx015 f and h, rlrx018 a and b, rlrx020a, b, c, d, e, f, and g (NARC1), and rlrx022 f and h (NARC2). In a preferred embodiment, the functional subarray is in increments of about 100 sequences. In a more preferred embodiment, the subarray is in increments of about 500 sequences. In a still more preferred embodiment, the subarray is in increments of about 1000 sequences.

These functional subarrays and incremental numbers of nucleic acid sequences in such functional subarrays can be derived from any of the sequences described herein, which includes both novel and known sequences, or can be derived exclusively from sequences disclosed herein and can comprise only the novel genes disclosed herein.

Accordingly, the invention encompasses subarrays derived from the brain-biased library comprising at least the incremental number of sequences, as described above or functional subarrays. As discussed, in one embodiment, one or more novel genes is comprised in the increment. Further, as discussed, in another embodiment the subarray is assembled with the proviso that the novel gene is not rlrx015 f and h, rlrx018 a and b, rlrx020a, b, c, d, e, f, and g (NARC1), and rlrx022 f and h (NARC2).

Accordingly, the invention is further directed to a functional array as described above comprising at least the incremental numbers of sequences, as described above. In one embodiment, the subarray contains at least one novel gene as designated herein. In another embodiment, the array is assembled with the proviso that the novel gene is not rlrx015 f and h, rlrx018 a and b, rlrx020 a, b, c, d, e, f, and g (NARC1), and rlrx022 f and h (NARC2).

In one embodiment of the invention, the functional subarray comprises nucleic acid sequences expressed in programmed cell death as disclosed herein.

The array comprises not only the specific designated sequences but also variants of these sequences, as described herein. As described, variants include, allelic variants, homologs from other loci in the same animal, orthologs, and sequences sufficiently similar such that they fulfill the requisites for sequence similarity/homology as described herein.

Further, the array not only comprises the specific designated sequences, but also comprises fragments thereof. As described herein, the range of fragments will vary depending upon the specific sequence involved. Accordingly, the range of fragments is considerable, for example, 10, 15, 20, 25, 30, 35, 40, 45, 50, 55, 60, 65, 70, 75, 80, 85, 90, 95, 100, 125, 150, 200, 250, 300, 350, 400, 450, 500, 550, 600, 650, 700, 750, 800, 850, 900, 950, 1000 etc. In no way, however, is a fragment to be construed as having a sequence identical to that which may be found in the prior art.

The array can be used to assay expression of one or more genes in the array.

In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development and differentiation, tumor progression, progression of other diseases, in vitro processes, such as cellular transformation and senescence, autonomic neural and neurological processes, such as, for example, pain and appetite, and cognitive functions, such as learning or memory.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

In one embodiment, the array, and particularly subarrays containing one or more of the nucleic acid sequences related to programmed cell death, are useful for diagnosing disease or predisposition to disease involving apoptosis. These disorders include, but are not limited to, those discussed in detail herein. In addition, the array or subarrays created therefrom are useful for diagnosing active disorders of the central nervous system or for predicting the tenancy to develop such disorders. Disorders of the central nervous system include, but are not limited to, those disclosed in detail herein. Furthermore, the array and subarrays thereof are useful for diagnosing an active disorder or predicting the tendency to develop a disorder including, but not limited to, disorders involving secretion/synaptic vesicle release, cell proliferation, cytoskeletal reorganization, stress response/hormone response; and calcium signal transduction.

The array is also useful for ascertaining expression of one or more genes in model systems in vitro or in vivo. Various model systems have been developed to study normal and abnormal processes, including, but not limited to, apoptosis.

Apoptosis can be actively induced in animal cells by a diverse array of triggers that range from ionizing radiation to hypothermia to viral infections to immune reactions. Majno et al. (1995) Amer. J. Pathol. 146:3-15; Hockenberry et al. (1995) Bio Essays 17:631-638; Thompson et al. Science 267: 1456-1462 (1995).

Transgenic mouse models have been developed for familial amyotrophic lateral sclerosis, familial Alzheimer's disease and Huntington's disease, reviewed in Price et al. (1998) Science 282:1079-1083. Amyotrophic lateral sclerosis is the most common adult onset motor neuron disease. Alzheimer's disease is the most common cause of dementia in adult life. It is associated with the damage of regions and neurocircuits critical for cognition and memory, including neurons in the neocortex, hippocampus, amygdala, basal forebrain cholinergic system, and brain stem monoaminergic nuclei. Neurological diseases that are associated with autosomal dominant trinucleotide repeat mutations include Huntington's disease, several spinal cerebellar ataxias and dentatorubral pallidoluysian atrophy. SCA-1 and SCA-3 or Machado-Joseph disease are characterized by ataxia and lack of coordination. In Huntington's disease, symptoms are related to degeneration of subsets of striatal and cortical neurons. Apoptosis is thought to play a role in the degeneration of these cells. In SCA-1, SCA-3, and in dentatorubral pallidoluysian atrophy, a variety of cell populations, and particularly cells in the cerebellum, have been shown to degenerate. See Price et al. above, which is incorporated by reference in its entirety for the teachings of model systems related to neurodegenerative diseases.

Mouse models have been developed for non-obese diabetic mice, to study disease progression for the treatment of autoimmune diabetes mellitus. Bellgrau et al. (1995) Nature 377:630-632. Models have also been developed in mice wherein the mice lack one or two copies of the p53 gene. Study of these mice has shown that apoptosis is involved in suppressing tumor development in vivo. Lozano et al. (1998) Semin. Canc. Biol. 8:337-344. Another animal model relevant to the study of apoptosis involves the targeted gene disruption of caspase genes creating caspase gene knockout mice. Colussi et al. (1999) J. Immun. Cell. Biol. 77:58-63. A further mouse model pertains to cold injury in mice, such injury inducing neuronal apoptosis. Murakami et al. (1999) Prog. Neurobiol. 57:289-299.

Knockout mice have been created for Apaf1. In these mice, defects are found in essentially all tissues whose development depends on cell death, including loss of interdigital webs, formation of the palate, control of neuron cell number, and development of the lens and retina. Cecconi et al. (1998) Cell 94:727-737.

Caspase knockout mice have also been achieved for caspase 1, 2, 3, and 9. Green (1998) Cell 94:695-698.

The array allows the simultaneous determination of a battery of genes involved in these processes and thus provides multiple candidates for in vivo verification and clinical testing. Because the array allows the determination of expression of multiple genes, it provides a powerful tool to ascertain coordinate gene expression, that is co-expression of two or more genes in a time and/or tissue-specific manner, both qualitatively and quantitatively. Thus, genes can be grouped on the basis of their expression per se and/or level of expression. This allows the classification of genes into functional categories even when the gene is completely uncharacterized with respect to function. Accordingly, if a first gene is expressed coordinately with a second gene whose function is known, a putative function can be assigned to that first gene. This first gene thus provides a new target for affecting that function in a diagnostic or therapeutic context. The larger the number of genes in an array, the greater is the probability that numerous known genes having the same or similar function will be expressed. In this case, the coordinate expression of one or more novel genes (with respect to function and/or structure) strongly allows discovery of genes in the same functional category as the known genes.

Accordingly, the array of the invention provides for "internal control" groups of genes whose functions are known and can thus be used to identify genes as being in the same functional category of the control group if they are coordinated expressed.

As an alternative to relying on such internal control groups, external control groups can be added to the array. The genes in such a group would have a known function. Genes coordinately expressed with these genes would thus be prima facie involved in the same function.

Therefore, the array provides a method not only for discovering novel genes having a specific function but also for assigning function to genes whose function is unknown or assigning to a known gene an additional function, previously unknown for that gene.

Accordingly, as disclosed and exemplified herein, previously characterized genes were grouped into new functional categories (i.e., previously the function was not known to be possessed by that gene). Furthermore, several uncharacterized genes could be functionally classified on the basis of coordinate expression with the "internal control group of genes". In a specific embodiment, disclosed and exemplified herein, genes related to programmed cell death in brain were selected. The array could, accordingly be used to select for genes related to other important biological processes, such as those disclosed herein. Nucleic acid from any tissue in any biological process is hybridized to nucleic acid sequences in an array. The expression pattern of genes in the array allows for their classification into functional groups based on specific expression patterns. Internal or external control genes (i.e. genes known to be expressed in the specific tissue/biological process) provide verification to classify other genes in the specific category.

Thus, the array is also useful for discovering genes involved in a biological process. This is specifically disclosed in the Examples, in which a subarray of the sequences described herein was developed. The subarray is composed of genes related to programmed cell death, especially in brain. Some of the genes were previously known to function in programmed cell death. Others were known per se, but not known to function in programmed cell death. Still others had not previously been characterized at the level of structure or expression.

The invention is thus directed to subarrays constructed by screening the array against various functional control groups, such as secretion/synaptic vesicle release, cell proliferation, secretion/synaptic vesicle release/cytoskeletal reorganization, stress response/hormone response, calcium signal transduction, apoptosis, and cytoskeleton/synapse cytoskeleton, or alternatively constructed, as exemplified herein, by screening against RNA (cDNA) from a specific biological sample, such as a programmed cell death model.

The subarray can be further divided based on related function or other parameters. In the present case, the designated NARC genes are of particular interest in programmed cell death. Therefore, in one embodiment the invention is directed to one or more of these genes, useful as disclosed herein. In one embodiment, they are useful as a control group for assigning function to other genes. Individually, they are subject to any of the various uses discussed herein.

Just as the array was useful for identifying programmed cell death genes, other relevant normal biological models include differentiation programs and disorders such as those disclosed herein.

The array is also useful for drug discovery. Candidate compounds can be used to screen cells and tissues in any of the biological contexts disclosed herein, such as pathology, development, differentiation, etc. Thus the expression of one or more genes in the array can be monitored by using the array to screen for RNA expression in a cell or tissue exposed to a candidate compound. Compounds can be selected on the basis of the overall effect on gene expression, not necessarily on the basis of its effect on a single gene. Thus, for example, where a compound is desired that affects a particular first gene or genes but has no effect on a second gene or genes, the array provides a way to globally monitor the effect on gene expression of a compound.

Alternatively, it may be desirable to target more than one gene, i.e. to modulate the expression of more than one gene. The array provides a way to discover compounds that will modulate a set of genes. All genes of the set can be upregulated or downregulated. Alternatively, some of the genes may be upregulated and others downregulated by the same compound. Moreover, compounds are discoverable that modulate desired genes to desired degrees.

In the context of drug discovery, functional subarrays of genes are especially useful. Thus, using the methods disclosed herein and those routinely available, groups of genes can be assembled based on their relationships to a specific biological function. The expression of this group of genes can be used for diagnostic purposes and to discover compounds relevant to the biological function. Thus, the subarray can provide the basis for discovering drugs relevant to treatment and diagnosis of disease, for example those disclosed herein.

In the present case, the group of genes whose expression is correlated with programmed cell death can be used to discover compounds that affect programmed cell death, and especially disorders in which programmed cell death is involved. These include but are not limited to those disclosed herein.

Apoptosis can be triggered by the addition of apoptosis-promoting ligands to a cell in culture or in vivo. In one embodiment of the invention, therefore, the arrays and subarrays described herein are useful to identify genes that respond to apoptosis-promoting ligands and conversely to identify ligands that act on genes involved in apoptosis. Apoptosis can also be triggered by decreasing or removing an apoptosis-inhibiting or survival-promoting ligand. Accordingly, apoptosis is triggered in view of the fact that the cell lacks a signal from a cell surface survival factor receptor. Ligands include, but are not limited to, FasL. Death-inhibiting ligands include, but are not limited to, IL-2. See Hetts et al. (1998) JAMA 279:300-307 (incorporated by reference in its entirety for teaching of ligands involved in active and passive apoptosis pathways.) Central in the pathway, and also serving as potential molecules for inducing (or releasing from inhibition) apoptosis pathways include FADD, caspases, human CED4 homolog (also called apoptotic protease activating factor 1), the Bcl-2 family of genes including, but not limited to, apoptosis promoting (for example, Bax and Bad) and apoptosis inhibiting (for example, Bcl-2 and Bcl-xl) molecules. See Hetts et al., above.

Multiple caspases upstream of caspase-3 can be inhibited by viral proteins such as cowpox, CrmA, and baculovirus, p35, synthetic tripeptides and tetrapeptides inhibit casepase-3 specifically (Hetts, above). Accordingly, the arrays and subarrays are useful for determining the modulation of gene expression in response to these agents.

The array is also useful for obtaining a set of human (or other animal) orthologs that can be used for drug discovery, treatment, diagnosis, and the other uses disclosed herein. The subarrays can be used to specifically create a corresponding human (or other animal) subarray that is relevant to a specific biological function. Accordingly, a method is provided for obtaining sets of genes from other organisms, which sets are correlated with, for example, disease or developmental disorders.

In a preferred embodiment of the invention, the arrays and subarrays disclosed herein are in a "microarray". The term "microarray" is intended to designate an array of nucleic acid sequences on a chip. This includes in situ synthesis of desired nucleic acid sequences directly on the chip material, or affixing previously chemically synthesized nucleic acid sequences or nucleic acid sequences produced by recombinant DNA methodology onto the chip material. In the case of recombinant DNA methodology, nucleic acids can include whole vectors containing desired inserts, such as phages and plasmids, the desired inserts removed from the vector as by, PCR cloning, cDNA synthesized from mRNA, mRNA modified to avoid degradation, and the like.

A series of state-of-the-art reviews of the technology for production of nucleic acid microarrays in various formats and examples of their utilization to address biological problems is provided in Nature Genetics, 21 Supplement, January 1999. These topics include molecular interactions on microarrays, expression profiling using cDNA microarrays, making and reading microarrays, high density synthetic oligonucleotide arrays, sequencing and mutation analysis using oligonucleotide microarrays, the use of microarrays in drug discovery and development, gene expression informatics, and use of arrays in population genetics. Various microarray substrates, methods for processing the substrates to affix the nucleic acids onto the substrates, processes for hybridization of the nucleic acid on the substrate to an external nucleic acid sample, methods for detection, and methods for analyzing expression data using specific algorithms have been widely disclosed in the art. References disclosing various microarray technologies are listed below.

Lashkari et al. (1997) "Yeast Microarrays for Genome Wide Parallel Genetic and Gene Expression Analysis", Proc. Natl. Acad. Sci. 94:13057-13062; Ramsay (1998) "DNA Chips: State-of-the-Art", Nature Biotechnology 16:40-44; Marshall et al. (1998) "DNA Chips: An Array of Possibilities", Nature Biotechnology 16:27-31; Wodicka et al. (1997) "Genome-Wide Expression Monitoring In *Saccharomyces Cerevisiae*", Nature Biotechnology 15:1359-1367; Southern et al. (1999) "Molecular Interactions On Microarrays", Nature Genetics 21(1):5-9; Duggan, et al. (1999) Nature Genetics 21(1):10-14; Cheung et al. (1999) "Making and Reading Microarrays", Nature Genetics 21(1):15-19; Lipshutz et al. (1999) "High Density Synthetic Oligonucleotide Arrays", Nature Genetics 21(1):20-24; Bowtell (1999) Nature Genetics 21:25-32; Brown et al. (1999) "Exploring the New World of the Genome with DNA Microarrays" Nature Genetics 21(1):33-37; Cole et al. (1999) "The Genetics of Cancer—A 3D Model" Nature Genetics 21(1):38-41; Hacia (1999) "Resequencing and Mutational Analysis Using Oligonucleotide Microarrays", Nature Genetics 21(1):42-47; Debouck et al. (1999) "DNA Microarrays in Drug Discovery and Development", Nature Genetics 21(1):48-50; Bassett, Jr. et al. (1999) "Gene Expression Informatics—It's All In Your Mine", Nature Genetics 21(1):51-55; Chakravarti (1999)

"Population Genetic—Making Sense Out of Sequence", Nature Genetics 21(1):56-60; Chee et al. (1996) "Accessing Genetic Information with High-Density DNA Arrays", Science 274:610-614; Lockhart et al. (1996) "Expression Monitoring by Hybridization to High-Density Oligonucleotide Arrays", Nature Biotechnology 14:1675-1680; Tamayo et al. (1999) "Interpreting Patterns of Gene Expression with Self-Organizing Maps: Methods and Application to Hematopoietic Differentiation", Proc. Natl. Acad. Sci. 96:2907-2912; Eisen et al. (1998) "Cluster Analysis and Display of Genome-Wide Expression Patterns", Proc. Natl. Acad. Sci. 95:14863-14868; Wen et al. (1998) "Large-Scale Temporal Gene Expression Mapping of Central Nervous System Development", Proc. Natl. Acad. Sci. 95:334-339; Ermolaeva et al. (1998) "Data Management and Analysis for Gene Expression Arrays", Nature Genetics 20:19-23; Wang et al. (1998) "A Strategy for Genome-Wide Gene Analysis: Integrated Procedure for Gene Identification", Proc. Natl. Acad. Sci. 95:11909-11914; U.S. Pat. No. 5,837,832; U.S. Pat. No. 5,861,242; WO 97/10363.

In the instant case, the microarray contains nucleic acid sequences on a Biodyne B filter. However, any medium, including those that are well-known and available to the person of ordinary skill in the art, to which nucleic acids can be affixed in a manner suitable to allow hybridization, are encompassed by the invention. This includes, but is not limited to, any of the membranes disclosed in the references above, which are incorporated herein for reference to those membranes, and other membranes that are commercially available, including but not limited to, nitrocellulose-1, supported nitrocellulose-1, and Biodyne A, which is a neutrally-charged nylon membrane suitable for Southern transfer and dot blotting procedures. (All are available from Life Technologies.)

SUMMARY

Programmed cell death (PCD) in rat cerebellar granule neurons (CGNs) induced by potassium (K+) withdrawal has been shown to depend on de novo RNA synthesis. The inventors characterized this transcriptional component of CGN programmed cell death using a custom-built brain-biased cDNA array representing over 7000 different rat genes. Consistent with carefully orchestrated mRNA regulation, the profiles of 234 differentially expressed genes segregated into distinct temporal groups (immediate early, early, middle, and late) encompassing genes involved in distinct physiological responses including cell-cell signaling, nuclear reorganization, apoptosis, and differentiation. A set of 64 genes, including 22 novel genes, were regulated by both K+ withdrawal and kainate treatment. Thus, by using array technology, they were able to broadly characterize physiological responses at the transcriptional level and identify novel genes induced by multiple models of programmed cell death.

BACKGROUND

In neurons, programmed cell death is an essential component of neuronal development (Jacobson et al. 1997; Pettmann and Henderson (1998); Pettmann and Henderson (1998) Neuron 20:633-747) and has been associated with many forms of neurodegeneration (Hetts (1998) Journal of the American Medical Association 279:300-307). In the cerebellum, granule cell development occurs postnatally. The final number of neurons represents the combined effects of additive processes such as cell division and subtractive processes such as target-related programmed cell death. Depolarization due to high concentrations (25 mM) of extracellular potassium (K+) promotes the survival of cerebellar granule neurons (CGNs) in vitro. CGNs maintained in serum containing medium with high K+ will undergo programmed cell death when switched to serum-free medium with low K+ (5 mM) (D'Mello et al. (1993) Proc. Natl. Acad. Sci. USA 90:10989-10993; Miller and Johnson (1996) Journal of Neueroscience 16:7487-7495). The resulting programmed cell death has a transcriptional component that can be blocked by inhibitors of new RNA synthesis (Galli et al. (1995) Journal of Neuroscience 15:1172-1179; and Schulz and Klockgether (1996) Journal of Neuroscience 16:4696-4706). Traditionally, the regulation of limited numbers of specific genes were characterized during CGN programmed cell death using Northern nucleic acid hybridization (e.g. PTZ-17, Roschier et al. (1998) Biochemical and Biophysical Research Communications 252:10-13), reverse transcription polymerase chain reaction (RT-PCR; e.g. c-jun, cyclophilin, cyclin D1, c-fos and caspase (Miller et al. (1997) Journal of Cell Biology 139:205-217), and in situ hybridization (e.g. RP-8; Owens et al. (1995) Developmental Brain Research 86:35-47).

High-density cDNA arrays have been successfully used to characterize genome-wide mRNA expression in yeast (Lashkari et al. (1997) Proc. Natl. Acad. Sci. USA 94:13057-13062; Wodicka et al. (1997) Nature Biotechnology 15:1997). In higher eukaryotes, the strategy has been to array as many sequences as possible from known genes, from expressed sequence tags (ESTs), or from uncharacterized cDNA clones from a library (Bowtell (1999) Nature Genetics 21:25-32; Duggan et al. (1999) Nature Genetics 21:10-14; Marshall and Hodgson (1998) Nature Biotechnology 16:27-31; and Ramsay (1998) Nature Biotechnology 16:40-44). Global RNA regulation during cellular processes including cell-cycle regulation (Cho et al. (1998) Molecular Cell 2:65-73, and Spellman et al. (1998) Mol. Biol. Cell. 95:14863-14868), fibroblast growth control (Iyer et al. (1999) Science 283:83-87), metabolic responses to growth medium (Derisi and Brown (1997) Science 278: 680-686), and germ cell development (Chu et al. (1998) Science 282:699-705) have been temporally monitored using arrays. The program of gene expression delineated in these studies demonstrated a correlation between common function and coordinate expression, and also provided a comprehensive, dynamic picture of the processes involved (Brown and Botstein (1999) Nature Genetics 21:33-37). For the cellular process of programmed cell death, a DNA chip has been used to identify twelve known genes as differentially expressed between two conditions, etoposide-treated and untreated cells (Wang et al. (1999) FEBS Letters 445:269-273).

A genome-wide approach for the comprehensive characterization of the transcriptional component of rat CGN programmed cell death and for identification of novel neuronal apoptosis genes requires an array consisting of both known and novel rat cDNAs. The inventors constructed a brain-biased and programmed cell death-enriched clone set by arraying ~7300 consolidated ESTs from two cDNA libraries cloned from rat frontal cortex and differentiated PC12 cells deprived of nerve growth factor (NGF), and >300 genes that are known markers for the central nervous system and/or programmed cell death. They reproducibly and simultaneously monitored the expression of the genes at 1, 3, 6, 12, and 24 hours after K+ withdrawal. They then categorized the regulated genes by time course expression pattern to identify cellular processes mobilized by CGN programmed cell death at the RNA level. In particular they focused on the expression profiles of many known pro- and anti-apoptotic regulatory proteins, including transcription factors, Bcl-2 family members, caspases, cyclins, heat shock proteins (HSPs), inhibitors of apoptosis (IAPs), growth factors and receptors, other signal transduction molecules, p53, superoxide dismutases (SODs), and other stress response genes. Finally, they compared the time courses of regulated genes induced by K+ withdrawal in the presence or absence of serum to those induced by glutamate toxicity. Thus, they identified a restricted set of relevant genes regulated by multiple models of programmed cell death in CGNs.

Results

Construction and Validation of a Brain-Biased cDNA Microarray

In order to characterize the transcriptional component of neuronal apoptosis in rat cerebellar granule neurons, the inventors constructed a cDNA array, called Smart Chip™ I, that contains primarily rat brain genes. Two cDNA libraries were cloned from rat frontal cortex and nerve growth factor-deprived rat PC12 cells to enrich for cDNAs expressed in the central nervous system and in one in vitro model of neuronal apoptosis. Expressed sequence tags (ESTs) from the 5'-end were identified for 8,304 clones in the cortical library and 5,680 in the PC12 library. These 13,984 ESTs were condensed into 7,399 unique sequence clusters by using the Basic Local Alignment Search Tool (BLAST) sequence comparison analysis (Altschul et al. 1990) to identify ESTs with overlapping sequence. One representative clone was chosen from each of 7,296 of the unique sequence clusters and prepared for PCR amplification using a robotic sample processor. In addition to the ESTs, PCR templates were prepared for 289 known DNA sequences, including negative controls, genes with known function in the CNS and/or during programmed cell death, and genes previously identified as regulated by CGN programmed cell death using differential display (data not shown). To check the fidelity of the set of array elements, a robotic sample processor was used to randomly choose 212 clones for sequencing. Ten clones produced poor sequence. The remaining 202 matched their seed sequence (data not shown), implicating 100% fidelity in sample tracking.

A sample volume of 20 nl from each of the 7584 PCR products was arrayed onto nylon filters at a density of ~64/cm2 using a pin robot. The arrayed DNA elements were denatured and covalently attached to the nylon filters for use in reverse Northern nucleic acid hybridization experiments. In a typical experiment, "radiolabeled RNA", 1 μg polyA RNA radiolabeled by 33P-dCTP incorporation during cDNA synthesis, was hybridized to triplicate arrays following RNA hydrolysis. Subsequently, the filters were washed and exposed to phosphoimage screens. Gene expression was quantified for each array element by digitizing the phosphoimage-captured hybridization signal intensity. An illustration that the coefficient of variation between triplicate hybridizations averaged less than 0.2 for genes whose intensities were above a threshold of 30-40 units is described herein. From control experiments when in vitro transcribed RNAs were deliberately spiked into samples, this threshold amounted to a copy number of less than 1 in 100,000 (data not shown).

Tissue Distribution of Brain-biased Smart Chip ESTs

To characterize the brain-biased cDNA array and possibly identify brain-specific genes, radiolabeled RNA from ten different normal rat tissues was hybridized to Smart Chip. Compared to heart, kidney, liver, lung, pancreas, skeletal muscle, smooth muscle, spleen, and testes, radiolabeled rat brain RNA produced more hybridization signal intensity against most of the brain-biased array elements. After data normalization and averaging between replicates, the threshold of detection was determined for each experiment and the number of genes detected for each tissue was tabulated. Most (6127 out of 7296) but not all of the ESTs were detected in at least one of the tissues profiled. The number of genes detected in brain was the highest. 582 genes appeared to be brain-specific, as defined by detection above threshold for brain but below threshold for any of the other nine tissues.

The Physiology of CGN KCl/Serum-withdrawal as Characterized by Transcription Profiling on Smart Chip Using the brain-biased, programmed cell death nucleic acid-enriched Smart Chip, global mRNA expression was profiled throughout a time course of KCl/serum-withdrawal-induced cell death in primary cultures of CGNs. The transcription-dependent CGN programmed cell death was coordinated, resulting in less than 30% survival at 24 hours post-withdrawal as quantified by cell counting (data not shown). RNA samples, designated "treated", were isolated at 1, 3, 6, 12, and 24 hours after switching post-natal day eight CGNs from medium containing 5% serum and 25 mM KCl to serum-free medium with mM KCl. For controls, the 5% serum/25 mM KCl medium was replaced, and "sham" RNA at 1, 3, 6, 12, and 24 hours was isolated.

Since the average coefficient of variation for gene expression intensities between triplicate hybridizations was less than 0.2, genes regulated at least three-fold during the time course (790 out of 6818 detected; data not shown) were further addressed. Using hierarchical clustering algorithms (see Experimental Procedures), the regulated genes were ordered based on their gene expression pattern across the ten experimental points (five time points, sham and treated). The hierarchy of relatedness between gene expression profiles are disclosed. The first major branch point segregated those genes regulated by sham treatment (first five columns), and those regulated by KCl/serum-withdrawal treatment only (last five columns). A majority of genes (556) were regulated by sham treatment. These genes included trk A, PSD-95, SV 2A, and VAMP 1, and were most likely induced by serum-add-back in the sham since the medium was exchanged at t=0 with unconditioned medium.

The expression pattern of 234 programmed cell death-induced genes that were regulated by KCl/serum-withdrawal only, and were not regulated by serum-add-back in the sham experiments ar described herein. Their coefficient of variation in expression level throughout the five serum-add-back experiments was less than 20%. Since the serum-add-back experiments were non-discriminating for these genes, the serum-add-back data were averaged to generate a single control data set for clustering with the KCl/serum withdrawal time course. Four apparent temporal regulation classes were designated immediate early (peaking at 1 hour followed by rapid decay), early (peaking at 3-6 hours), middle (peaking at 6-12 hours), and late (up-regulated at 24 hours). Almost all of the immediate early genes encoded proteins with known roles in regulating secretion and synaptic vesicle release including synaptotagmin, synaphin, NSG-1, calcium calmodulin-dependent kinase II; synapsin, complexin, LDL receptor, and fodrin. Histones 1, 2A, and 3 fell in the early class. Middle genes comprised several known genes induced by programmed cell death or stress, including caspase 3, the mammalian oxy R homolog, cytochrome c oxidase and protein phosphatase Wip-1. Functions encoded for by late genes could be effectors of survival mechanisms including inhibitory neurotransmission (GAD, GABA-A receptor, GABA transporter), cell adhesion (nexin, basement membrane protein 40, phosphacan, rat GRASP), down-regulation of excitatory neurotransmission (glutamate transporter, sodium-dependent glutamate/aspartate transporter), leukotriene metabolism (dithiolethione-induced NADP-dependent leukotriene B4 12-hydroxydegydrogenase, leukotriene A-4 hydrolase), protein stabilization (cysteine proteinase inhibitor cystatin C, N-alpha-acetyl transferase, CaBP2, elongation factor 1-gamma, APG-1), and ionic balance and cell volume (SLC12A integral membrane protein transporter). Based on four distinct waves of gene expression, the major transcriptional responses observed for KCl/serum-withdrawal included initial up-regulation of synaptic vesicle release/recycling, then, of histone biosynthesis, followed by various constituents of programmed cell death regulation and stress-response signaling, and finally, of multiple survival mechanisms. The apparent changes in transcription most likely also reflect changes in the relative cell populations, since late mRNAs may be markers of neurons and non-neuronal cells which have survived KCl/serum-withdrawal at 24 hours. Another contributing factor may be the presence of two populations of dying neurons that respond with different kinetics to serum versus KCl withdrawal, as has been described by other groups.

Neuronal Apoptosis Regulated Candidates (NARCs) Regulated by Multiple Models of Programmed Cell Death 112 novel ESTs were significantly regulated by KCl/serum-withdrawal in rat CGNs (data not shown). Some exhibited similar expression profiles throughout KCl/serum-withdrawal and serum-add-back to genes with known function during programmed cell death, such as caspase 3. The temporally-coupled expression of these novel genes may reflect related functionality with caspase 3, since they probably share common RNA regulatory elements, including those regulating initiation, elongation, processing, and/or stability. Apparent coordinate transcriptional up-regulation of synaptic vesicle release/recycling possibly reflects a physiological response to near cessation of synaptic transmission that may or may not contribute to the programmed cell death pathway. To help further distinguish genes that are specifically regulated in response to programmed cell death, CGN programmed cell death induced by glutamate (excitatory neurotransmitter) toxicity was studied. In addition, the effect of KCl-withdrawal alone on gene expression was examined. This was done under defined medium conditions to minimize the effect of serum on the sham and treated samples.

Rat CGNs from post-natal day seven pups were isolated as before and plated into basal medium Eagle containing "high", 10% dialysed fetal bovine serum, and "high", 25 mM KCl. After two days in culture, the medium was replaced with neurobasal medium supplemented with "low", 0.5% serum, and high KCl. To initiate KCl-withdrawal on day eight, the KCl concentration was switched to 5 mM for the treated samples. The same low serum, high KCl, neurobasal medium was replaced in the controls to minimize gene induction by high serum. For the glutamate toxicity experiment, the cells were treated for 30 min in sodium-free Locke's medium with or without 100 μM kainate for treated samples and controls, respectively.

After isolation from treated and control samples at 1, 3, 6, and 12 hours after KCl-withdrawal and 2, 4, 6, 12 hours after kainate treatment, mRNA was subjected to expression profiling analysis on Smart Chip I. An illustration of the changes in gene expression that occur over time when CGNs are induced to undergo programmed cell death by KCl/serum-withdrawal, KCl-withdrawal alone, or kainate treatment is disclosed. In the scatter plots, due to differential expression, large numbers of regulated genes migrated away from a line of slope one when withdrawn (W) or treated (T) samples were compared to control (C). The sham treated cells for the KCl/serum-withdrawal clearly responded to basal medium serum-add-back, whereas shams for KCl-withdrawal alone and kainate treatment did not respond to conditioned neurobasal medium add-back. Profiling across the mRNA levels of thousands of genes provided a clear index of changes in overall cell physiology.

In general, apparent changes in gene expression were less robust in the cells cultured on neurobasal medium. The number of genes detected above threshold was similar for all three paradigms, 6634, 7017, and 6818, respectively, for KCl-withdrawal, kainate treatment, and KCl/serum withdrawal (data not shown). Yet the number of genes regulated by at least three-fold during KCl-withdrawal and kainate treatment was only 156 and 167, respectively (data not shown), compared to the 790 discussed above for KCl/serum withdrawal.

A hierarchical clustering algorithm was used to order the regulated genes based on their gene expression pattern across all CGN programmed cell death paradigms investigated. Twenty-six individual profiling experiments in duplicate or triplicate were performed across the 7584 rat genes on Smart Chip I using mRNA isolated from 5 serum-add-back time points, 5 KCl/serum-withdrawal time points, 4 time points each for sham and KCl-withdrawal, and 4 time points each for sham and kainate treatment.

The expression clusters generated by one hierarchical clustering algorithm are described herein. The inset shows a specific group of genes having similar expression patterns. This group includes genes known to be regulated in programmed cell death, for example caspase 3 and Wip 1, as well as other nucleic acid sequences on the array not previously known to be regulated. Those sequences meeting specific criteria were designated "neuronal apoptosis regulated candidate" (NARC). Criteria for designating such genes were based on specific expression criteria. Nucleic acid sequences having an expression pattern similar to genes known to be involved in apoptosis were designated as NARC sequences. The sequences of the rat neuronal apoptosis regulated candidates NARC SC1 (SEQ ID NO:18), NARC 10A (SEQ ID NO:21), NARC 1 (SEQ ID NO:22), NARC 12 (SEQ ID NO:23), NARC 13 (SEQ ID NO:24), NARC17 (SEQ ID NO:25), NARC 25 (SEQ ID NO:26), NARC 3 (SEQ ID NO:27), NARC 4 (SEQ ID NO:28), NARC 7 (SEQ ID NO:29 and 30), NARC 8 (SEQ ID NO:31), NARC 11 (SEQ ID NO:35 and 36), NARC 14A (SEQ ID NO:37), NARC 15 (SEQ ID NO:38), NARC 16 (SEQ ID NO:39), NARC 19 (SEQ ID NO:40), NARC 20 (SEQ ID NO:41), NARC 26 (SEQ ID NO:42), NARC 27 (SEQ ID NO:43), NARC 28 (SEQ ID NO:44), NARC 30 (SEQ ID NO:45), NARC 5 (SEQ ID NO:46), NARC 6 (SEQ ID NO:47), and NARC 9 (SEQ ID NO:48); and the human neuronal apoptosis regulated candidate homologs NARC 10C (SEQ ID NO:19), NARC 8B (SEQ ID NO:20), NARC 9 (SEQ ID NO:32), NARC2A (SEQ ID NO:33), NARC 16B (SEQ ID NO:34), NARC 1C (SEQ ID NO:49), NARC 1A (SEQ ID NO:50), and NARC 25 (SEQ ID NO:51) are set forth in the Sequence Listing.

Gene Expression Validation by RT-PCR

Although the reproducibility in transcription profiling experiments was quite high (average CV<0.2), the gene expression regulation of known and novel genes was validated by semi-quantitative RT-PCR. The rat CGN model system was used to independently validate the expression of several NARC genes that had shown expression (when hybridized with sequences on the chip) related to programmed cell death. Reverse transcriptase-assisted PCR was performed to assess expression of NARC1-7, 9, 12, 13, 15, and 16. Experimental samples received KCl withdrawal treatment. Control samples show cells receiving no treatment. The PCR reactions contained 10, 5, 2.5, 1.3, and 0.7 ng of total RNA each. The RT-PCR protocol is disclosed in the exemplary material herein. NARC 1, 2, 4, 5, 7, 9, 12, 13, 15, and 16 all showed significant increases in expression levels within 3-6 hours following KCl withdrawal.

NARC1 and NARC2 Regulation in vivo During Cerebellar Development

Two novel neuronal apoptosis regulated candidates, NARC1 and NARC2, were validated by in situ hybridization and shown to be coordinately up-regulated with caspase 3 during postnatal development when increased apoptosis is associated with synapse consolidation in the cerebellum (not shown).

Experimental Procedures

BLAST Sequence Comparison Analysis

ESTs determined for the 5'-end of cDNA clones picked from two cDNA libraries, rat frontal cortex (8,304 clones) and NGF-deprived differentiated PC12 cells (5,680 clones), ranged from 100-1000 nt in sequence length and averaged 500 nt (data not shown). Sequence comparisons were done using BLAST (Altschul et al. 1990). Contiguous matches defined a sequence cluster. Large clusters were checked by hand to eliminate apparent chimeras. From 13,984 sequences inputted, the analysis identified 5,779 singletons and 1,620 larger clusters (data not shown). The 5'-most clone was selected from the larger clusters. Because two 96-well microtiter plates of clones were missing, a total of 7,296 out of the 7,399 identified were selected for Smart Chip™ I.

cDNA Microarray Construction

Using a Genesis RSP 150 robotic sample processor (Tecan AG, Switzerland), bacterial cultures of individual EST clones from the two libraries were consolidated from 13,792 clones spanning 144 96-well microtiter plates to 7296 Smart Chip I clones spanning 76 plates. To prepare templates for array elements, oligonucleotide primers specific for vector sequences up- and downstream of the cloning site were used to amplify the cDNA insert by PCR. Following ethanol precipitation and concentration (to 1-10 mg/ml), the array element templates were resuspended in 3×SSC (1×SSC: 150 mM sodium chloride, 15 mM sodium citrate, pH 7.0). A sample volume of 20 nl from each template was arrayed onto nylon filters (Biodyne B, Gibco BRL Life Technologies, Gaithersburg, Md.) at a density of ~64/cm2 using a 96-well format pin robot (THOR). After the filters were dry, the arrayed DNA was denatured in 0.4 M sodium hydroxide, neutralized in 0.1 M Tris-HCl, pH 7.5, rinsed in 2×SSC, and dried to completion.

Array Hybridization

Rat poly A+ RNA was purchased from Clontech (Palo Alto, Calif.) for the organ recital or was isolated as total RNA from cultured CGNs using RNA STAT-60™ (Tel-Test, Inc., Friendswood, Tex.) and then prepared using Oligotex™ (Qiagen, Inc., Chatsworth, Calif.). Re-annealed 1 μg mRNA and 1 μg oligo(dT)30 was incubated at 50° C. for 30 min with SuperScript™ II as recommended by Gibco in the presence of 0.5 mM each deoxynucleotide dATP, dGTP, and dTTP, and 100 μCi α33P-dCTP (2000-4000 Ci/mmol; NEN™ M Life Science Products, Boston, Mass.). After purification over Chroma Spin™+TE-30 columns (Clontech), the labeled cDNA was annealed with 10 μg poly(dA)>200 and 10 μg rat Cot-1 DNA (prepared as described in Britten et al. (1974) Methods in Enzymology 29:263-418). At 2×106 cpm/ml, the annealed cDNA mixture was added to array filters in pre-annealing solution containing 100 mg/ml sheared salmon sperm DNA in 7% SDS (sodium dodecyl sulfate), 0.25 M sodium phosphate, 1 mM ethylenediaminetetraacetic acid, and 10% formamide. Following over night hybridization at 65° C. in a rotisserie-style incubator (Robbins Scientific, Sunnyvale, Calif.), the array filters were washed twice for 15 min at 22° C. in 2×SSC, 1% SDS, twice for 30 min at 65° C. in 0.2×SSC, 0.5% SDS, and twice for 15 min at 22° C. in 2×SSC. The array filters were then dried and exposed to phosphoimage screens for 48 h. The radioactive hybridization signals were captured with a Fuji BAS 2500 phosphoimager and quantified using Array Visions software (Imaging Research Inc., Canada). Array hybridizations for the organ recital, the CGN KCl only-withdrawal, and the CGN kainate treatment experiments were performed in triplicate; for the CGN KCl/serum-withdrawal, they were performed in duplicate.

Transcription Profiling Data Analysis

For replicate array hybridizations, the distribution of signal intensities across all rat genes was normalized to a median of 100. Replicate measurements were averaged and a coefficient of variation (CV; standard deviation/mean for triplicates or the absolute value of the difference/mean for duplicates) was determined for each gene. The detection threshold was chosen for each hybridization experiment by graphing the moving average (with a window of 200) for CV versus mean gene expression intensity. The threshold was defined as the intensity at which lower intensities exhibited an average CV that was greater than 0.3. For most experiments, this threshold ranged from 10 to 40, and the number of genes detected above threshold ranged from 70% to 95%.

CGN Cell Culture

CGNs were prepared from seven day old rat pups as previously described (Johnson and Miller (1996) Journal of Neuroscience 16:74877-7495). Briefly, cerebella were isolated, and meningeal layers and blood vessels were removed under a dissecting scope. Dissociated cells were plated at a density of 2.3×105 cells/cm2 in basal medium Eagle (BME; Gibco) supplemented with 25 mM KCl, 10% dialyzed fetal bovine serum (Summit Biotechnology lot #04D35, Ft. Collins, Colo.), 100 U/ml penicillin, and 100 μg/ml streptomycin. Aphidicolin (Sigma, St. Louis, Mo.) was added to the cultures at 3.3 μg/ml, 24 hours after initial plating to reduce the number of non-neuronal cells to less than 1-5%.

For KCl/serum-withdrawal experiments, after seven days in culture, the treated cells were switched to 5 mM KCl, BME, no serum, while the shams received a medium replacement. By 24 hours post-withdrawal, less than 30% of the cells were surviving as assayed by Hoechts cell counts (data not shown). This apparent cell death could be rescued by actinomycin D at 2 μg/ml (data not shown).

For the KCl-withdrawal alone and kainate treatment experiments, on day two in culture, the medium was replaced with neurobasal medium (Gibco) supplemented with 25 mM KCl, 0.5% dialyzed fetal bovine serum, B27 supplement (Gibco), 0.5 mM L-glutamine (Gibco), 0.1 mg/ml AlbuMAX I (Gibco), 100 U/ml penicillin, 100 μg/ml streptomycin, and 3.3 μg/ml aphidicolin. On day seven, KCl-withdrawal was initiated by replacing the medium with 5 mM KCl while the shams received 25 mM. By 24 hours post-withdrawal, 40% of the cells were surviving as assayed by Hoechts cell counts (data not shown). As previously described, glutamate toxicity was induced by replacing the medium for 30 min with 5 mM KCl, 100 μM kainic acid (Sigma) in sodium free Locke's buffer, while the shams received no kainic acid (Coyle et al. (1996) Neuroscience 74:675-683). After 30 min, the supplemented neurobasal medium was replaced. By 12 hours post-withdrawal, 30% of the cells were surviving as assayed by Hoechts cell counts (data not shown). The KCl-withdrawal induced cell death was rescued by actinomycin D, whereas the kainate-induced was not.

Expression Data Clustering Algorithms

After normalization and averaging of the KCl/serum-withdrawal data, 790 genes passed the following criteria over the 10 time points (5 treated, 5 sham) for input into heirarchical clustering analysis: 1. detection, maximum intensity greater than 30; 2. noise filter, the difference between maximum and minimum intensity greater than 30; and 3. regulation, fold induction between maximum and minimum intensity of at least 3 (data not shown). Hierarchical clusters were ordered based on Euclidian distances. 234 out of 790 genes that passed the significance filter described above were not regulated in the controls based on CV less than 0.2 for all five control time points (data not shown).

RT-PCR

Oligonucleotide primer sequences specific for each EST validated by RT-PCR were selected from quality sequence regions and designed to obtain a melting temperature of 55-60° C. as predicted by PrimerSelect software (DNASTAR, Inc., Madison, Wis.) based on DNA stability measurements by (Breslauer et al. (1986) Proc. Natl. Acad. Sci. USA 83:3746-3750). The Stratagene Opti-Prime™ Kit (La Jolla, Calif.) was used to determine optimal RT-PCR amplification conditions for each primer pair. RT-PCR reactions on 2-fold serially diluted CGN programmed cell death cDNA were set up using the Genesis RSP 150 robotic sample processor and incorporating the optimal buffer conditions for each primer pair. Every robot run included primers specific for housekeeping genes to control for day to day differences in cDNA template dilutions. The number of cycles was adjusted to obtain a linear range of amplification by comparing the amount of product made from the serially diluted templates as assessed by agarose gel electrophoresis.

Preparation of Array on Nylon

Procedure for Generating Labeled First Strand cDNA Using Superscript II Reverse Transcriptase 10 mL (100 mCi) 33P α-dCTP was dried down by SpeedVac.

In a separate tube, the following components were mixed:

1.0 ug Poly A+ RNA or 10 ug Total RNA
1 uL 1 ug/uL oligo-dT(30)
x uL DEPC—H2O, to 10 uL The above sample was heated at 70° C. for 4 minutes and then placed on ice.

3. 8 uL from the oligo/RNA mixture (#2) was removed and used to resuspend the dried 3P3. The following components were added to the reaction:

4 uL 5× First Strand Buffer (comes with Superscript II RT)
2 uL 100 mM DTT
1 uL 10 mM dAGT-TPs
1 uL 0.1 mM cold dCTP
1 uL Rnase Inhibitor
1 uL Superscript II RT The reaction was incubated for 30 minutes at 50° C.

4. After incubation, 2 uL 0.5 M NaOH, and 2 uL 10 mM EDTA were added. The reaction was heated at 65° C., for 10 minutes to degrade RNA template.

The volume was brought to 50 uL (i.e., add 26 uL H2O).

5. One Choma-Spin+TE 30 column (Clontech, #K1321) was prepared for every probe made.

Air bubbles were removed from the column.

b. The break-away end of the column was removed and the column placed in an empty 2 mL tube and spun for 5 minutes at 700 g (in Eppendorf 5415C "3.5").

c. The column was removed and the flow-through discarded.

The column was placed in clean tube. The probe was added slowly to the center of the column bed without disturbing the matrix so that the liquid did not touch the side of the column and flow down the edge of the column wall.

The probe was eluted by spinning the column as above.

Hybridization

1. The hybridization chamber was preheated to 65° C.

2. 10 mL of 10% Formamide Church Buffer was added. This was placed in the hybridization chamber for around 15 minutes.

3. Sheared salmon sperm DNA was denatured at 95° C. for 5 minutes, placed on ice, and then added to the hybridization mixture at a final concentration of 100 ug/mL. Prehybridization was for 1.5 hours.

4. The amount of probe was calculated necessary to achieve 2×106 cpm/mL for 10 mL.

The Cot Annealing Reactions (per bottle) were as follows:

Rat probe with Rat Filters:
10 ug Poly dA (>200 nt)
10 ug Rat Cot 10 DNA
25 uL 20×SSC
probe+water to 100 uL Mouse probe with Rat Filters:
10 ug Poly dA (>200 nt)
10 ug Mouse Cot 1 DNA
25 uL 20×SSC
probe+water to 100 uL
Also added 5 ug Rat Cot 10 DNA to the prehybridization.

Human probe with Human Filters:
10 ug Poly dA (>200 nt)
10 ug Human Cot 1 DNA
25 uL 20×SSC
probe+water to 100 uL The probe was heated to 95° C., and then probe was allowed to preanneal at 65° C., for 1.5 hours.

6. The probe was added to prehybridizing filters (directly to the solution and not onto the filters) and hybridization was for approximately 20 hours.

Washing

1. Probe was removed.

2. Three quick washes were performed with preheated 2×SSC/1% SDS, 65° C. (washes could be done in roller bottles).

3. Two washes were performed for 15 minutes each with preheated high stringency wash buffer:

0.5×SSC, 0.1% SDS for cross species washes
0.5×SSC, 0.1% SDS for normal washes
0.1×SSC, 0.1% SDS for very high stringency washes 4. After the high stringency washes, the filters were rinsed in a large square petri dish in 2×SSC, no SDS. For experiments in which many filters are used, the 2×SSC is frequently changed so there is no residual SDS left on the filters.

5. The filters were removed from the 2×SSC and placed on Whatman filter paper. Filters were baked at 85° C. for 1 hour or longer. Screens were protected against any moisture. Filters were placed on a blank phosphorimager screen. No yellowed phosphoimager screens were used since they may not respond to exposure linearly. Screens had been erased on a light box for no less than 20 minutes.

6. Blots were exposed to the screen at least 48 hours or as necessary.

Scanning Filters on Fuji Phosphorimager

1. Gradation 16 bit, Resolution 50 m, Dynamic Range S4000, select Read and Launch Image Gauge. Image was saved on the hard drive.

APPENDIX I

10% Formamide-Church Buffer:

59.6 mL water
70 mL 20% SDS
50 mL 2M NaPO4 pH 7.2
20 mL Ultrapure Formamide
0.4 mL 0.5M EDTA pH 8.0

The above components were added to water, mixed, and filtered through a 0.2 um filter.

RT-PCR Protocol

1. For one PCR reaction mix, the following components were used:

| | |
|---|---|
| 28 ul | 5X First Strand Buffer |
| 14 ul | 0.1M DTT |
| 4 ul | dNTPs (20 mM) |
| 7 ul | Rnase Inhibitor |
| 7 ul | Superscript II |

This buffer can be stored at −80° C. for 3 months.

2. Total RNA was reversed transcribed as follows:

| | |
|---|---|
| 1.4 ug | Total RNA (DNAsed) |
| 14 ul | Random Primers (50 ng/ul--Gibco) |

Water was added to 60 ul. The mixture was incubated at 70° C. for 10 minutes and then placed on ice for 2 minutes. 60 ul of the RT Reaction Mix was added. Incubation was at room temperature for 10 minutes, then 50° C. for 30 minutes, then 90° C. for 10 minutes. The sample was diluted with 480 ul water to result in long per 5 ul.

3. The PCR reaction was performed with the following ingredients:

| | |
|---|---|
| 5 ul | 4x PCR Buffer |
| 5 ul | cDNA (at 10 ng/5 ul) |
| 5 ul | 1 uM Primer Pair |
| 5 ul | Enzyme Cocktail (0.2 ul Hot Start Taq, 1 ul 2 mM dNTPs, 3.8 ul water |

Cycling was as follows:

| | |
|---|---|
| 95° C. | 15 minutes |
| 94° C. | 30 seconds |
| 52° C. | 30 seconds |
| 72° C. | 1 minute |
| Cycle | 26-30 times |
| 72° C. | 10 minutes |
| 4° C. | Hold |

Cerebellar granule cell isolation was performed according to the method disclosed in Johnson et al. (1996) J. Neurosci. 16:74877-7495.

The induction of apoptosis in neurites induced by kainate is described in Neurosci. 75:675-683 (1996). The procedure shown in this reference was followed.

The following parameters were checked:

(1) Cerebellum granule neuron viability following potassium and serum withdrawal at time points corresponding to PCR-based methods for differential gene expression (Hoechst stain).

(2) Effects of 2 ug/ml actinomycin D on potassium and serum withdrawal at 24 hours on cerebellar granule neurons; viability by Hoeschst stained cell counts.

(3) Time course of kainate-induced cell death for parallel analysis of PCR-based method for differential gene expression of CGN Poly A mRNA.

(4) Time course of kainate-induced (30 minute exposure) apoptosis in CGNs; analysis by Hoechst cell counts.

(5) Time course of potassium withdrawal apoptosis in CGNs in defined media for PCR-based method for differential gene expression of analysis by Hoechst counts.

While this invention has been particularly shown and described with reference to preferred embodiments thereof, it will be understood by those skilled in the art that various changes in form and details may be made therein without departing from the spirit and scope of the invention as defined by the appended claims.

V. METHODS AND COMPOSITIONS FOR THE DIAGNOSIS AND TREATMENT OF CELLULAR PROLIFERATION DISORDERS USING 86604

Background of the Invention

The present invention provides methods and compositions for the diagnosis and treatment of cellular proliferation disorders, e.g., cancer, including, but not limited to colon, ovarian, and lung cancer. The present invention is based, at least in part, on the discovery that 86604, an aminotransferase molecule, is differentially expressed in tumor cells, e.g., colon, lung, and ovary tumor cells, as compared to normal cells, e.g., normal colon, lung, and ovary cells, and thus is useful in the diagnosis and treatment of cellular proliferation disorders, e.g., cancer, including, but not limited to, colon, lung, and ovary cancer. Human 86604 was also found to be upregulated in colon polyps and carcinomas as compared to normal colon tissue. The present invention is also based, at least in part, on the discovery that 86604 is differentially expressed in cell based models of cellular proliferation. In a cell based model wherein the activated k-ras allele in human colon cancer cell line HCT-116 has been disrupted, 86604 is down regulated, which indicates that expression of 86604 is decreased in cells which have slowed proliferation in vitro and in vivo and reduced expression of the c-myc oncogene. 86604 is also differentially expressed in cells which have been synchronized in the G2 phase, indicating that 86604 is expressed in proliferating cells.

Without intending to be limited by mechanism, it is believed that the 86604 molecules, by participating in amino acid transport and degradation and cellular metabolism, modulate cellular proliferation and are, therefore, useful as targets and therapeutic agents for the modulation of cellular proliferation, and the treatment, diagnosis, or prognosis of cellular proliferation disorders, such as cancer.

Accordingly, the present invention provides methods for the diagnosis and treatment of cellular proliferation disorders, e.g., cancer, including, but not limited to, ovarian, lung, and colon cancer.

In one aspect, the invention provides methods for identifying a compound capable of treating a cellular proliferation disorder, e.g., cancer, including, but not limited to colon, ovarian, and lung cancer. The method includes assaying the ability of the compound to modulate 86604 nucleic acid expression or 86604 polypeptide activity. In one embodiment, the ability of the compound to modulate nucleic acid expression or 86604 polypeptide activity is determined by detecting modulation of cellular proliferation, e.g., proliferation of a tumor cell. In another embodiment, the ability of the compound to modulate nucleic acid expression or 86604 polypeptide activity is determined by detecting modulation of amino acid degradation or amino acid transport in a cell, e.g., a tumor cell.

In another aspect, the invention provides methods for identifying a compound capable of modulating a 86604 activity, e.g., cellular proliferation, differentiation, cellular metabolism, or amino acid transport or degradation. The method includes contacting a cell expressing a 86604 nucleic acid or polypeptide (e.g., a colon tumor cell, a lung tumor cell, or an ovarian tumor cell) with a test compound and assaying the ability of the test compound to modulate 86604 nucleic acid expression or 86604 polypeptide activity.

Another aspect of the invention provides a method for modulating a cellular growth, differentiation or proliferation process, amino acid transport or amino acid degradation. The method includes contacting a cell with an 86604 modulator, for example, an anti-86604 antibody, an 86604 polypeptide comprising the amino acid sequence of SEQ ID NO:52 or a fragment thereof, an 86604 polypeptide comprising an amino acid sequence which is at least 90 percent identical to the amino acid sequence of SEQ ID NO:52, an isolated naturally occurring allelic variant of a polypeptide consisting of the amino acid sequence of SEQ ID NO:52, a small molecule, an antisense 86604 nucleic acid molecule, a nucleic acid molecule of SEQ ID NO:53 or a fragment thereof, or a ribozyme.

In yet another aspect, the invention features a method for treating a subject having a cellular proliferation disorder, e.g., a cellular proliferation disorder, characterized by aberrant 86604 polypeptide activity or aberrant 86604 nucleic acid expression such as cancer. In a preferred embodiment, the cellular proliferation disorder is colon, lung, or ovarian cancer. The method includes administering to the subject a therapeutically effective amount of an 86604 modulator, e.g., in a pharmaceutically acceptable formulation or by using a gene therapy vector. Embodiments of this aspect of the invention include the 86604 modulator being a small molecule, an anti-86604 antibody, a 86604 polypeptide comprising the amino acid sequence of SEQ ID NO:52 or a fragment thereof, a 86604 polypeptide comprising an amino acid sequence which is at least 90 percent identical to the amino acid sequence of SEQ ID NO:52, an isolated naturally occurring allelic variant of a polypeptide consisting of the amino acid sequence of SEQ ID NO:52, an antisense 86604 nucleic acid molecule, a nucleic acid molecule of SEQ ID NO:53 or a fragment thereof, or a ribozyme.

In another aspect, the invention provides a method for modulating, e.g., increasing or decreasing, cellular proliferation in a subject by administering to the subject a 86604 modulator.

Also featured are methods of regulating metastasis in a subject or inhibiting tumor progression in a subject which include administering to the subject an effective amount of an 86604 modulator (e.g., an 86604 inhibitor).

Other features and advantages of the invention will be apparent from the following detailed description and claims.

The present invention provides methods and compositions for the diagnosis and treatment of cellular proliferation disorders, e.g., cancer, including, but not limited to, colon, ovarian, and lung cancer. The present invention is based, at least in part, on the discovery that a human aminotransferase molecule, referred to herein as "86604," is differentially expressed in tumor cells, e.g., colon, lung, and ovary tumor cells and in colon cells which have metastasized to the liver, as compared to normal cells. Human 86604 was also found to be upregulated in colon polyps and carcinomas as compared to normal colon tissue. Moreover, cell-based assays, as described herein, have linked the expression 86604 with cellular proliferation. For example, in a cell based model wherein the activated k-ras allele in human colon cancer cell line HCT-116 has been disrupted, 86604 is down regulated, indicating decreased expression of human 86604 in cells which have slowed proliferation in vitro and in vivo and which exhibit reduced expression of the oncogene c-myc. In addition, human 86604 shows differential expression in cells which have been synchronized in the G2 phase, indicating expression of 86604 in proliferating cells.

The 86604 molecule is a member of the aminotransferase type I family having significant identity and similarity to the multifunctional protein glutamine transaminase K (GTK), also referred to as cystein conjugate β-lyase (described in Perry, et al. (1995) FEBS Lett. 360:277-80). GTK has been identified as having three activities: cystein conjugate β-lyase activity, glutamine transaminase K activity, and kynurenine aminotransferase activity. GTK catalyzes the conversion of L-glutamine and phenylpyruvate to 2-oxoglutaramate and L-phenylalanine. It has also been suggested that glutamine transaminase K is involved in amino acid transport across cell membranes. The 86604 molecules of the instant invention have aminotransferase activity and function to catalyze the transfer of amino groups from glutamine, leading to amino acid degradation. The 86604 molecules also function to transport amino acids between the cytoplasm and the mitochondria. Without intending to be limited by mechanism, it is believed that the 86604 molecules, by modulating amino acid degradation and amino acid transport, modulate cellular metabolism, growth, and proliferation.

For example, inhibition of 86604 may decrease amino acid transport and degradation causing cellular metabolism to decrease, thereby leading to decreased cellular growth and proliferation. Accordingly, the 86604 molecules of the present invention provide novel diagnostic targets and therapeutic agents for cellular proliferation disorders, e.g., cancer. In a preferred embodiment, the 86604 molecules of the present invention provide novel diagnostic targets and therapeutic agents for colon cancer, lung cancer, and ovarian cancer.

As used herein, a "cellular proliferation disorder" includes a disease or disorder that affects a cellular growth, differentiation, or proliferation process. As used herein, a "cellular growth, differentiation or proliferation process" is a process by which a cell increases in number, size or content, by which a cell develops a specialized set of characteristics which differ from that of other cells, or by which a cell moves closer to or further from a particular location or stimulus. A cellular growth, differentiation, or proliferation process includes amino acid transport and degradation and other metabolic processes of a cell. A cellular proliferation disorder may be characterized by aberrantly regulated cellular growth, proliferation, differentiation, or migration. Cellular proliferation disorders include tumorigenic disease or disorders. As used herein, a "tumorigenic disease or disorder" includes a disease or disorder characterized by aberrantly regulated cellular growth, proliferation, differentiation, adhesion, or migration, which may result in the production of or tendency to produce tumors. As used herein, a "tumor" includes a normal benign or malignant mass of tissue. Examples of cellular growth or proliferation disorders include, but are not limited to, cancer, e.g., carcinoma, sarcoma, or leukemia, examples of which include, but are not limited to, colon, ovarian, lung, breast, endometrial, uterine, hepatic, gastrointestinal, prostate, and brain cancer; tumorigenesis and metastasis; skeletal dysplasia; and hematopoietic and/or myeloproliferative disorders.

"Differential expression", as used herein, includes both quantitative as well as qualitative differences in the temporal and/or tissue expression pattern of a gene. Thus, a differentially expressed gene may have its expression activated or inactivated in normal versus cellular growth or proliferation disease states. The degree to which expression differs in normal versus cellular growth or proliferation disease states or control versus experimental states need only be large enough to be visualized via standard characterization techniques, e.g., quantitative PCR, Northern analysis, Taqman™ analysis, transcriptional profiling, or subtractive hybridization. The expression pattern of a differentially expressed gene may be used as part of a prognostic or diagnostic cellular proliferation disorder evaluation, or may be used in methods for identifying compounds useful for the treatment of cellular proliferation disorder. In addition, a differentially expressed gene involved in cellular proliferation disorders may represent a target gene such that modulation of the expression level of this gene or the activity of the gene product may act to ameliorate a cellular growth or proliferation disorder. Compounds that modulate target gene expression or activity of the target gene product can be used in the treatment of cellular proliferation disorders. Although the 86604 genes described herein may be differentially expressed with respect to cellular proliferation disorders, and/or their products may interact with gene products important to cellular proliferation disorders, the genes may also be involved in mechanisms important to additional tumor cell processes.

As used interchangeably herein, "86604 activity," "biological activity of 86604" or "functional activity of 86604," includes an activity exerted by a 86604 protein, polypeptide or nucleic acid molecule on a 86604 responsive cell or tissue, e.g., a tumor cell, or on a 86604 protein substrate, as determined in vivo, or in vitro, according to standard techniques. 86604 activity can be a direct activity, such as an association with a 86604-target molecule. As used herein, a "substrate" or "target molecule" or "binding partner" is a molecule with which a 86604 protein binds or interacts in nature, such that 86604-mediated function, e.g., modulation of amino acid transport or amino acid degradation, is achieved. A 86604 target molecule can be a non-86604 molecule or a 86604 protein or polypeptide. Examples of such target molecules include proteins in the same signaling path as the 86604 protein, e.g., proteins which may function upstream (including both stimulators and inhibitors of activity) or downstream of the 86604 protein in a pathway involving regulation of cellular growth, proliferation or differentiation. Alternatively, a 86604 activity is an indirect activity, such as a cellular signaling activity mediated by interaction of the 86604 protein with a 86604 target molecule. The biological activities of 86604 are described herein. For example, the 86604 proteins can have one or more of the following activities: 1) they modulate amino acid transport; 2) they modulate amino acid degradation; 3) they modulate cellular metabolism; 4) they catalyze transamination and β-elimination reactions of cysteine S-conjugates; 5) they modulate thiolate, pyruvate, and/or ammonia production; 6) they modulate cellular growth; and 7) they modulate cellular proliferation.

Various aspects of the invention are described in further detail in the following subsections:

Screening Assays

The invention provides methods (also referred to herein as "screening assays") for identifying modulators, i.e., candidate or test compounds or agents (e.g., peptides, peptidomimetics, small molecules, ribozymes, or 86604 antisense molecules) which bind to 86604 proteins, have a stimulatory or inhibitory effect on 86604 expression or 86604 activity, or have a stimulatory or inhibitory effect on the expression or activity of a 86604 target molecule. Compounds identified using the assays described herein may be useful for treating cellular proliferation disorders.

Candidate/test compounds include, for example, 1) peptides such as soluble peptides, including Ig-tailed fusion peptides and members of random peptide libraries (see, e.g., Lam, K. S. et al. (1991) Nature 354:82-84; Houghten, R. et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, F(ab')2, Fab expression library fragments, and epitope-binding fragments of antibodies); and 4) small organic and inorganic molecules (e.g., molecules obtained from combinatorial and natural product libraries).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. EngI. 33:2059; Carell et al. (1994) Angew. Chem. Int. Ed. EngI. 33:2061; and Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

Assays that may be used to identify compounds that modulate 86604 activity include assays to determine the ability of 86604 to convert L-phenylalanine and α-keto-γ-methiolbutyrate to phenylpyruvate and L-methionine in the presence of a candidate or test compound (as described in, for example, Cooper, A. J. L. and Meister, A. (1985) Meth. Enzymol. 113:344-349 and Nakamura, et al. (1996) Anal. Biochem. 234(1):19-22). In addition, assays for kynurenine aminotransferase activity and/or cysteine conjugate β-lyase activity as described in U.S. Pat. No. 6,136,572 may be used to identify compounds that modulate 86604 activity. Assays which measure the concentration of 2-oxoglutaramate and L-phenylalanine in a cell may also be used to identify compounds which modulate 86604 expression or activity. Other assays to identify compounds that modulate 86604 activity include assays for measurement of amino acid degradation, assays for measurement of production of thiolates, pyruvate and ammonia by cells expressing 86604, or other assays known in the relevant art to measure aminotransferase activity, e.g., glutamine transaminase activity.

Cellular proliferation assays that may be used to identify compounds that modulate 86604 activity include assays such as the acid phosphatase assay for cell number as described in Connolly et al. (1986) Anal. Biochem. 152, 136-140 and the MTT assay as described in Loveland, B. E. et al., (1992) Biochem. Int., 27:501-510, which utilizes colorimetric assays to quantitate viable cells, e.g., the cellular reduction of the tetrazolium salt, MTT, to formazan by mitochondrial succinate dehydrogenase. Other assays for cellular proliferation include clonogenic assays, assays for 3H-thymidine uptake, assays measuring the incorporation of radioactively labeled nucleotides into DNA, or other assays which are known in the art for measuring cellular proliferation. Moreover, inhibition of cellular growth in vivo, e.g., in a patient with cancer, can be detected by any standard method for detecting tumors such as by x-ray or imaging analysis of a tumor size, or by observing a reduction in mutant p53 protein production or in the production of any known cell-specific or tumor marker within a biopsy or tissue sample. Determining the ability of a test compound to modulate 86604 activity can be accomplished by monitoring, for example, cell progression through the cell cycle. For example, the cell can be a tumor cell, e.g., a colon tumor cell, a lung tumor cell, or an ovary tumor cell.

In one aspect, an assay is a cell-based assay in which a cell which expresses a 86604 protein or biologically active portion thereof is contacted with a test compound and the ability of the test compound to modulate 86604 activity is determined. In a preferred embodiment, the biologically active portion of the 86604 protein includes a domain or motif that can modulate amino acid transport or degradation, cellular metabolism, or cellular growth or proliferation. Determining the ability of the test compound to modulate 86604 activity can be accomplished by monitoring, for example, the production of one or more specific metabolites (e.g., thiolates, pyruvate, and/or ammonia) in a cell which expresses 86604 (see, e.g., Saada et al. (2000) Biochem Biophys. Res. Commun. 269: 382-386) or by monitoring cell metabolism, cellular growth, cellular proliferation, or cellular differentiation. The cell, for example, can be of mammalian origin, e.g., a tumor cell such as a lung, ovary, or colon tumor cell.

The ability of the test compound to modulate 86604 binding to a substrate or to bind to 86604 can also be determined. Determining the ability of the test compound to modulate 86604 binding to a substrate can be accomplished, for example, by coupling the 86604 substrate with a radioisotope or enzymatic label such that binding of the 86604 substrate to 86604 can be determined by detecting the labeled 86604 substrate in a complex. Alternatively, 86604 could be coupled with a radioisotope or enzymatic label to monitor the ability of a test compound to modulate 86604 binding to a 86604 substrate in a complex. Determining the ability of the test compound to bind 86604 can be accomplished, for example, by coupling the compound with a radioisotope or enzymatic label such that binding of the compound to 86604 can be determined by detecting the labeled 86604 compound in a complex. For example, 86604 substrates can be labeled with 125I, 35S, 14C, or 3H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with 86604 without the labeling of any of the interactants. For example, a microphysiometer can be used to detect the interaction of a compound with 86604 without the labeling of either the compound or the 86604 molecule (McConnell, H. M. et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 86604.

The ability of a 86604 modulator to modulate, e.g., inhibit or increase, 86604 activity can also be determined through screening assays which identify modulators which either increase or decrease amino acid transport or degradation, cellular metabolism, cellular growth, or cellular proliferation. In one embodiment, the invention provides for a screening assay involving contacting cells which express a 86604 protein or polypeptide with a test compound, and examining the cells for cellular growth or proliferation. For example, cells expressing a 86604 protein or polypeptide can be contacted with a test compound and subsequently quantitated to measure cellular growth and/or proliferation as described in, for example, Loveland, B. E. et al, (1992) Biochem. Int., 27:501-510, or by measuring the incorporation of radioactively labeled nucleotides into DNA, or by measuring the number of cells present compared to a control cell. The number of cells can be measured, for example, by dry/wet weight measurement, by counting the cells via optical density, using a counting chamber, or by using other assays for cellular proliferation as described herein or known in the art.

Because 86604 expression is increased in tumors, including metastatic tumors, and is regulated during the cell cycle, compounds which modulate cellular proliferation, growth, and/or differentiation can be identified by the ability to modulate 86604 expression. To determine whether a test compound modulates 86604 expression, a cell which expresses 86604 (e.g., a lung tumor cell, an ovary tumor cell, a colon tumor cell, or a corresponding normal cell) is contacted with a test compound, and the ability of the test compound to modulate 86604 expression can be determined by measuring 86604 mRNA by, e.g., Northern Blotting, quantitative PCR (e.g., Taqman), or in vitro transcriptional assays. To perform an in vitro transcriptional assay, the full length promoter and enhancer of 86604 can be linked to a reporter gene such as chloramphenicol acetyltransferase (CAT) or luciferase and introduced into host cells. The same host cells can then be transfected with or contacted with the test compound. The effect of the test compound can be measured by reporter gene activity and comparing it to reporter gene activity in cells which do not contain the test compound. An increase or decrease in reporter gene activity indicates a modulation of 86604 expression and is, therefore, an indicator of the ability of the test compound to modulate cellular proliferation, growth, and/or differentiation in, e.g., tumor cells.

The above described assay for testing the ability of a test compound to modulate 86604 expression can also be used to test the ability of the 86604 molecule to modulate cellular proliferation. If a test compound can modulate 86604 expression it can most likely modulate the cellular growth or proliferation, e.g., tumor cellular growth or proliferation.

In vitro cell-based models for cancer may also be used to identify compounds that modulate 86604 activity and/or to confirm the ability of the test compound to modulate the activity of a 86604 molecule. For example, cell lines may be transiently or stably transfected with tumor suppressors and oncogenes, e.g., including, but not limited, to wild type or mutated p53, Smad4, p16, p14, c-myc, and k-ras, which are genes known to be associated with cancer progression or inhibition, e.g., colon, lung, breast, or ovarian cancer progression or inhibition. These cell lines can then be used to evaluate expression or activity of 86604 in the presence or absence of a test compound using the methods described herein. For example, the following human mammary epithelial cell lines are available for use in vitro models and/or in xenograft models in mice: HMEC, MCF-7, T-47D, ZR-75, MDA-MB-231, MDA-MB-MC-2, MDA-MB-435, BT-549, SkBr3, MDA-MB-468, MCF10A, MCF10AT.c11, MCF10AT.c13, MCF10AT1, MCF10AT3B, MCF10CA1.c1, Hs578T, and HCC1937. The following colon cell lines are available for use in in vitro models and/or in xenograft models in mice: HCT-116, SW480, CC-ML3, KM12C, KM12SM, HT29, DLD-1, HCC-2998, COLO-205, HCT-15, SW-620, and KM20L2. The following lung cell lines are available for use in in vitro models and/or in xenograft models in mice: NCI-H345, NCI-H69, and NCI-H125. The following ovarian cell lines are available for use in in vitro models and/or in xenograft models in mice: SKOV3, SKOV3, OVCAR-3, and OVCAR-4

In vitro cell-based models for breast cancer include, for example, the MCF10A cell line transformed with k-ras, a cell-based system of mammary epithelial malignancy; treating human breast epithelial cells (MCF10A) with growth factors, including EGF and IGF1 growth factors; and reintroduction of BRCA1 expression into HCC1937 cells.

In vitro cell-based models for ovarian cancer include, for example, treatment of the ovarian cancer cell lines, SKOV3 and SKOV3/Variant (which are a variant of the parental SKOV3 ovarian cancer cell line that are cisplatin resistant), with either Epidermal Growth Factor (EGF) or the growth factor Heregulin (Hrg) for 15, 30 and 60 minutes in the absence of serum; and stable expression of p53 in a previously null cell line (SKOV-3 and SKOV3-Var).

In vitro cell-based models for lung cancer include, for example, tumor suppressor models such as reintroduction of p53 into NCI-H125 cells, a lung tumor cell line that is null for p53; expression of p16 and p14, distinct tumor suppressors derived from the same genetic locus, both of which are commonly silenced in lung tumors, in the lung tumor cell lines NCI-H460 and A549, which normally lack expression of these genes; and expression of the pRb gene, which is commonly deleted in small cell lung cancer in small cell tumor lines. Other cell-based models include a stably transformed bronchial epithelial cell line with activated k-ras gene. In addition, growth factor models may also be used. For example, NCI-H69 and NCI-H345 small cell lung carcinoma (SCLC) cells may be treated with a substance P analogue (SPA) that acts as a broad spectrum neuropeptide receptor inhibitor. Genes that were downregulated after SPA treatment were flagged for further study to determine if their expression is critical for tumor cell proliferation. SCLC cells that express both the c-kit tyrosine kinase receptor and its ligand, SCF, may be treated with the kinase inhibitor STI-571. It has been demonstrated that selective growth inhibition upon 571 treatment of cell lines expressing both the receptor and ligand, suggesting that they function in an autocrine feedback loop to stimulate tumor cell proliferation.

In vitro cell-based models for colon cancer include, for example, SW480 cells stably or transiently transfected with Smad4. Smad4 is a candidate tumor suppressor gene mutated in a subset of colon carcinomas. Smad4 functions in the signal transduction of TGF-β molecules. It is well known that the TGF-β superfamily is involved in growth inhibition. Smad4 mutation/loss in colon cell lines provides the hypothesis that Smad4 may be a modulator of cell adhesion and invasion. Another cell line useful in the methods of the invention are NCM425 cells stably or transiently transfected with β-catenin. Mutations of the APC gene are responsible for tumor formation in sporadic and familial forms of colorectal cancer. APC binds β-catenin and regulates the cytoplasmic levels of β-catenin. When APC is mutated, β-catenin accumulates in the cytoplasm and translocates into the nucleus. Once in the nucleus it interacts with LEF/TCF molecules and regulates gene expression. Genes regulated by the β-catenin/LEF complex, like c-myc and cyclin D1, are involved in tumorigenesis. Also useful in the methods of the invention are cells stably or transiently transfected with p53. p53 is a well-known tumor suppressor which is mutated in >50% of colorectal cancer tumors. Still other cell lines useful in the methods of the invention include transient or stable transfections of WISP-1 into NCM425 colon cancer cells, transient or stable transfections of DCC, Cox2, and/or APC into various cells.

Cell lines such as HCT-116 and DLD-1 may also be transformed with k-ras and used in the method of the invention. Point mutations that activate the k-ras oncogene are found in 50% of human colon cancers. Activated k-ras may regulate cell proliferation in colorectal tumors. Disrupting the activated k-ras allele in HCT-116 and DLD-1 cells morphologically alters differentiation, causes loss of anchorage independent growth, slows proliferation in vitro and in vivo and reduces expression of c-myc. Expression of 86604 was found to be downregulated in k-ras disrupted HCT-116 cells.

Abnormalities in cell cycle regulation and its checkpoints lead to the development of malignant cells. The loss of a cell's ability to respond to signals that regulate cell proliferation and cell cycle arrest is a common mechanism of cancer. Accordingly, for the study of specific time point within the cell cycle, cell lines such as the colon cancer cell lines HCT116, DLD-1, and NCM425, for example, may be synchronized with agents such as mimosine (G1 block), mimosine (G1/S block) and nocodazole (G2/M block). Cell synchronization in relation to p53 status may also be studied in cells of varying p53 status (SKOV-3 (null), OVCAR-3 or OVCAR-4 (mutant), and HEY (wildtype)).

In yet another embodiment, an assay of the present invention is a cell-free assay in which a 86604 protein or biologically active portion thereof is contacted with a test compound and the ability of the test compound to bind to or to modulate (e.g., stimulate or inhibit) the activity of the 86604 protein or biologically active portion thereof is determined. Preferred biologically active portions of the 86604 proteins to be used in assays of the present invention include fragments which participate in interactions with non-86604 molecules, e.g., fragments with high surface probability scores. Binding of the test compound to the 86604 protein can be determined either directly or indirectly as described above. Determining the ability of the 86604 protein to bind to a test compound can also be accomplished using a technology such as real-time Biomolecular Interaction Analysis (BIA) (Sjolander, S, and Urbaniczky, C. (1991) Anal. Chem. 63:2338-2345; Szabo et al. (1995) Curr. Opin. Struct. Biol. 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In more than one embodiment of the above assay methods of the present invention, it may be desirable to immobilize either 86604 or a 86604 target molecule to facilitate separation of complexed from uncomplexed forms of one or both of the proteins, as well as to accommodate automation of the assay. Binding of a test compound to a 86604 protein, or interaction of a 86604 protein with a 86604 target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/86604 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 86604 protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of 86604 binding or activity determined using standard techniques.

Other techniques for immobilizing proteins on matrices can also be used in the screening assays of the invention. For example, either a 86604 protein or a 86604 target molecule can be immobilized utilizing conjugation of biotin and streptavidin. Biotinylated 86604 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with 86604 protein or target molecules but which do not interfere with binding of the 86604 protein to its target molecule can be derivatized to the wells of the plate, and unbound target or 86604 protein is trapped in the wells by antibody conjugation. Methods for detecting such complexes, in addition to those described above for the GST-immobilized complexes, include immunodetection of complexes using antibodies reactive with the 86604 protein or target molecule, as well as enzyme-linked assays which rely on detecting an enzymatic activity associated with the 86604 protein or target molecule.

In yet another aspect of the invention, the 86604 protein or fragments thereof can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with 86604 ("86604-binding proteins" or "86604-bp) and are involved in 86604 activity. Such 86604-binding proteins are also likely to be involved in the propagation of signals by the 86604 proteins or 86604 targets as, for example, downstream elements of a 86604-mediated signaling pathway. Alternatively, such 86604-binding proteins are likely to be 86604 inhibitors.

The two-hybrid system is based on the modular nature of most transcription factors, which consist of separable DNA-binding and activation domains. Briefly, the assay utilizes two different DNA constructs. In one construct, the gene that codes for a 86604 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 86604-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 86604 protein.

In another aspect, the invention pertains to a combination of two or more of the assays described herein. For example, a modulating agent can be identified using a cell-based or a cell-free assay, and the ability of the agent to modulate the activity of a 86604 protein can be confirmed in vivo, e.g., in an animal such as an animal model for a cellular proliferation disorder, e.g., cancer. Examples of animal models of cancer include transplantable models (e.g., xenografts). Xenografts for colon cancer can be performed with the following cell lines: HCT-116, HT-29, SW-480, SW-620, Colon 26, DLD1, Caco2, colo205, T84, and KM12. Xenografts for lung cancer can be performed with the following cell lines: NCI-H125, NCI-H460, A549, NCI-H69, and NCI-H345. Xenografts for ovarian cancer can be performed with the SKOV3 and HEY cell lines. Xenografts for breast cancer can be performed with, for example, MCF10AT cells, which can be grown as subcutaneous or orthotopic (cleared mammary fat pad) xenografts in mice. MCF10AT xenografts produce tumors that progress in a manner analogous to human breast cancer. Estrogen stimulation has also been shown to accelerate tumor progression in this model. MCF10AT xenografted tumors representing stages hyperplasia, carcinoma in situ, and invasive carcinoma will be isolated expression profiling. A metastatic subclone of the human breast cancer cell line MDA-MB-231 that metastasizes to brain, lung and bone can also be grown in vitro and in vivo at various sites (i.e. subcutaneously, orthotopically, in bone following direct bone injection, in bone following intracardiac injection). MCF-7 and T-47D are other mammary adenocarcinoma cell lines that can be grown as xenografts. All of these cells can be transplanted into immunocompromised mice such as SCID or nude mice, for example.

Orthotopic metastasis mouse models may also be utilized. For example, the HCT-116 human colon carcinoma cell line can be grown as a subcutaneous or orthotopic xenograft (intracaecal injection) in athymic nude mice. Rare liver and lung metastases can be isolated, expanded in vitro, and re-implanted in vivo. A limited number of iterations of this process can be employed to isolate highly metastatic variants of the parental cell line. Standard and subtracted cDNA libraries and probes can be generated from the parental and variant cell lines to identify genes associated with the acquisition of a metastatic phenotype. This model can be established using several alternative human colon carcinoma cell lines, including SW480 and KM12C.

Also useful in the methods of the invention are mis-match repair models (MMRs). Hereditary nonpolyposis colon cancer (HNPCC), which is caused by germline mutations in MSH2 & MLH1, genes involved in DNA mismatch repair, accounts for 5-15% of colon cancer cases. Mouse models have been generated carrying null mutations in the MLH1, MSH2 and MSH3 genes.

Other animal models for cancer include transgenic models (e.g., B66-Min/+ mouse); chemical induction models, e.g., carcinogen (e.g., azoxymethane, 2-dimethylhydrazine, or N-nitrosodimethylamine) treated rats or mice; models of liver metastasis from colon cancer such as that described by Rashidi et al. (2000) Anticancer Res 20(2A):715; and cancer cell implantation or inoculation models as described in, for example, Fingert et al. (1987) Cancer Res 46(14):3824-9 and Teraoka et al. (1995) Jpn J Cancer Res 86(5):419-23. Furthermore, experimental model systems are available for the study of, for example, ovarian cancer (Hamilton, T C et al. Semin Oncol (1984) 11:285-298; Rahman, N A et al. Mol Cell Endocrinol (1998) 145:167-174; Beamer, W G et al. Toxicol Pathol (1998) 26:704-710), gastric cancer (Thompson, J et al. Int J Cancer (2000) 86:863-869; Fodde, R et al. Cytogenet Cell Genet (1999) 86:105-111), breast cancer (Li, M et al. Oncogene (2000) 19:1010-1019; Green, J E et al. Oncogene (2000) 19:1020-1027), melanoma (Satyamoorthy, K et al. Cancer Metast Rev (1999) 18:401-405), and prostate cancer (Shirai, T et al. Mutat Res (2000) 462:219-226; Bostwick, D G et al. Prostate (2000) 43:286-294). Mouse models for colon cancer include the APCmin mouse, a highly characterized genetic model of human colorectal carcinogeneis; the APC1638N mouse, which was generated by introducing a PGK-neomycin gene at codon 1638 of the APC gene and develops aberrant crypt foli after 6-8 weeks which ultimately progress to carcinomas by 4 months of age; and the Smad3−/− mouse which develops colon carcinomas that histopathologically resemble human disease.

Other animal based models for studying tumorigenesis in vivo are well known in the art (reviewed in Animal Models of Cancer Predisposition Syndromes, Hiai, H. and Hino, O. (eds.) 1999, Progress in Experimental Tumor Research, Vol. 35; Clarke A R Carcinogenesis (2000) 21:435-41) and include, for example, carcinogen-induced tumors (Rithidech, K et al. Mutat Res (1999) 428:33-39; Miller, M L et al. Environ Mol Mutagen (2000) 35:319-327), as well as animals bearing mutations in growth regulatory genes, for example, oncogenes (e.g., ras) (Arbeit, J M et al. Am J Pathol (1993) 142:1187-1197; Sinn, E et al. Cell (1987) 49:465-475; Thorgeirsson, S S et al. Toxicol Lett (2000) 112-113:553-555) and tumor suppressor genes (e.g., p53) (Vooijs, M et al. Oncogene (1999) 18:5293-5303; Clark A R Cancer Metast Rev (1995) 14:125-148; Kumar, T R et al. J Intern Med (1995) 238:233-238; Donehower, L A et al. (1992) Nature 356215-221).

Furthermore, this invention pertains to uses of novel compounds identified by the above-described screening assays for treatments as described herein. In one embodiment, the invention features a method of treating a subject having a cellular growth or proliferation disorder that involves administering to the subject an 86604 modulator such that treatment occurs. In another embodiment, the invention features a method of treating a subject having cancer, e.g., colon cancer, lung cancer, or ovarian cancer, that involves treating a subject with an 86604 modulator, such that treatment occurs. Preferred 86604 modulators include, but are not limited to, 86604 proteins or biologically active fragments, 86604 nucleic acid molecules, 86604 antibodies, ribozymes, and 86604 antisense oligonucleotides designed based on the 86604 nucleotide sequences disclosed herein, as well as peptides, organic and non-organic small molecules identified as being capable of modulating 86604 expression and/or activity, for example, according to at least one of the screening assays described herein.

Moreover, a 86604 modulator identified as described herein (e.g., an antisense 86604 nucleic acid molecule, a 86604-specific antibody, or a small molecule) can be used in an animal model to determine the efficacy, toxicity, or side effects of treatment with such a modulator. Alternatively, a 86604 modulator identified as described herein can be used in an animal model to determine the mechanism of action of such a modulator.

Any of the compounds, including but not limited to compounds such as those identified in the foregoing assay systems, may be tested for the ability to ameliorate cellular growth or proliferation disorder symptoms. Cell-based and animal model-based assays for the identification of compounds exhibiting such an ability to ameliorate cellular growth or proliferation disorder systems are described herein.

In one aspect, cell-based systems, as described herein, may be used to identify compounds which may act to ameliorate cellular growth or proliferation disorder symptoms, for example, reduction in tumor burden, tumor size, tumor cellular growth, differentiation, and/or proliferation, and invasive and/or metastatic potential before and after treatment. For example, such cell systems may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed cells. After exposure, the cells are examined to determine whether one or more of the cellular growth or proliferation disorder cellular phenotypes has been altered to resemble a more normal or more wild type, non-cellular growth or proliferation disorder phenotype. Cellular phenotypes that are associated with cellular growth and/or proliferation disorders include aberrant proliferation, growth, and migration, anchorage independent growth, and loss of contact inhibition.

In addition, animal-based cellular growth or proliferation disorder systems, such as those described herein, may be used to identify compounds capable of ameliorating cellular growth or proliferation disorder symptoms. Such animal models may be used as test substrates for the identification of drugs, pharmaceuticals, therapies, and interventions which may be effective in treating cellular growth or proliferation disorders. For example, animal models may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed animals. The response of the animals to the exposure may be monitored by assessing the reversal of cellular growth or proliferation disorders, or symptoms associated therewith, for example, reduction in tumor burden, tumor size, and invasive and/or metastatic potential before and after treatment.

With regard to intervention, any treatments which reverse any aspect of cellular growth or proliferation disorder symptoms should be considered as candidates for human cellular growth or proliferation disorder therapeutic intervention. Dosages of test compounds may be determined by deriving dose-response curves.

Additionally, gene expression patterns may be utilized to assess the ability of a compound to ameliorate cellular growth and/or proliferation disorder symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cellular growth, proliferation, differentiation, transformation, tumorigenesis, metastasis, and carcinogen exposure. Gene expression profiles may be generated, for example, by utilizing a differential display procedure, Northern analysis and/or RT-PCR. In one embodiment, 86604 gene sequences may be used as probes and/or PCR primers for the generation and corroboration of such gene expression profiles.

Gene expression profiles may be characterized for known states within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a cellular growth or proliferation disorder model system to more closely resemble the control system. Administration of a compound may, alternatively, cause the gene expression profile of a control system to begin to mimic a cellular growth and/or proliferation disorder state. Such a compound may, for example, be used in further characterizing the compound of interest, or may be used in the generation of additional animal models.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 86604 protein and/or nucleic acid expression as well as 86604 activity, in the context of a biological sample (e.g., blood, serum, cells, or tissue, e.g., tumor or carcinoma tissue) to thereby determine whether an individual is afflicted with a cellular proliferation disorder. The invention also provides for prognostic (or predictive) assays for determining whether an individual is at risk of developing a cellular proliferation disorder. For example, mutations in a 86604 gene can be assayed for in a biological sample. Such assays can be used for prognostic or predictive purpose to thereby prophylactically treat an individual prior to the onset of a cellular proliferation disorder.

Another aspect of the invention pertains to monitoring the influence of 86604 modulators (e.g., anti-86604 antibodies or 86604 ribozymes) on the expression or activity of 86604 in clinical trials.

These and other agents are described in further detail in the following sections.

A. Diagnostic Assays for Cellular Proliferation Disorders

To determine whether a subject is afflicted with a cellular proliferation disorder, a biological sample may be obtained from a subject and the biological sample may be contacted with a compound or an agent capable of detecting a 86604 protein or nucleic acid (e.g., mRNA or genomic DNA) that encodes a 86604 protein, in the biological sample. A preferred agent for detecting 86604 mRNA or genomic DNA is a labeled nucleic acid probe capable of hybridizing to 86604 mRNA or genomic DNA. The nucleic acid probe can be, for example, the 86604 nucleic acid set forth in SEQ ID NO:53, or a portion thereof, such as an oligonucleotide of at least 15, 20, 25, 30, 25, 40, 45, 50, 100, 250 or 500 nucleotides in length and sufficient to specifically hybridize under stringent conditions to 86604 mRNA or genomic DNA. Other suitable probes for use in the diagnostic assays of the invention are described herein.

A preferred agent for detecting 86604 protein in a sample is an antibody capable of binding to 86604 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect 86604 mRNA, protein, or genomic DNA in a biological sample in vitro as well as in vivo. For example, in vitro techniques for detection of 86604 mRNA include Northern hybridizations and in situ hybridizations. In vitro techniques for detection of 86604 protein include enzyme linked immunosorbent assays (ELISAs), Western blots, immunoprecipitations and immunofluorescence. In vitro techniques for detection of 86604 genomic DNA include Southern hybridizations. Furthermore, in vivo techniques for detection of 86604 protein include introducing into a subject a labeled anti-86604 antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting 86604 protein, mRNA, or genomic DNA, such that the presence of 86604 protein, mRNA or genomic DNA is detected in the biological sample, and comparing the presence of 86604 protein, mRNA or genomic DNA in the control sample with the presence of 86604 protein, mRNA or genomic DNA in the test sample.

B. Prognostic Assays for Cellular Proliferation Disorders

The present invention further pertains to methods for identifying subjects having or at risk of developing a cellular proliferation disorder associated with aberrant 86604 expression or activity.

As used herein, the term "aberrant" includes a 86604 expression or activity which deviates from the wild type 86604 expression or activity. Aberrant expression or activity includes increased or decreased expression or activity, as well as expression or activity which does not follow the wild type developmental pattern of expression or the subcellular pattern of expression. For example, aberrant 86604 expression or activity is intended to include the cases in which a mutation in the 86604 gene causes the 86604 gene to be under-expressed or over-expressed and situations in which such mutations result in a non-functional 86604 protein or a protein which does not function in a wild-type fashion, e.g., a protein which does not interact with a 86604 substrate, or one which interacts with a non-86604 substrate.

The assays described herein, such as the preceding diagnostic assays or the following assays, can be used to identify a subject having or at risk of developing a cellular proliferation disorder, e.g., cancer, such as for example, colon, lung, and ovarian cancer. A biological sample may be obtained from a subject and tested for the presence or absence of a genetic alteration. For example, such genetic alterations can be detected by ascertaining the existence of at least one of 1) a deletion of one or more nucleotides from a 86604 gene, 2) an addition of one or more nucleotides to a 86604 gene, 3) a substitution of one or more nucleotides of a 86604 gene, 4) a chromosomal rearrangement of a 86604 gene, 5) an alteration in the level of a messenger RNA transcript of a 86604 gene, 6) aberrant modification of a 86604 gene, such as of the methylation pattern of the genomic DNA, 7) the presence of a non-wild type splicing pattern of a messenger RNA transcript of a 86604 gene, 8) a non-wild type level of a 86604-protein, 9) allelic loss of a 86604 gene, and 10) inappropriate post-translational modification of a 86604-protein.

As described herein, there are a large number of assays known in the art which can be used for detecting genetic alterations in a 86604 gene. For example, a genetic alteration in a 86604 gene may be detected using a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a 86604 gene (see Abravaya et al. (1995) Nucleic Acids Res. 23:675-682). This method includes collecting a biological sample from a subject, isolating nucleic acid (e.g., genomic DNA, mRNA or both) from the sample, contacting the nucleic acid sample with one or more primers which specifically hybridize to a 86604 gene under conditions such that hybridization and amplification of the 86604 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 86604 gene from a biological sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 86604 can be identified by hybridizing biological sample derived and control nucleic acids, e.g., DNA or RNA, to high density arrays containing hundreds or thousands of oligonucleotide probes (Cronin, M. T. et al. (1996) Human Mutation 7:244-255; Kozal, M. J. et al. (1996) Nature Medicine 2:753-759). For example, genetic mutations in 86604 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows for the identification of point mutations. This step is followed by a second hybridization array that allows for the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 86604 gene in a biological sample and detect mutations by comparing the sequence of the 86604 in the biological sample with the corresponding wild-type (control) sequence. Examples of sequencing reactions include those based on techniques developed by Maxam and Gilbert (1977) Proc. Natl. Acad. Sci. USA 74:560) or Sanger (1977) Proc. Natl. Acad. Sci. USA 74:5463). It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the 86604 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type 86604 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad Sci USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 86604 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a 86604 sequence, e.g., a wild-type 86604 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 86604 genes. For example, single strand conformation polymorphism (SSCP) may be used to detect differences in electrophoretic mobility between mutant and wild type nucleic acids (Orita et al. (1989) Proc Natl. Acad. Sci. USA: 86:2766; see also Cotton (1993) Mutat. Res. 285:125-144 and Hayashi (1992) Genet. Anal. Tech. Appl. 9:73-79). Single-stranded DNA fragments of sample and control 86604 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

Furthermore, the prognostic assays described herein can be used to determine whether a subject can be administered a 86604 modulator (e.g., an agonist, antagonist, peptidomimetic, protein, peptide, nucleic acid, or small molecule) to effectively treat a cellular proliferation disorder.

C. Monitoring of Effects During Clinical Trials

The present invention further provides methods for determining the effectiveness of a 86604 modulator (e.g., a 86604 modulator identified herein) in treating a cellular proliferation disorder in a subject. For example, the effectiveness of a 86604 modulator in increasing 86604 gene expression, protein levels, or in upregulating 86604 activity, can be monitored in clinical trials of subjects exhibiting decreased 86604 gene expression, protein levels, or downregulated 86604 activity. Alternatively, the effectiveness of a 86604 modulator in decreasing 86604 gene expression, protein levels, or in downregulating 86604 activity, can be monitored in clinical trials of subjects exhibiting increased 86604 gene expression, protein levels, or 86604 activity. In such clinical trials, the expression or activity of a 86604 gene, and preferably, other genes that have been implicated in, for example, a cellular proliferation disorder can be used as a "read out" or marker of the phenotype of a particular cell.

For example, and not by way of limitation, genes, including 86604, that are modulated in cells by treatment with an agent which modulates 86604 activity (e.g., identified in a screening assay as described herein) can be identified. Thus, to study the effect of agents which modulate 86604 activity on subjects suffering from a cellular proliferation disorder in, for example, a clinical trial, cells can be isolated and RNA prepared and analyzed for the levels of expression of 86604 and other genes implicated in the cellular proliferation disorder. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of 86604 or other genes. In this way, the gene expression pattern can serve as a marker, indicative of the physiological response of the cells to the agent which modulates 86604 activity. This response state may be determined before, and at various points during treatment of the individual with the agent which modulates 86604 activity.

In a preferred embodiment, the present invention provides a method for monitoring the effectiveness of treatment of a subject with an agent which modulates 86604 activity (e.g., an agonist, antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of a 86604 protein, mRNA, or genomic DNA in the pre-administration sample; (iii) obtaining one or more post-administration samples from the subject; (iv) detecting the level of expression or activity of the 86604 protein, mRNA, or genomic DNA in the post-administration samples; (v) comparing the level of expression or activity of the 86604 protein, mRNA, or genomic DNA in the pre-administration sample with the 86604 protein, mRNA, or genomic DNA in the post administration sample or samples; and (vi) altering the administration of the agent to the subject accordingly. For example, increased administration of the agent may be desirable to increase the expression or activity of 86604 to higher levels than detected, i.e., to increase the effectiveness of the agent. Alternatively, decreased administration of the agent may be desirable to decrease expression or activity of 86604 to lower levels than detected, i.e. to decrease the effectiveness of the agent. According to such an embodiment, 86604 expression or activity may be used as an indicator of the effectiveness of an agent, even in the absence of an observable phenotypic response.

Methods of Treatment of Subjects Suffering from Cellular Proliferation Disorders The present invention provides for both prophylactic and therapeutic methods of treating a subject, e.g., a human, at risk of (or susceptible to) a cellular proliferation disorder such as cancer, e.g., colon, lung, or ovarian cancer. The term "treatment", as used herein, is defined as the application or administration of a therapeutic agent to a patient, or application or administration of a therapeutic agent to an isolated tissue or cell line from a patient, who has a disease or disorder, a symptom of a disease or disorder, or a predisposition toward a disease or disorder, with the purpose to cure, heal, alleviate, relieve, alter, remedy, ameliorate, improve or affect the disease or disorder, the symptoms of the disease or disorder, or the predisposition toward a disease or disorder, e.g., the cellular proliferation disorder. A therapeutic agent includes, but is not limited to, small molecules, peptides, antibodies, ribozymes and antisense oligonucleotides.

With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring an subject's prophylactic or therapeutic treatment with either the 86604 molecules of the present invention or 86604 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

A. Prophylactic Methods

In one aspect, the invention provides a method for preventing in a subject, a cellular proliferation disorder by administering to the subject an agent which modulates 86604 expression or 86604 activity, e.g., modulation of cellular proliferation, e.g., tumor cellular proliferation. Subjects at risk for a cellular proliferation disorder can be identified by, for example, any or a combination of the diagnostic or prognostic assays described herein. Administration of a prophylactic agent can occur prior to the manifestation of symptoms characteristic of aberrant 86604 expression or activity, such that a cellular proliferation disorder is prevented or, alternatively, delayed in its progression. Depending on the type of 86604 aberrancy, for example, a 86604, 86604 agonist or 86604 antagonist agent can be used for treating the subject. The appropriate agent can be determined based on screening assays described herein.

B. Therapeutic Methods

Another aspect of the invention pertains to methods for treating a subject suffering from a cellular proliferation disorder. These methods involve administering to a subject an agent which modulates 86604 expression or activity (e.g., an agent identified by a screening assay described herein), or a combination of such agents. In another embodiment, the method involves administering to a subject a 86604 protein or nucleic acid molecule as therapy to compensate for reduced, aberrant, or unwanted 86604 expression or activity.

Modulation, e.g., inhibition of 86604 activity is desirable in situations in which 86604 is abnormally upregulated and/or in which decreased 86604 activity is likely to have a beneficial effect, e.g., inhibition of amino acid degradation and transport and cellular growth and proliferation, thereby ameliorating a cellular proliferation disorder such as cancer, e.g., colon, lung, or ovarian cancer, in a subject.

The agents which modulate 86604 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates 86604 activity (e.g., a fragment of a 86604 protein or an anti-86604 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate 86604 activity can also be prepared in the form of suppositories (e.g., with conventional suppository bases such as cocoa butter and other glycerides) or retention enemas for rectal delivery.

In one embodiment, the agents that modulate 86604 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates 86604 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such 86604 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

C. Pharmacogenomics

In conjunction with the therapeutic methods of the invention, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an agent which modulates 86604 activity, as well as tailoring the dosage and/or therapeutic regimen of treatment with an agent which modulates 86604 activity.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate aminopeptidase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug target is known (e.g., a 86604 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a 86604 molecule or 86604 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of a subject. This knowledge, when applied to dosing or drug selection, can avoid adverse reactions or therapeutic failure and, thus, enhance therapeutic or prophylactic efficiency when treating a subject suffering from a cellular proliferation disorder with an agent which modulates 86604 activity.

Recombinant Expression Vectors and Host Cells Used in the Methods of the Invention The methods of the invention (e.g., the screening assays described herein) include the use of vectors, preferably expression vectors, containing a nucleic acid encoding a 86604 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 86604 proteins, mutant forms of 86604 proteins, fusion proteins, and the like).

The recombinant expression vectors to be used in the methods of the invention can be designed for expression of 86604 proteins in prokaryotic or eukaryotic cells. For example, 86604 proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 86604 activity assays, (e.g., direct assays or competitive assays described in detail below), or to generate antibodies specific for 86604 proteins. In a preferred embodiment, a 86604 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 86604 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, Reviews—Trends in Genetics, Vol. 1(1) 1986.

Another aspect of the invention pertains to the use of host cells into which a 86604 nucleic acid molecule of the invention is introduced, e.g., a 86604 nucleic acid molecule within a recombinant expression vector or a 86604 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 86604 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms “transformation” and “transfection” are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a 86604 protein. Accordingly, the invention further provides methods for producing a 86604 protein using the host cells of the invention. In one embodiment, the method comprises culturing the host cell of the invention (into which a recombinant expression vector encoding a 86604 protein has been introduced) in a suitable medium such that a 86604 protein is produced. In another embodiment, the method further comprises isolating a 86604 protein from the medium or the host cell.

Isolated Nucleic Acid Molecules Used in the Methods of the Invention

The coding sequence of the isolated human 86604 cDNA and the predicted amino acid sequence of the human 86604 polypeptide are shown in SEQ ID NO:53 and 52, respectively.

The methods of the invention include the use of isolated nucleic acid molecules that encode 86604 proteins or biologically active portions thereof, as well as nucleic acid fragments sufficient for use as hybridization probes to identify 86604-encoding nucleic acid molecules (e.g., 86604 mRNA) and fragments for use as PCR primers for the amplification or mutation of 86604 nucleic acid molecules. As used herein, the term “nucleic acid molecule” is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:53, or a portion thereof, can be isolated using standard molecular biology techniques and the sequence information provided herein. Using all or portion of the nucleic acid sequence of SEQ ID NO:53 as a hybridization probe, 86604 nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:53 can be isolated by the polymerase chain reaction (PCR) using synthetic oligonucleotide primers designed based upon the sequence of SEQ ID NO:53.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to 86604 nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:53, a complement of the nucleotide sequence shown in SEQ ID NO:53, or a portion of any of these nucleotide sequences. A nucleic acid molecule which is complementary to the nucleotide sequence shown in SEQ ID NO:53, is one which is sufficiently complementary to the nucleotide sequence shown in SEQ ID NO:53 such that it can hybridize to the nucleotide sequence shown in SEQ ID NO:53 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99% or more identical to the entire length of the nucleotide sequence shown in SEQ ID NO:53 or a portion of any of this nucleotide sequence.

Moreover, the nucleic acid molecules used in the methods of the invention can comprise only a portion of the nucleic acid sequence of SEQ ID NO:53, for example, a fragment which can be used as a probe or primer or a fragment encoding a portion of a 86604 protein, e.g., a biologically active portion of a 86604 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:53 of an anti-sense sequence of SEQ ID NO:53 or of a naturally occurring allelic variant or mutant of SEQ ID NO:53. In one embodiment, a nucleic acid molecule used in the methods of the present invention comprises a nucleotide sequence which is greater than 100, 100-200, 200-300, 300-400, 400-500, or more nucleotides in length and hybridizes under stringent hybridization conditions to a nucleic acid molecule of SEQ ID NO:53.

As used herein, the term “hybridizes under stringent conditions” is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH2PO4, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH2PO4, 7% SDS at about 65° C., followed by one or more washes at 0.02M NaH2PO4, 1% SDS at 65° C., see e.g., Church and Gilbert (1984) Proc. Natl. Acad. Sci. USA 81:1991-1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which mis-express a 86604 protein, such as by measuring a level of a 86604-encoding nucleic acid in a sample of cells from a subject e.g., detecting 86604 mRNA levels or determining whether a genomic 86604 gene has been mutated or deleted.

The methods of the invention further encompass the use of nucleic acid molecules that differ from the nucleotide sequence shown in SEQ ID NO:53 due to degeneracy of the genetic code and thus encode the same 86604 proteins as those encoded by the nucleotide sequence shown in SEQ ID NO:53. In another embodiment, an isolated nucleic acid molecule included in the methods of the invention has a nucleotide sequence encoding a protein having an amino acid sequence shown in SEQ ID NO:52.

The methods of the invention further include the use of allelic variants of human 86604, e.g., functional and non-functional allelic variants. Functional allelic variants are naturally occurring amino acid sequence variants of the human 86604 protein that maintain a 86604 activity. Functional allelic variants will typically contain only conservative substitution of one or more amino acids of SEQ ID NO:52, or substitution, deletion or insertion of non-critical residues in non-critical regions of the protein.

Non-functional allelic variants are naturally occurring amino acid sequence variants of the human 86604 protein that do not have a 86604 activity. Non-functional allelic variants will typically contain a non-conservative substitution, deletion, or insertion or premature truncation of the amino acid sequence of SEQ ID NO:52, or a substitution, insertion or deletion in critical residues or critical regions of the protein.

The methods of the present invention may further use non-human orthologues of the human 86604 protein. Orthologues of the human 86604 protein are proteins that are isolated from non-human organisms and possess the same 86604 activity.

The methods of the present invention further include the use of nucleic acid molecules comprising the nucleotide sequence of SEQ ID NO:53 or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of 86604 (e.g., the sequence of SEQ ID NO:52) without altering the biological activity, whereas an "essential" amino acid residue is required for biological activity. For example, amino acid residues that are conserved among the 86604 proteins of the present invention and other members of the aminotransferase family, e.g., the glutamine transaminase K family, are not likely to be amenable to alteration.

Mutations can be introduced into SEQ ID NO:53 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 86604 protein is preferably replaced with another amino acid residue from the same side chain family. Alternatively, in another embodiment, mutations can be introduced randomly along all or part of a 86604 coding sequence, such as by saturation mutagenesis, and the resultant mutants can be screened for 86604 biological activity to identify mutants that retain activity. Following mutagenesis of SEQ ID NO:53 the encoded protein can be expressed recombinantly and the activity of the protein can be determined using the assay described herein.

Another aspect of the invention pertains to the use of isolated nucleic acid molecules which are antisense to the nucleotide sequence of SEQ ID NO:53. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 86604 coding strand, or to only a portion thereof. In one embodiment, an antisense nucleic acid molecule is antisense to a "coding region" of the coding strand of a nucleotide sequence encoding a 86604. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding 86604. The term "noncoding region" refers to 5' and 3' sequences which flank the coding region that are not translated into amino acids (also referred to as 5' and 3' untranslated regions).

Given the coding strand sequences encoding 86604 disclosed herein, antisense nucleic acids of the invention can be designed according to the rules of Watson and Crick base pairing. The antisense nucleic acid molecule can be complementary to the entire coding region of 86604 mRNA, but more preferably is an oligonucleotide which is antisense to only a portion of the coding or noncoding region of 86604 mRNA. For example, the antisense oligonucleotide can be complementary to the region surrounding the translation start site of 86604 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules used in the methods of the invention are typically administered to a subject or generated in situ such that they hybridize with or bind to cellular mRNA and/or genomic DNA encoding a 86604 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule used in the methods of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215: 327-330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave 86604 mRNA transcripts to thereby inhibit translation of 86604 mRNA. A ribozyme having specificity for a 86604-encoding nucleic acid can be designed based upon the nucleotide sequence of a 86604 cDNA disclosed herein (i.e., SEQ ID NO:53). For example, a derivative of a Tetrahymena L-19 IVS RNA can be constructed in which the nucleotide sequence of the active site is complementary to the nucleotide sequence to be cleaved in a 86604-encoding mRNA. See, e.g., Cech et al. U.S. Pat. No. 4,987,071; and Cech et al. U.S. Pat. No. 5,116,742. Alternatively, 86604 mRNA can be used to select a catalytic RNA having a specific ribonuclease activity from a pool of RNA molecules. See, e.g., Bartel, D. and Szostak, J. W. (1993) Science 261:1411-1418.

Alternatively, 86604 gene expression can be inhibited by targeting nucleotide sequences complementary to the regulatory region of the 86604 (e.g., the 86604 promoter and/or enhancers) to form triple helical structures that prevent transcription of the 86604 gene in target cells. See generally, Helene, C. (1991) Anticancer Drug Des. 6(6): 569-84; Helene, C. et al. (1992) Ann. N.Y. Acad. Sci. 660:27-36; and Maher, L. J. (1992) Bioassays 14(12):807-15.

In yet another embodiment, the 86604 nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) Proc. Natl. Acad. Sci. 93:14670-675.

PNAs of 86604 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of 86604 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe et al. (1996) supra).

In another embodiment, PNAs of 86604 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 86604 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) Nucleic Acids Res. 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) Nucleic Acid Res. 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganic Med. Chem. Lett. 5: 1119-11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

Isolated 86604 Proteins and Anti-86604 Antibodies Used in the Methods of the Invention The methods of the invention include the use of isolated 86604 proteins, and biologically active portions thereof, as well as polypeptide fragments suitable for use as immunogens to raise anti-86604 antibodies. In one embodiment, native 86604 proteins can be isolated from cells or tissue sources by an appropriate purification scheme using standard protein purification techniques. In another embodiment, 86604 proteins are produced by recombinant DNA techniques. Alternative to recombinant expression, a 86604 protein or polypeptide can be synthesized chemically using standard peptide synthesis techniques.

As used herein, a "biologically active portion" of a 86604 protein includes a fragment of a 86604 protein having a 86604 activity. Biologically active portions of a 86604 protein include peptides comprising amino acid sequences sufficiently identical to or derived from the amino acid sequence of the 86604 protein, e.g., the amino acid sequence shown in SEQ ID NO:52, which include fewer amino acids than the full length 86604 proteins, and exhibit at least one activity of a 86604 protein. Typically, biologically active portions comprise a domain or motif with at least one activity of the 86604 protein. A biologically active portion of a 86604 protein can be a polypeptide which is, for example, 25, 50, 75, 100, 125, 150, 175, 200, 250, 300, 350, 400 or more amino acids in length. Biologically active portions of a 86604 protein can be used as targets for developing agents which modulate a 86604 activity.

In a preferred embodiment, the 86604 protein used in the methods of the invention has an amino acid sequence shown in SEQ ID NO:52. In other embodiments, the 86604 protein is substantially identical to SEQ ID NO:52, and retains the functional activity of the protein of SEQ ID NO:52, yet differs in amino acid sequence due to natural allelic variation or mutagenesis, as described in detail in subsection V above. Accordingly, in another embodiment, the 86604 protein used in the methods of the invention is a protein which comprises an amino acid sequence at least about 50%, 55%, 60%, 65%, 70%, 75%, 80%, 85%, 90%, 95%, 96%, 97%, 98%, 99% or more identical to SEQ ID NO:52.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 86604 amino acid sequence of SEQ ID NO:52 having 454 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444-453 (1970)) algorithm which has been incorporated into the GAP program in the GCG software package using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E.

Meyers and W. Miller (Comput. Appl. Biosci. 4:11-17 (1988)) which has been incorporated into the ALIGN program (version 2.0 or 2.0U), using a PAM120 weight residue table, a gap length penalty of 12 and a gap penalty of 4.

The methods of the invention may also use 86604 chimeric or fusion proteins. As used herein, a 86604 "chimeric protein" or "fusion protein" comprises a 86604 polypeptide operatively linked to a non-86604 polypeptide. An "86604 polypeptide" refers to a polypeptide having an amino acid sequence corresponding to a 86604 molecule, whereas a "non-86604 polypeptide" refers to a polypeptide having an amino acid sequence corresponding to a protein which is not substantially homologous to the 86604 protein, e.g., a protein which is different from the 86604 protein and which is derived from the same or a different organism. Within a 86604 fusion protein the 86604 polypeptide can correspond to all or a portion of a 86604 protein. In a preferred embodiment, a 86604 fusion protein comprises at least one biologically active portion of a 86604 protein. In another preferred embodiment, a 86604 fusion protein comprises at least two biologically active portions of a 86604 protein. Within the fusion protein, the term "operatively linked" is intended to indicate that the 86604 polypeptide and the non-86604 polypeptide are fused in-frame to each other. The non-86604 polypeptide can be fused to the N-terminus or C-terminus of the 86604 polypeptide.

For example, in one embodiment, the fusion protein is a GST-86604 fusion protein in which the 86604 sequences are fused to the C-terminus of the GST sequences. Such fusion proteins can facilitate the purification of recombinant 86604.

In another embodiment, this fusion protein is a 86604 protein containing a heterologous signal sequence at its N-terminus. In certain host cells (e.g., mammalian host cells), expression and/or secretion of 86604 can be increased through use of a heterologous signal sequence.

The 86604 fusion proteins used in the methods of the invention can be incorporated into pharmaceutical compositions and administered to a subject in vivo. The 86604 fusion proteins can be used to affect the bioavailability of a 86604 substrate. Use of 86604 fusion proteins may be useful therapeutically for the treatment of disorders caused by, for example, (i) aberrant modification or mutation of a gene encoding a 86604 protein; (ii) mis-regulation of the 86604 gene; and (iii) aberrant post-translational modification of a 86604 protein.

Moreover, the 86604-fusion proteins used in the methods of the invention can be used as immunogens to produce anti-86604 antibodies in a subject, to purify 86604 ligands and in screening assays to identify molecules which inhibit the interaction of 86604 with a 86604 substrate.

Preferably, a 86604 chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A 86604-encoding nucleic acid can be cloned into such an expression vector such that the fusion moiety is linked in-frame to the 86604 protein.

The present invention also pertains to the use of variants of the 86604 proteins which function as either 86604 agonists (mimetics) or as 86604 antagonists. Variants of the 86604 proteins can be generated by mutagenesis, e.g., discrete point mutation or truncation of a 86604 protein. An agonist of the 86604 proteins can retain substantially the same, or a subset, of the biological activities of the naturally occurring form of a 86604 protein. An antagonist of a 86604 protein can inhibit one or more of the activities of the naturally occurring form of the 86604 protein by, for example, competitively modulating a 86604-mediated activity of a 86604 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 86604 protein.

In one embodiment, variants of a 86604 protein which function as either 86604 agonists (mimetics) or as 86604 antagonists can be identified by screening combinatorial libraries of mutants, e.g., truncation mutants, of a 86604 protein for 86604 protein agonist or antagonist activity. In one embodiment, a variegated library of 86604 variants is generated by combinatorial mutagenesis at the nucleic acid level and is encoded by a variegated gene library. A variegated library of 86604 variants can be produced by, for example, enzymatically ligating a mixture of synthetic oligonucleotides into gene sequences such that a degenerate set of potential 86604 sequences is expressible as individual polypeptides, or alternatively, as a set of larger fusion proteins (e.g., for phage display) containing the set of 86604 sequences therein. There are a variety of methods which can be used to produce libraries of potential 86604 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 86604 sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of a 86604 protein coding sequence can be used to generate a variegated population of 86604 fragments for screening and subsequent selection of variants of a 86604 protein. In one embodiment, a library of coding sequence fragments can be generated by treating a double stranded PCR fragment of a 86604 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 86604 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 86604 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 86604 variants (Arkin and Yourvan (1992) Proc. Natl. Acad. Sci. USA 89:7811-7815; Delgrave et al. (1993) Protein Engineering 6(3):327-331).

The methods of the present invention further include the use of anti-86604 antibodies. An isolated 86604 protein, or a portion or fragment thereof, can be used as an immunogen to generate antibodies that bind 86604 using standard techniques for polyclonal and monoclonal antibody preparation. A full-length 86604 protein can be used or, alternatively, antigenic peptide fragments of 86604 can be used as immunogens. The antigenic peptide of 86604 comprises at least 8 amino acid residues of the amino acid sequence shown in SEQ ID NO:52 and encompasses an epitope of 86604 such that an antibody raised against the peptide forms a specific immune complex with the 86604 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 86604 that are located on the surface of the protein, e.g., hydrophilic regions, as well as regions with high antigenicity.

A 86604 immunogen is typically used to prepare antibodies by immunizing a suitable subject, (e.g., rabbit, goat, mouse, or other mammal) with the immunogen. An appropriate immunogenic preparation can contain, for example, recombinantly expressed 86604 protein or a chemically synthesized 86604 polypeptide. The preparation can further include an adjuvant, such as Freund's complete or incomplete adjuvant, or similar immunostimulatory agent. Immunization of a suitable subject with an immunogenic 86604 preparation induces a polyclonal anti-86604 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a 86604. Examples of immunologically active portions of immunoglobulin molecules include F(ab) and F(ab')2 fragments which can be generated by treating the antibody with an enzyme such as pepsin. The invention provides polyclonal and monoclonal antibodies that bind 86604 molecules. The term "monoclonal antibody" or "monoclonal antibody composition", as used herein, refers to a population of antibody molecules that contain only one species of an antigen binding site capable of immunoreacting with a particular epitope of 86604. A monoclonal antibody composition thus typically displays a single binding affinity for a particular 86604 protein with which it immunoreacts.

Polyclonal anti-86604 antibodies can be prepared as described above by immunizing a suitable subject with a 86604 immunogen. The anti-86604 antibody titer in the immunized subject can be monitored over time by standard techniques, such as with an enzyme linked immunosorbent assay (ELISA) using immobilized 86604. If desired, the antibody molecules directed against 86604 can be isolated from the mammal (e.g., from the blood) and further purified by well known techniques, such as protein A chromatography to obtain the IgG fraction. At an appropriate time after immunization, e.g., when the anti-86604 antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with a 86604 immunogen as described above, and the culture supernatants of the resulting hybridoma cells are screened to identify a hybridoma producing a monoclonal antibody that binds 86604.

Any of the many well known protocols used for fusing lymphocytes and immortalized cell lines can be applied for the purpose of generating an anti-86604 monoclonal antibody (see, e.g., G. Galfre et al. (1977) Nature 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 86604, e.g., using a standard ELISA assay.

Alternative to preparing monoclonal antibody-secreting hybridomas, a monoclonal anti-86604 antibody can be identified and isolated by screening a recombinant combinatorial immunoglobulin library (e.g., an antibody phage display library) with 86604 to thereby isolate immunoglobulin library members that bind 86604. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370-1372; Hay et al. (1992) Hum. Antibod. Hybridomas 3:81-85; Huse et al. (1989) Science 246: 1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc. Acid Res. 19:4133-4137; Barbas et al. (1991) Proc. Natl. Acad. Sci. USA 88:7978-7982; and McCafferty et al. (1990) Nature 348:552-554.

Additionally, recombinant anti-86604 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; Shaw et al. (1988) J. Natl. Cancer Inst. 80:1553-1559; Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

An anti-86604 antibody can be used to detect 86604 protein (e.g., in a cellular lysate or cell supernatant) in order to evaluate the abundance and pattern of expression of the 86604 protein. Anti-86604 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, □-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

Electronic Apparatus Readable Media and Arrays

Electronic apparatus readable media comprising a 86604 modulator of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 86604 modulators of the present invention.

A variety of software programs and formats can be used to store the marker information of the present invention on the electronic apparatus readable medium. For example, the nucleic acid sequence corresponding to the 86604 modulators can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the 86604 modulators of the present invention.

By providing the 86604 modulators of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a cellular proliferation disorder or a pre-disposition to a cellular proliferation disorder, wherein the method comprises the steps of determining the presence or absence of a 86604 modulator and based on the presence or absence of the 86604 modulator, determining whether the subject has a cellular proliferation disorder or a pre-disposition to cellular proliferation disorder and/or recommending a particular treatment for the cellular proliferation disorder or pre-cellular proliferation disorder condition.

The present invention further provides in an electronic system and/or in a network, a method for determining whether a subject has a cellular proliferation disorder or a pre-disposition to a cellular proliferation disorder associated with a 86604 modulator wherein the method comprises the steps of determining the presence or absence of the 86604 modulator, and based on the presence or absence of the 86604 modulator, determining whether the subject has a cellular proliferation disorder or a pre-disposition to a cellular proliferation disorder, and/or recommending a particular treatment for the cellular proliferation disorder or pre-cellular proliferation disorder condition. The method may further comprise the step of receiving phenotypic information associated with the subject and/or acquiring from a network phenotypic information associated with the subject.

The present invention also provides in a network, a method for determining whether a subject has a cellular proliferation disorder or a pre-disposition to a cellular proliferation disorder associated with a 86604 modulator, said method comprising the steps of receiving information associated with the 86604 modulator receiving phenotypic information associated with the subject, acquiring information from the network corresponding to the 86604 modulator and/or cellular proliferation disorder, and based on one or more of the phenotypic information, the 86604 modulator, and the acquired information, determining whether the subject has a cellular proliferation disorder or a pre-disposition to a cellular proliferation disorder. The method may further comprise the step of recommending a particular treatment for the cellular proliferation disorder or pre-cellular proliferation disorder condition.

The present invention also provides a business method for determining whether a subject has a cellular proliferation disorder or a pre-disposition to a cellular proliferation disorder, said method comprising the steps of receiving information associated with the 86604 modulator, receiving phenotypic information associated with the subject, acquiring information from the network corresponding to the 86604 modulator and/or cellular proliferation disorder, and based on one or more of the phenotypic information, the 86604 modulator, and the acquired information, determining whether the subject has a cellular proliferation disorder or a pre-disposition to a cellular proliferation disorder. The method may further comprise the step of recommending a particular treatment for the cellular proliferation disorder or pre-cellular proliferation disorder condition.

The invention also includes an array comprising a 86604 modulator of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of cellular proliferation disorder, progression of cellular proliferation disorder, and processes, such a cellular transformation associated with cellular proliferation disorder.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

This invention is further illustrated by the following examples which should not be construed as limiting. The contents of all references, patents and published patent applications cited throughout this application and the Sequence Listing are incorporated herein by reference.

EXAMPLES

Example 1

Tissue Distribution of 86604 mRNA using Taqman™ Analysis

This example describes the tissue distribution of human 86604 mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, including, for example, lung, ovary, breast, and colon tumor samples, and normal samples, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxy-fluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

A human panel comprising normal and tumorigenic tissues indicated broad distribution of human 86604 expression, with highest expression in normal brain cortex. Human 86604 expression was increased 7-fold in colon tumor samples as compared to normal colon tissue samples (Table 5).

TABLE 5

| Sample Number | Tissue Type | Relative Expression |
|---|---|---|
| 1 | Artery normal | 27.489 |
| 2 | Aorta diseased | 6.0872 |
| 3 | Vein normal | 11.2807 |
| 4 | Coronary SMC | 121.1612 |
| 5 | HUVEC | 188.8091 |
| 6 | Hemangioma | 16.12 |
| 7 | Heart normal | 7.4167 |
| 8 | Heart CHF | 5.2992 |
| 9 | Kidney | 58.7202 |
| 10 | Skeletal Muscle | 24.7745 |
| 11 | Adipose normal | 13.4151 |
| 12 | Pancreas | 122.4275 |
| 13 | primary osteoblasts | 41.6656 |
| 14 | Osteoclasts (diff) | 0.1002 |
| 15 | Skin normal | 29.462 |
| 16 | Brain Cortex normal | 230.0469 |
| 17 | Brain Hypothalamus normal | 55.7455 |
| 18 | Nerve | 30.1855 |
| 19 | DRG (Dorsal Root Ganglion) | 18.8407 |
| 20 | Breast normal | 45.4366 |
| 21 | Breast tumor | 11.8826 |
| 22 | Ovary Tumor | 25.471 |
| 23 | Prostate Normal | 34.7944 |
| 24 | Prostate Tumor | 45.5944 |
| 25 | Salivary glands | 9.0366 |
| 26 | Colon normal | 8.6685 |
| 27 | Colon Tumor | 56.1333 |
| 28 | Lung tumor | 84.7878 |
| 29 | Lung COPD | 6.5016 |
| 30 | Colon IBD | 2.3066 |
| 31 | Liver normal | 16.8629 |
| 32 | Liver fibrosis | 17.579 |
| 33 | Spleen normal | 5.7789 |
| 34 | Tonsil normal | 16.9802 |
| 35 | Lymph node normal | 15.1452 |
| 36 | Small intestine normal | 11.9653 |
| 37 | Macrophages | 0.2934 |
| 38 | Synovium | 1.6254 |
| 39 | BM-MNC | 3.4481 |
| 40 | Activated PBMC | 1.5975 |
| 41 | Neutrophils | 8.8814 |
| 42 | Megakaryocytes | 18.7106 |
| 43 | Erythroid | 130.7606 |
| 44 | positive control | 115.8235 |

A xenograft panel comprising breast, colon, lung and ovarian cancer cell lines as well as 293 and 293T cell lines was also tested. As shown in Table 6, expression of human 86604 was detected in cell lines of all origins, e.g., including colon, breast, lung, and ovarian cancer cell lines.

TABLE 6

| Sample Number | Tissue Type | Relative Expression |
|---|---|---|
| 1 | MCF-7 Breast T | 29.26 |
| 2 | ZR75 Breast T | 12.05 |
| 3 | T47D Breast T | 40.81 |
| 4 | MDA 231 Breast T | 3.89 |
| 5 | MDA 435 Breast T | 2.46 |
| 6 | SKBr3 Breast | 7.42 |
| 7 | DLD 1 ColonT (stage C) | 164.94 |
| 8 | SW480 Colon T (stage B) | 5.52 |
| 9 | SW620 ColonT (stage C) | 13.32 |
| 10 | HCT116 | 15.20 |
| 11 | HT29 | 0.66 |
| 12 | Colo 205 | 0.08 |
| 13 | NCIH125 | 11.40 |
| 14 | NCIH67 | 19.51 |
| 15 | NCIH322 | 42.25 |
| 16 | NCIH460 | 0.46 |
| 17 | A549 | 26.64 |
| 18 | NHBE | 39.83 |
| 19 | SKOV-3 ovary | 0.19 |
| 20 | OVCAR-3 ovary | 40.11 |
| 21 | 293 Baby Kidney | 69.11 |
| 22 | 293T Baby Kidney | 221.44 |

An oncology human panel comprising normal and solid tumor samples indicated overexpression of human 86604 in ovarian, lung, and colon tumors as compared to normal ovarian, lung, and colon samples (see Table 7). Notably, four out of four colon tumor samples tested had increased expression of human 86604 as compared to normal colon samples.

TABLE 7

| Sample Number | Tissue Type | Relative Expression |
|---|---|---|
| 1 | PIT 400 Breast N | 3.32 |
| 2 | PIT 372 Breast N | 3.91 |
| 3 | CHT 1228 Breast N | 1.93 |
| 4 | MDA 304 Breast T: MD-IDC | 0.40 |
| 5 | CHT 2002 Breast T: IDC | 0.62 |
| 6 | MDA 236-Breast T: PD-IDC(ILC?) | 0.00 |
| 7 | CHT 562 Breast T: IDC | 0.08 |
| 8 | NDR 138 Breast T ILC (LG) | 0.89 |
| 9 | CHT 1841 Lymph node (Breast met) | 0.52 |
| 10 | PIT 58 Lung (Breast met) | 0.00 |
| 11 | CHT 620 Ovary N | 4.58 |
| 12 | CHT 619 Ovary N | 5.92 |
| 13 | CLN 012 Ovary T | 8.82 |
| 14 | CLN 07 Ovary T | 3.44 |
| 15 | CLN 17 Ovary T | 25.74 |
| 16 | MDA 25 Ovary T | 13.70 |
| 17 | CLN 08 Ovary T | 4.00 |
| 18 | PIT 298 Lung N | 0.11 |
| 19 | MDA 185 Lung N | 0.24 |
| 20 | MPI 215 Lung T--SmC | 2.74 |

TABLE 7-continued

| Sample Number | Tissue Type | Relative Expression |
|---|---|---|
| 21 | MDA 259 Lung T-PDNSCCL | 10.13 |
| 22 | CHT 832 Lung T-PDNSCCL | 0.37 |
| 23 | MDA 262 Lung T-SCC | 50.07 |
| 24 | CHT 793 Lung T-ACA | 0.68 |
| 25 | CHT 331 Lung T-ACA | 3.11 |
| 26 | CHT 405 Colon N | 0.05 |
| 27 | CHT 1685 Colon N | 1.10 |
| 28 | CHT 371 Colon N | 0.17 |
| 29 | CHT 382 Colon T: MD | 7.76 |
| 30 | CHT 528 Colon T: MD | 6.94 |
| 31 | CLN 609 Colon T | 2.27 |
| 32 | NDR 210 Colon T: MD-PD | 15.41 |
| 33 | CHT 340 Colon-Liver Met | 1.44 |
| 34 | CHT 1637Colon-Liver Met | 0.39 |
| 35 | PIT 260 Liver N (female) | 0.25 |
| 36 | CHT 1653 Cervix Squamous CC | 3.30 |
| 37 | CHT 569 Cervix Squamous CC | 0.00 |
| 38 | A24 HMVEC-Arr | 0.70 |
| 39 | C48 HMVEC-Prol | 1.24 |
| 40 | Pooled Hemangiomas | 0.34 |
| 41 | HCT116N22 Normoxic | 19.64 |
| 42 | HCT116H22 Hypoxic | 16.46 |
| 43 | CHT 31 Prostate N | 0.54 |
| 44 | CHT 33 Prostate N | 1.30 |
| 45 | CHT 1269 Prostate T: St 5 | 0.78 |
| 46 | PIT 120 Prostate T: St 7 | 2.61 |

A panel comprising cells from in vitro oncogene cell models was also tested. These oncogene cell models comprise cell lines transiently and stably transfected with tumor suppressors and oncogenes known to be associated with cancer progression, e.g., colon cancer progression. As shown in Table 8, human 86604 is markedly overexpressed in human colon adenocarcinoma cells, e.g., DLD-1 cells, HCT-116 cells.

TABLE 8

| Sample Number | Tissue Type | Relative Expression |
|---|---|---|
| 1 | SMAD4-SW480 C | 7.87 |
| 2 | SMAD4-SW480 24 HR | 32.46 |
| 3 | SMAD4-SW480 48 HR | 29.16 |
| 4 | SMAD4-SW480 72 HR | 12.56 |
| 5 | L51747-MUCINOUS | 33.49 |
| 6 | HT29 NON-MUCINOUS | 1.72 |
| 7 | SW620 NON-MUCINOUS | 18.91 |
| 8 | CSC-1 NORMAL | 13.37 |
| 9 | NCM-460 NORMAL | 23.60 |
| 10 | HCT116 RER+ | 18.45 |
| 11 | SW480 RER−/− | 41.52 |
| 12 | CACO-RER−/− | 23.52 |
| 13 | JDLD-1 | 494.83 |
| 14 | JHCT116 | 83.62 |
| 15 | DKO1 | 333.32 |
| 16 | DKO4 | 395.02 |
| 17 | DKS-8 | 609.21 |
| 18 | HKe3 | 18.84 |
| 19 | HKh2 | 29.16 |
| 20 | HK2-6 | 56.92 |
| 21 | e3Ham#9 | 18.33 |
| 22 | APC5 −/− | 0.00 |
| 23 | APC6−/− | 2.00 |
| 24 | APC1+/+ | 0.31 |
| 25 | APC13+/+ | 0.61 |

A panel comprising normal colon samples, early stage adenocarcinoma samples, colon to liver metastasis samples, and normal liver samples was also tested. As shown in Table 9, expression of human 86604 was upregulated in 8 of 15 colon to liver metastasis samples tested.

TABLE 9

| Sample Number | Tissue Type | Relative Expression |
|---|---|---|
| 1 | CHT 371 Colon N | 0.03 |
| 2 | CHT 523 Colon N | 0.68 |
| 3 | NDR 104 Colon N | 1.16 |
| 4 | CHT 520 Colonic ACA-C | 3.88 |
| 5 | CHT 1365 Colonic ACA-C | 0.36 |
| 6 | CHT 382 Colonic ACA-B | 1.18 |
| 7 | CHT 122 Adenocarcinoma | 3.10 |
| 8 | CHT 077 Liver-Colon Mets | 4.61 |
| 9 | CHT 739 Liver-Colon Mets | 1.51 |
| 10 | CHT 755 Liver-Colon Mets | 2.50 |
| 11 | CHT001 Liver-Colon Mets | 0.71 |
| 12 | CHT 084 Liver-Colon Mets | 1.81 |
| 13 | CHT 113 Liver-Colon Mets | 0.06 |
| 14 | CHT 114 Liver-Colon Mets | 8.09 |
| 15 | CHT 127 Liver-Colon Mets | 9.75 |
| 16 | CHT 218 Liver-Colon Mets | 90.56 |
| 17 | CHT 220 Liver-Colon Mets | 156.58 |
| 18 | CHT 324 Liver-Colon Mets | 67.92 |
| 19 | CHT 530 Liver-Colon Met | 5.64 |
| 20 | CHT 849 Liver-Colon Met | 124.14 |
| 21 | CHT 1637 Liver-Colon Met | 5.51 |
| 22 | CHT131 Liver-Colon Met | 89.93 |
| 23 | NDR 165 Liver Normal | 2.21 |
| 24 | NDR 150 Liver Normal | 64.48 |
| 25 | PIT 236 Liver Normal | 4.63 |

An in vitro synchronized cell cycle panel was also tested (see Table 10). Abnormalities in cell cycle regulation and its checkpoints lead to the development of malignant cells. The loss of a cell's ability to respond to signals that regulate cell proliferation and cell cycle arrest is a common mechanism by which cancer develops. By synchronizing cell lines with drugs which cause cell cycle arrest, time points can be profiled to identify genes which are regulated in various stages of the cell cycle. Rapidly replicating human cells progress though the full cell cycle in about 24 hours (mitosis takes about 30 minutes, G1 takes about 9 hours, the S phase takes about 10 hours, and the G2 phase takes about 4.5 hours). Expression of human 86604 was tested at various time points in several cancer cell lines which were synchronized and induced to enter the cell cycle. Results show expression at all time points and increased expression in DLD-1 cells, which are human adenocarcinoma cells, with highest expression at t=15 hours.

TABLE 10

| Sample Number | Tissue Type | Relative Expression |
|---|---|---|
| 1 | HCT 116 Aphidl t = 0 | 30.50 |
| 2 | HCT 116 Aphidl t = 3 | 25.03 |
| 3 | HCT 116 Aphidl t = 6 | 24.69 |
| 4 | HCT 116 Aphidl t = 9 | 37.94 |
| 5 | HCT 116 Aphidl t = 12 | 37.55 |
| 6 | HCT 116 Aphidl t = 15 | 25.38 |
| 7 | HCT 116 Aphidl t = 18 | 23.04 |
| 8 | HCT 116 Aphidl t = 21 | 32.35 |
| 9 | HCT 116 Aphidl t = 24 | 26.28 |
| 10 | HCT 116 Noc t = 0 | 42.84 |
| 11 | HCT 116 Noc t = 3 | 43.43 |
| 12 | HCT 116 Noc t = 6 | 36.40 |
| 13 | HCT 116 Noc t = 9 | 29.87 |
| 14 | HCT 116 Noc t = 15 | 29.36 |
| 15 | HCT 116 Noc t = 18 | 31.03 |
| 16 | HCT 116 Noc t = 21 | 50.07 |
| 17 | HCT 116 Noc t = 24 | 58.72 |
| 18 | DLD noc t = 3 | 196.15 |
| 19 | DLD noc t = 9 | 246.56 |
| 20 | DLD noc t = 12 | 226.09 |

TABLE 10-continued

| Sample Number | Tissue Type | Relative Expression |
|---|---|---|
| 21 | DLD noc t = 15 | 260.62 |
| 22 | DLD noc t = 18 | 219.91 |
| 23 | DLD noc t = 21 | 209.50 |
| 24 | A549 Mimo t = 0 | 28.66 |
| 25 | A549 Mimo t = 3 | 32.58 |
| 26 | A549 Mimo t = 6 | 27.87 |
| 27 | A549 Mimo t = 9 | 36.91 |
| 28 | A549 Mimo t = 15 | 32.46 |
| 29 | A549 Mimo t = 18 | 27.49 |
| 30 | A549 Mimo t = 21 | 19.78 |
| 31 | A549 Mimo t = 24 | 37.42 |
| 32 | MCF10A Mimo t = 0 | 36.15 |
| 33 | MCF10A Mimo t = 3 | 17.52 |
| 34 | MCF10A Mimo t = 6 | 25.83 |
| 35 | MCF10A Mimo t = 9 | 22.17 |
| 36 | MCF10A Mimo t = 12 | 18.45 |
| 37 | MCF10A Mimo t = 18 | 15.15 |
| 38 | MCF10A Mimo t = 21 | 10.67 |
| 39 | MCF10A Mimo t = 24 | 10.90 |

A colonic ACA panel comprising samples from various stages of colon cancer including stage B adenocarcinoma samples, stage C adenocarcinoma samples, adenoma samples, colon to liver metastasis samples, abdominal colon metastasis samples, normal colon samples, and normal liver samples was also tested (see Table 11). Results show some overexpression of human 86604 in early stage tumors and overexpression of human 86604 in liver metastasis samples.

TABLE 11

| Sample Number | Tissue Type | Relative Expression |
|---|---|---|
| 1 | CHT 410 Colon N | 3.85 |
| 2 | CHT 425 Colon N | 3.83 |
| 3 | CHT 371 Colon N | 3.89 |
| 4 | NDR 211 Colon N | 0.30 |
| 5 | CHT 122 Adenomas | 5.80 |
| 6 | CHT 887 Adenomas | 26.64 |
| 7 | CHT 414 Colonic ACA-B | 4.29 |
| 8 | CHT 841 Colonic ACA-B | 1.78 |
| 9 | CHT 890 Colonic ACA-B | 0.74 |
| 10 | CHT 377 Colonic ACA-B | 2.17 |
| 11 | CHT 520 Colonic ACA-C | 13.46 |
| 12 | CHT 596 Colonic ACA-C | 0.99 |
| 13 | CHT 907 Colonic ACA-C | 4.53 |
| 14 | CHT 372 Colonic ACA-C | 10.27 |
| 15 | NDR 210 Colonic ACA-C | 1.46 |
| 16 | CHT 1365 Colonic ACA-C | 1.19 |
| 17 | CLN 741 Liver N | 7.04 |
| 18 | NDR 165 Liver N | 1.92 |
| 19 | NDR 150 Liver N | 4.04 |
| 20 | PIT 236 Liver N | 1.66 |
| 21 | CHT 1878 Liver N | 3.79 |
| 22 | CHT 119 Col Liver Met | 37.81 |
| 23 | CHT 131 Col Liver Met | 24.10 |
| 24 | CHT 218 Col Liver Met | 16.92 |
| 25 | CHT 739 Col Liver Met | 17.58 |
| 26 | CHT 755 Col Liver Met | 11.32 |
| 27 | CHT 215 Col Abdominal Met | 0.19 |

Analysis of 86604 cDNA expression in HCT-116 human colon carcinoma cells in which the k-ras gene has been disrupted was also investigated. Point mutations that activate the k-ras oncogene are found in 50% of human colon cancers. Disrupting the activated k-ras allele in HCT-116 and DLD-1 cells morphologically alters differentiation, causes loss of anchorage independent growth, slows proliferation in vitro and in vivo and reduces expression of c-myc. Results show that 86604 expression is down regulated when k-ras is disrupted compared to wild type HCT-116 cells, demonstrating that expression of human 86604 is decreased in cells which have slowed proliferation in vitro and in vivo and which exhibit reduced expression of the oncogene c-myc. Therefore, expression 86604 may be regulated by k-ras.

TABLE 12

| Sample Number | Tissue Type | Relative Expression |
|---|---|---|
| 1 | JHCT116 | 83.62 |
| 2 | HK2-6 | 56.92 |
| 3 | HKe3 | 18.84 |
| 4 | HKh2 | 29.16 |

Analysis of 86604 cDNA expression in cell cycle regulated HCT-116 human colon carcinoma cells was also investigated. Cell cycle was regulated by administering mimosine or nocodazole, which regulates the cell cycle in the G1 and G2/M phases, receptively. Results show human 86604 expression during the G2 phase of the cell cycle in HCT-116 cells.

TABLE 13

| Sample Number | Tissue Type | Relative Expression |
|---|---|---|
| 1 | HCT 116 Aphidl t = 0 | 30.50 |
| 2 | HCT 116 Aphidl t = 3 | 25.03 |
| 3 | HCT 116 Aphidl t = 6 | 24.69 |
| 4 | HCT 116 Aphidl t = 9 | 37.94 |
| 5 | HCT 116 Aphidl t = 12 | 37.55 |
| 6 | HCT 116 Aphidl t = 15 | 25.38 |
| 7 | HCT 116 Aphidl t = 18 | 23.04 |
| 8 | HCT 116 Aphidl t = 21 | 32.35 |
| 9 | HCT 116 Aphidl t = 24 | 26.28 |
| 10 | HCT 116 Noc t = 0 | 42.84 |
| 11 | HCT 116 Noc t = 3 | 43.43 |
| 12 | HCT 116 Noc t = 6 | 36.40 |
| 13 | HCT 116 Noc t = 9 | 29.87 |
| 14 | HCT 116 Noc t = 15 | 29.36 |
| 15 | HCT 116 Noc t = 18 | 31.03 |
| 16 | HCT 116 Noc t = 21 | 50.07 |
| 17 | HCT 116 Noc t = 24 | 58.72 |

The foregoing data reveal a significant up-regulation of 86604 mRNA in carcinomas, in particular colon carcinomas, colon metastases to the liver, ovary carcinomas, and lung carcinomas. Moreover, these data link the expression of 86604 with cellular proliferation. Given that 86604 is expressed in a variety of tumors, with significant up-regulation in tumor samples as compared to normal samples, and that 86604 is expressed during cellular proliferation, it is believed that inhibition of 86604 activity may inhibit tumor formation or progression, especially in colon, ovarian, or lung tumors.

Example 2

Tissue Distribution of 86604 mRNA Using In Situ Analysis

For in situ analysis, various tissues, e.g., tissues obtained from normal colon, liver, breast, and lung and colon, breast, and lung tumors, and colon metastases to the liver were first frozen on dry ice. Ten-micrometer-thick sections of the tissues were post-fixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with 35S-radiolabeled (5×107 cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

In situ hybridization results indicated expression in none of two normal colon tissue samples tested, in one of one adenoma sample tested, three of five colon tumor samples tested, three of five liver metastases to the liver tested, and in none of two normal liver samples tested. Results further indicate no expression in one normal breast tissue sample tested and moderate expression in one of two breast tumor tissue samples tested. Results also indicated no expression in one normal lung tissue tested, and moderate expression in one of three lung tumor tissues tested. These results, which confirm the expression pattern shown by Taqman analysis described above, indicate that 86604 is differentially expressed in colon tumors and liver metastases as compared to normal colon and liver tissue; in breast tumors as compared to normal breast tissue; and in lung tumors as compared to normal lung tissue. Therefore, inhibition of 86604 may inhibit tumor progression or formation, especially in colon tumors.

Example 3

Expression of Recombinant 86604 Protien in Bacterial Cells

In this example, human 86604 is expressed as a recombinant glutathione-S-transferase (GST) fusion polypeptide in *E. coli* and the fusion polypeptide is isolated and characterized. Specifically, 86604 is fused to GST and this fusion polypeptide is expressed in *E. coli*, e.g., strain PEB199. Expression of the GST-86604 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 86604 Protien in COS Cells

To express the human 86604 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 86604 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 86604 DNA sequence is amplified by PCR using two primers. The 5' primer contains the restriction site of interest followed by approximately twenty nucleotides of the 86604 coding sequence starting from the initiation codon; the 3' end sequence contains complementary sequences to the other restriction site of interest, a translation stop codon, the HA tag or FLAG tag and the last 20 nucleotides of the 86604 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 86604 gene is inserted in the correct orientation. The ligation mixture is transformed into *E. coli* cells (strains HB101, DH5□, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 86604-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 86604 polypeptide is detected by radiolabelling (35S-methionine or 35S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with 35S-methionine (or 35S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific monoclonal antibody. Precipitated polypeptides are then analyzed by SDS-PAGE.

Alternatively, DNA containing the 86604 coding sequence is cloned directly into the polylinker of the pcDNA/Amp vector using the appropriate restriction sites. The resulting plasmid is transfected into COS cells in the manner described above, and the expression of the 86604 polypeptide is detected by radiolabelling and immunoprecipitation using an 86604 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

VI. METHODS AND COMPOSITIONS FOR THE TREATMENT AND DIAGNOSIS OF CELLULAR PROLIFERATIVE DISORDERS USING 32222

Background of the Invention

The present invention provides methods and compositions for the diagnosis and treatment of cellular proliferative disorders (e.g., tumorigenic disease, such as, lung tumors, colon tumors, ovarian tumors and breast tumors). The present invention is based, at least in part, on the discovery that the hydrolase 32222 is differentially expressed in tumor tissue samples as compared to its expression in normal tissue samples which express wild-type p53. Specifically, the expression of 32222 was repressed upon activation of an engineered p53/estrogen-receptor fusion protein in H125 (lung tumor) cells. The correlation between p53 activation and 32222 down-regulation was confirmed using Taqman™ analysis. The present invention is also based, at least in part, on the discovery that the 32222 gene is significantly upregulated in breast, lung, and colon tumors, as compared to normal tissue from these organs.

In one aspect, the invention provides methods for identifying a compound capable of treating a cellular proliferative disorder, e.g., lung tumors, colon tumors, and breast tumors. The method includes assaying the ability of the compound to modulate 32222 nucleic acid expression or 32222 polypeptide activity. In one embodiment, the ability of the compound to modulate 32222 nucleic acid expression or 32222 polypeptide activity is determined by detecting modulation of cellular proliferation. In another embodiment, the ability of the compound to modulate 32222 nucleic acid expression or 32222 polypeptide activity is determined by detecting modulation of the breakdown of a metabolic intermediate, e.g., a polypeptide, a nucleic acid, or a lipid in a cell.

In another aspect, the invention provides methods for identifying a compound capable of modulating a cellular growth, differentiation or proliferation process in a cell. The method includes contacting a cell expressing a 32222 nucleic acid or polypeptide (e.g., an epithelial cell derived from lung, breast, or colon tissues) with a test compound and assaying the ability of the test compound to modulate the expression of a 32222 nucleic acid or the activity of a 32222 polypeptide.

In a further aspect, the invention features a method for modulating a cellular growth, differentiation or proliferation process in a cell. The method includes contacting a cell (e.g., a lung, breast, or a colon cell) with a 32222 modulator, for example, an anti-32222 antibody, a 32222 polypeptide comprising the amino acid sequence of SEQ ID NO:54, or a fragment thereof, a 32222 polypeptide comprising an amino acid sequence which is at least 90 percent identical to the amino acid sequence of SEQ ID NO:54, an isolated naturally occurring allelic variant of a polypeptide consisting of the amino acid sequence of SEQ ID NO:54, a small molecule, an antisense 32222 nucleic acid molecule, a nucleic acid molecule of SEQ ID NO:55 or 56, or a fragment thereof, or a ribozyme.

In yet another aspect, the invention features a method for treating a subject having a cellular proliferative disorder, e.g., a cellular proliferative disorder characterized by aberrant 32222 polypeptide activity or aberrant 32222 nucleic acid expression, such as, a lung tumor, an ovarian tumor, a colon tumor, or a breast tumor. The method includes administering to the subject a therapeutically effective amount of a 32222 modulator (e.g., using a pharmaceutically acceptable formulation or a gene therapy vector). In one embodiment, the 32222 modulator may be a small molecule, an anti-32222 antibody, a 32222 polypeptide comprising the amino acid sequence of SEQ ID NO:54, or a fragment thereof, a 32222 polypeptide comprising an amino acid sequence which is at least 90 percent identical to the amino acid sequence of SEQ ID NO:54, an isolated naturally occurring allelic variant of a polypeptide consisting of the amino acid sequence of SEQ ID NO:54, an antisense 32222 nucleic acid molecule, a nucleic acid molecule of SEQ ID NO:55 or 56, or a fragment thereof, or a ribozyme.

In another aspect, the invention provides a method for modulating, e.g., increasing or decreasing, cellular proliferation in a subject by administering to the subject a 32222 modulator.

Other features and advantages of the invention will be apparent from the following detailed description and claims.

Table 14 shows reduced expression of 32222 in NCI-H125 lung tumor cells expressing the p53 tumor suppressor gene (H125 p53) as compared to a vector only control (H125 vector), as determined by transcriptional profiling analysis.

Table 15 shows reduced expression of 32222 in NCI-H125 lung tumor cells expressing the p53 tumor suppressor gene (H125 p53) as compared to a vector only control (H125 vector), at 96 hours after transient p53 activation.

Table 16 shows 32222 expression in a lung model panel. 3222 expression was analyzed in different clinical samples, such as, lung tumors or cell lines, e.g., H69 (small cell lung carcinoma), NCI-H125 (lung tumor cells expressing wild-type p53) or H125 p53ER (lung tumor cells which express inducible p53ER protein).

Table 17 shows 32222 expression in epithelial cells derived from normal and tumorigenic lung, breast, ovary, and colon tissues.

Table 18 shows 32222 mRNA expression in various tissues using Taqman™ analysis.

Table 19 shows 32222 expression in xenograph-friendly cells.

Table 20 shows 32222 expression in tumor and normal tissues derived from various tissues.

TABLE 14

| Sample | Relative Expression |
|---|---|
| p53ER day2 + 4HT | 0.73 |
| p53ER day2 untreat | 5.39 |
| pERvc day2 + 4HT | 4.14 |
| pERvc day2 untreat | 3.77 |

TABLE 15

| Tissue Type | Relative Expression |
|---|---|
| H125 Incx 96 hr | 15.15 |
| H125 p53 96 hr | 4.55 |

TABLE 16

| Tissue Type | Relative Expression |
|---|---|
| NHBE | 16.7 |
| A549 (BA) | 18.7 |
| H460 (LCLC) | 14.4 |
| H23 (AC) | 15.1 |
| H522 (AC) | 94.5 |
| H125 (AC/SCC) | 37.6 |
| H520 (SCC) | 22 |
| H69 (SCLC) | 29.7 |
| H345 (SCLC) | 27.4 |
| H460 INCX 24 hr | 21.2 |
| H460 p16 24 hr | 17.1 |
| H460 INCX 48 hr | 30.1 |
| H460 p16 48 hr | 21.7 |
| H460 INCX Stable Plas | 15.9 |
| H460 p16 Stable Plas | 14.8 |
| H460 NA-Agar | 17.5 |
| H460 Incx stable Agar | 19.6 |
| H460 p16 stable Agar | 19.9 |
| H125 Incx 96 hr | 11.6 |
| H125 p53 96 hr | 12.7 |
| H345 Mock 144 hr | 23.2 |
| H345 Gluc 144 hr | 34.9 |
| H345 VIP 144 hr | 18.8 |

TABLE 17

| Tissue Type | Relative Expression |
|---|---|
| PIT 400 Breast N | 10.60 |
| ONC 038 Breast N | 2.66 |
| CHT 1228 Breast N | 8.82 |
| NDR 005 Breast Tum: IDC-MD/PD | 24.35 |
| CHT 2002 Breast T: IDC | 7.39 |
| CHT 564 Breast Tum: IDC-PD | 26.74 |
| CHT 562 Breast T: IDC | 1.74 |
| NDR 138 Breast T ILC (LG) | 19.71 |
| CHT 1841 Lymph node (Breast met) | 2.56 |
| PIT 58 Lung (Breast met) | 0.75 |
| CHT 620 Ovary N | 7.26 |
| CHT 619 Ovary N | 12.05 |
| CLN 012 Ovary T: PD-PS | 14.78 |
| CHT 2432 Ovary T: MD-PS | 2.57 |
| CLN 17 Ovary T: PD-PS | 8.29 |
| CHT 2434 Ovary T: PD-AC | 9.79 |
| CLN 08 Ovary T: MD/PD-PS | 1.77 |
| PIT 298 Lung N | 0.26 |
| PIT 270 Lung N | 0.19 |
| CLN 930 Lung N | 1.64 |
| MPI 215 Lung T--SmC | 25.65 |
| CHT 793 Lung T: MD-SCC | 6.11 |
| CHT 832 Lung T: PD-NSCLC | 1.01 |
| CHT 211 Lung T: WD-AC | 8.43 |
| CHT 1371 Lung T: MD-AC | 2.18 |
| CHT 331 Lung T: MD-AC | 3.89 |
| NDR 104 Colon N | 2.61 |
| CHT 1685 Colon N | 2.06 |
| CHT 371 Colon N | 2.86 |
| CHT 382 Colon T: MD | 14.38 |
| CHT 528 Colon T: MD | 14.58 |
| CLN 609 Colon T | 2.13 |
| NDR 210 Colon T: MD-PD | 16.35 |
| CHT 340 Colon-Liver Met | 15.46 |
| CHT 1637Colon-Liver Met | 5.62 |
| PIT 260 Liver N (female) | 0.45 |
| CHT 1653 Cervix Squamous CC | 5.88 |
| CHT 569 Cervix Squamous CC | 0.12 |
| A24 HMVEC-Arr | 2.70 |
| C48 HMVEC-Prol | 4.07 |
| Pooled Hemangiomas | 0.24 |
| HCT116N22 Normoxic | 27.02 |
| HCT116H22 Hypoxic | 19.92 |

TABLE 18

| Tissue Type | Relative Expression |
|---|---|
| Artery normal | 1.4649 |
| Aorta diseased | 0 |
| Vein normal | 0.4063 |
| Coronary SMC | 5.7389 |
| HUVEC | 16.8046 |
| Hemangioma | 1.7121 |
| Heart normal | 0.8043 |
| Heart CHF | 12.6038 |
| Kidney | 34.3154 |
| Skeletal Muscle | 19.8461 |
| Liver normal | 12.5602 |
| Small intestine normal | 3.4962 |
| Adipose normal | 9.7526 |
| Pancreas | 13.139 |
| primary osteoblasts | 4.03 |
| Bladder-Female normal | 0.3574 |
| Adrenal Gland normal | 11.2807 |
| Pituitary Gland normal | 8.3732 |
| Spinal cord normal | 3.1619 |
| Brain Cortex normal | 13.2763 |
| Brain Hypothalamus normal | 9.585 |
| Nerve | 0 |
| DRG (Dorsal Root Ganglion) | 4.3493 |
| Breast normal | 5.6599 |
| Breast tumor/IDC | 2.5241 |
| Ovary normal | 0.7401 |
| Ovary Tumor | 4.41 |
| Prostate BPH | 1.6827 |
| Prostate Adenocarcinoma | 8.4607 |
| Colon normal | 4.8259 |
| Colon Adenocarcinoma | 5.4861 |
| Lung normal | 0.1775 |
| Lung tumor | 18.9718 |
| Lung COPD | 0.2004 |
| Colon IBD | 0 |
| Synovium | 0 |
| Tonsil normal | 0.2318 |
| Lymph node normal | 0.5609 |
| Liver fibrosis | 26.1871 |
| Spleen normal | 0 |
| Macrophages | 0 |
| Progenitors (erythroid, megakaryocyte, neutrophil) | 2.3227 |
| Megakaryocytes | 0 |
| Activated PBMC | 0.016 |
| Neutrophils | 0 |
| Erythroid | 21.0505 |
| positive control | 15.0928 |

TABLE 19

| Tissue Type | Relative Expression |
|---|---|
| MCF-7 Breast T | 161.0 |
| ZR75 Breast T | 105.8 |
| T47D Breast T | 38.2 |
| MDA 231 Breast T | 25.8 |
| SKBr3 Breast | 27.7 |
| DLD 1 ColonT (stage C) | 52.7 |
| SW480 Colon T (stage B) | 23.1 |
| HCT116 | 46.2 |
| HT29 | 9.5 |
| Colo 205 | 10.2 |
| NCIH125 | 49.4 |
| NCIH67 | 75.1 |
| NCIH322 | 42.4 |
| NCIH460 | 17.1 |
| A549 | 106.9 |
| NHBE | 64.9 |
| SKOV-3 ovary | 6.2 |
| OVCAR-3 ovary | 12.7 |

TABLE 20

| Tissue Type | Relative Expression |
|---|---|
| PIT 400 Breast N | 10.60 |
| ONC 038 Breast N | 2.66 |
| CHT 1228 Breast N | 8.82 |
| NDR 005 Breast Tum: IDC-MD/PD | 24.35 |
| CHT 2002 Breast T: IDC | 7.39 |
| CHT 564 Breast Tum: IDC-PD | 26.74 |
| CHT 562 Breast T: IDC | 1.74 |
| NDR 138 Breast T ILC (LG) | 19.71 |
| CHT 1841 Lymph node (Breast met) | 2.56 |
| PIT 58 Lung (Breast met) | 0.75 |
| CHT 620 Ovary N | 7.26 |
| CHT 619 Ovary N | 12.05 |
| CLN 012 Ovary T: PD-PS | 14.78 |
| CHT 2432 Ovary T: MD-PS | 2.57 |
| CLN 17 Ovary T: PD-PS | 8.29 |
| CHT 2434 Ovary T: PD-AC | 9.79 |
| CLN 08 Ovary T: MD/PD-PS | 1.77 |
| PIT 298 Lung N | 0.26 |
| PIT 270 Lung N | 0.19 |
| CLN 930 Lung N | 1.64 |
| MPI 215 Lung T--SmC | 25.65 |
| CHT 793 Lung T: MD-SCC | 6.11 |
| CHT 832 Lung T: PD-NSCLC | 1.01 |
| CHT 211 Lung T: WD-AC | 8.43 |
| CHT 1371 Lung T: MD-AC | 2.18 |
| CHT 331 Lung T: MD-AC | 3.89 |
| NDR 104 Colon N | 2.61 |
| CHT 1685 Colon N | 2.06 |
| CHT 371 Colon N | 2.86 |
| CHT 382 Colon T: MD | 14.38 |
| CHT 528 Colon T: MD | 14.58 |
| CLN 609 Colon T | 2.13 |
| NDR 210 Colon T: MD-PD | 16.35 |
| CHT 340 Colon-Liver Met | 15.46 |
| CHT 1637Colon-Liver Met | 5.62 |
| PIT 260 Liver N (female) | 0.45 |
| CHT 1653 Cervix Squamous CC | 5.88 |
| CHT 569 Cervix Squamous CC | 0.12 |
| A24 HMVEC-Arr | 2.70 |
| C48 HMVEC-Prol | 4.07 |
| Pooled Hemangiomas | 0.24 |
| HCT116N22 Normoxic | 27.02 |
| HCT116H22 Hypoxic | 19.92 |

The present invention provides methods and compositions for the diagnosis and treatment of cellular proliferative disorders, e.g., lung tumors, ovarian tumors, colon tumors, and breast tumors. p53 tumor suppressor gene mutations occur with high frequency in a broad spectrum of human cancers (Hollstein M. D. et al., (1991) Science 253: 49-53). Germ-line mutations of the p53 gene (the L1-Fraumeni syndrome) predispose a subject to diverse types of cancers (Malkin D. et al., (1990) Science 250: 1233-1238). A normal cell has a low level of the p53 protein, because of the short half-life of this protein, and the fact that this protein is typically found in a latent form. The levels and activity of p53 increase in response to cellular stress, such as DNA damage by irradiation or chemotherapeutic agents, activation of oncogenes or viral infection, hypoxia, or very low levels of ribonucleoside triphosphate pools. Subsequently, activated p53 mediates cell cycle arrest or programmed cell death (apoptosis), depending on the cell type or the presence of activated oncogenes. This results in the elimination of clones of cells that contain mutations and the prevention of a high mutation rate in cells (Levine A. J. (1997) Cell 88: 323-331; Prives C. and Hall P. A. (1999) J. Pathol. 187: 112-126). Wild-type p53 has been shown to block the transformation by activated oncogenes and inhibit tumor cell growth in vitro (Finlay C. P. et al., (1989) Cell 57: 1083-1093; Michalovitz D. et al., (1990) Cell 62: 671-680). Additionally, p53's function as a tumor suppressor is supported by the observation that p53 null mice, generated by homologous targeting, are susceptible to spontaneous development of tumors at a young age (Lozano G., and Liu G. (1998) Semin. Cancer Biol. 8: 337-344).

Among the genes that are down-regulated by p53 are genes which are members of the hydrolase family. It has been demonstrated that tumors occurring in mice which overexpress MMTV-v-Ha-ras or MMTV-c-myc transgenes or mice heterozygous for p53 gene disruption, all show elevated thymidine-DNA glycosylase and methyl transferase expression specific to the transformed tissue (Niederreither K. et al., (1998) Oncogene 17, 1577-85).

Hydrolases play important roles in the synthesis and breakdown of nearly all major metabolic intermediates, including polypeptides, nucleic acids, and lipids. As such, their activity contributes to the ability of the cell to grow and differentiate, to proliferate, to adhere and move, and to interact and communicate with other cells. Hydrolases also are important in the conversion of pro-proteins and pro-hormones to their active forms, the inactivation of peptides, the biotransformation of compounds (e.g., a toxin or carcinogen), antigen presentation, and the regulation of synaptic transmission.

The present invention is based, at least in part, on the discovery that the hydrolase 32222 is differentially expressed in tumor tissue samples as compared to its expression in normal tissue samples which express wild-type p53. Specifically, the expression of 32222 was repressed upon activation of an engineered p53/estrogen-receptor fusion protein in H125 (lung tumor) cells. The correlation between p53 activation and 32222 down-regulation was confirmed using Taqman™ analysis. The present invention is also based, at least in part, on the discovery that the 32222 gene is significantly upregulated in breast, lung, and colon tumors, as compared to normal tissue from these organs (see Table 17).

Accordingly, the present invention provides methods and compositions for treating, diagnosing or prognosing cellular proliferative disorders. As used herein, a "cellular proliferation disorder" includes a disease or disorder that affects a cellular growth, differentiation, or proliferation process. As used herein, a "cellular growth, differentiation or proliferation process" is a process by which a cell increases in number, size or content, by which a cell develops a specialized set of characteristics which differ from that of other cells, or by which a cell moves closer to or further from a particular location or stimulus. A cellular growth, differentiation, or proliferation process includes amino acid transport and degradation and other metabolic processes of a cell. A cellular proliferation disorder may be characterized by aberrantly regulated cellular growth, proliferation, differentiation, or migration. Cellular proliferation disorders include tumorigenic disease or disorders. As used herein, a "tumorigenic disease or disorder" includes a disease or disorder characterized by aberrantly regulated cellular growth, proliferation, differentiation, adhesion, or migration, which may result in the production of or tendency to produce tumors. As used herein, a "tumor" includes a normal benign or malignant mass of tissue. Examples of cellular growth or proliferation disorders include, but are not limited to, cancer, e.g., carcinoma, sarcoma, or leukemia, examples of which include, but are not limited to, colon, ovarian, lung, breast, endometrial, uterine, hepatic, gastrointestinal, prostate, and brain cancer; tumorigenesis and metastasis; skeletal dysplasia; and hematopoietic and/or myeloproliferative disorders.

"Differential expression", as used herein, includes both quantitative as well as qualitative differences in the temporal and/or tissue expression pattern of a gene. Thus, a differentially expressed gene may have its expression activated or inactivated in normal versus tumorigenic disease conditions (for example, in an experimental tumorigenic disease system). The degree to which expression differs in normal versus tumorigenic disease or control versus experimental states need only be large enough to be visualized via standard characterization techniques, e.g., quantitative PCR, Northern analysis, or subtractive hybridization. The expression pattern of a differentially expressed gene may be used as part of a prognostic or diagnostic tumorigenic disease evaluation, or may be used in methods for identifying compounds useful for the treatment of tumorigenic disease. In addition, a differentially expressed gene involved in a tumorigenic disease may represent a target gene such that modulation of the level of target gene expression or of target gene product activity may act to ameliorate a tumorigenic disease condition. Compounds that modulate target gene expression or activity of the target gene product can be used in the treatment of tumorigenic disease.

The present invention is based, at least in part, on the discovery of a hydrolase molecule, referred to herein as "32222" nucleic acid and protein molecule, is differentially regulated by the p53 gene. 32222 molecule is a member of a family of enzymes which are capable of catalyzing the hydrolytic cleavage of a chemical bond (e.g., a chemical bond within a biological molecule). Thus, this 32222 molecule may play a role in or function in a variety of metabolic and cellular processes, e.g., proliferation, growth, differentiation, migration, survival and in tumorigenic disease, e.g., lung tumors, ovarian tumors, colon tumors, and breast tumors.

As used herein, the term "hydrolase" includes a molecule which is involved in the hydrolytic cleavage of a bond within a biological molecule (e.g., a peptide, a lipid, or a nucleic acid). Hydrolase molecules are involved in the anabolism and catabolism of metabolically important biomolecules, including the metabolism of biochemical molecules necessary for energy production or storage, and for intra- or inter-cellular signaling, as well as the detoxification of potentially harmful compounds (e.g., toxins, carcinogens). Examples of hydrolases include fungal, bacterial and pancreatic lipases, acetylcholinesterases, serine carboxypeptidases, haloalkane dehalogenases, dienelactone hydrolases, A2 bromoperoxidases, and thioesterases. As hydrolases, the 32222 molecules provide methods and compositions for developing diagnostic targets and therapeutic agents to control hydrolase-associated disorders.

As used interchangeably herein, an "32222 activity", "biological activity of 32222" or "32222-mediated activity", includes an activity exerted by a 32222 protein, polypeptide or nucleic acid molecule on a 32222 responsive cell or tissue, or on a 32222 protein substrate, as determined in vivo, or in vitro, according to standard techniques. In one embodiment, a 32222 activity is a direct activity, such as an association with a 32222 target molecule. As used herein, a "target molecule" or "binding partner" is a molecule with which a 32222 protein binds or interacts in nature, such that 32222 mediated function is achieved. A 32222 target molecule can be a non-32222 molecule or a 32222 protein or polypeptide. In an exemplary embodiment, a 32222 target molecule is a 32222 substrate (e.g., a peptide, a lipid, a nucleic acid, or a vitamin). Alternatively, a 32222 activity is an indirect activity, such as a cellular signaling activity mediated by interaction of the 32222 protein with a 32222 ligand or substrate. The biological activities of 32222 are described herein. For example, 32222 molecules may have one or more of the following activities: (1) they modulate the cleavage, e.g., hydrolytic cleavage, of a chemical bond within a biochemical molecule; (2) they cleave a biochemical molecule that is associated with the regulation of one or more cellular processes, such as a peptide, a nucleic acid, a lipid or a vitamin, (3) they modulate the anabolism and catabolism of metabolically important biomolecules, including the metabolism of biochemical molecules necessary for energy production or storage, and for intra- or inter-cellular signaling, as well as the detoxification of potentially harmful compound.

Screening Assays:

The invention provides a method (also referred to herein as a "screening assay") for identifying modulators, i.e., candidate or test compounds or agents (e.g., peptides, peptidomimetics, small molecules or other drugs) which bind to 32222 proteins, have a stimulatory or inhibitory effect on, for example, 32222 expression or 32222 activity, or have a stimulatory or inhibitory effect on, for example, the expression or activity of a 32222 substrate.

Compounds identified via assays such as those described herein may be useful, for example, for ameliorating a 32222 associated disorder, such as, a cellular proliferative disorder, e.g., cancer. In instances whereby a cellular proliferative disorder results from an overall lower level of 32222 gene expression and/or 32222 protein in a cell or tissue, compounds which accentuate or amplify the expression and/or activity of the 32222 protein may ameliorate symptoms. In other instances, mutations within the 32222 gene may cause aberrant types or excessive amounts of 32222 proteins to be made which have a deleterious effect that leads to a cellular proliferative disease. Similarly, physiological conditions may cause an increase in 32222 gene expression leading to a cellular proliferative disease. In such cases, compounds that inhibit or decrease the expression and/or activity of 32222 may ameliorate symptoms. Assays for testing the effectiveness of compounds identified by techniques are discussed herein.

In one embodiment, the invention provides assays for screening candidate or test compounds which are substrates of a 32222 protein or polypeptide or biologically active portion thereof (e.g., peptides, lipids, or nucleic acids). In another embodiment, the invention provides assays for screening candidate or test compounds which bind to or modulate the activity of a 32222 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al., (1993) Proc. Natl. Acad. Sci. U.S.A. 90:6909; Erb et al., (1994) Proc. Natl. Acad. Sci. USA 91:11422; Zuckermann et al., (1994). J. Med. Chem. 37:2678; Cho et al., (1993) Science 261:1303; Carrell et al., (1994) Angew. Chem. Int. Ed. Engl. 33:2059; Carell et al., (1994) Angew. Chem. Int. Ed. EngI. 33:2061; and in Gallop et al., (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al., (1992) Proc Natl Acad Sci USA 89:1865-1869) or on phage (Scott and Smith (1990) Science 249:386-390); (Devlin (1990) Science 249:404-406); (Cwirla et al., (1990) Proc. Natl. Acad. Sci. 87:6378-6382); (Felici (1991) J. Mol. Biol. 222:301-310); (Ladner supra.).

In one embodiment, an assay is a cell-based assay in which a cell which expresses a 32222 protein or biologically active portion thereof is contacted with a test compound and the ability of the test compound to modulate 32222 activity is determined. Determining the ability of the test compound to modulate 32222 activity can be accomplished by monitoring, for example, cell progression through the cell cycle, or the production of one or more specific metabolites in a cell which expresses 32222. The cell, for example, can be of mammalian origin, e.g., an epithelial cell. The ability of the test compound to modulate 32222 binding to a substrate (e.g., a peptide, lipid or nucleic acid) or to bind to 32222 can also be determined. Determining the ability of the test compound to modulate 32222 binding to a substrate can be accomplished, for example, by coupling the 32222 substrate with a radioisotope or enzymatic label such that binding of the 32222 substrate to 32222 can be determined by detecting the labeled 32222 substrate in a complex.

Cellular proliferation assays that may be used to identify compounds that modulate 32222 activity include assays such as the acid phosphatase assay for cell number as described in Connolly et al. (1986) Anal. Biochem. 152, 136-140 and the MTT assay as described in Loveland, B. E. et al., (1992) Biochem. Int., 27:501-510, which utilizes colorimetric assays to quantitate viable cells, e.g., the cellular reduction of the tetrazolium salt, MTT, to formazan by mitochondrial succinate dehydrogenase. Other assays for cellular proliferation include clonogenic assays, assays for 3H-thymidine uptake, assays measuring the incorporation of radioactively labeled nucleotides into DNA, or other assays which are known in the art for measuring cellular proliferation. Moreover, inhibition of cellular growth in vivo, e.g., in a patient with cancer, can be detected by any standard method for detecting tumors such as by x-ray or imaging analysis of a tumor size, or by observing a reduction in mutant p53 protein production or in the production of any known cell-specific or tumor marker within a biopsy or tissue sample. Determining the ability of a test compound to modulate 32222 activity can be accomplished by monitoring, for example, cell progression through the cell cycle. For example, the cell can be a tumor cell, e.g., a colon tumor cell, a lung tumor cell, or an ovary tumor cell.

In one aspect, an assay is a cell-based assay in which a cell which expresses a 32222 protein or biologically active portion thereof is contacted with a test compound and the ability of the test compound to modulate 32222 activity is determined. In a preferred embodiment, the biologically active portion of the 32222 protein includes a domain or motif that can modulate amino acid transport or degradation, cellular metabolism, or cellular growth or proliferation. Determining the ability of the test compound to modulate 32222 activity can be accomplished by monitoring, for example, the production of one or more specific metabolites (e.g., the hydrolytic cleavage of N-glycosidic bond can be monitored by kinetic isotope measurements) in a cell which expresses 32222 (see, e.g., Werner R. M et al. (2000) Biochemistry 21: 14054-64) or by monitoring cell metabolism, cellular growth, cellular proliferation, or cellular differentiation. The cell, for example, can be of mammalian origin, e.g., a tumor cell such as a lung, ovary, or colon tumor cell.

In another embodiment, an assay is a cell-based assay comprising contacting a cell expressing wild-type p53 regulated 32222 protein or biologically active portion is contacted with a test compound and determining the ability of the test compound to modulate 32222 activity. Determining the ability of the test compound to modulate 32222 activity can be accomplished by monitoring, for example, cell progression through the cell cycle, or the production of one or more specific metabolites in a cell which expresses 32222. The cell, for example, can be of mammalian origin, e.g., an epithelial cell. The ability of the test compound to modulate 32222 binding to a substrate (e.g., a peptide, lipid or nucleic acid) or to bind to 32222 can also be determined. Determining the ability of the test compound to modulate 32222 binding to a substrate can be accomplished, for example, by coupling the 32222 substrate with a radioisotope or enzymatic label such that binding of the 32222 substrate to 32222 can be determined by detecting the labeled 32222 substrate in a complex. In yet another embodiment, an assay is a cell-based assay in which a cell (e.g., a cell which lacks p53 expression) which expresses a 32222 protein or biologically active portion thereof is contacted with a test compound and the ability of the test compound to modulate 32222 activity is determined. Determining the ability of the test compound to modulate 32222 activity can be accomplished by monitoring, for example, cell progression through the cell cycle, or the production of one or more specific metabolites. The cell, for example, can be of mammalian origin, e.g., an epithelial cell. The ability of the test compound to modulate 32222 binding to a substrate (e.g., a peptide, lipid or nucleic acid) or to bind to 32222 can also be determined. Determining the ability of the test compound to modulate 32222 binding to a substrate can be accomplished, for example, by coupling the 32222 substrate with a radioisotope or enzymatic label such that binding of the 32222 substrate to 32222 can be determined by detecting the labeled 32222 substrate in a complex.

Alternatively, 32222 could be coupled with a radioisotope or enzymatic label to monitor the ability of a test compound to modulate 32222 binding to a 32222 substrate in a complex. Determining the ability of the test compound to bind 32222 can be accomplished, for example, by coupling the compound with a radioisotope or enzymatic label such that binding of the compound to 32222 can be determined by detecting the labeled compound in a complex. For example, compounds (e.g., 32222 substrates) can be labeled with 125I, 35S, 14C, or 3H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a 32222 substrate) to interact with 32222 without the labeling of any of the interactants. For example, a microphysiometer can be used to detect the interaction of a compound with 32222 without the labeling of either the compound or the 32222. McConnell, H. M. et al., (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 32222.

In another embodiment, an assay is a cell-based assay comprising contacting a cell expressing a 32222 target molecule (e.g., a 32222 substrate) with a test compound and determining the ability of the test compound to modulate (e.g., stimulate or inhibit) the activity of the 32222 target molecule. Determining the ability of the test compound to modulate the activity of a 32222 target molecule can be accomplished, for example, by determining the ability of the 32222 protein to bind to or interact with the 32222 target molecule.

Determining the ability of the 32222 protein, or a biologically active fragment thereof, to bind to or interact with a 32222 target molecule can be accomplished by one of the methods described above for determining direct binding. In a preferred embodiment, determining the ability of the 32222 protein to bind to or interact with a 32222 target molecule can be accomplished by determining the activity of the target molecule. For example, the activity of the target molecule can be determined by detecting induction of a cellular response (i.e., cell proliferation, migration and/or survival activity), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a 32222 protein or biologically active portion thereof is contacted with a test compound and the ability of the test compound to bind to the 32222 protein or biologically active portion thereof is determined. Preferred biologically active portions of the 32222 proteins to be used in assays of the present invention include fragments which participate in interactions with non-32222 molecules, e.g., fragments with high surface probability scores. Binding of the test compound to the 32222 protein can be determined either directly or indirectly as described above. In a preferred embodiment, the assay includes contacting the 32222 protein or biologically active portion thereof with a known compound which binds 32222 to form an assay mixture, contacting the assay mixture with a test compound, and determining the ability of the test compound to interact with a 32222 protein, wherein determining the ability of the test compound to interact with a 32222 protein comprises determining the ability of the test compound to preferentially bind to 32222 or biologically active portion thereof as compared to the known compound.

In another embodiment, the assay is a cell-free assay in which a 32222 protein or biologically active portion thereof is contacted with a test compound and the ability of the test compound to modulate (e.g., stimulate or inhibit) the activity of the 32222 protein or biologically active portion thereof is determined. Determining the ability of the test compound to modulate the activity of a 32222 protein can be accomplished, for example, by determining the ability of the 32222 protein to bind to a 32222 target molecule by one of the methods described above for determining direct binding. Determining the ability of the 32222 protein to bind to a 32222 target molecule can also be accomplished using a technology such as real-time Biomolecular Interaction Analysis (BIA). Sjolander, S. and Urbaniczky, C. (1991) Anal. Chem. 63:2338-2345 and Szabo et al., (1995) Curr. Opin. Struct. Biol. 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a 32222 protein can be accomplished by determining the ability of the 32222 protein to further modulate the activity of a downstream effector of a 32222 target molecule. For example, the activity of the effector molecule on an appropriate target can be determined or the binding of the effector to an appropriate target can be determined as previously described.

In yet another embodiment, the cell-free assay involves contacting a 32222 protein or biologically active portion thereof with a known compound (e.g., a 32222 substrate) which binds the 32222 protein to form an assay mixture, contacting the assay mixture with a test compound, and determining the ability of the test compound to interact with the 32222 protein, wherein determining the ability of the test compound to interact with the 32222 protein comprises determining the ability of the 32222 protein to preferentially bind to or modulate the activity of a 32222 target protein, e.g., catalyze the cleavage, e.g., the hydrolytic cleavage, of a chemical bond within the target protein.

In more than one embodiment of the above assay methods of the present invention, it may be desirable to immobilize either 32222 or its target molecule to facilitate separation of complexed from uncomplexed forms of one or both of the proteins, as well as to accommodate automation of the assay. Binding of a test compound to a 32222 protein, or interaction of a 32222 protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/32222 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 32222 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of 32222 binding or activity determined using standard techniques.

Other techniques for immobilizing proteins on matrices can also be used in the screening assays of the invention. For example, either a 32222 protein or a 32222 target molecule can be immobilized utilizing conjugation of biotin and streptavidin. Biotinylated 32222 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with 32222 protein or target molecules but which do not interfere with binding of the 32222 protein to its target molecule can be derivatized to the wells of the plate, and unbound target or 32222 protein trapped in the wells by antibody conjugation. Methods for detecting such complexes, in addition to those described above for the GST-immobilized complexes, include immunodetection of complexes using antibodies reactive with the 32222 protein or target molecule, as well as enzyme-linked assays which rely on detecting an enzymatic activity associated with the 32222 protein or target molecule.

In another embodiment, modulators of 32222 expression are identified in a method wherein a cell is contacted with a candidate compound and the expression of 32222 mRNA or protein in the cell is determined. The level of expression of 32222 mRNA or protein in the presence of the candidate compound is compared to the level of expression of 32222 mRNA or protein in the absence of the candidate compound. The candidate compound can then be identified as a modulator of 32222 expression based on this comparison. For example, when expression of 32222 mRNA or protein is greater (statistically significantly greater) in the presence of the candidate compound than in its absence, the candidate compound is identified as a stimulator of 32222 mRNA or protein expression. Alternatively, when expression of 32222 mRNA or protein is less (statistically significantly less) in the presence of the candidate compound than in its absence, the candidate compound is identified as an inhibitor of 32222 mRNA or protein expression. The level of 32222 mRNA or protein expression in the cells can be determined by methods described herein for detecting 32222 mRNA or protein.

In a preferred embodiment, modulators of 32222 expression are identified in a method wherein a cell expressing wild-type p53 or a cell lacking wild-type p53 expression (e.g., p53 mutant or p53−/− cell) is contacted with a candidate compound and the expression of 32222 mRNA or protein in the cell is determined. The level of expression of 32222 mRNA or protein in the presence of the candidate compounds is compared to the level of expression of 32222 mRNA or protein in the absence of the candidate compound. The candidate compound can then be identified as a modulator of 32222 expression based on this comparison. For example, when expression of 32222 mRNA or protein is greater (statistically significantly greater) in the presence of the candidate compound than in its absence, the candidate compound is identified as a stimulator of 32222 mRNA or protein expression. Alternatively, when expression of 32222 mRNA or protein is less (statistically significantly less) in the presence of the candidate compound than in its absence, the candidate compound is identified as an inhibitor of 32222 mRNA or protein expression. The level of 32222 mRNA or protein expression in the cells can be determined by methods described herein for detecting 32222 mRNA or protein In yet another aspect of the invention, the 32222 proteins can be used as "bait proteins" in a two-hybrid assay or three-hybrid assay (see, e.g., U.S. Pat. No. 5,283,317; Zervos et al., (1993) Cell 72:223-232; Madura et al., (1993) J. Biol. Chem. 268:12046-12054; Bartel et al., (1993) Biotechniques 14:920-924; Iwabuchi et al., (1993) Oncogene 8:1693-1696; and Brent WO94/10300), to identify other proteins, which bind to or interact with 32222 ("32222 binding proteins" or "32222-bp") and are involved in 32222 activity. Such 32222 binding proteins are also likely to be involved in the propagation of signals by the 32222 proteins or 32222 targets as, for example, downstream elements of a 32222-mediated signaling pathway. Alternatively, such 32222 binding proteins are likely to be 32222 inhibitors.

The two-hybrid system is based on the modular nature of most transcription factors, which consist of separable DNA-binding and activation domains. Briefly, the assay utilizes two different DNA constructs. In one construct, the gene that codes for a 32222 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 32222-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 32222 protein.

In another aspect, the invention pertains to a combination of two or more of the assays described herein. For example, a modulating agent can be identified using a cell-based or a cell free assay, and the ability of the agent to modulate the activity of a 32222 protein can be confirmed in vivo, e.g., in an animal such as an animal model for cellular transformation and/or tumorigenesis, or an animal model for a metabolic disorder.

This invention further pertains to novel agents identified by the above-described screening assays. Accordingly, it is within the scope of this invention to further use an agent identified as described herein in an appropriate animal model. For example, an agent identified as described herein (e.g., a 32222 modulating agent, an antisense 32222 nucleic acid molecule, a 32222-specific antibody, or a 32222 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to ameliorate symptoms of, for example, a cellular proliferative disorder. Cell-based and animal model-based assays for the identification of compounds exhibiting an ability to ameliorate the symptoms of a cellular proliferative disorder are described herein.

In one aspect, cell-based systems, as described herein, may be used to identify compounds which may act to ameliorate symptoms of a cellular proliferative disorder. For example, such cell systems may be exposed to a test compound (e.g., suspected of exhibiting an ability to ameliorate symptoms of a cellular proliferative disorder), at a sufficient concentration and for a time sufficient to elicit amelioration of symptoms of a cellular proliferative disorder in the exposed cells. After exposure, the cells are examined to determine whether one or more of the cellular phenotypes associated with a cellular proliferative disorder has been altered to resemble a normal or wild type, non-cellular proliferative disorder phenotype. Cellular phenotypes that are associated with cellular proliferative disorders include aberrant proliferation and survival, migration, anchorage independent growth, and loss of contact inhibition.

In addition, animal-based models of cellular proliferative disorders, such as those described herein, may be used to identify compounds capable of ameliorating symptoms of a cellular proliferative disorder. Such animal models may also be used to test substrates for the identification of drugs, pharmaceuticals, therapies, and interventions which may be effective in treating a cellular proliferative disorder. For example, animal models may be exposed to a test compound at a sufficient concentration and for a time sufficient to ameliorate symptoms of a cellular proliferative disorder in the exposed animals. The response of the animals to the exposure may be monitored by assessing amelioration of symptoms of a cellular proliferative disorder, for example, reduction in tumor size, invasive and/or metastatic potential, as well as tumor burden, before and after treatment.

With regard to intervention, any treatments which reverse any aspect of a cellular proliferative disorder should be considered as candidates for human disease therapeutic intervention. Dosages of test agents may be determined by deriving dose-response curves.

Additionally, gene expression patterns may be utilized to assess the ability of a compound to ameliorate symptoms of a cellular proliferative disorder. For example, the expression pattern of one or more genes may form part of a "gene expression profile" or "transcriptional profile" which may be then in such an assessment. "Gene expression profile" or "transcriptional profile", as used herein, includes the pattern of mRNA expression obtained for a given tissue or cell type under a given set of conditions. Such conditions may include, but are not limited to, cell proliferation, differentiation, transformation, tumorigenesis and metastasis. Gene expression profiles may be generated, for example, by utilizing a differential display procedure, Northern analysis and/or RT-PCR. In one embodiment, 32222 gene sequences may be used as probes and/or PCR primers for the generation and corroboration of such gene expression profiles.

Gene expression profiles may be characterized for known states, for example, a tumorigenic/disease state or normal state, within the cell- and/or animal-based model systems. Subsequently, these known gene expression profiles may be compared to ascertain the effect of a test compound on modifying such gene expression profiles.

For example, administration of a test compound may cause the gene expression profile of a cellular proliferative disorder model system to more closely resemble the control system. Administration of a test compound may, alternatively, cause the gene expression profile of a control system to begin to mimic a cellular proliferative disorder state. Such a test compound may, for example, be used in further characterizing the test compound of interest, or may be used in the generation of additional animal models.

Cells that contain and express 32222 gene sequences which encode a 32222 protein, and further, exhibit cellular phenotypes associated with a cellular proliferative disorder, may be used to identify compounds that exhibit cellular growth modulatory activity. Such cells include tumor cell lines, such as those exemplified herein, as well as generic mammalian cell lines such as COS cells. Further, such cells may include recombinant cell lines derived from a transgenic or a knockout animal (e.g., p53−/− animal). For example, animal models of tumorigenesis, such as those discussed above, may be used to generate cell lines that can be used as cell culture models for this disorder. While primary cultures derived from transgenic or knockout animals may be utilized, the generation of continuous cell lines is preferred. For examples of techniques which may be used to derive a continuous cell line from the transgenic animals, see Small et al., (1985) Mol. Cell. Biol. 5:642-648.

Alternatively, cells of a cell type known to be involved in cellular proliferative disorder may be transfected with sequences capable of increasing or decreasing the amount of 32222 gene expression within the cell. For example, 32222 gene sequences may be introduced into, and overexpressed in, the genome of the cell of interest, or, if endogenous 32222 gene sequences are present, they may be either overexpressed or, alternatively, disrupted in order to underexpress or inactivate 32222 gene expression.

In order to overexpress a 32222 gene, the coding portion of the 32222 gene may be ligated to a regulatory sequence which is capable of driving gene expression in the cell type of interest. Such regulatory regions will be well known to those of skill in the art, and may be utilized in the absence of undue experimentation. Recombinant methods for expressing target genes are described above.

For underexpression of an endogenous 32222 gene sequence, such a sequence may be isolated and engineered such that when reintroduced into the genome of the cell type of interest, the endogenous 32222 alleles will be inactivated. Preferably, the engineered 32222 sequence is introduced via gene targeting such that the endogenous 32222 sequence is disrupted upon integration of the engineered 32222 sequence into the cell's genome. Transfection of host cells with 32222 genes is discussed, above.

In an another embodiment, overexpression or underexpression of 32222 molecule may be regulated indirectly by compounds regulating the expression of p53 molecule. Wild-type p53 molecule may be transfected into a cell, p53 may be further engineered to include other regulatory elements which may then act as a regulatory switch to test for compounds which turn on or off the p53 expression, thereby regulating the expression of the 32222 molecule.

Cells treated with test compounds or transfected with 32222 genes can be examined for phenotypes associated with a cellular proliferative disorder, e.g., dysregulated proliferation and migration, anchorage independent growth, and loss of contact inhibition.

Transfection of a 32222 nucleic acid may be accomplished by using standard techniques (described herein and in, for example, Ausubel (1989) supra). Transfected cells should be evaluated for the presence of the recombinant 32222 gene sequences, for expression and accumulation of 32222 mRNA, and for the presence of recombinant 32222 protein production. In instances wherein a decrease in 32222 gene expression is desired, standard techniques may be used to demonstrate whether a decrease in endogenous 32222 gene expression and/or in 32222 protein production is achieved.

Cellular models for the study of cellular proliferative disorder are known in the art, and include cell lines derived from clinical tumors, cells exposed to carcinogenic agents, and cell lines with genetic alterations in growth regulatory genes, for example, oncogenes (e.g., ras) and tumor suppressor genes (e.g., p53).

In another aspect, the invention pertains to a combination of two or more of the assays described herein. For example, a modulating agent can be identified using a cell-based or a cell-free assay, and the ability of the agent to modulate the activity of a 32222 protein can be confirmed in vivo, e.g., in an animal such as an animal model for a cellular proliferation disorder, e.g., cancer. Examples of animal models of cancer include transplantable models (e.g., xenografts). Xenografts for colon cancer can be performed with the following cell lines: HCT-116, HT-29, SW-480, SW-620, Colon 26, DLD1, Caco2, colo205, T84, and KM12. Xenografts for lung cancer can be performed with the following cell lines: NCI-H125, NCI-H460, A549, NCI-H69, and NCI-H345. Xenografts for ovarian cancer can be performed with the SKOV3 and HEY cell lines. Xenografts for breast cancer can be performed with, for example, MCF10AT cells, which can be grown as subcutaneous or orthotopic (cleared mammary fat pad) xenografts in mice. MCF10AT xenografts produce tumors that progress in a manner analogous to human breast cancer. Estrogen stimulation has also been shown to accelerate tumor progression in this model. MCF10AT xenografted tumors representing stages hyperplasia, carcinoma in situ, and invasive carcinoma will be isolated expression profiling. A metastatic subclone of the human breast cancer cell line MDA-MB-231 that metastasizes to brain, lung and bone can also be grown in vitro and in vivo at various sites (i.e. subcutaneously, orthotopically, in bone following direct bone injection, in bone following intracardiac injection). MCF-7 and T-47D are other mammary adenocarcinoma cell lines that can be grown as xenografts. All of these cells can be transplanted into immunocompromised mice such as SCID or nude mice, for example.

Orthotopic metastasis mouse models may also be utilized. For example, the HCT-116 human colon carcinoma cell line can be grown as a subcutaneous or orthotopic xenograft (intracaecal injection) in athymic nude mice. Rare liver and lung metastases can be isolated, expanded in vitro, and re-implanted in vivo. A limited number of iterations of this process can be employed to isolate highly metastatic variants of the parental cell line. Standard and subtracted cDNA libraries and probes can be generated from the parental and variant cell lines to identify genes associated with the acquisition of a metastatic phenotype. This model can be established using several alternative human colon carcinoma cell lines, including SW480 and KM12C.

Also useful in the methods of the invention are mis-match repair models (MMRs). Hereditary nonpolyposis colon cancer (HNPCC), which is caused by germline mutations in MSH2 & MLH1, genes involved in DNA mismatch repair, accounts for 5-15% of colon cancer cases. Mouse models have been generated carrying null mutations in the MLH1, MSH2 and MSH3 genes.

Other animal models for cancer include transgenic models (e.g., B66-Min/+mouse); chemical induction models, e.g., carcinogen (e.g., azoxymethane, 2-dimethylhydrazine, or N-nitrosodimethylamine) treated rats or mice; models of liver metastasis from colon cancer such as that described by Rashidi et al. (2000) Anticancer Res 20(2A):715; and cancer cell implantation or inoculation models as described in, for example, Fingert et al. (1987) Cancer Res 46(14):3824-9 and Teraoka et al. (1995) Jpn J Cancer Res 86(5):419-23. Furthermore, experimental model systems are available for the study of, for example, ovarian cancer (Hamilton, T C et al. Semin Oncol (1984) 11:285-298; Rahman, N A et al. Mol Cell Endocrinol (1998) 145:167-174; Beamer, W G et al. Toxicol Pathol (1998) 26:704-710), gastric cancer (Thompson, J et al. Int J Cancer (2000) 86:863-869; Fodde, R et al. Cytogenet Cell Genet (1999) 86:105-111), breast cancer (Li, M et al. Oncogene (2000) 19:1010-1019; Green, J E et al. Oncogene (2000) 19:1020-1027), melanoma (Satyamoorthy, K et al. Cancer Metast Rev (1999) 18:401-405), and prostate cancer (Shirai, T et al. Mutat Res (2000) 462:219-226; Bostwick, D G et al. Prostate (2000) 43:286-294). Mouse models for colon cancer include the APCmin mouse, a highly characterized genetic model of human colorectal carcinogene is; the APC1638N mouse, which was generated by introducing a PGK-neomycin gene at codon 1638 of the APC gene and develops aberrant crypt foli after 6-8 weeks which ultimately progress to carcinomas by 4 months of age; and the p53−/− mouse which develops colon carcinomas that histopathologically resemble human disease.

Other animal based models for studying tumorigenesis in vivo are well known in the art (reviewed in Animal Models of Cancer Predisposition Syndromes, Hiai, H and Hino, O (eds.) 1999, Progress in Experimental Tumor Research, Vol. 35; Clarke A R Carcinogenesis (2000) 21:435-41) and include, for example, carcinogen-induced tumors (Rithidech, K et al., Mutat Res (1999) 428:33-39; Miller, M L et al., Environ Mol Mutagen (2000) 35:319-327), injection and/or transplantation of tumor cells into an animal, as well as animals bearing mutations in growth regulatory genes, for example, oncogenes (e.g., ras) (Arbeit, J M et al., Am J Pathol (1993) 142:1187-1197; Sinn, E et al., Cell (1987) 49:465-475; Thorgeirsson, S S et al., Toxicol Lett (2000) 112-113:553-555) and tumor suppressor genes (e.g., p53) (Vooijs, M et al., Oncogene (1999) 18:5293-5303; Clark A R Cancer Metast Rev (1995) 14:125-148; Kumar, T R et al., J Intern Med (1995) 238:233-238; Donehower, L A et al., (1992) Nature 356215-221). Furthermore, experimental model systems are available for the study of, for example, ovarian cancer (Hamilton, T C et al., Semin Oncol (1984) 11:285-298; Rahman, N A et al., Mol Cell Endocrinol (1998) 145:167-174; Beamer, W G et al., Toxicol Pathol (1998) 26:704-710), gastric cancer (Thompson, J et al., Int J Cancer (2000) 86:863-869; Fodde, R et al., Cytogenet Cell Genet (1999) 86:105-111), breast cancer (Li, M et al., Oncogene (2000) 19:1010-1019; Green, J E et al., Oncogene (2000) 19:1020-1027), melanoma (Satyamoorthy, K et al., Cancer Metast Rev (1999) 18:401-405), and prostate cancer (Shirai, T et al., Mutat Res (2000) 462:219-226; Bostwick, D G et al., Prostate (2000) 43:286-294).

Additionally, gene expression patterns may be utilized to assess the ability of a compound to ameliorate tumorigenic disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cell proliferation, differentiation, transformation, tumorigenesis, metastasis, and carcinogen exposure. Gene expression profiles may be generated, for example, by utilizing a differential display procedure, Northern analysis and/or RT-PCR. In one embodiment, 32222 gene sequences may be used as probes and/or PCR primers for the generation and corroboration of such gene expression profiles.

Gene expression profiles may be characterized for known states, such as, tumorigenic disease or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a tumorigenic disease model system to more closely resemble the control system. Administration of a compound may, alternatively, cause the gene expression profile of a control system to begin to mimic a tumorigenic disease state. Such a compound may, for example, be used in further characterizing the compound of interest, or may be used in the generation of additional animal models.

Models for studying tumorigenesis in vivo include carcinogen-induced tumors, injection and/or transplantation of tumor cells into an animal, as well as animals bearing mutations in growth regulatory genes.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 32222 protein and/or nucleic acid expression as well as 32222 activity, in the context of a biological sample (e.g., blood, serum, cells, tissue) to thereby determine whether an individual is afflicted with a disease or disorder, or is at risk of developing a disorder, associated with aberrant or unwanted 32222 expression or activity, e.g., a cellular proliferative disorder. The invention also provides for prognostic (or predictive) assays for determining whether an individual is at risk of developing a disorder associated with 32222 protein, nucleic acid expression or activity. For example, mutations in a 32222 gene can be assayed in a biological sample. Such assays can be used for prognostic or predictive purpose to thereby phophylactically treat an individual prior to the onset of a disorder characterized by or associated with 32222 protein, nucleic acid expression or activity.

Another aspect of the invention pertains to monitoring the influence of agents (e.g., drugs, compounds) on the expression or activity of 32222 in clinical trials.

These and other agents are described in further detail in the following sections.

A. Diagnostic Assays for Tumorigenic Disorders

An exemplary method for detecting the presence or absence of 32222 protein or nucleic acid in a biological sample involves obtaining a biological sample from a test subject and contacting the biological sample with a compound or an agent capable of detecting 32222 protein or nucleic acid (e.g., mRNA, or genomic DNA) that encodes 32222 protein such that the presence of 32222 protein or nucleic acid is detected in the biological sample. A preferred agent for detecting 32222 mRNA or genomic DNA is a labeled nucleic acid probe capable of hybridizing to 32222 mRNA or genomic DNA. The nucleic acid probe can be, for example, the 32222 nucleic acid set forth in SEQ ID NO:55 or 56, or a portion thereof, such as an oligonucleotide of at least 15, 30, 50, 100, 250 or 500 nucleotides in length and sufficient to specifically hybridize under stringent conditions to 32222 mRNA or genomic DNA. Other suitable probes for use in the diagnostic assays of the invention are described herein.

A preferred agent for detecting 32222 protein is an antibody capable of binding to 32222 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect 32222 mRNA, protein, or genomic DNA in a biological sample in vitro as well as in vivo. For example, in vitro techniques for detection of 32222 mRNA include Northern hybridizations and in situ hybridizations. In vitro techniques for detection of 32222 protein include enzyme linked immunosorbent assays (ELISAs), Western blots, immunoprecipitations and immunofluorescence. In vitro techniques for detection of 32222 genomic DNA include Southern hybridizations. Furthermore, in vivo techniques for detection of 32222 protein include introducing into a subject a labeled anti-32222 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting 32222 protein, mRNA, or genomic DNA, such that the presence of 32222 protein, mRNA or genomic DNA is detected in the biological sample, and comparing the presence of 32222 protein, mRNA or genomic DNA in the control sample with the presence of 32222 protein, mRNA or genomic DNA in the test sample.

The invention also encompasses kits for detecting the presence of 32222 in a biological sample. For example, the kit can comprise a labeled compound or agent capable of detecting 32222 protein or mRNA in a biological sample; means for determining the amount of 32222 in the sample; and means for comparing the amount of 32222 in the sample with a standard. The compound or agent can be packaged in a suitable container. The kit can further comprise instructions for using the kit to detect 32222 protein or nucleic acid.

B. Prognostic Assays for Tumorigenic Disorders

The diagnostic methods described herein can furthermore be utilized to identify subjects having or at risk of developing a disease or disorder associated with aberrant or unwanted 32222 expression or activity, e.g., a tumorigenic disorder. As used herein, the term "aberrant" includes a 32222 expression or activity which deviates from the wild type 32222 expression or activity. Aberrant expression or activity includes increased or decreased expression or activity, as well as expression or activity which does not follow the wild type developmental pattern of expression or the subcellular pattern of expression.

For example, aberrant 32222 expression or activity is intended to include the cases in which a mutation in the 32222 gene causes the 32222 gene to be under-expressed or over-expressed and situations in which such mutations result in a non-functional 32222 protein or a protein which does not function in a wild-type fashion, e.g., a protein which does not interact with a 32222 substrate, or one which interacts with a non-32222 substrate.

As used herein, the term "unwanted" includes an unwanted phenomenon involved in a biological response such as cellular proliferation. For example, the term unwanted includes a 32222 expression or activity which is undesirable in a subject.

The assays described herein, such as the preceding diagnostic assays or the following assays, can be utilized to identify a subject having or at risk of developing a disorder associated with a misregulation in 32222 protein activity or nucleic acid expression, such as a cell proliferation, growth, differentiation, survival, or migration disorder. Alternatively, the prognostic assays can be utilized to identify a subject having or at risk for developing a disorder associated with a misregulation in 32222 protein activity or nucleic acid expression, such as a cell proliferation, growth, differentiation, survival, or migration disorder. Thus, the present invention provides a method for identifying a disease or disorder associated with aberrant or unwanted 32222 expression or activity in which a test sample is obtained from a subject and 32222 protein or nucleic acid (e.g., mRNA or genomic DNA) is detected, wherein the presence of 32222 protein or nucleic acid is diagnostic for a subject having or at risk of developing a disease or disorder associated with aberrant or unwanted 32222 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 32222 expression or activity. For example, such methods can be used to determine whether a subject can be effectively treated with an agent for a cell proliferation, growth, differentiation, survival, or migration disorder. Thus, the present invention provides methods for determining whether a subject can be effectively treated with an agent for a disorder associated with aberrant or unwanted 32222 expression or activity in which a test sample is obtained and 32222 protein or nucleic acid expression or activity is detected (e.g., wherein the abundance of 32222 protein or nucleic acid expression or activity is diagnostic for a subject that can be administered the agent to treat a disorder associated with aberrant or unwanted 32222 expression or activity).

The methods of the invention can also be used to detect genetic alterations in a 32222 gene, thereby determining if a subject with the altered gene is at risk for a disorder characterized by misregulation in 32222 protein activity or nucleic acid expression, such as a cell proliferation, growth, differentiation, survival, or migration disorder. In preferred embodiments, the methods include detecting, in a sample of cells from the subject, the presence or absence of a genetic alteration characterized by at least one of an alteration affecting the integrity of a gene encoding a 32222 protein, or the mis-expression of the 32222 gene. For example, such genetic alterations can be detected by ascertaining the existence of at least one of 1) a deletion of one or more nucleotides from a 32222 gene; 2) an addition of one or more nucleotides to a 32222 gene; 3) a substitution of one or more nucleotides of a 32222 gene, 4) a chromosomal rearrangement of a 32222 gene; 5) an alteration in the level of a messenger RNA transcript of a 32222 gene, 6) aberrant modification of a 32222 gene, such as of the methylation pattern of the genomic DNA, 7) the presence of a non-wild type splicing pattern of a messenger RNA transcript of a 32222 gene, 8) a non-wild type level of a 32222 protein, 9) allelic loss of a 32222 gene, and 10) inappropriate post-translational modification of a 32222 protein. As described herein, there are a large number of assays known in the art which can be used for detecting alterations in a 32222 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al., (1988) Science 241:1077-1080; and Nakazawa et al., (1994) Proc. Natl. Acad. Sci. USA 91:360-364), the latter of which can be particularly useful for detecting point mutations in a 32222 gene (see Abravaya et al., (1995) Nucleic Acids Res 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a 32222 gene under conditions such that hybridization and amplification of the 32222 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874-1878), transcriptional amplification system (Kwoh, D. Y. et al., (1989) Proc. Natl. Acad. Sci. USA 86:1173-1177), Q-Beta Replicase (Lizardi, P. M. et al., (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 32222 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 32222 can be identified by hybridizing a sample and control nucleic acids, e.g., DNA or RNA, to high density arrays containing hundreds or thousands of oligonucleotides probes (Cronin, M. T. et al., (1996) Human Mutation 7: 244-255; Kozal, M. J. et al., (1996) Nature Medicine 2: 753-759). For example, genetic mutations in 32222 can be identified in two dimensional arrays containing light-generated DNA probes as described in Cronin, M. T. et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 32222 gene and detect mutations by comparing the sequence of the sample 32222 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al., (1996) Adv. Chromatogr. 36:127-162; and Griffin et al., (1993) Appl. Biochem. Biotechnol. 38:147-159).

Other methods for detecting mutations in the 32222 gene include methods in which protection from cleavage agents is used to detect mismatched bases in RNA/RNA or RNA/DNA heteroduplexes (Myers et al., (1985) Science 230:1242). In general, the art technique of “mismatch cleavage” starts by providing heteroduplexes of formed by hybridizing (labeled) RNA or DNA containing the wild-type 32222 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al., (1988) Proc. Natl. Acad Sci USA 85:4397; Saleeba et al., (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 32222 cDNAs obtained from samples of cells. For example, the mutY enzyme of *E. coli* cleaves A at G/A mismatches and the thymidine DNA glycosylase from HeLa cells cleaves T at G/T mismatches (Hsu et al., (1994) Carcinogenesis 15:1657-1662). According to an exemplary embodiment, a probe based on a 32222 sequence, e.g., a wild-type 32222 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 32222 genes. For example, single strand conformation polymorphism (SSCP) may be used to detect differences in electrophoretic mobility between mutant and wild type nucleic acids (Orita et al., (1989) Proc Natl. Acad. Sci. USA: 86:2766, see also Cotton (1993) Mutat. Res. 285:125-144; and Hayashi (1992) Genet. Anal. Tech. Appl. 9:73-79). Single-stranded DNA fragments of sample and control 32222 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al., (1985) Nature 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al., (1986) Nature 324:163); Saiki et al., (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al., (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al., (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 32222 gene.

Furthermore, any cell type or tissue in which 32222 is expressed may be utilized in the prognostic assays described herein.

C. Monitoring of Effects During Clinical Trials

Monitoring the influence of agents (e.g., drugs) on the expression or activity of a 32222 protein (e.g., the modulation of cell proliferation and/or survival) can be applied not only in basic drug screening, but also in clinical trials. For example, the effectiveness of an agent determined by a screening assay as described herein to increase 32222 gene expression, protein levels, or upregulate 32222 activity, can be monitored in clinical trials of subjects exhibiting decreased 32222 gene expression, protein levels, or down-regulated 32222 activity. Alternatively, the effectiveness of an agent determined by a screening assay to decrease 32222 gene expression, protein levels, or downregulate 32222 activity, can be monitored in clinical trials of subjects exhibiting increased 32222 gene expression, protein levels, or upregulated 32222 activity. In such clinical trials, the expression or activity of a 32222 gene, and preferably, other genes that have been implicated in, for example, a 32222-associated disorder can be used as a "read out" or markers of the phenotype of a particular cell.

For example, and not by way of limitation, genes, including 32222, that are modulated in cells by treatment with an agent (e.g., compound, drug or small molecule) which modulates 32222 activity (e.g., identified in a screening assay as described herein) can be identified. Thus, to study the effect of agents on 32222-associated disorders (e.g., disorders characterized by deregulated cell proliferation and/or migration), for example, in a clinical trial, cells can be isolated and RNA prepared and analyzed for the levels of expression of 32222 and other genes implicated in the 32222-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of 32222 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a 32222 protein, mRNA, or genomic DNA in the preadministration sample; (iii) obtaining one or more post-administration samples from the subject; (iv) detecting the level of expression or activity of the 32222 protein, mRNA, or genomic DNA in the post-administration samples; (v) comparing the level of expression or activity of the 32222 protein, mRNA, or genomic DNA in the pre-administration sample with the 32222 protein, mRNA, or genomic DNA in the post administration sample or samples; and (vi) altering the administration of the agent to the subject accordingly. For example, increased administration of the agent may be desirable to increase the expression or activity of 32222 to higher levels than detected, i.e., to increase the effectiveness of the agent. Alternatively, decreased administration of the agent may be desirable to decrease expression or activity of 32222 to lower levels than detected, i.e. to decrease the effectiveness of the agent. According to such an embodiment, 32222 expression or activity may be used as an indicator of the effectiveness of an agent, even in the absence of an observable phenotypic response.

Methods of Treatment of Subjects Suffering from Tumorigenic Disorders

The present invention provides for both prophylactic and therapeutic methods of treating a subject at risk of (or susceptible to) a disorder or having a disorder associated with aberrant or unwanted 32222 expression or activity, e.g., a hydrolase-associated disorder such as a cell proliferation, growth, differentiation, survival, or migration disorder. The term "treatment", as used herein, is defined as the application or administration of a therapeutic agent to a patient, or application or administration of a therapeutic agent to an isolated tissue or cell line from a patient, who has a disease or disorder, a symptom of a disease or disorder, or a predisposition toward a disease or disorder, with the purpose to cure, heal, alleviate, relieve, alter, remedy, ameliorate, improve or affect the disease or disorder, the symptoms of the disease or disorder, or the predisposition toward a disease or disorder, e.g., the cellular proliferation disorder. A therapeutic agent includes, but is not limited to, small molecules, peptides, antibodies, ribozymes and antisense oligonucleotides. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the 32222 molecules of the present invention or 32222 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

A. Prophylactic Methods

In one aspect, the invention provides a method for preventing in a subject, a disease or condition associated with an aberrant or unwanted 32222 expression or activity, by administering to the subject a 32222 or an agent which modulates 32222 expression or at least one 32222 activity. Subjects at risk for a disease which is caused or contributed to by aberrant or unwanted 32222 expression or activity can be identified by, for example, any or a combination of diagnostic or prognostic assays as described herein. Administration of a prophylactic agent can occur prior to the manifestation of symptoms characteristic of the 32222 aberrancy, such that a disease or disorder is prevented or, alternatively, delayed in its progression. Depending on the type of 32222 aberrancy, for example, a 32222, 32222 agonist or 32222 antagonist agent can be used for treating the subject. The appropriate agent can be determined based on screening assays described herein.

B. Therapeutic Methods

Another aspect of the invention pertains to methods for treating a subject suffering from a cellular proliferative disorder. These methods involve administering to a subject an agent which modulates 32222 expression or activity (e.g., an agent identified by a screening assay described herein), or a combination of such agents. In another embodiment, the method involves administering to a subject a 32222 protein or nucleic acid molecule as therapy to compensate for reduced, aberrant, or unwanted 32222 expression or activity.

Stimulation of 32222 activity is desirable in situations in which 32222 is abnormally downregulated and/or in which increased 32222 activity is likely to have a beneficial effect, i.e., a decrease in cell proliferation or survival, thereby ameliorating a cellular proliferative disorder such as AIDS or immunosupressive disorders. Likewise, inhibition of 32222 activity is desirable in situations in which 32222 is abnormally upregulated and/or in which decreased 32222 activity is likely to have a beneficial effect, e.g., a decrease in cell proliferation or survival, thereby ameliorating a cellular proliferative disorder such as tumor in a subject.

The agents which modulate 32222 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates 32222 activity (e.g., a fragment of a 32222 protein or an anti-32222 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate 32222 activity can also be prepared in the form of suppositories (e.g., with conventional suppository bases such as cocoa butter and other glycerides) or retention enemas for rectal delivery.

In one embodiment, the agents that modulate 32222 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates 32222 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such 32222 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg cellular proliferative, preferably about 0.01 to 25 mg/kg cellular proliferative, more preferably about 0.1 to 20 mg/kg cellular proliferative, and even more preferably about 1 to 10 mg/kg, 2 to 9 mg/kg, 3 to 8 mg/kg, 4 to 7 mg/kg, or 5 to 6 mg/kg cellular proliferative. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg cellular proliferative, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, cellular proliferative, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985); Hellstrom et al., "Antibodies For Drug Delivery", in Controlled Drug Delivery (2nd Ed.), Robinson et al., (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al., (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al., (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

C. Pharmacogenomics

In conjunction with the therapeutic methods of the invention, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an agent which modulates 32222 activity, as well as tailoring the dosage and/or therapeutic regimen of treatment with an agent which modulates 32222 activity.

Pharmacogenomics deals with clinically significant hereditary variations in the response to drugs due to altered drug disposition and abnormal action in affected persons. See, for example, Eichelbaum, M. et al., (1996) Clin. Exp. Pharmacol. Physiol. 23(10-11): 983-985 and Linder, M. W. et al., (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a 32222 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a 32222 molecule or 32222 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a 32222 molecule or 32222 modulator, such as a modulator identified by one of the exemplary screening assays described herein.

This invention is further illustrated by the following examples which should not be construed as limiting. The contents of all references, patents and published patent applications cited throughout this application, are incorporated herein by reference.

Recombinant Expression Vectors and Host Cells Used in the Methods of the Invention The methods of the invention (e.g., the screening assays described herein) include the use of vectors, preferably expression vectors, containing a nucleic acid encoding a 32222 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 32222 proteins, mutant forms of 32222 proteins, fusion proteins, and the like).

The recombinant expression vectors to be used in the methods of the invention can be designed for expression of 32222 proteins in prokaryotic or eukaryotic cells. For example, 32222 proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 32222 activity assays, (e.g., direct assays or competitive assays described in detail below), or to generate antibodies specific for 32222 proteins. In a preferred embodiment, a 32222 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 32222 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, Reviews-Trends in Genetics, Vol. 1(1) 1986.

Another aspect of the invention pertains to the use of host cells into which a 32222 nucleic acid molecule of the invention is introduced, e.g., a 32222 nucleic acid molecule within a recombinant expression vector or a 32222 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 32222 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a 32222 protein. Accordingly, the invention further provides methods for producing a 32222 protein using the host cells of the invention. In one embodiment, the method comprises culturing the host cell of the invention (into which a recombinant expression vector encoding a 32222 protein has been introduced) in a suitable medium such that a 32222 protein is produced. In another embodiment, the method further comprises isolating a 32222 protein from the medium or the host cell.

Isolated Nucleic Acid Molecules Used in the Methods of the Invention

The cDNA sequence of the isolated human 32222 gene and the predicted amino acid sequence of the human 32222 polypeptide are shown in SEQ ID NO:55 and 56 respectively.

The methods of the invention include the use of isolated nucleic acid molecules that encode 32222 proteins or biologically active portions thereof, as well as nucleic acid fragments sufficient for use as hybridization probes to identify 32222-encoding nucleic acid molecules (e.g., 32222 mRNA) and fragments for use as PCR primers for the amplification or mutation of 32222 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:55 or 56, or a portion thereof, can be isolated using standard molecular biology techniques and the sequence information provided herein. Using all or portion of the nucleic acid sequence of SEQ ID NO:55 or 56 as a hybridization probe, 32222 nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:55 or 56 can be isolated by the polymerase chain reaction (PCR) using synthetic oligonucleotide primers designed based upon the sequence of SEQ ID NO:55 or 56.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to 32222 nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:55 or 56, a complement of the nucleotide sequence shown in SEQ ID NO:55 or 56, or a portion of any of these nucleotide sequences. A nucleic acid molecule which is complementary to the nucleotide sequence shown in SEQ ID NO:55 or 56, is one which is sufficiently complementary to the nucleotide sequence shown in SEQ ID NO:55 or 56 such that it can hybridize to the nucleotide sequence shown in SEQ ID NO:55 or 56 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or more identical to the entire length of the nucleotide sequence shown in SEQ ID NO:55 or 56, or a portion of any of this nucleotide sequence.

Moreover, the nucleic acid molecules used in the methods of the invention can comprise only a portion of the nucleic acid sequence of SEQ ID NO:55 or 56, for example, a fragment which can be used as a probe or primer or a fragment encoding a portion of a 32222 protein, e.g., a biologically active portion of a 32222 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:55 or 56 or an anti-sense sequence of SEQ ID NO:55 or 56, or of a naturally occurring allelic variant or mutant of SEQ ID NO:55 or 56. In one embodiment, a nucleic acid molecule used in the methods of the present invention comprises a nucleotide sequence which is greater than 50, 50-100, 100-200, 200-300, 300-400, 400-500, 500-600, 600-700, 700-800, 800-900, 900-1000, 1000-1100 or more nucleotides in length and hybridizes under stringent hybridization conditions to a nucleic acid molecule of SEQ ID NO:55 or 56.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further preferred, non-limiting example of stringent hybridization conditions includes hybridization at 6×SSC at 45° C., followed by one or more washes in 0.2×SSC, 0.1% SDS at 65° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH2PO4, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH2PO4, 7% SDS at about 65° C., followed by one or more washes at 0.02M NaH2PO4, 1% SDS at 65° C., see e.g., Church and Gilbert (1984) Proc. Natl. Acad. Sci. USA 81:1991-1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a 32222 protein, such as by measuring a level of a 32222-encoding nucleic acid in a sample of cells from a subject e.g., detecting 32222 mRNA levels or determining whether a genomic 32222 gene has been mutated or deleted.

The methods of the invention further encompass the use of nucleic acid molecules that differ from the nucleotide sequence shown in SEQ ID NO:55 or 56 due to degeneracy of the genetic code and thus encode the same 32222 proteins as those encoded by the nucleotide sequence shown in SEQ ID NO:55 or 56. In another embodiment, an isolated nucleic acid molecule included in the methods of the invention has a nucleotide sequence encoding a protein having an amino acid sequence shown in SEQ ID NO:54.

The methods of the invention further include the use of allelic variants of huma 32222, e.g., functional and non-functional allelic variants. Functional allelic variants are naturally occurring amino acid sequence variants of the huma 32222 protein that maintain a 32222 activity. Functional allelic variants will typically contain only conservative substitution of one or more amino acids of SEQ ID NO:54, or substitution, deletion or insertion of non-critical residues in non-critical regions of the protein.

Non-functional allelic variants are naturally occurring amino acid sequence variants of the huma 32222 protein that do not have a 32222 activity. Non-functional allelic variants will typically contain a non-conservative substitution, deletion, or insertion or premature truncation of the amino acid sequence of SEQ ID NO:54, or a substitution, insertion or deletion in critical residues or critical regions of the protein.

The methods of the present invention may further use non-human orthologues of the huma 32222 protein. Orthologues of the huma 32222 protein are proteins that are isolated from non-human organisms and possess the same 32222 activity.

The methods of the present invention further include the use of nucleic acid molecules comprising the nucleotide sequence of SEQ ID NO:55 or 56, or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of 32222 (e.g., the sequence of SEQ ID NO:54) without altering the biological activity, whereas an "essential" amino acid residue is required for biological activity. For example, amino acid residues that are conserved among the 32222 proteins of the present invention and other members of the short-chain dehydrogenase family are not likely to be amenable to alteration.

Mutations can be introduced into SEQ ID NO:55 or 56 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 32222 protein is preferably replaced with another amino acid residue from the same side chain family. Alternatively, in another embodiment, mutations can be introduced randomly along all or part of a 32222 coding sequence, such as by saturation mutagenesis, and the resultant mutants can be screened for 32222 biological activity to identify mutants that retain activity. Following mutagenesis of SEQ ID NO:55 or 56, the encoded protein can be expressed recombinantly and the activity of the protein can be determined using an assay described herein.

Another aspect of the invention pertains to the use of isolated nucleic acid molecules which are antisense to the nucleotide sequence of SEQ ID NO:55 or 56. An “antisense” nucleic acid comprises a nucleotide sequence which is complementary to a “sense” nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 32222 coding strand, or to only a portion thereof. In one embodiment, an antisense nucleic acid molecule is antisense to a “coding region” of the coding strand of a nucleotide sequence encoding a 32222. The term “coding region” refers to the region of the nucleotide sequence comprising codons which are translated into amino acid residues. In another embodiment, the antisense nucleic acid molecule is antisense to a “noncoding region” of the coding strand of a nucleotide sequence encoding 32222. The term “noncoding region” refers to 5' and 3' sequences which flank the coding region that are not translated into amino acids (also referred to as 5' and 3' untranslated regions).

Given the coding strand sequences encoding 32222 disclosed herein, antisense nucleic acids of the invention can be designed according to the rules of Watson and Crick base pairing. The antisense nucleic acid molecule can be complementary to the entire coding region of 32222 mRNA, but more preferably is an oligonucleotide which is antisense to only a portion of the coding or noncoding region of 32222 mRNA. For example, the antisense oligonucleotide can be complementary to the region surrounding the translation start site of 32222 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules used in the methods of the invention are typically administered to a subject or generated in situ such that they hybridize with or bind to cellular mRNA and/or genomic DNA encoding a 32222 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule used in the methods of the invention is an $\alpha$-anomeric nucleic acid molecule. An $\alpha$-anomeric nucleic acid molecule forms specific double-stranded hybrids with complementary RNA in which, contrary to the usual $\beta$-units, the strands run parallel to each other (Gaultier et al., (1987) Nucleic Acids Res. 15:6625-6641). The antisense nucleic acid molecule can also comprise a 2'-o-methylribonucleotide (Inoue et al., (1987) Nucleic Acids Res. 15:6131-6148) or a chimeric RNA-DNA analogue (Inoue et al., (1987) FEBS Lett. 215: 327-330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) Nature 334:585-591)) can be used to catalytically cleave 32222 mRNA transcripts to thereby inhibit translation of 32222 mRNA. A ribozyme having specificity for a 32222-encoding nucleic acid can be designed based upon the nucleotide sequence of a 32222 cDNA disclosed herein (i.e., SEQ ID NO:55 or 56). For example, a derivative of a Tetrahymena L-19 IVS RNA can be constructed in which the nucleotide sequence of the active site is complementary to the nucleotide sequence to be cleaved in a 32222-encoding mRNA. See, e.g., Cech et al., U.S. Pat. No. 4,987,071; and Cech et al., U.S. Pat. No. 5,116,742. Alternatively, 32222 mRNA can be used to select a catalytic RNA having a specific ribonuclease activity from a pool of RNA molecules. See, e.g., Bartel, D. and Szostak, J. W. (1993) Science 261:1411-1418.

Alternatively, 32222 gene expression can be inhibited by targeting nucleotide sequences complementary to the regulatory region of the 32222 (e.g., the 32222 promoter and/or enhancers) to form triple helical structures that prevent transcription of the 32222 gene in target cells. See generally, Helene, C. (1991) Anticancer Drug Des. 6(6): 569-84; Helene, C. et al., (1992) Ann. N.Y. Acad. Sci. 660:27-36; and Maher, L. J. (1992) Bioessays 14(12):807-15.

In yet another embodiment, the 32222 nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) Bioorg. Med. Chem. 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. and Nielsen (1996) supra and Perry-O'Keefe et al., (1996) Proc. Natl. Acad. Sci. USA 93:14670-675.

PNAs of 32222 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of 32222 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup and Nielsen (1996) supra)); or as probes or primers for DNA sequencing or hybridization (Hyrup and Nielsen (1996) supra; Perry-O'Keefe et al., (1996) supra).

In another embodiment, PNAs of 32222 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 32222 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al., (1996) Nucleic Acids Res. 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al., (1989) Nucleic Acids Res. 17: 5973-88). PNA monomers are then coupled in a stepwise manner to produce a chimeric molecule with a 5' PNA segment and a 3' DNA segment (Finn et al., (1996) supra). Alternatively, chimeric molecules can be synthesized with a 5' DNA segment and a 3' PNA segment (Petersen, K. H. et al., (1975) Bioorganic Med. Chem. Lett. 5: 1119-11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al., (1989) Proc. Natl. Acad. Sci. USA 86:6553-6556; Lemaitre et al., (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., (1988) Biotechniques 6:958-976) or intercalating agents. (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

Isolated 32222 Proteins and Anti-32222 Antibodies Used in the Methods of the Invention The methods of the invention include the use of isolated 32222 proteins, and biologically active portions thereof, as well as polypeptide fragments suitable for use as immunogens to raise anti-32222 antibodies. In one embodiment, native 32222 proteins can be isolated from cells or tissue sources by an appropriate purification scheme using standard protein purification techniques. In another embodiment, 32222 proteins are produced by recombinant DNA techniques. Alternative to recombinant expression, a 32222 protein or polypeptide can be synthesized chemically using standard peptide synthesis techniques.

As used herein, a "biologically active portion" of a 32222 protein includes a fragment of a 32222 protein having a 32222 activity. Biologically active portions of a 32222 protein include peptides comprising amino acid sequences sufficiently identical to or derived from the amino acid sequence of the 32222 protein, e.g., the amino acid sequence shown in SEQ ID NO:54, which include fewer amino acids than the full length 32222 proteins, and exhibit at least one activity of a 32222 protein. Typically, biologically active portions comprise a domain or motif with at least one activity of the 32222 protein. A biologically active portion of a 32222 protein can be a polypeptide which is, for example, 25, 50, 75, 100, 125, 150, 175, 200, 250, 300 or more amino acids in length. Biologically active portions of a 32222 protein can be used as targets for developing agents which modulate a 32222 activity.

In a preferred embodiment, the 32222 protein used in the methods of the invention has an amino acid sequence shown in SEQ ID NO:54. In other embodiments, the 32222 protein is substantially identical to SEQ ID NO:54, and retains the functional activity of the protein of SEQ ID NO:54, yet differs in amino acid sequence due to natural allelic variation or mutagenesis, as described in detail in subsection V above. Accordingly, in another embodiment, the 32222 protein used in the methods of the invention is a protein which comprises an amino acid sequence at least about 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or more identical to SEQ ID NO:54.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 32222 amino acid sequence of SEQ ID NO:54 having 311 amino acid residues, at least 93, preferably at least 124, more preferably at least 156, even more preferably at least 187, and even more preferably at least 218, 249, 280 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid “identity” is equivalent to amino acid or nucleic acid “homology”). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444-453 (1970)) algorithm which has been incorporated into the GAP program in the GCG software package using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (Comput. Appl. Biosci. 4:11-17 (1988)) which has been incorporated into the ALIGN program (version 2.0 or 2.0U), using a PAM120 weight residue table, a gap length penalty of 12 and a gap penalty of 4.

The methods of the invention may also use 32222 chimeric or fusion proteins. As used herein, a 32222 “chimeric protein” or “fusion protein” comprises a 32222 polypeptide operatively linked to a non-32222 polypeptide. A “32222 polypeptide” refers to a polypeptide having an amino acid sequence corresponding to a 32222 molecule, whereas a “non-32222 polypeptide” refers to a polypeptide having an amino acid sequence corresponding to a protein which is not substantially homologous to the 32222 protein, e.g., a protein which is different from the 32222 protein and which is derived from the same or a different organism. Within a 32222 fusion protein the 32222 polypeptide can correspond to all or a portion of a 32222 protein. In a preferred embodiment, a 32222 fusion protein comprises at least one biologically active portion of a 32222 protein. In another preferred embodiment, a 32222 fusion protein comprises at least two biologically active portions of a 32222 protein. Within the fusion protein, the term “operatively linked” is intended to indicate that the 32222 polypeptide and the non-32222 polypeptide are fused in-frame to each other. The non-32222 polypeptide can be fused to the N-terminus or C-terminus of the 32222 polypeptide.

For example, in one embodiment, the fusion protein is a GST-32222 fusion protein in which the 32222 sequences are fused to the C-terminus of the GST sequences. Such fusion proteins can facilitate the purification of recombinant 32222. In another embodiment, this fusion protein is a 32222 protein containing a heterologous signal sequence at its N-terminus. In certain host cells (e.g., mammalian host cells), expression and/or secretion of 32222 can be increased through use of a heterologous signal sequence.

The 32222 fusion proteins used in the methods of the invention can be incorporated into pharmaceutical compositions and administered to a subject in vivo. The 32222 fusion proteins can be used to affect the bioavailability of a 32222 substrate. Use of 32222 fusion proteins may be useful therapeutically for the treatment of disorders caused by, for example, (i) aberrant modification or mutation of a gene encoding a 32222 protein; (ii) mis-regulation of the 32222 gene; and (iii) aberrant post-translational modification of a 32222 protein.

Moreover, the 32222-fusion proteins used in the methods of the invention can be used as immunogens to produce anti-32222 antibodies in a subject, to purify 32222 ligands and in screening assays to identify molecules which inhibit the interaction of 32222 with a 32222 substrate.

Preferably, a 32222 chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). A 32222-encoding nucleic acid can be cloned into such an expression vector such that the fusion moiety is linked in-frame to the 32222 protein.

The present invention also pertains to the use of variants of the 32222 proteins which function as either 32222 agonists (mimetics) or as 32222 antagonists. Variants of the 32222 proteins can be generated by mutagenesis, e.g., discrete point mutation or truncation of a 32222 protein. An agonist of the 32222 proteins can retain substantially the same, or a subset, of the biological activities of the naturally occurring form of a 32222 protein. An antagonist of a 32222 protein can inhibit one or more of the activities of the naturally occurring form of the 32222 protein by, for example, competitively modulating a 32222-mediated activity of a 32222 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 32222 protein.

In one embodiment, variants of a 32222 protein which function as either 32222 agonists (mimetics) or as 32222 antagonists can be identified by screening combinatorial libraries of mutants, e.g., truncation mutants, of a 32222 protein for 32222 protein agonist or antagonist activity. In one embodiment, a variegated library of 32222 variants is generated by combinatorial mutagenesis at the nucleic acid level and is encoded by a variegated gene library. A variegated library of 32222 variants can be produced by, for example, enzymatically ligating a mixture of synthetic oligonucleotides into gene sequences such that a degenerate set of potential 32222 sequences is expressible as individual polypeptides, or alternatively, as a set of larger fusion proteins (e.g., for phage display) containing the set of 32222 sequences therein. There are a variety of methods which can be used to produce libraries of potential 32222 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 32222 sequences. Methods for synthesizing degenerate oligonucleotides are known in the art (see, e.g., Narang, S. A. (1983) Tetrahedron 39:3; Itakura et al., (1984) Annu. Rev. Biochem. 53:323; Itakura et al., (1984) Science 198:1056; Ike et al., (1983) Nucleic Acid Res. 11:477).

In addition, libraries of fragments of a 32222 protein coding sequence can be used to generate a variegated population of 32222 fragments for screening and subsequent selection of variants of a 32222 protein. In one embodiment, a library of coding sequence fragments can be generated by treating a double stranded PCR fragment of a 32222 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 32222 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 32222 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 32222 variants (Arkin and Youvan (1992) Proc. Natl. Acad. Sci. USA 89:7811-7815; Delagrave et al., (1993) Prot. Eng. 6(3):327-331).

The methods of the present invention further include the use of anti-32222 antibodies. An isolated 32222 protein, or a portion or fragment thereof, can be used as an immunogen to generate antibodies that bind 32222 using standard techniques for polyclonal and monoclonal antibody preparation. A full-length 32222 protein can be used or, alternatively, antigenic peptide fragments of 32222 can be used as immunogens. The antigenic peptide of 32222 comprises at least 8 amino acid residues of the amino acid sequence shown in:64 and encompasses an epitope of 32222 such that an antibody raised against the peptide forms a specific immune complex with the 32222 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 32222 that are located on the surface of the protein, e.g., hydrophilic regions, as well as regions with high antigenicity.

A 32222 immunogen is typically used to prepare antibodies by immunizing a suitable subject, (e.g., rabbit, goat, mouse, or other mammal) with the immunogen. An appropriate immunogenic preparation can contain, for example, recombinantly expressed 32222 protein or a chemically synthesized 32222 polypeptide. The preparation can further include an adjuvant, such as Freund's complete or incomplete adjuvant, or similar immunostimulatory agent. Immunization of a suitable subject with an immunogenic 32222 preparation induces a polyclonal anti-32222 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a 32222. Examples of immunologically active portions of immunoglobulin molecules include F(ab) and F(ab')2 fragments which can be generated by treating the antibody with an enzyme such as pepsin. The invention provides polyclonal and monoclonal antibodies that bind 32222 molecules. The term "monoclonal antibody" or "monoclonal antibody composition", as used herein, refers to a population of antibody molecules that contain only one species of an antigen binding site capable of immunoreacting with a particular epitope of 32222. A monoclonal antibody composition thus typically displays a single binding affinity for a particular 32222 protein with which it immunoreacts.

Polyclonal anti-32222 antibodies can be prepared as described above by immunizing a suitable subject with a 32222 immunogen. The anti-32222 antibody titer in the immunized subject can be monitored over time by standard techniques, such as with an enzyme linked immunosorbent assay (ELISA) using immobilized 32222. If desired, the antibody molecules directed against 32222 can be isolated from the mammal (e.g., from the blood) and further purified by well known techniques, such as protein A chromatography to obtain the IgG fraction. At an appropriate time after immunization, e.g., when the anti-32222 antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al., (1981) J. Immunol. 127:539-46; Brown et al., (1980) J. Biol. Chem. 255:4980-83; Yeh et al., (1976) Proc. Natl. Acad. Sci. USA 76:2927-31; and Yeh et al., (1982) Int. J. Cancer 29:269-75), the more recent human B cell hybridoma technique (Kozbor et al., (1983) Immunol. Today 4:72), the EBV-hybridoma technique (Cole et al., (1985)

Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387-402; Gefter, M. L. et al., (1977) Somat. Cell Genet. 3:231-36). Briefly, an immortal cell line (typically a myeloma) is fused to lymphocytes (typically splenocytes) from a mammal immunized with a 32222 immunogen as described above, and the culture supernatants of the resulting hybridoma cells are screened to identify a hybridoma producing a monoclonal antibody that binds 32222.

Any of the many well known protocols used for fusing lymphocytes and immortalized cell lines can be applied for the purpose of generating an anti-32222 monoclonal antibody (see, e.g., G. Galfre et al., (1977) Nature 266:55052; Gefter et al., (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 32222, e.g., using a standard ELISA assay.

Alternative to preparing monoclonal antibody-secreting hybridomas, a monoclonal anti-32222 antibody can be identified and isolated by screening a recombinant combinatorial immunoglobulin library (e.g., an antibody phage display library) with 32222 to thereby isolate immunoglobulin library members that bind 32222. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication WO 92/20791; Markland et al., PCT International Publication No. WO 92/15679; Breitling et al., PCT International Publication WO 93/01288; McCafferty et al., PCT International Publication No. WO 92/01047; Garrard et al., PCT International Publication No. WO 92/09690; Ladner et al., PCT International Publication No. WO 90/02809; Fuchs et al., (1991) Bio/Technology 9:1370-1372; Hay et al., (1992) Hum. Antibod. Hybridomas 3:81-85; Huse et al., (1989) Science 246:1275-1281; Griffiths et al., (1993) EMBO J. 12:725-734; Hawkins et al., (1992) J. Mol. Biol. 226:889-896; Clarkson et al., (1991) Nature 352:624-628; Gram et al., (1992) Proc. Natl. Acad. Sci. USA 89:3576-3580; Garrard et al., (1991) Biotechnology (NY) 9:1373-1377; Hoogenboom et al., (1991) Nucleic Acids Res. 19:4133-4137; Barbas et al., (1991) Proc. Natl. Acad. Sci. USA 88:7978-7982; and McCafferty et al., (1990) Nature 348:552-554.

Additionally, recombinant anti-32222 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al., International Application No. PCT/US86/02269; Akira, et al., European Patent Application 184,187; Taniguchi, M., European Patent Application 171,496; Morrison et al., European Patent Application 173,494; Neuberger et al., PCT International Publication No. WO 86/01533; Cabilly et al., U.S. Pat. No. 4,816,567; Cabilly et al., European Patent Application 125,023; Better et al., (1988) Science 240:1041-1043; Liu et al., (1987) Proc. Natl. Acad. Sci. USA 84:3439-3443; Liu et al., (1987) J. Immunol. 139:3521-3526; Sun et al., (1987) Proc. Natl. Acad. Sci. USA 84:214-218; Nishimura et al., (1987) Cancer Res. 47:999-1005; Wood et al., (1985) Nature 314:446-449; Shaw et al., (1988) J. Natl. Cancer Inst. 80:1553-1559; Morrison, S. L. (1985) Science 229:1202-1207; Oi et al., (1986) BioTechniques 4:214; Winter U.S. Pat. No. 5,225,539; Jones et al., (1986) Nature 321:552-525; Verhoeyen et al., (1988) Science 239:1534; and Beidler et al., (1988) J. Immunol. 141:4053-4060.

An anti-32222 antibody can be used to detect 32222 protein (e.g., in a cellular lysate or cell supernatant) in order to evaluate the abundance and pattern of expression of the 32222 protein. Anti-32222 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

Electronic Apparatus Readable Media and Arrays

Electronic apparatus readable media comprising a 32222 modulator of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 32222 modulators of the present invention.

A variety of software programs and formats can be used to store the marker information of the present invention on the electronic apparatus readable medium. For example, the nucleic acid sequence corresponding to the 32222 modulators can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the 32222 modulators of the present invention.

By providing the 32222 modulators of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a cellular proliferative disorder or a pre-disposition to a cellular proliferative disorder, wherein the method comprises the steps of determining the presence or absence of a 32222 modulator and based on the presence or absence of the 32222 modulator, determining whether the subject has a cellular proliferative disorder or a pre-disposition to a cellular proliferative disorder and/or recommending a particular treatment for the cellular proliferative disorder or pre-cellular proliferative disorder condition.

The present invention further provides in an electronic system and/or in a network, a method for determining whether a subject has a cellular proliferative disorder or a pre-disposition to a cellular proliferative disorder associated with a 32222 modulator wherein the method comprises the steps of determining the presence or absence of the 32222 modulator, and based on the presence or absence of the 32222 modulator, determining whether the subject has a cellular proliferative disorder or a pre-disposition to a cellular proliferative disorder, and/or recommending a particular treatment for the cellular proliferative disorder or pre-cellular proliferative disorder condition. The method may further comprise the step of receiving phenotypic information associated with the subject and/or acquiring from a network phenotypic information associated with the subject.

The present invention also provides in a network, a method for determining whether a subject has a cellular proliferative disorder or a pre-disposition to a cellular proliferative disorder associated with a 32222 modulator, said method comprising the steps of receiving information associated with the 32222 modulator receiving phenotypic information associated with the subject, acquiring information from the network corresponding to the 32222 modulator and/or cellular proliferative disorder, and based on one or more of the phenotypic information, the 32222 modulator, and the acquired information, determining whether the subject has a cellular proliferative disorder or a pre-disposition to a cellular proliferative disorder. The method may further comprise the step of recommending a particular treatment for the cellular proliferative disorder or pre-cellular proliferative disorder condition.

The present invention also provides a business method for determining whether a subject has a cellular proliferative disorder or a pre-disposition to a cellular proliferative disorder, said method comprising the steps of receiving information associated with the 32222 modulator, receiving phenotypic information associated with the subject, acquiring information from the network corresponding to the 32222 modulator and/or cellular proliferative disorder, and based on one or more of the phenotypic information, the 32222 modulator, and the acquired information, determining whether the subject has a cellular proliferative disorder or a pre-disposition to a cellular proliferative disorder. The method may further comprise the step of recommending a particular treatment for the cellular proliferative disorder or pre-cellular proliferative disorder condition.

The invention also includes an array comprising a 32222 modulator of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of cellular proliferative disorder, progression of cellular proliferative disorder, and processes, such a cellular transformation associated with cellular proliferative disorder.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

This invention is further illustrated by the following examples which should not be construed as limiting. The contents of all references, patents and published patent applications cited throughout this application and the Sequence Listing, are incorporated herein by reference.

EXAMPLES

Example 1

Identification of 32222 as a Regulator of Tumorgenesis

In order to determine whether the 32222 molecules of the present invention are involved in tumorigenesis, gene expression in a lung tumor cell line that is null for the p53 protein was examined. A p53/estrogen receptor fusion protein (p53ER) was introduced into a lung tumor cell line that is null for the p53 protein. The p53 activity of this fusion protein was induced by addition of the estrogen analogue tamoxifen (4HT) to the cell culture medium. The results of these experiments have demonstrated that 32222 activity was down-regulated by the induced p53 activity. Regulation of 32222 expression by the p53 molecule was also observed in cells derived from colon, breast, and ovary tumor samples.

Example 2

Tissue Distribution Analysis of Human 32222 mRNA Using Transcriptional Profiling A 30K array was profiled with probes generated from NCI-H125 cells transiently expressing p53 and those infected with a control vector. This experiment revealed that cells expressing p53 showed reduced levels of 32222 expression as compared to the vector controls (H125 control vector) (see Table 14). These results were confirmed by transcription profiling experiments comparing gene expression patterns in the NCI-H125 lung tumor cell line with and without functional p53 expression at 96 hours (Table 15).

In addition to the high expression of the 32222 molecule in tumors derived from lung tissues, high levels of 32222 expression were observed in epithelial tumors derived from breast, ovary, and colon tissues (see Table 20).

Example 3

Tissue Distribution of Human 32222 by In Situ Analysis

For in situ analysis, various tissues, e.g., tissues obtained from normal colon, breast, lung, and ovarian normal tissue, as well as colon, breast, lung, and ovarian tumors and colon metastases to the liver, were first frozen on dry ice. Ten-micrometer-thick sections of the tissues were post-fixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with 35S-radiolabeled (5×107 cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

In situ hybridization results indicated expression of 32222 in all tumor types, with no expression in normal tissue counterparts. Expression was detected in 2 out of 2 breast tumors, 8 out of 8 lung tumors, 4 out of 4 colon tumors (including 2 primary tumors and 2 colon metastasis to the liver), and in 1 out of 1 ovary tumor tested.

Example 4

Tissue Distribution of Human 32222 mRNA Using Tagman™ Analysis

This example describes the tissue distribution of human 32222 mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq GoId™ DNA Polymerase to cleave a TaqMan™ probe during PCR. Briefly, cDNA was generated from the samples of interest, e.g., lung, ovary, colon, and breast normal and tumor samples, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Data obtained from the Taqman™ analysis demontrated a significant up-regulation of 32222 mRNA in tumors (T), breast, lung, and colon tumors, in particular, as compared to the respective normal (N) tissues. Given that the mRNA for 32222 is expressed in a variety of tumors, with significant up-regulation in tumor samples in comparison to normal samples, it is believed that inhibition of 32222 activity may inhibit tumor progression by, for example, inhibiting energy production and cellular growth and proliferation.

A further experiment revealed that 32222 mRNA is expressed at high levels in most of the xenograft-friendly cell lines tested. These cell lines can be grown as subcutaneous or orthotopic xenografts in mice and are capable of producing tumors analogous to human tumors, tested using Taqman™ analysis (see Table 16).

Example 5

Expression of Recombinant 32222 Plypeptide in Bacterial Cells

In this example, human 32222 is expressed as a recombinant glutathione-S-transferase (GST) fusion polypeptide in *E. coli* and the fusion polypeptide is isolated and characterized. Specifically, 32222 is fused to GST and this fusion polypeptide is expressed in *E. coli*, e.g., strain PEB199. Expression of the GST-32222 fusion polypeptide in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 6

Expression of Recombinant 32222 Polypeptide in COS Cells

To express the human 32222 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 32222 polypeptide and an HA tag (Wilson et al., (1984) Cell 37:767) or a FLAG tag fused in-frame to its 3' end of the fragment is cloned into the polylinker region of the vector, thereby placing the expression of the recombinant polypeptide under the control of the CMV promoter.

To construct the plasmid, the human 32222 DNA sequence is amplified by PCR using two primers. The 5' primer contains the restriction site of interest followed by approximately twenty nucleotides of the 32222 coding sequence starting from the initiation codon; the 3' end sequence contains complementary sequences to the other restriction site of interest, a translation stop codon, the HA tag or FLAG tag and the last 20 nucleotides of the 32222 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 32222 gene is inserted in the correct orientation. The ligation mixture is transformed into *E. coli* cells (strains HB101, DH5□, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the human 32222-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the IC54420 polypeptide is detected by radiolabelling (35S-methionine or 35S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labelled for 8 hours with 35S-methionine (or 35S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the human 32222 coding sequence is cloned directly into the polylinker of the pcDNA/Amp vector using the appropriate restriction sites. The resulting plasmid is transfected into COS cells in the manner described above, and the expression of the 32222 polypeptide is detected by radiolabelling and immunoprecipitation using a 32222-specific monoclonal antibody.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound which binds to a polypeptide selected from the group consisting of:

a) a polypeptide comprising the amino acid sequence of SEQ ID NO:4; and b) a polypeptide encoded by a nucleic acid molecule comprising the nucleotide sequence of SEQ ID NO:5;

the method comprising the steps of:

i) combining a cell expressing the polypeptide with a test compound; and ii) determining whether the polypeptide binds to the test compound.

2. The method of claim 1, wherein the binding of the test compound to the polypeptide is detected by a method selected from the group consisting of:

a) detection of binding by direct detecting of test compound/polypeptide binding;

b) detection of binding using a competition binding assay.

3. The method claim 1, wherein the compound identified is an agent that inhibits the activity of the polypeptide.

4. The method of claim 1, wherein the polypeptide comprises the amino acid sequence of SEQ ID NO:4.

5. The method of claim 1, wherein the polypeptide is encoded by a nucleic acid molecule comprising the nucleotide sequence of SEQ ID NO:5.

* * * * *

SEQUENCE LISTING

<160> NUMBER OF SEQ ID NOS: 56

<210> SEQ ID NO 1
<211> LENGTH: 2686
<212> TYPE: DNA
<213> ORGANISM: Homo Sapiens
<220> FEATURE:
<221> NAME/KEY: misc_feature
<222> LOCATION: (1)...(2686)
<223> OTHER INFORMATION: n = A,T,C or G

<400> SEQUENCE: 1

```
atccacgctt ttgcntgacc cttgcttggt tcaacttana ggtctttgtt tcggttttct      60
tgttnngcnc cggttacaga tccaaagttt tgaaaaaacc anaaaagtna nctggtaagt     120
taagtctttt ttgtctttta tttccagntc cnggaatccg ggtggttggt gcaaantcaa     180
aaganttgtt cctcaagtga atgttgcntt tacttcttag gcntgtacgg aaagtgttat     240
ttttgtttta aaagctggga attcttanta cgacttcact atagggagtc gacccacgcg     300
tccggcgagt ctccatggcg gtggcggcgg cagctgcggc gggacccgtg ttctggaggc     360
gactgctggg cctcctgcct ggccgcccag ggctggccgc gctcctggga cgcctgtccg     420
accgcctcgg caggaaccgg gaccgccagc gcaggaggtc accatggctg ttattggctc     480
ccttgctgtc cccagctgtt ccccaggtca cctccccacc ttgctgcctg tgtccagaag     540
gcgtgcaccg gttccagtgg atcagaaacc tggttccaga atttggagtc tccagttctc     600
acgttagggt gctttcttcc ccggcagagt tttcgagctc catgaagggg cagataagag     660
tagccaagag gcgggtcgtg atggcatccc tctacctggg gacaggtcct ttggaacagg     720
agctggtgga ctgcctggaa agtactctag aaaagtcact ccaagcaaag tttccttcaa     780
atctcaaggt ctccattctc ttagacttca cgcggggctc acgaggtcgg aagaactccc     840
gcacaatgct gctcccactc ctgcggaggt tcccagagca ggtccgagtc tccctctttc     900
acacgccgca cctccgtggg ctgcttcggc tcctcatccc tgagcgcttc aacgagacca     960
tcggcctcca gcacattaag gtgtacctct tcgacaacag cgtcatcttg agcggtgcaa    1020
acctgagtga ctcctacttc accaaccgcc aggaccgcta cgtgttcctg caggactgtg    1080
cggagattgc cgacttcttc acggagctgg tggacgcggt gggggatgtg tccctgcagc    1140
tgcaggggga cgacacggtg caggtggtgg atgggatggt gcatccttac aaaggggacc    1200
gggccgagta ctgcaaggca gccaataaga gggtcatgga tgtgatcaac tcagccagga    1260
cccgccagca gatgctgcat gcccagacct tccacagcaa ctctcttttg acccaggaag    1320
atgcagcagc tgctggggat cgcagaccag cccctgacac ctggatttat ccgctgattc    1380
agatgaagcc cttcgagatt caaatcgatg agattgtcac tgagaccctg ttgactgagg    1440
cggagcgcgg ggcaaaggtc tacctcacca ctggctattt caacctgacc caggcctaca    1500
tggacctggt cttgggcact cgggctgagt accagatcct gctggcctca ccagaggtga    1560
atggcttctt tggggccaag gggggtggccg gcgccatccc agcggcctat gtgcacatcg    1620
agcgacagtt cttcagtgag gtgtgcagcc tgggacagca ggagcgggtc cagcttcagg    1680
agtactggcg gaggggctgg acgttccacg ccaaaggcct ctggctgtac ctggcaggga    1740
gcagcctgcc ctgtctcacg ctgattggct ctcctaattt tgggtacagg tcagttcacc    1800
gggacctgga ggcccagatt gcgatcgtga cggagaacca ggccctgcag cagcagcttc    1860
accaggagca agagcagctc tacctgaggt caggtgtggt gtcctctgcc accttcgagc    1920
```

```
agccgagtcg ccaggtgaag ctgtgggtga agatggtgac tccactgatc aagaacttct   1980

tctgaggaca gacaggtgct gtctctagca tcacctctca gcacgatttt cccgagagtt   2040

cacaggaatg gccttgatga agatgacagg catggccggg gtcagctctt tcagccgcgc   2100

ttcagcgatg actccagtct gggtgtccca gcgagcccct gcagggacag tatggctgag   2160

ggtcaggtgt gctgccagta agtgagggag gggctggcag gaagggtggg gtcctcacac   2220

tccccgccct ytgcagagct gggctctacc ccaaaaggct tcaggccagc tgccacagct   2280

ggaagcagag gccttcgtag gtgatggcct gcatgttgta actaccccgt cccgctgggc   2340

tcaaggaaca gctcagctaa agccctcggg ttccatccgt ttaaatctgt ggcattttca   2400

gagcctcatc tgtcagcctt aatgtcagtg gcaggaagtc ataactccag ctaaaaatta   2460

cagagtaaag ttccctgatt cttaatgtgt aatgtctgcc ctatgtgtac atacacaata   2520

taattataca tctgtgcata taaatattgc ctttaaccag actgctatta tttctactcg   2580

ccctatttaa tggtgttttt atttcctgtc tgaaatctca aaataaacaa acatggagag   2640

cttaaaaaaa aaaaaaaagg gcggccgcta gactagtcta gagaaa                  2686
```

```
<210> SEQ ID NO 2
<211> LENGTH: 556
<212> TYPE: PRT
<213> ORGANISM: Homo Sapiens

<400> SEQUENCE: 2

Met Ala Val Ala Ala Ala Ala Ala Ala Gly Pro Val Phe Trp Arg Arg
 1               5                  10                  15

Leu Leu Gly Leu Leu Pro Gly Arg Pro Gly Leu Ala Ala Leu Leu Gly
            20                  25                  30

Arg Leu Ser Asp Arg Leu Gly Arg Asn Arg Asp Arg Gln Arg Arg Arg
        35                  40                  45

Ser Pro Trp Leu Leu Leu Ala Pro Leu Leu Ser Pro Ala Val Pro Gln
    50                  55                  60

Val Thr Ser Pro Pro Cys Cys Leu Cys Pro Glu Gly Val His Arg Phe
65                  70                  75                  80

Gln Trp Ile Arg Asn Leu Val Pro Glu Phe Gly Val Ser Ser Ser His
                85                  90                  95

Val Arg Val Leu Ser Ser Pro Ala Glu Phe Phe Glu Leu Met Lys Gly
            100                 105                 110

Gln Ile Arg Val Ala Lys Arg Arg Val Val Met Ala Ser Leu Tyr Leu
        115                 120                 125

Gly Thr Gly Pro Leu Glu Gln Glu Leu Val Asp Cys Leu Glu Ser Thr
    130                 135                 140

Leu Glu Lys Ser Leu Gln Ala Lys Phe Pro Ser Asn Leu Lys Val Ser
145                 150                 155                 160

Ile Leu Leu Asp Phe Thr Arg Gly Ser Arg Gly Arg Lys Asn Ser Arg
                165                 170                 175

Thr Met Leu Leu Pro Leu Leu Arg Arg Phe Pro Glu Gln Val Arg Val
            180                 185                 190

Ser Leu Phe His Thr Pro His Leu Arg Gly Leu Leu Arg Leu Leu Ile
        195                 200                 205

Pro Glu Arg Phe Asn Glu Thr Ile Gly Leu Gln His Ile Lys Val Tyr
    210                 215                 220

Leu Phe Asp Asn Ser Val Ile Leu Ser Gly Ala Asn Leu Ser Asp Ser
225                 230                 235                 240
```

```
Tyr Phe Thr Asn Arg Gln Asp Arg Tyr Val Phe Leu Gln Asp Cys Ala
                245                 250                 255

Glu Ile Ala Asp Phe Phe Thr Glu Leu Val Asp Ala Val Gly Asp Val
            260                 265                 270

Ser Leu Gln Leu Gln Gly Asp Asp Thr Val Gln Val Val Asp Gly Met
        275                 280                 285

Val His Pro Tyr Lys Gly Asp Arg Ala Glu Tyr Cys Lys Ala Ala Asn
    290                 295                 300

Lys Arg Val Met Asp Val Ile Asn Ser Ala Arg Thr Arg Gln Gln Met
305                 310                 315                 320

Leu His Ala Gln Thr Phe His Ser Asn Ser Leu Leu Thr Gln Glu Asp
                325                 330                 335

Ala Ala Ala Ala Gly Asp Arg Arg Pro Ala Pro Asp Thr Trp Ile Tyr
            340                 345                 350

Pro Leu Ile Gln Met Lys Pro Phe Glu Ile Gln Ile Asp Glu Ile Val
        355                 360                 365

Thr Glu Thr Leu Leu Thr Glu Ala Glu Arg Gly Ala Lys Val Tyr Leu
    370                 375                 380

Thr Thr Gly Tyr Phe Asn Leu Thr Gln Ala Tyr Met Asp Leu Val Leu
385                 390                 395                 400

Gly Thr Arg Ala Glu Tyr Gln Ile Leu Leu Ala Ser Pro Glu Val Asn
                405                 410                 415

Gly Phe Phe Gly Ala Lys Gly Val Ala Gly Ala Ile Pro Ala Ala Tyr
            420                 425                 430

Val His Ile Glu Arg Gln Phe Phe Ser Glu Val Cys Ser Leu Gly Gln
        435                 440                 445

Gln Glu Arg Val Gln Leu Gln Glu Tyr Trp Arg Arg Gly Trp Thr Phe
    450                 455                 460

His Ala Lys Gly Leu Trp Leu Tyr Leu Ala Gly Ser Ser Leu Pro Cys
465                 470                 475                 480

Leu Thr Leu Ile Gly Ser Pro Asn Phe Gly Tyr Arg Ser Val His Arg
                485                 490                 495

Asp Leu Glu Ala Gln Ile Ala Ile Val Thr Glu Asn Gln Ala Leu Gln
            500                 505                 510

Gln Gln Leu His Gln Glu Gln Glu Gln Leu Tyr Leu Arg Ser Gly Val
        515                 520                 525

Val Ser Ser Ala Thr Phe Glu Gln Pro Ser Arg Gln Val Lys Leu Trp
    530                 535                 540

Val Lys Met Val Thr Pro Leu Ile Lys Asn Phe Phe
545                 550                 555
```

<210> SEQ ID NO 3
<211> LENGTH: 1668
<212> TYPE: DNA
<213> ORGANISM: Homo Sapiens

<400> SEQUENCE: 3

```
atggcggtgg cggcggcagc tgcggcggga cccgtgttct ggaggcgact gctgggcctc      60

ctgcctggcc gcccagggct ggccgcgctc ctgggacgcc tgtccgaccg cctcggcagg     120

aaccgggacc gccagcgcag gaggtcacca tggctgttat tggctccctt gctgtcccca     180

gctgttcccc aggtcacctc ccccaccttgc tgcctgtgtc cagaaggcgt gcaccggttc    240

cagtggatca gaaacctggt tccagaattt ggagtctcca gttctcacgt tagggtgctt     300
```

-continued

```
tcttccccgg cagagttttt cgagctcatg aaggggcaga taagagtagc caagaggcgg    360

gtcgtgatgg catccctcta cctggggaca ggtcctttgg aacaggagct ggtggactgc    420

ctggaaagta ctctagaaaa gtcactccaa gcaaagtttc cttcaaatct caaggtctcc    480

attctcttag acttcacgcg gggctcacga ggtcggaaga actccacaat gctgctccca    540

ctcctgcgga ggttcccaga gcaggtccga gtctccctct ttcacacgcc gcacctccgt    600

gggctgcttc ggctcctcat ccctgagcgc ttcaacgaga ccatcggcct ccagcacatt    660

aaggtgtacc tcttcgacaa cagcgtcatc ttgagcggtg caaacctgag tgactcctac    720

ttcaccaacc gccaggaccg ctacgtgttc ctgcaggact gtgcggagat tgccgacttc    780

ttcacggagc tggtggacgc ggtgggggat gtgtccctgc agctgcaggg ggacgacacg    840

gtgcaggtgg tggatgggat ggtgcatcct tacaaagggg accgggccga gtactgcaag    900

gcagccaata agagggtcat ggatgtgatc aactcagcca ggacccgcca gcagatgctg    960

catgcccaga ccttccacag caactctctt ttgacccagg aagatgcagc agctgctggg   1020

gatcgcagac cagcccctga cacctggatt tatccgctga ttcagatgaa gcccttcgag   1080

attcaaatcg atgagattgt cactgagacc ctgttgactg aggcggagcg cggggcaaag   1140

gtctacctca ccactggcta tttcaacctg acccaggcct acatggacct ggtcttgggc   1200

actcgggctg agtaccagat cctgctggcc tcaccagagg tgaatggctt ctttggggcc   1260

aagggggtgg ccggcgccat cccagcggcc tatgtgcaca tcgagcgaca gttcttcagt   1320

gaggtgtgca gcctgggaca gcaggagcgg gtccagcttc aggagtactg gcggaggggc   1380

tggacgttcc acgccaaagg cctctggctg tacctggcag ggagcagcct gccctgtctc   1440

acgctgattg gctctcctaa ttttgggtac aggtcagttc accgggacct ggaggcccag   1500

attgcgatcg tgacggagaa ccaggccctg cagcagcagc ttcaccagga gcaagagcag   1560

ctctacctga ggtcaggtgt ggtgtcctct gccaccttcg agcagccgag tcgccaggtg   1620

aagctgtggg tgaagatggt gactccactg atcaagaact tcttctga                1668
```

```
<210> SEQ ID NO 4
<211> LENGTH: 372
<212> TYPE: PRT
<213> ORGANISM: Homo Sapiens

<400> SEQUENCE: 4

Met Ser Lys Ala Phe Gly Leu Leu Arg Gln Ile Cys Gln Ser Ile Leu
 1               5                  10                  15

Ala Glu Ser Ser Gln Ser Pro Ala Asp Leu Glu Glu Lys Lys Glu Glu
            20                  25                  30

Asp Ser Asn Met Lys Arg Glu Gln Pro Arg Glu Arg Pro Arg Ala Trp
        35                  40                  45

Asp Tyr Pro His Gly Leu Val Gly Leu His Asn Ile Gly Gln Thr Cys
    50                  55                  60

Cys Leu Asn Ser Leu Ile Gln Val Phe Val Met Asn Val Asp Phe Thr
65                  70                  75                  80

Arg Ile Leu Lys Arg Ile Thr Val Pro Arg Gly Ala Asp Glu Gln Arg
                85                  90                  95

Arg Ser Val Pro Phe Gln Met Leu Leu Leu Leu Glu Lys Met Gln Asp
            100                 105                 110

Ser Arg Gln Lys Ala Val Arg Pro Leu Glu Leu Ala Tyr Cys Leu Gln
        115                 120                 125

Lys Cys Asn Val Pro Leu Phe Val Gln His Asp Ala Ala Gln Leu Tyr
```

-continued

```
    130                 135                 140

Leu Lys Leu Trp Asn Leu Ile Lys Asp Gln Ile Thr Asp Val His Leu
145                 150                 155                 160

Val Glu Arg Leu Gln Ala Leu Tyr Thr Ile Arg Val Lys Asp Ser Leu
                165                 170                 175

Ile Cys Val Asp Cys Ala Met Glu Ser Ser Arg Asn Ser Ser Met Leu
            180                 185                 190

Thr Leu Pro Leu Ser Leu Phe Asp Val Asp Ser Lys Pro Leu Lys Thr
        195                 200                 205

Leu Glu Asp Ala Leu His Cys Phe Phe Gln Pro Arg Glu Leu Ser Ser
    210                 215                 220

Lys Ser Lys Cys Phe Cys Glu Asn Cys Gly Lys Lys Thr Arg Gly Lys
225                 230                 235                 240

Gln Val Leu Lys Leu Thr His Leu Pro Gln Thr Leu Thr Ile His Leu
                245                 250                 255

Met Arg Phe Ser Ile Arg Asn Ser Gln Thr Arg Lys Ile Cys His Ser
            260                 265                 270

Leu Tyr Phe Pro Gln Ser Leu Asp Phe Ser Gln Ile Leu Pro Met Lys
        275                 280                 285

Arg Glu Ser Cys Asp Ala Glu Glu Gln Ser Gly Gly Gln Tyr Glu Leu
    290                 295                 300

Phe Ala Val Ile Ala His Val Gly Met Ala Asp Ser Gly His Tyr Cys
305                 310                 315                 320

Val Tyr Ile Arg Asn Ala Val Asp Gly Lys Trp Phe Cys Phe Asn Asp
                325                 330                 335

Ser Asn Ile Cys Leu Val Ser Trp Glu Asp Ile Gln Cys Thr Tyr Gly
            340                 345                 350

Asn Pro Asn Tyr His Trp Gln Glu Thr Ala Tyr Leu Leu Val Tyr Met
        355                 360                 365

Lys Met Glu Cys
    370
```

<210> SEQ ID NO 5
<211> LENGTH: 1869
<212> TYPE: DNA
<213> ORGANISM: Homo Sapiens

<400> SEQUENCE: 5

```
caccccgcgt ccgcagcagc ggaggctgga cgcttgcatg gcgcttgaga gattccatcg     60

tgcctggctc acataagcgc ttcctggaag tgaagtcgtg ctgtcctgaa cgcgggccag    120

gcagctgcgg cctgggggtt ttggagtgat cacgaatgag caaggcgttt gggctcctga    180

ggcaaatctg tcagtccatc ctggctgagt cctcgcagtc cccggcagat cttgaagaaa    240

agaaggaaga agacagcaac atgaagagag agcagcccag agagcgtccc agggcctggg    300

actaccctca tggcctggtt ggtttacaca acattggaca gacctgctgc cttaactcct    360

tgattcaggt gttcgtaatg aatgtggact tcaccaggat attgaagagg atcacggtgc    420

ccaggggagc tgacgagcag aggagaagcg tccctttcca gatgcttctg ctgctggaga    480

agatgcagga cagccggcag aaagcagtgc ggcccctgga gctggcctac tgcctgcaga    540

agtgcaacgt gcccttgttt gtccaacatg atgctgccca actgtacctc aaactctgga    600

acctgattaa ggaccagatc actgatgtgc acttggtgga gagactgcag gccctgtata    660

cgatccgggt gaaggactcc ttgatttgcg ttgactgtgc catggagagt agcagaaaca    720
```

-continued

```
gcagcatgct caccctccca ctttctcttt ttgatgtgga ctcaaagccc ctgaagacac    780

tggaggacgc cctgcactgc ttcttccagc ccagggagtt atcaagcaaa agcaagtgct    840

tctgtgagaa ctgtgggaag aagacccgtg ggaaacaggt cttgaagctg acccatttgc    900

cccagaccct gacaatccac ctcatgcgat tctccatcag gaattcacag acgagaaaga    960

tctgccactc cctgtacttc ccccagagct tggatttcag ccagatcctt ccaatgaagc   1020

gagagtcttg tgatgctgag gagcagtctg gagggcagta tgagcttttt gctgtgattg   1080

cgcacgtggg aatggcagac tccggtcatt actgtgtcta catccggaat gctgtggatg   1140

gaaaatggtt ctgcttcaat gactccaata tttgcttggt gtcctgggaa gacatccagt   1200

gtacctacgg aaatcctaac taccactggc aggaaactgc atatcttctg gtttacatga   1260

agatggagtg ctaatggaaa tgcccaaaac cttcagagat tgacacgctg tcattttcca   1320

tttccgttcc tggatctacg gagtcttcta agagattttg caatgaggag aagcattgtt   1380

ttcaaactat ataactgagc cttatttata attagggata ttatcaaaat atgtaaccat   1440

gaggcccctc aggtcctgat cagtcagaat ggatgctttc accagcagac ccggccatgt   1500

ggctgctcgg tcctgggtgc tcgctgctgt gcaagacatt agccctttag ttatgagcct   1560

gtgggaactt caggggttcc cagtggggag agcagtggca gtgggaggca tctgggggcc   1620

aaaggtcagt ggcagggggt atttcagtat tatacaactg ctgtgaccag acttgtatac   1680

tggctgaata tcagtgctgt ttgtaatttt tcactttgag aaccaacatt aattccatat   1740

gaatcaagtg ttttgtaact gctattcatt tattcagcaa atatttattg atcatctctt   1800

ctccataaga tagtgtgata aacacagtca tgaataaagt tattttccac aaaaaaaaaa   1860

aaaaaaagg                                                           1869
```

<210> SEQ ID NO 6
<211> LENGTH: 2175
<212> TYPE: DNA
<213> ORGANISM: Homo Sapiens

<400> SEQUENCE: 6

```
cacgcgtccg caaatttcct gattcttttg aattaggatt ccagatgggg gcctcatttc     60

tacagccccc aacattccta tagccgttat cactgccatc accactgcca ccagcatctt    120

cttgcagatt ccacccctgc tccccagaga cttcctgctt tgaaagtgag cagaaaggaa    180

gctctcagaa aaatctctag tggtggctgc cgtcgctcca gacaatcgga atcctgcctt    240

caccaccatg ggctggcttt ttctaaaggt tttgttggcg ggagtgagtt tctcaggatt    300

tctttatcct cttgtggatt tttgcatcag tgggaaaaca agaggacaga agccaaactt    360

tgtgattatt ttggccgatg acatggggtg gggtgacctg ggagcaaact gggcagaaac    420

aaaggacact gccaaccttg ataagatggc ttcggaggga atgaggtttg tggatttcca    480

tgcagctgcc tccacctgct caccctcccg ggcttccttg ctcaccggcc ggcttggcct    540

tcgcaatgga gtcacacgca actttgcagt cacttctgtg ggaggccttc cgctcaacga    600

gaccaccttg gcagaggtgc tgcagcaggc gggttacgtc actgggataa taggcaaatg    660

gcatcttgga caccacggct cttatcaccc caacttccgt ggttttgatt actactttgg    720

aatcccatat agccatgata tggctgtac tgatactcca ggctacaacc accctccttg    780

tccagcgtgt ccacagggtg atggaccatc aaggaacctt caaagagact gttacactga    840

cgtggccctc cctctttatg aaaacctcaa cattgtggag cagccggtga acttgagcag    900

ccttgcccag aagtatgctg agaaagcaac ccagttcatc cagcgtgcaa gcaccagcgg    960
```

```
gaggcccttc ctgctctatg tggctctggc ccacatgcac gtgcccttac ccgtgactca   1020

gctaccagca gcgccacggg gcagaagcct gtatggtgca gggctctggg agatggacag   1080

tctggtgggc cagatcaagg acaaagttga ccacacagtg aaggaaaaca cattcctctg   1140

gtttacagga gacaatggcc cgtgggctca gaagtgtgag ctagcgggca gtgtgggtcc   1200

cttcactgga ttttggcaaa ctcgtcaagg gggaagtcca gccaagcaga cgacctggga   1260

aggagggcac cgggtcccag cactggctta ctggcctggc agagttccag ttaatgtcac   1320

cagcactgcc ttgttaagcg tgctggacat tttttccaact gtggtagccc tggcccaggc   1380

cagcttacct caaggacggc gctttgatgg tgtggacgtc tccgaggtgc tctttggccg   1440

gtcacagcct gggcacaggg tgctgttcca ccccaacagc ggggcagctg gagagtttgg   1500

agccctgcag actgtccgcc tggagcgtta caaggccttc tacattaccg gtggagccag   1560

ggcgtgtgat gggagcacgg ggcctgagct gcagcataag tttcctctga ttttcaacct   1620

ggaagacgat accgcagaag ctgtgcccct agaaagaggt ggtgcggagt accaggctgt   1680

gctgcccgag gtcagaaagg ttcttgcaga cgtcctccaa gacattgcca acgacaacat   1740

ctccagcgca gattacactc aggacccttc agtaactccc tgctgtaatc cctaccaaat   1800

tgcctgccgc tgtcaagccg cataacagac caatttttat tccacgagga ggagtacctg   1860

gaaattaggc aagtttgctt ccaaatttca tttttaccct ctttacaaac acacgcttta   1920

gtttagtctt ggagtttagt tttggagtta gccttgcata tcccttctgt atcctgtccc   1980

tcctccacgc cgacccgaga gcagctgagc tgcgctggct ctgggcaggg agtgtgcctt   2040

aatgggaagc acacgggctt tggagtcagg cacaggtgcc agctccagct tttgaacttg   2100

ggcaattgtt taacctaacc tgcaagttga ttttgagggt taaataaagg catacatgaa   2160

aaaaaaaaaa aaaaa                                                    2175
```

<210> SEQ ID NO 7
<211> LENGTH: 4321
<212> TYPE: DNA
<213> ORGANISM: Homo Sapiens
<220> FEATURE:
<221> NAME/KEY: misc_feature
<222> LOCATION: (1)...(4321)
<223> OTHER INFORMATION: n = A,T,C or G

<400> SEQUENCE: 7

```
cccacgcgtc cggctaatga atcttggggc cggtgtcggg ccggggcggc ttgatcggca     60

actaggaaac cccaggcgca gaggccagga gcgagggcag cgaggatcag aggccaggcc    120

ttcccggctg ccggcgctcc tcggaggtca gggcagatga ggaacatgac tctcccccctt   180

cggaggagga aggaagtccc gctgccacct tatctctgct cctctgcctc ctccctgttc    240

ccagagcttt ttctctagag aagattttga aggcggcttt tgtgctgacg gccacccacc    300

atcatctaaa gaagataaac ttggcaaatg acatgcaggt tcttcaaggc agaataattg    360

cagaaaatct tcaaaggacc ctatctgcag atgttctgaa tacctctgag aatagagatt    420

gattattcaa ccaggatacc taattcaaga actccagaaa tcaggagacg gagacatttt    480

gtcagttttg caacattgga ccaaatacaa tgaagtattc ttgctgtgct ctggttttgg    540

ctgtcctggg cacagaattg ctgggaagcc tctgttcgac tgtcagatcc ccgaggttca    600

gaggacggat acagcaggaa cgaaaaaaca tccgacccaa cattattctt gtgcttaccg    660

atgatcaaga tgtggagctg ggtccctgc aagtcatgaa caaaacgaga aagattatgg    720
```

-continued

```
aacatggggg ggccaccttc atcaatgcct ttgtgactac acccatgtgc tgcccgtcac    780
ggtcctccat gctcaccggg aagtatgtgc acaatcacaa tgtctacacc aacaacgaga    840
actgctcttc cccctcgtgg caggccatgc atgagcctcg gacttttgct gtatatctta    900
acaacactgg ctacagaaca gcctttttttg gaaaatacct caatgaatat aatggcagct    960
acatcccccc tgggtggcga gaatggcttg gattaatcaa gaattctcgc ttctataatt   1020
acactgtttg tcgcaatggc atcaaagaaa agcatggatt tgattatgca aaggactact   1080
tcacagactt aatcactaac gagagcatta attacttcaa aatgtctaag agaatgtatc   1140
cccataggcc cgttatgatg gtgatcagcc acgctgcgcc ccacggcccc gaggactcag   1200
ccccacagtt ttctaaactg taccccaatg cttcccaaca cataactcct agttataact   1260
atgcaccaaa tatggataaa cactggatta tgcagtacac aggaccaatg ctgcccatcc   1320
acatggaatt tacaaacatt ctacagcgca aaaggctcca gactttgatg tcagtggatg   1380
attctgtgga gaggctgtat aacatgctcg tggagacggg ggagctggag aatacttaca   1440
tcatttacac cgccgaccat ggttaccata ttgggcagtt tggactggtc aaggggaaat   1500
ccatgccata tgactttgat attcgtgtgc cttttttttat tcgtggtcca agtgtagaac   1560
caggatcaat agtcccacag atcgttctca acattgactt ggcccccacg atcctggata   1620
ttgctgggct cgacacacct cctgatgtgg acggcaagtc tgtcctcaaa cttctggacc   1680
cagaaaagcc aggtaacagg tttcgaacaa acaagaaggc caaaatttgg cgtgatacat   1740
tcctagtgga aagaggcaaa tttctacgta agaaggaaga atccagcaag aatatccaac   1800
agtcaaatca cttgcccaaa tatgaacggg tcaaagaact atgccagcag gccaggtacc   1860
agacagcctg tgaacaaccg gggcagaagt ggcaatgcat tgaggataca tctggcaagc   1920
ttcgaattca caagtgtaaa ggacccagtg acctgctcac agtccggcag agcacgcgga   1980
acctctacgc tcgcggcttc catgacaaag acaaagagtg cagttgtagg gagtctggtt   2040
accgtgccag cagaagccaa agaaagagtc aacggcaatt cttgagaaac caggggactc   2100
caaagtacaa gcccagattt gtccatactc ggcagacacg ttccttgtcc gtcgaatttg   2160
aaggtgaaat atatgacata aatctggaag aagaagaaga attgcaagtg ttgcaaccaa   2220
gaaacattgc taagcgtcat gatgaaggcc acaaggggcc aagagatctc caggcttcca   2280
gtggtggcaa caggggcagg atgctggcag atagcagcaa cgccgtgggc ccacctacca   2340
ctgtccgagt gacacacaag tgttttattc ttcccaatga ctctatccat tgtgagagag   2400
aactgtacca atcggccaga gcgtggaagg accataaggc atacattgac aaagagattg   2460
aagctctgca agataaaatt aagaatttaa gagaagtgag aggacatctg aagagaagga   2520
agcctgagga atgtagctgc agtaaacaaa gctattacaa taaagagaaa ggtgtaaaaa   2580
agcaagagaa attaaagagc catcttcacc cattcaagga ggctgctcag gaagtagata   2640
gcaaactgca actttttcaag gagaacaacc gtaggaggaa gaaggagagg aaggagaaga   2700
gacggcagag gaagggggaa gagtgcagcc tgcctggcct cacttgcttc acgcatgaca   2760
acaaccactg gcagacagcc ccgttctgga acctgggatc tttctgtgct tgcacgagtt   2820
ctaacaataa cacctactgg tgtttgcgta cagttaatga gacgcataat tttcttttct   2880
gtgagtttgc tactggcttt ttggagtatt ttgatatgaa tacagatcct tatcagctca   2940
caaatacagt gcacacggta gaacgaggca ttttgaatca gctacacgta caactaatgg   3000
agctcagaag ctgtcaagga tataagcagt gcaacccaag acctaagaat cttgatgttg   3060
gaaataaaga tggaggaagc tatgacctac acagaggaca gttatgggat ggatgggaag   3120
```

```
gttaatcagc cccgtctcac tgcagacatc aactggcaag gcctagagga gctacacagt   3180
gtgaatgaaa acatctatga gtacagacaa aactacagac ttagtctggt ggactggact   3240
aattacttga aggatttaga tagagtattt gcactgctga agagtcacta tgagcaaaat   3300
aaaacaaata agactcaaac tgctcaaagt gacgggttct tggttgtctc tgctgagcac   3360
gctgtgtcaa tggagatggc ctctgctgac tcagatgaag acccaaggca taaggttggg   3420
aaaacacctc atttgacctt gccagctgac cttcaaaccc tgcatttgaa ccgaccaaca   3480
ttaagtccag agagtaaact tgaatggaat aacgacattc cagaagttaa tcatttgaat   3540
tctgaacact ggagaaaaac cgaaaaatgg acggggcatg aagagactaa tcatctggaa   3600
accgatttca gtggcgatgg catgacagag ctagagctcg ggcccagccc caggctgcag   3660
cccattcgca ggcacccgaa agaacttccc cagtatggtg gtcctggaaa ggacattttt   3720
gaagatcaac tatatcttcc tgtgcattcc gatggaattt cagttcatca gatgttcacc   3780
atggccaccg cagaacaccg aagtaattcc agcatagcgg ggaagatgtt gaccaaggtg   3840
gagaagaatc acgaaaagga gaagtcacag cacctagaag gcagcgcctc ctcttcactc   3900
tcctctgatt agatgaaact gttaccttac cctaaacaca gtatttcttt ttaacttttt   3960
tatttgtaaa ctaataaagg kaatcacagc caccaacatt ccaagctacc ctgggtacct   4020
ttgtgcagta gaagctagtg agcatgtgag caagcggtgt gcacacggag actcatcgtt   4080
ataatttact atctgccaag gagtagaaag aaaggctggg gatatttggg ttggctttgg   4140
ktttgatttt ttgcttggtt ggttggtttg kactaaaaca gtattatctt ttgaatatcg   4200
tagggacata arkwwwwwmm wkktwwtcma wymrakakgs ywrrawkggg stytytskkr   4260
kstmwamwyk wscmccyskk rwwawtywyw mmywcmykyt ssstgrykrn ktaatgaagt   4320
t                                                                   4321
```

<210> SEQ ID NO 8
<211> LENGTH: 2877
<212> TYPE: DNA
<213> ORGANISM: Homo Sapiens

<400> SEQUENCE: 8

```
ccacgcgtcc gcccacgcgt ccggctgcca cgccgcgtct caggctggcc gggctgagcc     60
ggggaagagg gagcaaaggc ggcgcagggc ctgcgcttag gcagcgggag gcagctcggc    120
gcgggcctga cctccccaga gcgccccgct gcggccgagc agatccggcc cagccgtccg    180
gcagccagtc ccggaccaga cactggaccg tccccggggg gcgctgaact ccctcgcagc    240
atccgagccg gcgggccggt ggtgcgccct gggcgcgcga ggtggtgagg ccccaggagc    300
ccggcgcgcc gggacacgcg ggccggcttg gcgatgcaca ccctcactgg cttctctctg    360
gtcagcctgc tcagcttcgg ctacctgtcc tgggactggg ccaagccgag cttcgtggcc    420
gacgggcccg gggaggctgg cgagcagccc tcggccgctc cgccccagcc tccccacatc    480
atcttcatcc tcacggacga ccaaggctac cacgacgtgg gctaccatgg ttcagatatc    540
gagaccccta cgctggacag gctggcggcc aagggggtca agttggagaa ttattacatc    600
cagcccatct gcacgccttc gcggagccag ctcctcactg gcaggtacca gatccacaca    660
ggactccagc attccatcat ccgcccacag cagcccaact gcctgcccct ggaccaggtg    720
acactgccac agaagctgca ggaggcaggt tattccaccc atatggtggg caagtggcac    780
ctgggcttct accggaagga gtgtctgccc acccgtcggg gcttcgacac cttcctgggc    840
```

-continued

```
tcgctcacgg gcaatgtgga ctattacacc tatgacaact gtgatggccc aggcgtgtgc    900

ggcttcgacc tgcacgaggg tgagaatgtg gcctgggggc tcagcggcca gtactccact    960

atgctttacg cccagcgcgc cagccatatc ctggccagcc acagccctca gcgtcccctc   1020

ttcctctatg tggccttcca ggcagtacac acacccctgc agtcccctcg tgagtacctg   1080

taccgctacc gcaccatggg caatgtggcc cggcggaagt acgcggccat ggtgacctgc   1140

atggatgagg ctgtgcgcaa catcacctgg gccctcaagc gctacggttt ctacaacaac   1200

agtgtcatca tcttctccag tgacaatggt ggccagactt tctcgggggg cagcaactgg   1260

ccgctccgag gacgcaaggg cacttattgg gaaggtggcg tgcggggcct aggctttgtc   1320

cacagtcccc tgctcaagcg aaagcaacgg acaagccggg cactgatgca catcactgac   1380

tggtacccga ccctggtggg tctggcaggt ggtaccacct cagcagccga tgggctagat   1440

ggctacgacg tgtggccggc catcagcgag ggccgggcct caccacgcac ggagatcctg   1500

cacaacattg acccactcta caaccatgcc cagcatggct ccctggaggg cggctttggc   1560

atctggaaca ccgccgtgca ggctgccatc cgcgtgggtg agtggaagct gctgacagga   1620

gaccccggct atggcgattg gatcccaccg cagacactgg ccaccttccc gggtagctgg   1680

tggaacctgg aacgaatggc cagtgtccgc caggccgtgt ggctcttcaa catcagtgct   1740

gacccttatg aacgggagga cctggctggc cagcggcctg atgtggtccg caccctgctg   1800

gctcgcctgg ccgaatataa ccgcacagcc atcccggtac gctacccagc tgagaacccc   1860

cgggctcatc ctgactttaa tgggggttgg gggccctggg ccagtgatga ggaagaggag   1920

gaagaggaag ggagggctcg aagcttctcc cggggtcgtc gcaagaaaaa atgcaagatt   1980

tgcaagcttc gatccttttt ccgtaaactc aacaccaggc taatgtccca acggatctga   2040

tggtggggag ggagaaaact gtcctttaga ggatcttccc agttggaggg tgtagagtcc   2100

cttggttgaa cagggtaggg agcctggata ggagtgggtg ggaataaacc agactgggat   2160

gcctgtgtct cagtcctgcc tcctcacgga cttgctctgt gacctcaggt gacccacatg   2220

agcttttagc ctcagtttcc tcatctgtaa aatgagctct aatgactttg tgactctttg   2280

gtgtggccct ggagcctggg gccacggtgg agttcctggc cggccttgcc acttgacaac   2340

tcctttaagg cttccccctt aacacgggat ccctgtggtg gtgtttggga gttgcctgga   2400

ggcaactcca agcctggccc ccagctgaag catggcaatc tggctgctct ctacagggac   2460

ccccaagcgc tgtgggtgga gggcaggggt cggggggggtt gaccttcttg ggtcttcaca  2520

tggcctaggc cagtcctccg gtcagactgg tgtcaggcac cgtggtgcaa aattcctctt   2580

ctggcccctc cagtacccag agaaactggc tgggccatta actgctgcag caccaagggt   2640

ggtagaaaga gctgtgaaga gcccccaaac cagtaccagg acacctgggt tctcctgtga   2700

cctggggcac agttcttgcc ctctaggcct tgatttcccc acctgcaagt ggggatgcca   2760

gccctggctc tgcctccttc atgaggctct ggaagactgg ccaaggttgt ggaggagctt   2820

gtgaacttga ttaaagtgtc gtaacatgga aaaaaaaaaa aaaaaaaaaa agggcgg      2877
```

<210> SEQ ID NO 9
<211> LENGTH: 2253
<212> TYPE: DNA
<213> ORGANISM: Homo Sapiens

<400> SEQUENCE: 9

```
cacgcgtccg cccacgcgtc cgtggagata ttaacttttt tcttttttttt tttccttggt   60

ggaagctgct ctagggaggg gggaggagga ggagaaagtg aaatgtgctg gagaagagcg    120
```

-continued

```
agccctcctt gttcttccgg agtcccatcc attaagccat cacttctgga agattaaagt    180

tgtcggacat ggtgacagct gagaggagag gaggatttct tgccaggtgg agagtcttca    240

ccgtctgttg ggtgcatgtg tgcgcccgca gcggcgcggg gcgcgtggtt ctccgcgtgg    300

agtctcacct gggacctgag tgaatggctc ccaggggctg tgcggggcat ccgcctccgc    360

cttctccaca ggcctgtgtc tgtcctggaa agatgctagc aatgggggcg ctggcaggat    420

tctggatcct ctgcctcctc acttatggtt acctgtcctg ggccaggcc ttagaagagg    480

aggaagaagg ggccttacta gctcaagctg gagagaaact agagcccagc acaacttcca    540

cctcccagcc ccatctcatt ttcatcctag cggatgatca gggatttaga gatgtgggtt    600

accacggatc tgagattaaa acacctactc ttgacaagct cgctgccgaa ggagttaaac    660

tggagaacta ctatgtccag cctatttgca caccatccag gagtcagttt attactggaa    720

agtatcagat acacaccgga cttcaacatt ctatcataag acctacccaa cccaactgtt    780

tacctctgga caatgccacc ctacctcaga aactgaagga ggttggatat tcaacgcata    840

tggtcggaaa atggcacttg ggtttttaca gaaaagaatg catgcccacc agaagaggat    900

ttgatacctt ttttggttcc cttttgggaa gtggggatta ctatacacac tacaaatgtg    960

acagtcctgg gatgtgtggc tatgacttgt atgaaaacga caatgctgcc tgggactatg   1020

acaatggcat atactccaca cagatgtaca ctcagagagt acagcaaatc ttagcttccc   1080

ataaccccac aaagcctata tttttatata ttgcctatca agctgttcat tcaccactgc   1140

aagctcctgg caggtatttc gaacactacc gatccattat caacataaac aggaggagat   1200

atgctgccat gctttcctgc ttagatgaag caatcaacaa cgtgacattg gctctaaaga   1260

cttatggttt ctataacaac agcattatca tttactcttc agataatggt ggccagccta   1320

cggcaggagg gagtaactgg cctctcagag gtagcaaagg aacatattgg gaaggaggga   1380

tccgggctgt aggctttgtg catagcccac ttctgaaaaa caagggaaca gtgtgtaagg   1440

aacttgtgca catcactgac tggtacccca ctctcatttc actggctgaa ggacagattg   1500

atgaggacat tcaactagat ggctatgata tctgggagac cataagtgag ggtcttcgct   1560

caccccgagt agatattttg cataacattg accccatata caccaaggca aaaaatggct   1620

cctgggcagc aggctatggg atctggaaca ctgcaatcca gtcagccatc agagtgcagc   1680

actggaaatt gcttacagga aatcctggct acagcgactg ggtccccccct cagtctttca   1740

gcaacctggg accgaaccgg tggcacaatg aacggatcac cttgtcaact ggcaaaagtg   1800

tatggctttt caacatcaca gccgacccat atgagagggt ggacctatct aacaggtatc   1860

caggaatcgt gaagaagctc ctacggaggc tctcacagtt caacaaaact gcagtgccgg   1920

tcaggtatcc ccccaaagac cccagaagta accctaggct caatggaggg gtctggggac   1980

catggtataa agaggaaacc aagaaaaaga agccaagcaa aaatcaggct gagaaaaagc   2040

aaaagaaaag caaaaaaaag aagaagaaac agcagaaagc agtctcaggt tcaacttgcc   2100

attcaggtgt tacttgtgga taagcacaaa tatttcctgt ttggttaaac tttaatcagt   2160

tcttatcttt catctgtttc ctaggtaaac cagcaaattt ggctcgataa tatcgctggc   2220

ctaagcgtca ggcttgtttt catgctgtgc cac                                2253
```

<210> SEQ ID NO 10
<211> LENGTH: 525
<212> TYPE: PRT
<213> ORGANISM: Homo Sapiens

<400> SEQUENCE: 10

```
Met Gly Trp Leu Phe Leu Lys Val Leu Leu Ala Gly Val Ser Phe Ser
 1               5                  10                  15

Gly Phe Leu Tyr Pro Leu Val Asp Phe Cys Ile Ser Gly Lys Thr Arg
            20                  25                  30

Gly Gln Lys Pro Asn Phe Val Ile Ile Leu Ala Asp Asp Met Gly Trp
        35                  40                  45

Gly Asp Leu Gly Ala Asn Trp Ala Glu Thr Lys Asp Thr Ala Asn Leu
    50                  55                  60

Asp Lys Met Ala Ser Glu Gly Met Arg Phe Val Asp Phe His Ala Ala
65                  70                  75                  80

Ala Ser Thr Cys Ser Pro Ser Arg Ala Ser Leu Leu Thr Gly Arg Leu
                85                  90                  95

Gly Leu Arg Asn Gly Val Thr Arg Asn Phe Ala Val Thr Ser Val Gly
            100                 105                 110

Gly Leu Pro Leu Asn Glu Thr Thr Leu Ala Glu Val Leu Gln Gln Ala
        115                 120                 125

Gly Tyr Val Thr Gly Ile Ile Gly Lys Trp His Leu Gly His His Gly
    130                 135                 140

Ser Tyr His Pro Asn Phe Arg Gly Phe Asp Tyr Tyr Phe Gly Ile Pro
145                 150                 155                 160

Tyr Ser His Asp Met Gly Cys Thr Asp Thr Pro Gly Tyr Asn His Pro
                165                 170                 175

Pro Cys Pro Ala Cys Pro Gln Gly Asp Gly Pro Ser Arg Asn Leu Gln
            180                 185                 190

Arg Asp Cys Tyr Thr Asp Val Ala Leu Pro Leu Tyr Glu Asn Leu Asn
        195                 200                 205

Ile Val Glu Gln Pro Val Asn Leu Ser Ser Leu Ala Gln Lys Tyr Ala
    210                 215                 220

Glu Lys Ala Thr Gln Phe Ile Gln Arg Ala Ser Thr Ser Gly Arg Pro
225                 230                 235                 240

Phe Leu Leu Tyr Val Ala Leu Ala His Met His Val Pro Leu Pro Val
                245                 250                 255

Thr Gln Leu Pro Ala Ala Pro Arg Gly Arg Ser Leu Tyr Gly Ala Gly
            260                 265                 270

Leu Trp Glu Met Asp Ser Leu Val Gly Gln Ile Lys Asp Lys Val Asp
        275                 280                 285

His Thr Val Lys Glu Asn Thr Phe Leu Trp Phe Thr Gly Asp Asn Gly
    290                 295                 300

Pro Trp Ala Gln Lys Cys Glu Leu Ala Gly Ser Val Gly Pro Phe Thr
305                 310                 315                 320

Gly Phe Trp Gln Thr Arg Gln Gly Gly Ser Pro Ala Lys Gln Thr Thr
                325                 330                 335

Trp Glu Gly Gly His Arg Val Pro Ala Leu Ala Tyr Trp Pro Gly Arg
            340                 345                 350

Val Pro Val Asn Val Thr Ser Thr Ala Leu Leu Ser Val Leu Asp Ile
        355                 360                 365

Phe Pro Thr Val Val Ala Leu Ala Gln Ala Ser Leu Pro Gln Gly Arg
    370                 375                 380

Arg Phe Asp Gly Val Asp Val Ser Glu Val Leu Phe Gly Arg Ser Gln
385                 390                 395                 400

Pro Gly His Arg Val Leu Phe His Pro Asn Ser Gly Ala Ala Gly Glu
                405                 410                 415
```

```
Phe Gly Ala Leu Gln Thr Val Arg Leu Glu Arg Tyr Lys Ala Phe Tyr
            420                 425                 430

Ile Thr Gly Gly Ala Arg Ala Cys Asp Gly Ser Thr Gly Pro Glu Leu
        435                 440                 445

Gln His Lys Phe Pro Leu Ile Phe Asn Leu Glu Asp Asp Thr Ala Glu
    450                 455                 460

Ala Val Pro Leu Glu Arg Gly Gly Ala Glu Tyr Gln Ala Val Leu Pro
465                 470                 475                 480

Glu Val Arg Lys Val Leu Ala Asp Val Leu Gln Asp Ile Ala Asn Asp
                485                 490                 495

Asn Ile Ser Ser Ala Asp Tyr Thr Gln Asp Pro Ser Val Thr Pro Cys
            500                 505                 510

Cys Asn Pro Tyr Gln Ile Ala Cys Arg Cys Gln Ala Ala
        515                 520                 525


<210> SEQ ID NO 11
<211> LENGTH: 871
<212> TYPE: PRT
<213> ORGANISM: Homo Sapiens

<400> SEQUENCE: 11

Met Lys Tyr Ser Cys Cys Ala Leu Val Leu Ala Val Leu Gly Thr Glu
 1               5                  10                  15

Leu Leu Gly Ser Leu Cys Ser Thr Val Arg Ser Pro Arg Phe Arg Gly
            20                  25                  30

Arg Ile Gln Gln Glu Arg Lys Asn Ile Arg Pro Asn Ile Ile Leu Val
        35                  40                  45

Leu Thr Asp Asp Gln Asp Val Glu Leu Gly Ser Leu Gln Val Met Asn
    50                  55                  60

Lys Thr Arg Lys Ile Met Glu His Gly Gly Ala Thr Phe Ile Asn Ala
65                  70                  75                  80

Phe Val Thr Thr Pro Met Cys Cys Pro Ser Arg Ser Ser Met Leu Thr
                85                  90                  95

Gly Lys Tyr Val His Asn His Asn Val Tyr Thr Asn Asn Glu Asn Cys
            100                 105                 110

Ser Ser Pro Ser Trp Gln Ala Met His Glu Pro Arg Thr Phe Ala Val
        115                 120                 125

Tyr Leu Asn Asn Thr Gly Tyr Arg Thr Ala Phe Phe Gly Lys Tyr Leu
    130                 135                 140

Asn Glu Tyr Asn Gly Ser Tyr Ile Pro Pro Gly Trp Arg Glu Trp Leu
145                 150                 155                 160

Gly Leu Ile Lys Asn Ser Arg Phe Tyr Asn Tyr Thr Val Cys Arg Asn
                165                 170                 175

Gly Ile Lys Glu Lys His Gly Phe Asp Tyr Ala Lys Asp Tyr Phe Thr
            180                 185                 190

Asp Leu Ile Thr Asn Glu Ser Ile Asn Tyr Phe Lys Met Ser Lys Arg
        195                 200                 205

Met Tyr Pro His Arg Pro Val Met Met Val Ile Ser His Ala Ala Pro
    210                 215                 220

His Gly Pro Glu Asp Ser Ala Pro Gln Phe Ser Lys Leu Tyr Pro Asn
225                 230                 235                 240

Ala Ser Gln His Ile Thr Pro Ser Tyr Asn Tyr Ala Pro Asn Met Asp
                245                 250                 255

Lys His Trp Ile Met Gln Tyr Thr Gly Pro Met Leu Pro Ile His Met
```

-continued

```
            260                 265                 270

Glu Phe Thr Asn Ile Leu Gln Arg Lys Arg Leu Gln Thr Leu Met Ser
        275                 280                 285

Val Asp Asp Ser Val Glu Arg Leu Tyr Asn Met Leu Val Glu Thr Gly
    290                 295                 300

Glu Leu Glu Asn Thr Tyr Ile Ile Tyr Thr Ala Asp His Gly Tyr His
305                 310                 315                 320

Ile Gly Gln Phe Gly Leu Val Lys Gly Lys Ser Met Pro Tyr Asp Phe
                325                 330                 335

Asp Ile Arg Val Pro Phe Phe Ile Arg Gly Pro Ser Val Glu Pro Gly
            340                 345                 350

Ser Ile Val Pro Gln Ile Val Leu Asn Ile Asp Leu Ala Pro Thr Ile
        355                 360                 365

Leu Asp Ile Ala Gly Leu Asp Thr Pro Pro Asp Val Asp Gly Lys Ser
    370                 375                 380

Val Leu Lys Leu Leu Asp Pro Glu Lys Pro Gly Asn Arg Phe Arg Thr
385                 390                 395                 400

Asn Lys Lys Ala Lys Ile Trp Arg Asp Thr Phe Leu Val Glu Arg Gly
                405                 410                 415

Lys Phe Leu Arg Lys Lys Glu Glu Ser Ser Lys Asn Ile Gln Gln Ser
            420                 425                 430

Asn His Leu Pro Lys Tyr Glu Arg Val Lys Glu Leu Cys Gln Gln Ala
        435                 440                 445

Arg Tyr Gln Thr Ala Cys Glu Gln Pro Gly Gln Lys Trp Gln Cys Ile
    450                 455                 460

Glu Asp Thr Ser Gly Lys Leu Arg Ile His Lys Cys Lys Gly Pro Ser
465                 470                 475                 480

Asp Leu Leu Thr Val Arg Gln Ser Thr Arg Asn Leu Tyr Ala Arg Gly
                485                 490                 495

Phe His Asp Lys Asp Lys Glu Cys Ser Cys Arg Glu Ser Gly Tyr Arg
            500                 505                 510

Ala Ser Arg Ser Gln Arg Lys Ser Gln Arg Gln Phe Leu Arg Asn Gln
        515                 520                 525

Gly Thr Pro Lys Tyr Lys Pro Arg Phe Val His Thr Arg Gln Thr Arg
    530                 535                 540

Ser Leu Ser Val Glu Phe Glu Gly Glu Ile Tyr Asp Ile Asn Leu Glu
545                 550                 555                 560

Glu Glu Glu Glu Leu Gln Val Leu Gln Pro Arg Asn Ile Ala Lys Arg
                565                 570                 575

His Asp Glu Gly His Lys Gly Pro Arg Asp Leu Gln Ala Ser Ser Gly
            580                 585                 590

Gly Asn Arg Gly Arg Met Leu Ala Asp Ser Ser Asn Ala Val Gly Pro
        595                 600                 605

Pro Thr Thr Val Arg Val Thr His Lys Cys Phe Ile Leu Pro Asn Asp
    610                 615                 620

Ser Ile His Cys Glu Arg Glu Leu Tyr Gln Ser Ala Arg Ala Trp Lys
625                 630                 635                 640

Asp His Lys Ala Tyr Ile Asp Lys Glu Ile Glu Ala Leu Gln Asp Lys
                645                 650                 655

Ile Lys Asn Leu Arg Glu Val Arg Gly His Leu Lys Arg Arg Lys Pro
            660                 665                 670

Glu Glu Cys Ser Cys Ser Lys Gln Ser Tyr Tyr Asn Lys Glu Lys Gly
        675                 680                 685
```

```
Val Lys Lys Gln Glu Lys Leu Lys Ser His Leu His Pro Phe Lys Glu
    690                 695                 700

Ala Ala Gln Glu Val Asp Ser Lys Leu Gln Leu Phe Lys Glu Asn Asn
705                 710                 715                 720

Arg Arg Arg Lys Lys Glu Arg Lys Glu Lys Arg Arg Gln Arg Lys Gly
                725                 730                 735

Glu Glu Cys Ser Leu Pro Gly Leu Thr Cys Phe Thr His Asp Asn Asn
            740                 745                 750

His Trp Gln Thr Ala Pro Phe Trp Asn Leu Gly Ser Phe Cys Ala Cys
        755                 760                 765

Thr Ser Ser Asn Asn Asn Thr Tyr Trp Cys Leu Arg Thr Val Asn Glu
    770                 775                 780

Thr His Asn Phe Leu Phe Cys Glu Phe Ala Thr Gly Phe Leu Glu Tyr
785                 790                 795                 800

Phe Asp Met Asn Thr Asp Pro Tyr Gln Leu Thr Asn Thr Val His Thr
                805                 810                 815

Val Glu Arg Gly Ile Leu Asn Gln Leu His Val Gln Leu Met Glu Leu
            820                 825                 830

Arg Ser Cys Gln Gly Tyr Lys Gln Cys Asn Pro Arg Pro Lys Asn Leu
        835                 840                 845

Asp Val Gly Asn Lys Asp Gly Gly Ser Tyr Asp Leu His Arg Gly Gln
    850                 855                 860

Leu Trp Asp Gly Trp Glu Gly
865                 870


<210> SEQ ID NO 12
<211> LENGTH: 569
<212> TYPE: PRT
<213> ORGANISM: Homo Sapiens

<400> SEQUENCE: 12

Met His Thr Leu Thr Gly Phe Ser Leu Val Ser Leu Leu Ser Phe Gly
 1               5                  10                  15

Tyr Leu Ser Trp Asp Trp Ala Lys Pro Ser Phe Val Ala Asp Gly Pro
            20                  25                  30

Gly Glu Ala Gly Glu Gln Pro Ser Ala Ala Pro Pro Gln Pro Pro His
        35                  40                  45

Ile Ile Phe Ile Leu Thr Asp Asp Gln Gly Tyr His Asp Val Gly Tyr
    50                  55                  60

His Gly Ser Asp Ile Glu Thr Pro Thr Leu Asp Arg Leu Ala Ala Lys
65                  70                  75                  80

Gly Val Lys Leu Glu Asn Tyr Tyr Ile Gln Pro Ile Cys Thr Pro Ser
                85                  90                  95

Arg Ser Gln Leu Leu Thr Gly Arg Tyr Gln Ile His Thr Gly Leu Gln
            100                 105                 110

His Ser Ile Ile Arg Pro Gln Gln Pro Asn Cys Leu Pro Leu Asp Gln
        115                 120                 125

Val Thr Leu Pro Gln Lys Leu Gln Glu Ala Gly Tyr Ser Thr His Met
    130                 135                 140

Val Gly Lys Trp His Leu Gly Phe Tyr Arg Lys Glu Cys Leu Pro Thr
145                 150                 155                 160

Arg Arg Gly Phe Asp Thr Phe Leu Gly Ser Leu Thr Gly Asn Val Asp
                165                 170                 175

Tyr Tyr Thr Tyr Asp Asn Cys Asp Gly Pro Gly Val Cys Gly Phe Asp
```

-continued

```
            180                 185                 190

Leu His Glu Gly Glu Asn Val Ala Trp Gly Leu Ser Gly Gln Tyr Ser
        195                 200                 205

Thr Met Leu Tyr Ala Gln Arg Ala Ser His Ile Leu Ala Ser His Ser
    210                 215                 220

Pro Gln Arg Pro Leu Phe Leu Tyr Val Ala Phe Gln Ala Val His Thr
225                 230                 235                 240

Pro Leu Gln Ser Pro Arg Glu Tyr Leu Tyr Arg Tyr Arg Thr Met Gly
                245                 250                 255

Asn Val Ala Arg Arg Lys Tyr Ala Ala Met Val Thr Cys Met Asp Glu
            260                 265                 270

Ala Val Arg Asn Ile Thr Trp Ala Leu Lys Arg Tyr Gly Phe Tyr Asn
        275                 280                 285

Asn Ser Val Ile Ile Phe Ser Ser Asp Asn Gly Gly Gln Thr Phe Ser
    290                 295                 300

Gly Gly Ser Asn Trp Pro Leu Arg Gly Arg Lys Gly Thr Tyr Trp Glu
305                 310                 315                 320

Gly Gly Val Arg Gly Leu Gly Phe Val His Ser Pro Leu Leu Lys Arg
                325                 330                 335

Lys Gln Arg Thr Ser Arg Ala Leu Met His Ile Thr Asp Trp Tyr Pro
            340                 345                 350

Thr Leu Val Gly Leu Ala Gly Gly Thr Thr Ser Ala Ala Asp Gly Leu
        355                 360                 365

Asp Gly Tyr Asp Val Trp Pro Ala Ile Ser Glu Gly Arg Ala Ser Pro
    370                 375                 380

Arg Thr Glu Ile Leu His Asn Ile Asp Pro Leu Tyr Asn His Ala Gln
385                 390                 395                 400

His Gly Ser Leu Glu Gly Gly Phe Gly Ile Trp Asn Thr Ala Val Gln
                405                 410                 415

Ala Ala Ile Arg Val Gly Glu Trp Lys Leu Leu Thr Gly Asp Pro Gly
            420                 425                 430

Tyr Gly Asp Trp Ile Pro Pro Gln Thr Leu Ala Thr Phe Pro Gly Ser
        435                 440                 445

Trp Trp Asn Leu Glu Arg Met Ala Ser Val Arg Gln Ala Val Trp Leu
    450                 455                 460

Phe Asn Ile Ser Ala Asp Pro Tyr Glu Arg Glu Asp Leu Ala Gly Gln
465                 470                 475                 480

Arg Pro Asp Val Val Arg Thr Leu Leu Ala Arg Leu Ala Glu Tyr Asn
                485                 490                 495

Arg Thr Ala Ile Pro Val Arg Tyr Pro Ala Glu Asn Pro Arg Ala His
            500                 505                 510

Pro Asp Phe Asn Gly Gly Ala Trp Gly Pro Trp Ala Ser Asp Glu Glu
        515                 520                 525

Glu Glu Glu Glu Glu Gly Arg Ala Arg Ser Phe Ser Arg Gly Arg Arg
    530                 535                 540

Lys Lys Lys Cys Lys Ile Cys Lys Leu Arg Ser Phe Phe Arg Lys Leu
545                 550                 555                 560

Asn Thr Arg Leu Met Ser Gln Arg Ile
                565
```

<210> SEQ ID NO 13
<211> LENGTH: 599
<212> TYPE: PRT
<213> ORGANISM: Homo Sapiens

<400> SEQUENCE: 13

```
Met Ala Pro Arg Gly Cys Ala Gly His Pro Pro Pro Pro Ser Pro Gln
 1               5                  10                  15

Ala Cys Val Cys Pro Gly Lys Met Leu Ala Met Gly Ala Leu Ala Gly
            20                  25                  30

Phe Trp Ile Leu Cys Leu Leu Thr Tyr Gly Tyr Leu Ser Trp Gly Gln
        35                  40                  45

Ala Leu Glu Glu Glu Glu Glu Gly Ala Leu Leu Ala Gln Ala Gly Glu
    50                  55                  60

Lys Leu Glu Pro Ser Thr Thr Ser Thr Ser Gln Pro His Leu Ile Phe
65                  70                  75                  80

Ile Leu Ala Asp Asp Gln Gly Phe Arg Asp Val Gly Tyr His Gly Ser
                85                  90                  95

Glu Ile Lys Thr Pro Thr Leu Asp Lys Leu Ala Ala Glu Gly Val Lys
            100                 105                 110

Leu Glu Asn Tyr Tyr Val Gln Pro Ile Cys Thr Pro Ser Arg Ser Gln
        115                 120                 125

Phe Ile Thr Gly Lys Tyr Gln Ile His Thr Gly Leu Gln His Ser Ile
    130                 135                 140

Ile Arg Pro Thr Gln Pro Asn Cys Leu Pro Leu Asp Asn Ala Thr Leu
145                 150                 155                 160

Pro Gln Lys Leu Lys Glu Val Gly Tyr Ser Thr His Met Val Gly Lys
                165                 170                 175

Trp His Leu Gly Phe Tyr Arg Lys Glu Cys Met Pro Thr Arg Arg Gly
            180                 185                 190

Phe Asp Thr Phe Phe Gly Ser Leu Leu Gly Ser Gly Asp Tyr Tyr Thr
        195                 200                 205

His Tyr Lys Cys Asp Ser Pro Gly Met Cys Gly Tyr Asp Leu Tyr Glu
    210                 215                 220

Asn Asp Asn Ala Ala Trp Asp Tyr Asp Asn Gly Ile Tyr Ser Thr Gln
225                 230                 235                 240

Met Tyr Thr Gln Arg Val Gln Gln Ile Leu Ala Ser His Asn Pro Thr
                245                 250                 255

Lys Pro Ile Phe Leu Tyr Ile Ala Tyr Gln Ala Val His Ser Pro Leu
            260                 265                 270

Gln Ala Pro Gly Arg Tyr Phe Glu His Tyr Arg Ser Ile Ile Asn Ile
        275                 280                 285

Asn Arg Arg Arg Tyr Ala Ala Met Leu Ser Cys Leu Asp Glu Ala Ile
    290                 295                 300

Asn Asn Val Thr Leu Ala Leu Lys Thr Tyr Gly Phe Tyr Asn Asn Ser
305                 310                 315                 320

Ile Ile Ile Tyr Ser Ser Asp Asn Gly Gly Gln Pro Thr Ala Gly Gly
                325                 330                 335

Ser Asn Trp Pro Leu Arg Gly Ser Lys Gly Thr Tyr Trp Glu Gly Gly
            340                 345                 350

Ile Arg Ala Val Gly Phe Val His Ser Pro Leu Leu Lys Asn Lys Gly
        355                 360                 365

Thr Val Cys Lys Glu Leu Val His Ile Thr Asp Trp Tyr Pro Thr Leu
    370                 375                 380

Ile Ser Leu Ala Glu Gly Gln Ile Asp Glu Asp Ile Gln Leu Asp Gly
385                 390                 395                 400

Tyr Asp Ile Trp Glu Thr Ile Ser Glu Gly Leu Arg Ser Pro Arg Val
```

```
                405                 410                 415

Asp Ile Leu His Asn Ile Asp Pro Ile Tyr Thr Lys Ala Lys Asn Gly
            420                 425                 430

Ser Trp Ala Ala Gly Tyr Gly Ile Trp Asn Thr Ala Ile Gln Ser Ala
        435                 440                 445

Ile Arg Val Gln His Trp Lys Leu Leu Thr Gly Asn Pro Gly Tyr Ser
    450                 455                 460

Asp Trp Val Pro Pro Gln Ser Phe Ser Asn Leu Gly Pro Asn Arg Trp
465                 470                 475                 480

His Asn Glu Arg Ile Thr Leu Ser Thr Gly Lys Ser Val Trp Leu Phe
                485                 490                 495

Asn Ile Thr Ala Asp Pro Tyr Glu Arg Val Asp Leu Ser Asn Arg Tyr
            500                 505                 510

Pro Gly Ile Val Lys Lys Leu Leu Arg Arg Leu Ser Gln Phe Asn Lys
        515                 520                 525

Thr Ala Val Pro Val Arg Tyr Pro Pro Lys Asp Pro Arg Ser Asn Pro
    530                 535                 540

Arg Leu Asn Gly Gly Val Trp Gly Pro Trp Tyr Lys Glu Glu Thr Lys
545                 550                 555                 560

Lys Lys Lys Pro Ser Lys Asn Gln Ala Glu Lys Lys Gln Lys Lys Ser
                565                 570                 575

Lys Lys Lys Lys Lys Lys Gln Gln Lys Ala Val Ser Gly Ser Thr Cys
            580                 585                 590

His Ser Gly Val Thr Cys Gly
        595
```

<210> SEQ ID NO 14
<211> LENGTH: 1578
<212> TYPE: DNA
<213> ORGANISM: Homo Sapiens

<400> SEQUENCE: 14

```
atgggctggc tttttctaaa ggttttgttg gcgggagtga gtttctcagg atttctttat      60

cctcttgtgg atttttgcat cagtgggaaa acaagaggac agaagccaaa ctttgtgatt     120

attttggccg atgacatggg gtggggtgac ctgggagcaa actgggcaga aacaaaggac     180

actgccaacc ttgataagat ggcttcggag ggaatgaggt ttgtggattt ccatgcagct     240

gcctccacct gctcaccctc ccgggcttcc ttgctcaccg gccggcttgg ccttcgcaat     300

ggagtcacac gcaactttgc agtcacttct gtgggaggcc ttccgctcaa cgagaccacc     360

ttggcagagg tgctgcagca ggcgggttac gtcactggga taataggcaa atggcatctt     420

ggacaccacg gctcttatca ccccaacttc cgtggttttg attactactt tggaatccca     480

tatagccatg atatgggctg tactgatact ccaggctaca accaccctcc ttgtccagcg     540

tgtccacagg gtgatggacc atcaaggaac cttcaaagag actgttacac tgacgtggcc     600

ctccctcttt atgaaaacct caacattgtg gagcagccgg tgaacttgag cagccttgcc     660

cagaagtatg ctgagaaagc aacccagttc atccagcgtg caagcaccag cgggaggccc     720

ttcctgctct atgtggctct ggcccacatg cacgtgccct tacccgtgac tcagctacca     780

gcagcgccac ggggcagaag cctgtatggt gcagggctct gggagatgga cagtctggtg     840

ggccagatca aggacaaagt tgaccacaca gtgaaggaaa acacattcct ctggtttaca     900

ggagacaatg gcccgtgggc tcagaagtgt gagctagcgg gcagtgtggg tcccttcact     960

ggatttggc aaactcgtca agggggaagt ccagccaagc agacgacctg ggaaggaggg    1020
```

```
caccgggtcc cagcactggc ttactggcct ggcagagttc cagttaatgt caccagcact   1080

gccttgttaa gcgtgctgga catttttcca actgtggtag ccctggccca ggccagctta   1140

cctcaaggac ggcgctttga tggtgtggac gtctccgagg tgctctttgg ccggtcacag   1200

cctgggcaca gggtgctgtt ccaccccaac agcggggcag ctggagagtt tggagccctg   1260

cagactgtcc gcctggagcg ttacaaggcc ttctacatta ccggtggagc cagggcgtgt   1320

gatgggagca cggggcctga gctgcagcat aagtttcctc tgattttcaa cctggaagac   1380

gataccgcag aagctgtgcc cctagaaaga ggtggtgcgg agtaccaggc tgtgctgccc   1440

gaggtcagaa aggttcttgc agacgtcctc caagacattg ccaacgacaa catctccagc   1500

gcagattaca ctcaggaccc ttcagtaact ccctgctgta atccctacca aattgcctgc   1560

cgctgtcaag ccgcataa                                                 1578
```

<210> SEQ ID NO 15
<211> LENGTH: 2616
<212> TYPE: DNA
<213> ORGANISM: Homo Sapiens

<400> SEQUENCE: 15

```
atgaagtatt cttgctgtgc tctggttttg gctgtcctgg gcacagaatt gctgggaagc     60

ctctgttcga ctgtcagatc cccgaggttc agaggacgga tacagcagga acgaaaaaac    120

atccgaccca acattattct tgtgcttacc gatgatcaag atgtggagct ggggtccctg    180

caagtcatga acaaaacgag aaagattatg gaacatgggg gggccacctt catcaatgcc    240

tttgtgacta cacccatgtg ctgcccgtca cggtcctcca tgctcaccgg gaagtatgtg    300

cacaatcaca atgtctacac caacaacgag aactgctctt ccccctcgtg gcaggccatg    360

catgagcctc ggacttttgc tgtatatctt aacaacactg gctacagaac agcctttttt    420

ggaaaatacc tcaatgaata taatggcagc tacatccccc ctgggtggcg agaatggctt    480

ggattaatca agaattctcg cttctataat tacactgttt gtcgcaatgg catcaaagaa    540

aagcatggat ttgattatgc aaaggactac ttcacagact taatcactaa cgagagcatt    600

aattacttca aaatgtctaa gagaatgtat ccccataggc ccgttatgat ggtgatcagc    660

cacgctgcgc cccacggccc cgaggactca gccccacagt tttctaaact gtaccccaat    720

gcttcccaac acataactcc tagttataac tatgcaccaa atatggataa acactggatt    780

atgcagtaca caggaccaat gctgcccatc cacatggaat ttacaaacat tctacagcgc    840

aaaaggctcc agactttgat gtcagtggat gattctgtgg agaggctgta taacatgctc    900

gtggagacgg gggagctgga gaatacttac atcatttaca ccgccgacca tggttaccat    960

attgggcagt ttggactggt caaggggaaa tccatgccat atgactttga tattcgtgtg   1020

ccttttttta ttcgtggtcc aagtgtagaa ccaggatcaa tagtcccaca gatcgttctc   1080

aacattgact tggcccccac gatcctggat attgctgggc tcgacacacc tcctgatgtg   1140

gacggcaagt ctgtcctcaa acttctggac ccagaaaagc caggtaacag gtttcgaaca   1200

aacaagaagg ccaaaatttg gcgtgataca ttcctagtgg aaagaggcaa atttctacgt   1260

aagaaggaag aatccagcaa gaatatccaa cagtcaaatc acttgcccaa atatgaacgg   1320

gtcaaagaac tatgccagca ggccaggtac cagacagcct gtgaacaacc ggggcagaag   1380

tggcaatgca ttgaggatac atctggcaag cttcgaattc acaagtgtaa aggacccagt   1440

gacctgctca cagtccggca gagcacgcgg aacctctacg ctcgcggctt ccatgacaaa   1500
```

-continued

```
gacaaagagt gcagttgtag ggagtctggt taccgtgcca gcagaagcca aagaaagagt   1560
caacggcaat tcttgagaaa ccaggggact ccaaagtaca agcccagatt tgtccatact   1620
cggcagacac gttccttgtc cgtcgaattt gaaggtgaaa tatatgacat aaatctggaa   1680
gaagaagaag aattgcaagt gttgcaacca agaaacattg ctaagcgtca tgatgaaggc   1740
cacaaggggc caagagatct ccaggcttcc agtggtggca acaggggcag gatgctggca   1800
gatagcagca acgccgtggg cccacctacc actgtccgag tgacacacaa gtgttttatt   1860
cttcccaatg actctatcca ttgtgagaga gaactgtacc aatcggccag agcgtggaag   1920
gaccataagg catacattga caaagagatt gaagctctgc aagataaaat taagaattta   1980
agagaagtga gaggacatct gaagagaagg aagcctgagg aatgtagctg cagtaaacaa   2040
agctattaca ataaagagaa aggtgtaaaa aagcaagaga aattaaagag ccatcttcac   2100
ccattcaagg aggctgctca ggaagtagat agcaaactgc aacttttcaa ggagaacaac   2160
cgtaggagga agaaggagag gaaggagaag agacggcaga ggaaggggga agagtgcagc   2220
ctgcctggcc tcacttgctt cacgcatgac aacaaccact ggcagacagc cccgttctgg   2280
aacctgggat ctttctgtgc ttgcacgagt tctaacaata acacctactg gtgtttgcgt   2340
acagttaatg agacgcataa ttttcttttc tgtgagtttg ctactggctt tttggagtat   2400
tttgatatga atacagatcc ttatcagctc acaaatacag tgcacacggt agaacgaggc   2460
attttgaatc agctacacgt acaactaatg gagctcagaa gctgtcaagg atataagcag   2520
tgcaacccaa gacctaagaa tcttgatgtt ggaaataaag atggaggaag ctatgaccta   2580
cacagaggac agttatggga tggatgggaa ggttaa                             2616
```

<210> SEQ ID NO 16
<211> LENGTH: 1710
<212> TYPE: DNA
<213> ORGANISM: Homo Sapiens

<400> SEQUENCE: 16

```
atgcacaccc tcactggctt ctctctggtc agcctgctca gcttcggcta cctgtcctgg     60
gactgggcca agccgagctt cgtggccgac gggcccgggg aggctggcga gcagccctcg    120
gccgctccgc cccagcctcc ccacatcatc ttcatcctca cggacgacca aggctaccac    180
gacgtgggct accatggttc agatatcgag accccctacgc tggacaggct ggcggccaag    240
ggggtcaagt tggagaatta ttacatccag cccatctgca cgccttcgcg gagccagctc    300
ctcactggca ggtaccagat ccacacagga ctccagcatt ccatcatccg cccacagcag    360
cccaactgcc tgcccctgga ccaggtgaca ctgccacaga agctgcagga ggcaggttat    420
tccacccata tggtgggcaa gtggcacctg ggcttctacc ggaaggagtg tctgcccacc    480
cgtcggggct tcgacacctt cctgggctcg ctcacgggca atgtggacta ttacacctat    540
gacaactgtg atggcccagg cgtgtgcggc ttcgacctgc acgagggtga gaatgtggcc    600
tgggggctca gcggccagta ctccactatg ctttacgccc agcgcgccag ccatatcctg    660
gccagccaca gccctcagcg tcccctcttc ctctatgtgg ccttccaggc agtacacaca    720
cccctgcagt cccctcgtga gtacctgtac cgctaccgca ccatgggcaa tgtggcccgg    780
cggaagtacg cggccatggt gacctgcatg gatgaggctg tgcgcaacat cacctgggcc    840
ctcaagcgct acggtttcta caacaacagt gtcatcatct tctccagtga caatggtggc    900
cagactttct cgggggcag caactggccg ctccgaggac gcaagggcac ttattgggaa    960
ggtggcgtgc ggggcctagg ctttgtccac agtcccctgc tcaagcgaaa gcaacggaca   1020
```

```
agccgggcac tgatgcacat cactgactgg tacccgaccc tggtgggtct ggcaggtggt   1080
accacctcag cagccgatgg gctagatggc tacgacgtgt ggccggccat cagcgagggc   1140
cgggcctcac cacgcacgga gatcctgcac aacattgacc cactctacaa ccatgcccag   1200
catggctccc tggagggcgg ctttggcatc tggaacaccg ccgtgcaggc tgccatccgc   1260
gtgggtgagt ggaagctgct gacaggagac cccggctatg gcgattggat cccaccgcag   1320
acactggcca ccttcccggg tagctggtgg aacctggaac gaatggccag tgtccgccag   1380
gccgtgtggc tcttcaacat cagtgctgac ccttatgaac gggaggacct ggctggccag   1440
cggcctgatg tggtccgcac cctgctggct cgcctggccg aatataaccg cacagccatc   1500
ccggtacgct acccagctga gaacccccgg gctcatcctg actttaatgg gggtgcttgg   1560
gggccctggg ccagtgatga ggaagaggag gaagaggaag ggagggctcg aagcttctcc   1620
cggggtcgtc gcaagaaaaa atgcaagatt tgcaagcttc gatccttttt ccgtaaactc   1680
aacaccaggc taatgtccca acggatctga                                     1710
```

<210> SEQ ID NO 17
<211> LENGTH: 1800
<212> TYPE: DNA
<213> ORGANISM: Homo Sapiens

<400> SEQUENCE: 17

```
atggctccca ggggctgtgc ggggcatccg cctccgcctt ctccacaggc ctgtgtctgt     60
cctggaaaga tgctagcaat gggggcgctg gcaggattct ggatcctctg cctcctcact    120
tatggttacc tgtcctgggg ccaggcctta gaagaggagg aagaaggggc cttactagct    180
caagctggag agaaactaga gcccagcaca acttccacct cccagcccca tctcattttc    240
atcctagcgg atgatcaggg atttagagat gtgggttacc acggatctga gattaaaaca    300
cctactcttg acaagctcgc tgccgaagga gttaaactgg agaactacta tgtccagcct    360
atttgcacac catccaggag tcagtttatt actggaaagt atcagataca caccggactt    420
caacattcta tcataagacc tacccaaccc aactgtttac ctctggacaa tgccacccta    480
cctcagaaac tgaaggaggt tggatattca acgcatatgg tcggaaaatg gcacttgggt    540
ttttacagaa aagaatgcat gcccaccaga agaggatttg atacctttt tggttccctt     600
ttgggaagtg ggattacta tacacactac aaatgtgaca gtcctgggat gtgtggctat     660
gacttgtatg aaaacgacaa tgctgcctgg gactatgaca atggcatata ctccacacag    720
atgtacactc agagagtaca gcaaatctta gcttcccata accccacaaa gcctatattt    780
ttatatattg cctatcaagc tgttcattca ccactgcaag ctcctggcag gtatttcgaa    840
cactaccgat ccattatcaa cataaacagg aggagatatg ctgccatgct ttcctgctta    900
gatgaagcaa tcaacaacgt gacattggct ctaaagactt atggtttcta taacaacagc    960
attatcattt actcttcaga taatggtggc cagcctacgg caggagggag taactggcct   1020
ctcagaggta gcaaaggaac atattgggaa ggagggatcc gggctgtagg ctttgtgcat   1080
agcccacttc tgaaaaacaa gggaacagtg tgtaaggaac ttgtgcacat cactgactgg   1140
taccccactc tcatttcact ggctgaagga cagattgatg aggacattca actagatggc   1200
tatgatatct gggagaccat aagtgagggt cttcgctcac cccgagtaga tattttgcat   1260
aacattgacc ccatatacac caaggcaaaa aatggctcct gggcagcagg ctatgggatc   1320
tggaacactg caatccagtc agccatcaga gtgcagcact ggaaattgct tacaggaaat   1380
```

-continued

```
cctggctaca gcgactgggt toccccctcag tctttcagca acctgggacc gaaccggtgg   1440

cacaatgaac ggatcacctt gtcaactggc aaaagtgtat ggcttttcaa catcacagcc   1500

gacccatatg agagggtgga cctatctaac aggtatccag gaatcgtgaa gaagctccta   1560

cggaggctct cacagttcaa caaaactgca gtgccggtca ggtatccccc caaagacccc   1620

agaagtaacc ctaggctcaa tggaggggtc tggggaccat ggtataaaga ggaaaccaag   1680

aaaaagaagc caagcaaaaa tcaggctgag aaaaagcaaa agaaaagcaa aaaaaagaag   1740

aagaaacagc agaaagcagt ctcaggttca acttgccatt caggtgttac ttgtggataa   1800
```

<210> SEQ ID NO 18
<211> LENGTH: 2019
<212> TYPE: DNA
<213> ORGANISM: Homo Sapiens

<400> SEQUENCE: 18

```
gcggcgcagc accgcgggct ccccgcccgc cgctgccggg agtgggacgg ggccggccgt     60

gagctgcgca ccggctgcgg gagccggccg gctgctgcag cccatccgcg ccacggtgcc    120

ctaccagctc ctgcggggca gccagcacag ccccacgcgc cccgccgccg ccgccgcgct    180

cggcagtctc ccagggccca gcggggcccg tggccctagc ccgtccagcc cgactccacc    240

gccggccact gccccagccg agcaggcgcc tcgcgccaag ggccgcccga gacggtcccc    300

cgagagccag cggaggagca gctcacctga gagacggagt cccggctcgc ccgtgtgcag    360

agtggacaga ccaaaatctc agcaaattcg aaactctagt acaataaggc gaacctcttc    420

tttggatacg ataacaggac cttacctcac aggacagtgg ccacgtgacc ctcatgttca    480

ctacccttcg tgcatgaaag ataaagcgac tcagacacct agctgttggg cagaggaggg    540

agcagaaaaa cgatcacatc agcgctctgc gtcatgggga agtgctgatc aactgaaaga    600

gcagattgcc aaactcaggc agcagttaca gcgcagcaag cagagcagtc ggcacagtag    660

agagaaagat cgacagtcac ctctccatgg caaccacata ccgatcagtc atactcaggc    720

tattgggtcc aggtcagtcc ctatgcctct gtcaaacata tccgtgccaa aatcctctgt    780

ttcccgtgtg ccctgcaatg tagaagggat aagtcctgaa ctggaaaagg tattcatcaa    840

agaaaacaat gggaaggaag aagtatccaa gccgttggat ataccagatg gtcgaagagc    900

cccgctccct gcgcactaca ggagcagtag tacccgaagc atagataccc agacaccttc    960

tgtccaagag cgcagcagta gctgcagcag ccactcccct tgtgtgtccc cattttgtcc   1020

tccggaatcc caggatggaa gtccttgttc aacagaagat ttgctgtatg atcgtgataa   1080

agacagtggg agtagctcac cgttacccaa gtatgcttca tctcccaaac caaacaacag   1140

ctacatgttc aaacgggagc ccccagaggg atgtgagcga gtgaaggtct ttgaggaaat   1200

ggcgtctcgt cagcctatct cggcccctct cttttcatgt cctgacaaaa acaaggttaa   1260

tttcatccca accggatcag ctttctgtcc tgtaaaactt ctaggccctc tcttacctgc   1320

ctctgacctg atgctcaaga actctcctaa ttctggccag agctcagctc tggccacact   1380

aaccgtagag cagctctcct cccgggtctc cttcacgtcc ctttctgatg acaccagcac   1440

cgcagactcc ctggagccct ctgtccagca gccatctcag cagcagcagc tcctgcagga   1500

tttgcaggca gaggaacaca tctccactca gaactatgtg atgatctaaa gcagaggggg   1560

agctggcctc cgcccatgtt ccatggatcg ggaatgagat ctcagacatc tatctgcatg   1620

gagtgacaaa ctttctgaac accaccacca acagcaaaat acttagcatc ataaaatagc   1680

tattaacact gatcttggca gggaccgact tctattcagc agtttttgtg gaaagcagta   1740
```

```
atgcttgcaa aaatgtgtgt gtcattcagc atttaagtgg agactatgca tttcatagta   1800

tgtctgacag actagtactg tgtcctgtgt tttgttccaa atttttcagt atgaataagc   1860

tctacttcaa aaagttgcct gtctaagtag aaaatgtctt gctgtgtttt gtcctatgga   1920

aaatactgta cttcaggatt atgtttacaa ttgatccagg tgtttgtttc taacttctat   1980

aatacataca atgcaaaaaa aaaaaaaaag ggcggccgc                          2019
```

<210> SEQ ID NO 19
<211> LENGTH: 2034
<212> TYPE: DNA
<213> ORGANISM: Homo Sapiens

<400> SEQUENCE: 19

```
gtcgacccac gcgtccggca agatctctct ggaccagctc gggtgcaggg cctctgcggg     60

agccctccta gacctctgcg gcttctcctc taacatggcc gactcggaaa accaggggcc    120

tgcggagcct agccaggcgg cggcagcggc ggaggcagcg gcagaggagg taatggcgga    180

aggcggtgcg cagggtggag actgtgacag cgcggctggt gaccctgaca gcgcggctgg    240

tcagatggct gaggagcccc agacccctgc agagaatgcc ccaaagccga aaaatgactt    300

tatcgagagc ctgcctaatt cggtgaaatg ccgagtcctg gccctcaaaa agctgcagaa    360

gcgatgcgat aagatagaag ccaaatttga taaggaattt caggctctgg aaaaaaagta    420

taatgacatc tataagcccc tactcgccaa gatccaagag ctcaccggcg agatggaggg    480

gtgtgcatgg accttggagg gggaggagga ggaggaagag gagtacgagg atgacgagga    540

ggagggggaa gacgaggagg aggaggaggc tgcggcagag gctgccgcgg gggccaaaca    600

tgacgatgcc cacgccgaga tgcctgatga cgccaagaag taagggggc agagatggat     660

gaagagaaag cccacgaaga aaaaagcctg gttttgtttt tcccagaata tcgatggact    720

taaaaaggct caggtttttg accaaaatac aatgtgaatt tattctgaca ttcctaaaat    780

agattaaatt aaagcaatta gatcctggcc agctcgattc aaatttgact ttcattttga    840

acataataaa tatatcaaaa ggtgttaaag aaaactgaat taaacccaaa attatgtttt    900

catggtctct tctctgagga ttgaggttta caaagggtgt tagcagatgc gaagtaaaga    960

acgtcacttt gaaacccatt catcacacag catacgctac acatggaaca cccaagccat   1020

gactgaacac gttctcagtg cttaattctt aaatttcttt actcatgaca tttcgcagtg   1080

cagagaaggc agaacccaag aaaaacgtca tctttgagac tttgcttttg taacgcagac   1140

atcagcttta cacttcacag gagattgatg gcattgagga agattgcaat ggagatcatg   1200

acactactgt taataaggcc aggaaaactg ccatttcaag ttctgaaaaa tgttttgagt   1260

atttgaattt agagaaacaa catggttcca agaaggaggg tgtaaaacct gtaaaatact   1320

gtcaacatat gtattcatta gttacaatct catgtttgtg ttttcttagt actgtctatt   1380

tacaaacacg taaaaaatac cccaaatatg tttaagtatt aaatcacttt acctagcgtt   1440

ttagaaatat taatttactt gaagagatgt agaatgtagc aaattatgta aagcatgtgt   1500

atccagcgtt atgtactttg cgccttgtga cgtctttctg tcatgtagct tttagggtgt   1560

agctgtgaaa atcatcagaa ctcttcactg aagctaatgt ttggaaaaaa tatatacttg   1620

aagaaccaat ccaagtgtgt gcccctaccc ccagctcaga agtagaaagg gtttaagttt   1680

gcttgtatta gctgtgcctt cattattttg ctatgtaaat gtgacatatt aattataaaa   1740

tggtgcataa tcaaatttta ctgcttgagg acagatgcat acagtaagga tttttaggaa   1800
```

gaatatattt aatgtaaaga ctcttagctt ctgtgtgggt tttgaattat gtgtgagcca 1860
gtgatctata aagaaacata agcttaaagt tgtttatcac tgtggtgtta ataaaacagt 1920
attttcaaaa aataaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaagggcgg ccgc 2034

<210> SEQ ID NO 20
<211> LENGTH: 1407
<212> TYPE: DNA
<213> ORGANISM: Homo Sapiens

<400> SEQUENCE: 20
gtcgacccac gcgtccggtt ggagcgagca tgtgggtctg cagtaccctg tggcgggtgc 60 gaaccccgc ccggcagtgg cgggggctgc tcccagcttc tggctgtcac ggacctgccg 120
cctcctccta ctccgcatcc gccgagcctg cccgggtccg ggcgcttgtc tatgggcacc 180
acggggatcc agccaaggtc gtcgaactca agaacctgga gctagctgct gtgagaggat 240
cagatgtccg tgtgaagatg ctggcggccc ctatcaatcc atctgacata aatatgatcc 300
aaggaaacta cggactcctt cctgaactgc ctgctgttgg agggaacgaa ggtgttgcac 360
aggtggtagc ggtgggcagc aatgtgaccg ggctgaagcc aggagactgg gtgattccag 420
caaatgctgg tttaggaacc tggcggaccg aggctgtgtt cagcgaggaa gcactgatcc 480
aagttccgag tgacatccct cttcagagcg ctgccaccct gggtgtcaat ccctgcacag 540
cctacaggat gttgatggat ttcgagcaac tgcagccagg ggattctgtc atccagaatg 600
catccaacag cggagtgggg caagcggtca tccagatcgc cgcagccctg ggcctaagaa 660
ccatcaatgt ggtccgagac agacctgata tccagaagct gagtgacaga ctgaagagtc 720
tgggggctga gcatgtcatc acagaagagg agctaagaag gcccgaaatg aaaaacttct 780
ttaaggacat gccccagcca cggcttgctc tcaactgtgt tggtgggaaa agctccacag 840
agctgctgcg gcagttagcg cgtggaggaa ccatggtaac ctatgggggg atggccaagc 900
agcccgtcgt agcctctgtg agcctgctca tttttaagga tctcaaactt cgaggctttt 960
ggttgtccca gtggaagaag gatcacagtc cagaccagtt caaggagctg atcctcacac 1020
tgtgcgatct catccgccga ggccagctca cagcccctgc ctgctcccag gtcccgctgc 1080
aggactacca gtctgccttg gaagcctcca tgaagccctt catatcttca aagcagattc 1140
tcaccatgtg atcatcccaa aagagctgga gtgacatggg aggggaggcg gatctgaggg 1200
gctgggtgca ggcccctcag ttggggctcc caccttcccc agactactgt tctcctcact 1260
gcctcttcct attaggagga tggtgaagcc agccacggtt ttccccaggg ccagccttaa 1320
ggtatctaat aaagtctgaa ctctcccttc caaaaaaaaa aaaaaaaaaa aaaaaaaaaa 1380
aaaaaaaaaa aaaaaaaggg cggccgc 1407

<210> SEQ ID NO 21
<211> LENGTH: 1791
<212> TYPE: DNA
<213> ORGANISM: Rattus norvegicus

<400> SEQUENCE: 21
gtcgacccac gcgtccggct gatcgaggct gaccttccaa acctagatgg ttgctggtcc 60
tgcacatgag tggaaatata ttcatggaga aacttccatg atgcacagta tctgccgttc 120
ttcagtcctc tgtctttctt tgtcattcag ttctgggcat tgagcagccg cagtcacagc 180
tgcaggacct ctctggacca gctcagtcgc agactgcgca accaccagac cactgcggca 240

-continued

```
aacaagccca gctgagccaa gcaatagcga tggccgaccc cgagaagcag ggacccgctg    300
agagccgcgc cgaggacgag gtaatggagg gcgctcaggg tggcgaggat gcagcaaccg    360
gtgacagtgc cactgcaccc gcggccgagg agccccaggc cccgcggag aatgcgccca     420
agcccaaaaa tgactttatc gagagcttgc ccaatcccgt caagtgccgg gttctggcgc    480
tcaaaaagct gcagaagcgc tgcgataaga tcgaggcgaa atttgacaag gaattccagg    540
ctctggagaa gaagtacaat gatatctaca agcccctact cgccaagatc caggaactca    600
ccggagagat ggagggctgc gcgtggaccc tggagggaga ggatgatgaa gacgacgagg    660
aagaagatga ggaggaggaa gaagaggagg ctgcagctgg cgcaactggg ggtcccgact    720
ctgccgagaa gtgagcacag cagctgacag acttgagact gatgaaaggt tgtcagttag    780
atgggaatta aagtgcgtca cacgttgaaa tccattcatc acactacacc ttaacaccca    840
agctaagaca gaactcttct caatgcttaa ttcttcagtt tctttacatt tcccagcgca    900
gaggaagagg aacccaagaa cgacgtcatc tttaagactt ttgcttttgc aaacccagac    960
atcagcttta cactccagag gagacaaggc atggaggaag gctggactga cagcatttac   1020
tgtttatgtg gctagaaaaa ctgccatttc aagttgtgaa aaatgttttg aatatttgaa   1080
tttacagaaa gaacacggtt ccaaaaataa gggtgtattc catgtataat attgtcaaca   1140
cgtgttcatc tgtaatggtc tcatgttatc tgttttcttg gtagtgtttg tttacaaaat   1200
cgtaaaaatt accccaaatg ttttaagtat taaattccct tatagcattt tagaaatata   1260
atttacttga agagatgtag aatgtagcaa ttctgtaaag catgtgtatc cagtgttgcc   1320
tagtttgact ttgtgaagtc tttttgtctt gtagctttta gcaagtagct gtgaaaacca   1380
tcagaactcc tcaatgaagc taatgtttgg aaaaaagtat atacttgaag aaccaaccca   1440
agtgtgtatc cccaacccca gctcagaaat aggaaggatt taagtttgct tgtattagct   1500
gtgccttcat tattttgcta tgtaaatgtg acttattaaa tggtgcataa tcaaatttta   1560
ttgcttgagg acaaaaatgg cataaaggga agacttttgg gaaaaagaca tttaatgtaa   1620
aggcctttag cttctttgtg ggttttgaac tatctgtgaa tcaatgttct gtaaagaaac   1680
acaaacgtaa agttgtttac cactgtggtg ttaacaaaac agtattttca aaaataaaaa   1740
aaacttgtta ttctgaaaaa aaaaaaaaaa aaaaaaaaaa agggcggccg c            1791
```

<210> SEQ ID NO 22
<211> LENGTH: 1057
<212> TYPE: DNA
<213> ORGANISM: Rattus norvegicus

<400> SEQUENCE: 22

```
agcggacagg accagtgaag aagccacggt agctgctgcc atctgctgcc ggagccggcc     60
ttcggcaaag gcctcctggg ttcaccagtg acagcctcag gcaggcattg tacctgtggc    120
tggacgcaga gatggacgtc ctggctctct tgtgtctagc caaaagtggg gagactctgc    180
ctgggggaac ttggcgtctc atcctgggta cccattcctg gtgtatgtgt ggggaagcac    240
ctccttcatg gtcagggggc ctgtgcttgg ccttctgcca tcgaagatgt taagctatag    300
ttggctttgg ccagctgctc cagtatatca gaacctgaga gcacttgcta caaggctagt    360
gttcaggcct taggcctcca gagtgaatgt atcctgcagg aagataatga tggatcgtga    420
cccttgacgg tcaccccccct cccccaggtc agatgtcacc agactagaac agtatctgaa    480
agctgctggg gccactcaca gcttgcttac tctggagaca gcattttggg ctccctgatt    540
```

-continued

```
aatgcagatc agttctgccc acctccaggg gtggatccag ctgtgaggct cacctgtatc    600

ttccagatgt tctcatctgc tgcaccgaag gctctggccc tgctcaggag aacacgctac    660

gaactcctag ctgactctgt ttgcactgga gaaccacaca gggcttaccc cactaccctg    720

tgcactgact ggcttcactt tatggaggaa gagacagggc cagagaagca atgtcatgca    780

gccagtgatg ctaggacata aatccagagt ggctggccct gaagccatgc ctcttggcaa    840

tgccaggctg ggcatcctat ttttgaagca aacaaaaaat gagaggacag gctgtgcttc    900

agcggcttgt tcctggacct atgctccctt agccccagtc ccacggatta tgtggagagt    960

ggaggagcaa cagagggcga ctgtactaag gccacacaag tcgacaagaa cacctatatc   1020

cttttgacct cttctgcttt tttatagtaa gctttcc                            1057
```

<210> SEQ ID NO 23
<211> LENGTH: 2250
<212> TYPE: DNA
<213> ORGANISM: Rattus norvegicus

<400> SEQUENCE: 23

```
cactagccta gagcctgaag gtatttctcc atatggacat gatgtctcac cctccaacca     60

tggattctaa accctgccag atgttccagc cttgatctct ttgctactta cccctatatc    120

tggaggattc agtgggagag ccttgcaagg taataccagg ctctccctgt gaccagctga    180

ggactcatct gcccccacag tgccaacaag gacccccccct ctggaaagga ggtcagattg   240

cagttccagg tattggggag gctgatcagc tgtctcccag gtggcaagaa gtttagtgaa    300

gctaaggtac tccatcttgg ggaccctgtt ggagtagctc actgactaga aaacccttaa    360

gaacctccac tgcctactga atctcatccc ttctcatcag ccctcaatca ggactcttca    420

cttcttggga agcttctctg ggccagaagt gagcatggcc tctgtcctgc actgtcctgt    480

tccattcata ctcactggtt tgactagaca ttctccaaaa gcagaacgga gatggatgcg    540

agagagaagc aggaggagac cttaatgtca gctttggagc atccccaaat tccaagaagg    600

ctcccctgct agtgaacagt agtcacccct tcccactgtc ttggactttg gtaaatttac    660

cccagagtgg ccagcatttg atccagacac agactaaagg attgattgtt acccgaagtc    720

atgtcactgg gtagcagcag ggtctgctcc tgactcatgc tgccactaca gctccctgtc    780

tcctcctgac tgtctgcttc agggccccctg gcccctggct gccttgatcc ttggcttctg  840

gcactcacct actctctttt attgagcatc tctgggtgag ccctccctcc cctctgggcc    900

tccacctcca gaaagagttg taatctgagt aggccctgga gttcctcatt tcgtttgagc    960

tcccgatgcc tactagcaat gggccgacca gatcacaagc agctgaagct tggtcttcaa   1020

gggcatgcct tttccatggc cgagaggaca gacaggcttc accagaaggg gtactgaggg   1080

agagaagaat gtaaacagaa tctagttaag acaggaacac agaattgctc ttgtggggtt   1140

ggttgtccat gatcttgaag gttctctagg tcaattcccc agtttctaaa gactaggcct   1200

ctctagggta ccaggaagac tcaagaccag taagtaaggt tgattgatgg catgcgttcc   1260

tgattggcag cagagtgctc tcctgactcc ttcagccact ataactgccc tcttcctcct   1320

aatcctcctg actgactgac tgcttcaggg ccattggctt tttccaccag agcacgactc   1380

tgtcctgagg ctttatctca cgtgacacta ggcaacatta gcaagtttac ctaccgaaca   1440

cctgcactgg gaatggtgtt ataaggaaga gagagaggtg tgaaagagaa cacctctctg   1500

cttctgctgg gaagcaggca ttagtgggac agtgtcacta ctgagctcag gtacccagca   1560

tgaagtgacc aggaagatct ctggagaggg atggtttgag ctgggcttca gaagatcaat   1620
```

-continued

```
catatcagac aggaggggca caggctcgac tctaaaggtc ccctaaggac cgctctttca   1680
aagaactcct gtgtctaaaa ctcctgctcc aatgggtgtg agcttgaggg gggccaccag   1740
ctcaacttcc ttttctagtg cagctctccg ggtcccaaga tcgtggcatg gagtccacta   1800
agctaggcca ttttatatat gagcatcaga acggaatttt tcagtgccaa acaatctgag   1860
gcaaagccag aggcaggcca gaggacattt ttgttttatt ttgttgagtt ctcgtgttat   1920
caagacctac ctcccacccc aagtagccca ggacaagtgg agcagaaact cagatgagaa   1980
cataagaatg tgaaaaacag tatccatgga gaactagttc cagcccaccc ctcaccctcc   2040
agcataccaa aatcttgtgt agaatggtgt agtatttgca tataatgatg catattctcc   2100
tatacacttt aaatggtctc tagagtacgt ataatgccta atatgatgta aacgctatgt   2160
cagcccttac acagtgttgt tgtaataatg acaagaaaaa taaaaaaaaa aaaaaaaaaa   2220
aaaaaaaaaa aaaaaaaaag gggcggccgc                                     2250
```

<210> SEQ ID NO 24
<211> LENGTH: 2046
<212> TYPE: DNA
<213> ORGANISM: Rattus norvegicus

<400> SEQUENCE: 24

```
gtcgacccac gcgtccggtt tttattactt taattattgt tataaaaagc ctgccatttt     60
taatatgtgg tttggggaat ttttgtttgt ttttcctgtt tgggggtttc ctttgttttt    120
tgtttttttt ctggatttaa aaaaaaaaaa aacaaaacct tgcttttagt gtttgtactg    180
ctgctggtca gaatgttaaa acgctgaagt tctaggaaat aggagagctc gcctgtgcag    240
cattccacac agcagggcta agggggcacc taggtctggt cagctgtcca gggcatggtg    300
acccatgagc agcaggaact tggcacagct ctggcagctg agctcctgag acaggcacag    360
ctctggcaga gagctccaca ctgggggatc tcccttccca gtttcaagtc ctcagtcagg    420
gctgaccaac ttgaaagaga tcctcttcct gccagagcct gtgactatcc tccatcacgg    480
ggggggggag aggaggcaga gcctaccctt ggccaccagg ctcaatggct gtacagagca    540
gctgccttgc agtctgtccc caccctgctc tacccccaac cccttgctct gcctgccaag    600
agtcttctag acaaggaagt gccaccagta ctgtcagcag tcaacaaagc accttcctct    660
gcctacagcc agtcagagat ggtccaaagg agagcagagg ctgcacaccc tgggcaaagc    720
actgcccagt tttccagtta agtgctgcgt gcgctcagtg ttcctttccc aggctaagaa    780
cacaccgatg actggaagct tttgctaatc tgcttggcaa tggcttctgg gaaaggtagg    840
acccataact taagacatgc acagtctctc ccaccgtccc acaggagttc ccctggctga    900
gtatacgatc caaagcaagc catgccctcc caggtcagtc tggggcacaa gctgagccga    960
tgactagcaa tgcctatggc ctttcccttg cctgccctcc tccagcatct ccgcctgtgg   1020
agaccgagta cccccgtgct catacgtaaa gtgacaatca gaaccaggta caagccagga   1080
aagtggcagc tgactgccac tcagaccacg tggcgctttt cccatcccac ggtctcagag   1140
ctggacgagg ctaaatagaa cacagtagcc ccccttccca ggtactgcac cgtccctgga   1200
gatccctctg acccttccct gctacagatc tgctctgctc taggctggac tgtggaatta   1260
gcatgtacat ggaaatccca gtccttgacc atggcttccc actccacctg caagtgatag   1320
atgccatctg tcctgggtgt ctgatcagac ccgccaccat cacagatgag tgaccaagag   1380
gggggctgtc aacacctcgg tacatggtga tcttaaaacc acccaactgc accatcgcac   1440
```

-continued

```
cagactgtac ctctggggca cccagaacaa gccccaccct aacagtgggg gccacagcca   1500

ggcttccagc actgagtctc aaccagctaa gttgaatggc aaactcgatg cctccgcccc   1560

cacccctcag ctgcccaggc cccagcatgc agatggcctg cacagcaggc tcagcacctc   1620

tgaggtgtgc attagccact taacagcagc agtctgtact caagtacaaa agcttttact   1680

tcacgacttg ccgtagcctg tccccactgt ctgatccagt gcttaacttc aaccctagag   1740

tctgccttga ccctgaggag gcatctcact ggtttcgtac ttgtgtgtgc cctatgcctc   1800

actgctgggg ccgcgcaccc agacccagcc aggagggagg atgggtgcct cggtcgctct   1860

gggggcagtt tagatgctgt gaaattaaac ccgttctaag tgtacttgtt tgaattaact   1920

gtattgtaat attatttgtt gaatgtagta attaggtatt tatgaatata ttgctgtaat   1980

ttctgacatc ccaaaaataa aatcttccta aatcatgtta aaaaaaaaaa aaaaaagggc   2040

ggccgc                                                              2046
```

<210> SEQ ID NO 25
<211> LENGTH: 988
<212> TYPE: DNA
<213> ORGANISM: Rattus norvegicus

<400> SEQUENCE: 25

```
gttttagcac aggcttttttg aaccctctac ctgactcagc attttttatt ggtgaaaaaa     60

attccaggat gaagagccct gttttagaat gcaaataaag taagaggctt attttttaat    120

gttaggcaat tttgaaatct tatgcctttc tgcatgcatg acagtggaat gggcaactac    180

aaattccata ttgccattaa aatatattgg attatattag cattcacaga ttacttctag    240

ttaatgctgg gatttcattt ttgaataatg gcaccttcca tttgtacctc cattttctga    300

agtactttgg aacatatttt cattttagaa tatagttctt aagaattttc tacaaaatta    360

gtgaagaaac atagagaatg ctataaaaag gtgggtaggt gggttggttg gttggttcat    420

tggttcatat gactaaagag agtctctagt tttatctgtt gtactgtcat gctgaatacg    480

ttatcttttc agatagtttt taagagtatg tcttaggagc aatttgagga atgaaagtct    540

agaatcattt tattcagttg gttaataact tagtaagcat tgaatttctg ttggcattca    600

tattttttca ggaaggaata ttccaaatca cttatccaaa tactgatcca gatatttaac    660

cacaaatatt ttaaatagtt attttgtgaa agtccagaaa gtccagcaga atgaaataag    720

gaggtaacac ttttgtgaac aaaaattctc agccaacctt aaaggaacaa aactacatgc    780

aacttttctt actctgttct agtttgtctt actgacttat catttgtgtg attttgttaa    840

ggataatttt tgtcaagatg aatgtgttgt cttacatcta tataagagaa atttatgtaa    900

tccacatttg aataaataca tcaagattaa aaaaaaaaaa ccaaaaaaaa aaaaaaaaaa    960

aaaaaaaaaa aaaaaaaagg gcggccgc                                       988
```

<210> SEQ ID NO 26
<211> LENGTH: 974
<212> TYPE: DNA
<213> ORGANISM: Rattus norvegicus

<400> SEQUENCE: 26

```
tgctgggcca gggtgaggag gggccgagct gcgagcttgg gcgctgcagc ctgggcctgc     60

acgtctctgg ctctgagcga agccactggg aggagatgct aaaaaaccca cgccggcaga    120

tcgccatgtg gcaccaattg cacctgtagt ccacatgcct acacccaaag acagatgcaa    180

acatgttggc tgaggccagg aactcattcc tctcttactg tattcccaat actaaagagt    240
```

```
gagcagcatt ggcaggacag tgagcaggac tggcatgtca gggtcactca gaagactgtg    300

tgtcttgctc atctgtgttt tggaaaaaga tgtgcgtcag gtatactcag tagacagtcc    360

ctgctcacat tggtctaaag cagcagttct caacctgtgt gtcatggccc ctttggccac    420

cctctatctc caaaatattt acattgtgat tcataacagt agcaaaatta cagatatgaa    480

gtagcaatga aaatagttct gtggttggag attgccaaaa cacaagaaac tttattatag    540

ggtcacggca tttggaaggt tgagaactac tggctggcag caggtccctg ggccacgggg    600

gctcatgcca cactgatgct ctaggtggaa tacaccaggc tcctgtcctt aactagcaca    660

ggggttctgg agcaggaggg gctgcgcttg atgaggtccc ttcgacacta cccaggcaac    720

ctttccaccc ttgacctcca gaatctcaac actgggcagt atgaagacaa gagctctccg    780

cttacttctc cttttttaca tttctgctgt tcatatccca ctcttgaact gtactgtgtg    840

ttttgactgt tttatttaag gaattgatgt gggttttgtt tgtctttgat cacacgtaga    900

gtgccctttc cctggcagac ctaggttgcc gttcctctgg agtgtctgtg gcattctgag    960

gacaactgtc atgt                                                      974
```

<210> SEQ ID NO 27
<211> LENGTH: 637
<212> TYPE: DNA
<213> ORGANISM: Homo Sapiens

<400> SEQUENCE: 27

```
acagaaatgc atctgggtga gcatgtgctt atttgtatta ttctgaagct cctgagagtc     60

cctcaaagac ccatgctggg cctccccgtc accgagattg cctccgagaa cttctctcac    120

agaagcagga agaagagcac ttcactcctg cccacaggag cagcaactct gaattccgca    180

gccaagggct ctttctggct tgactcccag caaactgaag gttccaggga agaagtgtgg    240

attaattctc taaagagcct gcctttgtgt aagaccttct agatggtctg ccacttgctg    300

agtgggggca tcacagcctt atggtgagat gggttcaaaa gaacaaggtt cactgcgtgg    360

cttggcaaac acctgtgatc tgagtccatc tgagacagga atgaatcaga taatgagacc    420

ctatctgaaa gcaatcaata aaaggccaag gctgtattgg gtggtgtctg gcccccaatg    480

gcagtcatct attactaggt tttgcctctg acctggaatt tttgtgactg ctggataaga    540

ccctaaaata tatgctgggc tgttggacct cttgctcacc ccttccaacc tcgaggctag    600

gaatgggcgg gtacctgctt ccaaaagaaa gtgtctc                             637
```

<210> SEQ ID NO 28
<211> LENGTH: 875
<212> TYPE: DNA
<213> ORGANISM: Homo Sapiens
<220> FEATURE:
<221> NAME/KEY: misc_feature
<222> LOCATION: (1)...(875)
<223> OTHER INFORMATION: n = A,T,C or G

<400> SEQUENCE: 28

```
ggggggcgg atcgaccacg cgtccgcgaa gtcaccagta tggattccgg accgcctcat      60

cacatcatac aatcccaggg camgaaaagc agaaagtctc ccctcaacaa ccgacagcga    120

aagatgagag cggagcgtgc ctcattcctg atgacgccag acagctctga gcagcgcctc    180

acttctgctt tcaccaggct tcagctgcat ggtcgctcat ctaccacgct gttgccaact    240

tgggatcagc ttcaagaatt ggtctctgct gcaagagata gcgtgcttcc tctccgactc    300
```

-continued

```
ccagttactc cctccaatct tctcctgcta tgctttcact tctcttcacc cagggacatg    360

gttttttgat cctggcatag aggccattca tcatgcctcc tgtgtacttc gtagaggttc    420

ctggctgtca catttctgca cgatggtgaa caagtttgtt tttctgattc tcataacaag    480

aaaaggttaa gactaaacta tctaatcttc aaccccatcc aagatctgag gaggagaaat    540

gttgcctgaa taaaaggaaa ttcaaagcaa acagcttcca aacctaagaa atgacagaaa    600

ttgttggcta cactgggagt cagtcagcaa atattcctgt gtcactgtgg catccacctt    660

caactcactg ggccaggagc tctgacaaca atcctttgaa gcaggtcact tgaaggacta    720

tcctattttt tttccaaaaa ctgggacaca nacttcccca tgatcaactt ctgcacagtc    780

tggacagctt nctggcagca gtagaggttg gccctgcagc tttgggcang gcccatggac    840

aaagagattc gcacctgatg ggaacaatct taaaa                                875
```

```
<210> SEQ ID NO 29
<211> LENGTH: 2792
<212> TYPE: DNA
<213> ORGANISM: Rattus norvegicus

<400> SEQUENCE: 29

gtcactacaa cactggtgac atcacagagg atgccagaac tctctaggag acaatagaat     60

gtccaagaag ggacagctga tgtcatgggg agcagacttt gcctccctgc taatgttctc    120

cctgtactga gcataagcag aggtgccctt tccaggagac tttcctgggg cagagccact    180

gagcatctcc tgcttccaaa gccaaatttt cctcaaggct tgattataaa aaccttagta    240

attcctatgc atctaaatga atgtttcctt ccatatcttg ccccaaaatg tctcactaac    300

tcaaattgtc ctcattcacc aatgttagcc attaaaactt cctgagattt cacaccagct    360

tgaatatgca gtcaaaagtt ctcttgtctc attatgtaca ggtgctttaa atcacatcaa    420

gaaatagtct gcatggtagg ttacaacatg cgtgtgtgtt aggggaacac tcatgaagtc    480

atgtgcttag caatcgacaa ttgccagaaa attccttagg agaaagagtt gaagtcttta    540

aggtgctagg aaaagtgtgg agaccagttt gcagaggaaa atgcaatatt agagccacca    600

gtgaagggaa cctcatgctg cttgtggggt tctgctctct gcaccaatgt tgctaaagga    660

gcactgctca caggcctgag taacatgtac tatgagcttt tatcagaaaa ataaaataca    720

caagagatat agagggtgca tagaaacgtc taaaatgagg ctataaacat cgataagtgg    780

atagagcaag gtcccagcac ctgtacactg ggaaatggcc accccaccaa acacaaaagc    840

atctatcata gtaaaaaatg aatactttat agaatgcacc cactaacact gattgatcac    900

atccatagtt caaattttgg gggcaaattc atggccttaa ctatctttgt ctcaccttat    960

atagcaaaaa ataagaaaga acgagaaaag aaaaagtcaa aactaaaagc tcaagcttct   1020

catatgagga ttgcaggaag tgttatatgg gagtcagttc tgattaggcc attttacata   1080

gaacagtgca tagtgaccct taatgtgatg ggccctatat aaagcttttt gcaatattgg   1140

aattttaaca aacctcatcc agaacgtacg gaagaggcac catatgatca ccatgtgatc   1200

accatgtcct tactctgtat caggttattt ttctgcatcc ttgattgtca ggcatataac   1260

agcaacaacc tgaaatagct ggtagacatg taaaaacatg gccaaaacta tagttgtggg   1320

taacacacct caactgtgaa aggctaatgc tgtctgcaca gtccttggag gccactcttt   1380

taagcctatt tattgcaaag tgaaaggagg tttatctgag ctcaaagtga tcctggccag   1440

ccaggtagag ggcaacatgt gatacttgag accctgtttt aaaccagcac agaaatccac   1500

acttcattca aagcatcatc tacgaattct cgattattta ccattctctc cctaccagtc   1560
```

-continued

```
gtactgtttg gaatggtaga aaacaattgg aactgatctt tctattttaa ggaccttgat   1620
ctctcttttt ttaggtccac attaagagtg catacaaatg gacatcacca tctgaacatc   1680
ttagtattat ctactctgta tatatagcat aatactgtgc ctatgaaaat ctcaagcttc   1740
cttgagtgta gttgccccat caagaagtgt gaagttctga gttcaaaccc cagtgatgct   1800
ttaaagggac tagaagaaag ccatcagaga tactccactt ctttgtcctt agattaaatc   1860
aagttgacac aatgtgaacc tggtgggcta tttaaccatg catctttctc ccaaccccac   1920
ttccacgagt tcagtccatg gcagaattca tcccccacca tcctagatat ttctttgtat   1980
atttctacaa gagccaggtt tcttttttt taatagaatt agttgtagtc aatcaactgc   2040
tgccctatgt gagaaatgat tagtatctat tgcaacttac cacagtgtat ttgtgtatac   2100
aagtacatta ttggaaatcc agcattactg agggattgga aaccagtgct gtggccttgc   2160
ctttctgtgc ctcttcctgg ctcacaggca gcaggcggca gaccttgagt tcctcttcag   2220
ggacagagtg atgttgaatg ggcactgagc agtcagagaa acacagctga ggcagctcct   2280
ttcagttatc aaacacatca tctccttccc atcttaaggg ctactgctga ggtcttgccc   2340
ccatacctac cttaatagca gcgaatttgt tacacagcag ccagctcttt cctattgttc   2400
tgtaatacgc ctccacatca tggatgccaa gaaaaacact aacaaagaac aaaaaactct   2460
gacgttggac tgggtggtgc tggtcacata ccctgttatg ttctgtatga ggtttgttaa   2520
tcttaacaag ttccccaagt gtattcttca cataggaccc aatagattca aggaaaatag   2580
gaacaattat gtgtaaaatg gcctgagtca gggcccatag accgaagcat ttccagcact   2640
tgtgcatgag cccatgtgga ttttgcaatg agctgggcct agcaatgtcc agtacacagt   2700
tgtgagctgt tgctctggtt gaactgtatt ggtgtgtgca ttaataaact acacctattt   2760
aaatgaaaaa aaaaaaaaaa aagggcggcc gc                                 2792
```

<210> SEQ ID NO 30
<211> LENGTH: 617
<212> TYPE: DNA
<213> ORGANISM: Rattus norvegicus

<400> SEQUENCE: 30

```
gaattcggct tggaaagctg gtaccgcctg caggtaccgg tccggaattc ccgggtcgac     60
ccacgcgtcc ggggttccct ggctcccttt gttcaaccaa gaggaaatct gagtcaagcc    120
agttgagcta tcaagagcct aggccacacc tctccatgct ccccgaaccc aacacaccca    180
gaaacctgtg atttcttttc tcctgttttg acaagggacc acatatcaac acaaaattat    240
aatctccaca aggaatacaa atgtacagac gaattcggct tggaaagctg gtacgcctgc    300
aggtaccggt ccggctccca gaacaaagca ttcgtccgtg gaaattcaat tccttttcag    360
atgctccagt tgttgtggcc cattgctaga aaggtcagct taagcccgca gcccccccggt   420
aggaagctca aaatacactg cccagaactt actcaacatt ccccagaagt gctgtctttg    480
tccatcatta ctttgagacg aaaggctaga ctccttcact ttagtctctc cagaatcgac    540
attccccctc ccaaaacgct tgcgaagacg ggaaaacatg tcttagcttg taaccgccag    600
actcagactg agagaaa                                                   617
```

<210> SEQ ID NO 31
<211> LENGTH: 1475
<212> TYPE: DNA
<213> ORGANISM: Rattus norvegicus -continued

<400> SEQUENCE: 31

```
gtcgacccac gcgtccgccc acgcgtccgc ccacgcgtcc gcccacgcgt ccggttggtc     60
agccggcgac tgacaggggc gcgagcccgg gcacctctgc ttgcgagtct cctcgaggct    120
tggtgccgcc agggcaggac cacctcctcc tactccgctt tctcggagcc gtcgcgtgtg    180
cgggcgctgg tctatggcaa ccacggggat ccagccaagg tcatccacta taaaagcaga    240
acaatagtct gcaagctatt gaaatgggat ggaagctggc cggcctataa agcacttggc    300
agggagcctg gctgaacact cactgactga agaacctgga gctcactgct gtggaaggat    360
ctgacgtcca tgtgaagatg ctggcagccc ctatcaatcc atctgacata aatatgatcc    420
aagggaacta tggcctcctt cccaagctgc ctgctgttgg agggaatgaa ggtgttggac    480
aggtgatagc agtgggcagc agtgtgtctg gattgaagcc aggagattgg gtgatcccag    540
caaatgctgg tttgggaacc tggcggactg aggcggtgtt cagtgaggaa gcgctgattg    600
gagtccctaa ggacatccct ctccagagtg ctgccaccct aggtgtcaac ccctgcacag    660
cctacaggat gttggtggac tttgaacagc tacaaccagg ggactctgtc atccagaatg    720
cgtccaacag tggagtaggg caagcagtca ttcagatcgc ctcagccctt ggcctaaaga    780
ccatcaacgt gatccgagac agacctgaca tcaagaagct aactgacaga ctgaaggatc    840
taggagctga ttatgtcctc acagaggagg agataaggat gcccgagacc aaaaacatct    900
tcaaggacct gccgctgccc cgactggctc tcaactgtgt cggtgggaag agttccacag    960
agctgctccg gcacctagcg cccggaggaa ccatggtgac ctatggagga atggccaagc   1020
agcctgtaac agcctctgtg agtatgctca tttttaagga cctcaaactt cgtggctttt   1080
ggttgtccca gtggaagaag aaccatagtc cagatgagtt caaggagctg attctcattc   1140
tctgcaacct catccgccaa ggccagctca cagcccctgc ctggtccggg attccactgc   1200
aggactacca gcaggctttg gaagcctcca tgaagccttt tgtgtcttcg aagcagattc   1260
tcactatgtg attactccag aggaccagga ggaaagcagg agaggcaggc cagcaagatt   1320
ggctggctgc tggccctcca tgaggactcc agactgcctc accctcactg cctcttccta   1380
ccaggagggt gggaggccaa ccccagggtc cctaataaac cctggacttc ccaagtaaaa   1440
aaaaaaaaaa aaaaaaaaaa aaaaaaaaaa aaaaa                              1475
```

<210> SEQ ID NO 32
<211> LENGTH: 2738
<212> TYPE: DNA
<213> ORGANISM: Homo Sapiens

<400> SEQUENCE: 32

```
gtcgacccac gcgtccggag atatccttaa taagcgacaa tgagttcaag tgcaggcatt     60
cacagccgga gtgtggttat ggcttgcagc ctgatcgttg gacagagtac agcatacaga    120
cgatggaacc agataacctg gaactaatct ttgatttttt cgaagaagat ctcagtgagc    180
acgtagttca gggtgatgcc cttcctggac atgtgggtac agcttgtctc ttatcatcca    240
ccattgctga gagtggaaag agtgctggaa ttcttactct tcccatcatg agcagaaatt    300
cccggaaaac aataggcaaa gtgagagttg actatataat tattaagcca ttaccaggat    360
acagttgtga catgaaatct tcattttcca agtattggaa gccaagaata ccattggatg    420
ttggccatcg aggtgcagga aactctacaa caactgccca gctggctaaa gttcaagaaa    480
atactattgc ttctttaaga aatgctgcta gtcatggtgc agcctttgta gaatttgacg    540
tacacctttc aaaggacttt gtgcccgtgg tatatcatga tcttacctgt tgtttgacta    600
```

-continued

```
tgaaaaagaa atttgatgct gatccagttg aattatttga aattccagta aaagaattaa    660
catttgacca actccagttg ttaaagctca ctcatgtgac tgcactgaaa tctaaggatc    720
ggaaagaatc tgtggttcag gaggaaaatt ccttttcaga aaatcagcca tttccttctc    780
ttaagatggt tttagagtct ttgccagaag atgtagggtt taacattgaa ataaaatgga    840
tctgccagca aagggatgga atgtgggatg gtaacttatc aacatatttt gacatgaatc    900
tgtttttgga tataatttta aaaactgttt tagaaaattc tgggaagagg agaatagtgt    960
tttcttcatt tgatgcagat atttgcacaa tggttcggca aaagcagaac aaatatccga   1020
tactattttt aactcaagga aaatctgaga tttatcctga actcatggac ctcagatctc   1080
ggacaacccc cattgcaatg agctttgcac agtttgaaaa tctactgggg ataaatgtac   1140
atactgaaga cttgctcaga aacccatcct atattcaaga ggcaaaagct aagggactag   1200
tcatattctg ctggggtgat gataccaatg atcctgaaaa cagaaggaaa ttgaaggaac   1260
ttggagttaa tggtctaatt tatgatagga tatatgattg gatgcctgaa caaccaaata   1320
tattccaagt ggagcaattg gaacgcctga agcaggaatt gccagagctt aagagctgtt   1380
tgtgtcccac tgttagccgc tttgttccct catctttgtg tggggagtct gatatccatg   1440
tggatgccaa cggcattgat aacgtggaga atgcttagtt tttattgcac agaggtcatt   1500
ttgggggcgt gcaccgctgt tctgggtatt catttttcat cactgagcat tgttgatcta   1560
tgccttttgg gcttctcagt tcaatgaagc aataatgaag tatttaactc tttcactaca   1620
gttcttgcaa gtatgctatt taaattactt ggccaggtat aattgccagt cagtctcttt   1680
atagtgagaa aatttattgg ttagtaatat aaatatttta aactaaatat ataaatctat   1740
aatgttaaac atatgttcat taaaagcata gcactttgaa attaactata taaatagctc   1800
atatttacac ttacagcttt tcatttgatc aggtctgaaa tctttagcac ttaaggaaaa   1860
tgactatgca taattatacc tgaccatgaa aaaaataagt acctcaaatg catgcatttg   1920
cactggtgat tccaactgca caaatctttg tgccatcttg tatataggta ttttttacat   1980
gggttgacat gcacacaaca ccattttcat tcagtatgaa ccttgaggct gctgccattt   2040
ttccacttaa ccaaaccagc ctgaaggtga acctcgaaac ttgtttcata aatctttcaa   2100
aagttgtttt acatcaatgt taaaatttca aaatgctgca gggtaattta atgtataaaa   2160
tattagtaag aaaaagtatg tattgcatac ttagtagaat agatcacaac atacaaattc   2220
aattcagtgc atgctttagg tgttaagcat gagattgtac atgtttactg ttaggtcctt   2280
gcatctgtgg tgctaggtga gtatgagaag atgtcaagga ctggacgtat tttgttgcct   2340
aaaaaaaaaa ggctgtttgt aggcgtttta aatatgctta ttttgtgtgt ctctcactac   2400
ctattacaca ctgttgcttt gtgggtttgt tttgtatgtg cgtgtgttat acagtagtta   2460
aatttccatg cagaaaaata aatgtcctga attctcatat tagtattctt tattgtatat   2520
catgcatgta atttatttag aaatgtaggt cttactaaat gtatatgcat gtatttcaga   2580
ttatactagg atttcttgga ttagaagcag attgtgttaa ctgtaactta aagaatgaat   2640
gttaaataaa atgatacaga tttattttct tcattacaaa aaaaaaaaaa aaaaaaaaaa   2700
aaaaaaaaaa aaaaaaaaaa aaaaaaaagg gcggccgc                           2738
```

```
<210> SEQ ID NO 33
<211> LENGTH: 1664
<212> TYPE: DNA
<213> ORGANISM: Homo Sapiens
```

<400> SEQUENCE: 33

```
gcggccgcag ccccggccga gcaggcgccg cgggccaagg gccgcccgag acggtcccca      60

gagagccacc ggaggagcag ctcacctgag agacggagcc ccggctcgcc cgtgtgcaga     120

gcggacaagg caaaatctca gcaagttcgg acctctagta caataaggcg aacctcctct     180

ttggatacaa taacaggacc ttacctcaca ggacagtggc cacgggatcc tcatgttcac     240

tacccttcat gcatgaaaga caaagctact cagacaccta gctgttgggc agaagagggt     300

gcagaaaaga ggtcacatca gcgttctgcg tcatggggga gtgctgatca actaaaagag     360

atcgccaaac tgaggcagca actacaacgc agtaaacaga gtagtcgtca cagtaaggag     420

aaagatcgcc agtcacctct tcatggcaac catataacaa tcagtcacac tcaggctact     480

ggatcaaggt cagttcctat gccactgtca aatatatcag tgccaaaatc atctgtttcg     540

cgtgtgccct gcaatgtaga aggaataagt cctgaattag aaaaggtatt cattaaagaa     600

aataatggga aggaagaagt atccaagccg ttggacatac cagatggtcg aagagctcca     660

cttcctgctc attaccggag cagtagtact cgcagcattg acactcagac tccttctgtc     720

caggagcgca gcagtagctg cagcagtcat tcaccctgtg tctccccttt ttgtcccccg     780

gaatcccagg atggtagccc ttgctcaaca gaagatttgc tctatgatcg tgataaaggt     840

ctcgtcagcc tatctcggcc cctctctttt catgtcctga caaaaacaag gttaatttca     900

tcccaaccgg atcagctttc tgtcctgtaa aacttctagg ccccctctta cctgcttctg     960

accttatgct caagaactct cctaactctg gccagagctc agctttggca actctgaccg    1020

ttgagcagct ctcatcccgg gtttccttta cgtctctttc tgatgacacc agcacagcgg    1080

gctccatgga ggcctctgtc cagcagccat cccagcagca gcagctcctg caggaactgc    1140

agggtgagga ccacatctct gctcagaact atgtgatcat ctaaaaaagg gggagctggc    1200

ctccaccctg tgttccatgg attcggaaca agatttcaga catctgcatg agtgacaaac    1260

tttctgaaca ccaccaccac caataatact tatcagcatc ataaagtatc tcttaaacac    1320

tgatcttggc agggacggaa ctcctattca gcagtttttg tggaaagcag taatgcttgc    1380

aaaacgtgtg tgtcattcag cattttaagt ggagactatg catttcatag tatatttgac    1440

agattagtac tgtgtcctgt gttttgttcc agattcttca gtataaataa gctctatatc    1500

aaaaagttgc ctgtctaaat agaaaatgtc ttgctgtgtt ttgtcctatg gaaaatactg    1560

taattcagga ttatgtttac aattgatcca ggtgtttgtt tctaacttct gtaatacata    1620

caatgcaaaa aaaaaaaaaa aaaacggacg cgtgggtcga ctcc                     1664
```

<210> SEQ ID NO 34
<211> LENGTH: 3206
<212> TYPE: DNA
<213> ORGANISM: Homo Sapiens

<400> SEQUENCE: 34

```
gtcgacccac gcgtccgggc gaggcacgga cggcgggcgc ccggtacctc tgcccgcggt      60

cctcgctctc gggcggggcg gcggcgacgc ggacctgcgg actagcgaac ccggagcacg     120

acatcataaa ataaatccat cagaatgaca ccttctcagg ttgcctttga aataagagga     180

actcttttac caggagaagt ttttgcgata tgtggaagct gtgatgcttt gggaaactgg     240

aatcctcaaa atgctgtggc tcttcttcca gagaatgaca caggtgaaag catgctatgg     300

aaagcaacca ttgtactcag tagaggagta tcagttcagt atcgctactt caaagggtac     360

tttttagaac caaagactat cggtggtcca tgtcaagtga tagttcacaa gtgggagact     420
```

-continued

```
catctacaac cacgatcaat aacccccttta gaaagcgaaa ttattattga cgatggacaa    480
tttggaatcc acaatggtgt tgaaactctg gattctggat ggctgacatg tcagactgaa    540
ataagattac gtttgcatta ttctgaaaaa cctcctgtgt caataaccaa gaaaaaatta    600
aaaaaatcta gatttagggt gaagctgaca ctagaaggcc tggaggaaga tgacgatgat    660
agggtatctc ccactgtact ccacaaaatg tccaatagct tggagatatc cttaataagc    720
gacaatgagt tcaagtgcag gcattcacag ccggagtgtg gttatggctt gcagcctgat    780
cgttggacag agtacagcat acagacgatg gaaccagata acctggaact aatctttgat    840
tttttcgaag aagatctcag tgagcacgta gttcagggtg atgcccttcc tggacatgtg    900
ggtacagctt gtctcttatc atccaccatt gctgagagtg gaaagagtgc tggaattctt    960
actcttccca tcatgagcag aaattcccgg aaaacaatag gcaaagtgag agttgactat   1020
ataattatta agccattacc aggatacagt tgtgacatga aatcttcatt ttccaagtat   1080
tggaagccaa gaataccatt ggatgttggc catcgaggtg caggaaactc tacaacaact   1140
gcccagctgg ctaaagttca agaaaatact attgcttctt taagaaatgc tgctagtcat   1200
ggtgcagcct ttgtagaatt tgacgtacac ctttcaaagg actttgtgcc cgtggtatat   1260
catgatctta cctgttgttt gactatgaaa aagaaatttg atgctgatcc agttgaatta   1320
tttgaaattc cagtaaaaga attaacattt gaccaactcc agttgttaaa gctcactcat   1380
gtgactgcac tgaaatctaa ggatcggaaa gaatctgtgg ttcaggagga aaattccttt   1440
tcagaaaatc agccatttcc ttctcttaag atggttttag agtctttgcc agaagatgta   1500
gggtttaaca ttgaaataaa atggatctgc cagcaaaggg atggaatgtg ggatggtaac   1560
ttatcaacat attttgacat gaatctgttt ttggatataa ttttaaaaac tgttttagaa   1620
aattctggga agaggagaat agtgttttct tcatttgatg cagatatttg cacaatggtt   1680
cggcaaaagc agaacaaata tccgatacta tttttaactc aaggaaaatc tgagatttat   1740
cctgaactca tggacctcag atctcggaca acccccattg caatgagctt tgcacagttt   1800
gaaaatctac tggggataaa tgtacatact gaagacttgc tcagaaaccc atcctatatt   1860
caagaggcaa aagctaaggg actagtcata ttctgctggg gtgatgatac caatgatcct   1920
gaaaacagaa ggaaattgaa ggaacttgga gttaatggtc taatttatga taggatatat   1980
gattggatgc ctgaacaacc aaatatattc caagtggagc aattggaacg cctgaagcag   2040
gaattgccag agcttaagag ctgtttgtgt cccactgtta gccgctttgt tccctcatct   2100
ttgtgtgggg agtctgatat ccatgtggat gccaacggca ttgataacgt ggagaatgct   2160
tagtttttat tgcacagagg tcattttggg ggcgtgcacc gctgttctgg gtattcattt   2220
ttcatcactg agcattgttg atctatgcct tttgggcttc tcagttcaat gaagcaataa   2280
tgaagtattt aactctttca ctacagttct tgcaagtatg ctatttaaat tacttggcca   2340
ggtataattg ccagtcagtc tctttatagt gagaaaattt attggttagt aatataaata   2400
ttttaaacta aatatataaa tctataatgt taaacatatg ttcattaaaa gcatagcact   2460
ttgaaattaa ctatataaat agctcatatt tacacttaca gcttttcatt tgatcaggtc   2520
tgaaatcttt agcacttaag gaaaatgact atgcataatt atacctgacc atgaaaaaaa   2580
taagtacctc aaatgcatgc atttgcactg gtgattccaa ctgcacaaat ctttgtgcca   2640
tcttgtatat aggtattttt tacatgggtt gacatgcaca caacaccatt ttcattcagt   2700
atgaaccttg aggctgctgc catttttcca cttaaccaaa ccagcctgaa ggtgaacctc   2760
```

```
gaaacttgtt tcataaatct ttcaaaagtt gttttacatc aatgttaaaa tttcaaaatg   2820

ctgcagggta atttaatgta taaaatatta gtaagaaaaa gtatgtattg catacttagt   2880

agaatagatc acaacataca aattcaattc agtgcatgct ttaggtgtta agcatgagat   2940

tgtacatgtt tactgttagg tccttgcatc tgtggtgcta ggtgagtatg agaagatgtc   3000

aaggactgga cgtattttgt tgcctaaaaa aaaaaggctg tttgtaggcg ttttaaatat   3060

gcttattttg tgtgtctctc actacctatt acacactgtt gctttgtggg tttgttttgt   3120

atgtgcgtgt gttatacagt agttaaattt ccatgcagaa aaataaatgt cctgaattct   3180

caaaaaaaaa aaaaaagggc ggccgc                                          3206
```

<210> SEQ ID NO 35
<211> LENGTH: 1175
<212> TYPE: DNA
<213> ORGANISM: Homo Sapiens

<400> SEQUENCE: 35

```
gcggccgcct gctggccgga gcctatcacg ccgtagtgct gcgagagcgc gccgctcagt     60

gcctgcttct ggattgtcgc tccttcttcg ccttcaacgc cggccacatc gtgggctcag    120

tgaacgtgcg cttcagccac catctgcctt gcttacctca tgaggactaa ccgagtgaag    180

ctggacgagg cctttgagtt cgtgaagcag aggcggagta ttatctcccc caacttcagc    240

ttcatgggcc agctgctgca atttgagtcc caagtactgg cccctcactg ttctgcagaa    300

gctgggagcc cggccatggc tgtccttgac cggggcacct ctactacaac ggtcttcaac    360

ttccctgtct ccatccctgt tcaccccacg aacagtgccc tgaactacct tcaaagcccc    420

atcacaacct ctccgagctg ctgaagggcc aggggaggtg tagagtttca tgtgccaccg    480

ggacgacact cctcccatgg gaggagcaat gcaataactc tgggagaggc tcatgtgagc    540

tggtccttat ttatttaaca ccccccccca acacctcccg agttccactg agttcccaag    600

cagtcataac aatgacttga ccgcaagaca tttgctgaac tcagcccgtt cgggaccaat    660

atattgtggg tacatcgagc ccctctgaca aaacagggca gaagggaaag gactctgttt    720

gagccagttt cttcccttgc ctgtttttc tagaaacttc gtgcttgaca tacctaccag     780

tattaaccat tcccgatgac atacgcgtat gagagtttta ccttatttat ttttgtgtgg    840

gtgggtggtc tgccctcaca aatgtcattg tctactcata gaagaacgaa atacctcact    900

ttttgtgttt gcgtactgta ctatcttgta aatagaccca gagcaggctt tcagcactga    960

tggacgaagc cagtgttggt tgtttgtagc ttttagctat caacagttgt atgtttgttt   1020

atttatgatc tgaagtaata tatttcttct tctgagaaga cattttgtta ctaggatgac   1080

ttttttttta tacagcagaa taaattatga catttctatt gaaaaaaaaa aaaaaaaaaa   1140

aaaaaaccca cgcgtccgcg gacgcgtggg tcgac                                1175
```

<210> SEQ ID NO 36
<211> LENGTH: 1172
<212> TYPE: DNA
<213> ORGANISM: Rattus norvegicus

<400> SEQUENCE: 36

```
gcggccgcct gctggccgga gcctatcacg ccgtagtgct gcgagagcgc gccgctcagt     60

gcctgcttct ggattgtcgc tccttcttcg ccttcaacgc cggccacatc gtgggctcag    120

tgaacgtgcg cttcagccac catctgcctt gcttacctca tgaggactaa ccgagtgaag    180

ctggacgagg cctttgagtt cgtgaagcag aggcggagta tctcccccaa cttcagcttc    240
```

```
atgggccagc tgctgcaatt tgagtcccaa gtactggccc ctcactgttc tgcagaagct    300

gggagcccgg ccatggctgt ccttgaccgg ggcacctcta ctacaacggt cttcaacttc    360

cctgtctcca tccctgttca ccccacgaac agtgccctga actaccttca aagccccatc    420

acaacctctc cgagctgctg aagggccagg ggaggtgtag agtttcatgt gccaccggga    480

cgacactcct cccatgggag gagcaatgca ataactctgg gagaggctca tgtgagctgg    540

tccttattta tttaacaccc ccccccaaca cctccccgagt tccactgagt tcccaagcag   600

tcataacaat gacttgaccg caagacattt gctgaactca gcccgttcgg gaccaatata    660

ttgtgggtac atcgagcccc tctgacaaaa cagggcagaa gggaaaggac tctgtttgag    720

ccagtttctt cccttgcctg ttttttctag aaacttcgtg cttgacatac ctaccagtat    780

taaccattcc cgatgacata cgcgtatgag agttttacct tatttatttt tgtgtgggtg    840

ggtggtctgc cctcacaaat gtcattgtct actcatagaa gaacgaaata cctcactttt    900

tgtgtttgcg tactgtacta tcttgtaaat agacccagag caggctttca gcactgatgg    960

acgaagccag tgttggttgt ttgtagcttt tagctatcaa cagttgtatg tttgtttatt   1020

tatgatctga agtaatatat ttcttcttct gagaagacat tttgttacta ggatgacttt   1080

tttttatac agcagaataa attatgacat ttctattgaa aaaaaaaaaa aaaaaaaaaa    1140

aaacccacgc gtccgcggac gcgtgggtcg ac                                 1172
```

<210> SEQ ID NO 37
<211> LENGTH: 863
<212> TYPE: DNA
<213> ORGANISM: Rattus norvegicus

<400> SEQUENCE: 37

```
gtgacatgct gtctagtccg gtttcatctt ttttttaat gttgtttatt tttggatgta      60

caaaagaaaa attgggggga gggggtgatc tctgtagata ctcttgtact ttgaagttac    120

cggaaatgga acgggtctta aagcagaaag taacttttcc aaggaacaga tgcttgcgaa    180

ggccccccttc cttgtcttat tctccagaga caactgaaat ttagcttctt tgttgcagca   240

aagctctttg cccaggtgaa cactgaccac cgcgggtttt ctatgtcaga aagaagaaga    300

aaaacaaaaa catgctcgag ctttttctaa cctccccttg ggggtctgtt gtgcgaaccc    360

ctctttcttc aatatcgtgt cactttattc tctttaatgg actgtaacaa acaacaacaa    420

caatgtaatc acgagagtgc caaatatctt gaaacgccaa aaggcatttt ggtttccttt    480

tctcccctgt gctctgagtc ttcgtactgg aacgcttgga gtgtcttttc tgttatttat    540

aggggttctc ttaaggctct cgccagctgc ctgttttgca tggtatttgc aaaaaaaaaa    600

atgcctcttg cgtgaggaat cttttacttt tttttttttt atttgtttgc aactttggac    660

ctcaagaggt ccccaccccca gtcccagttc cttcttttct taattcttta ttctgtatgc   720

tgcaccttga accagcacac agggctattt ctccaatgta caataaagaa cttcctgtgt    780

ctccttaaaa aaaaaaaaaa aaaaaaaaaa aaaaaaaaaa aaaaaaaaaa aaaaaaaaaa    840

aaaaaaaaaa aaagggcggc cgc                                            863
```

<210> SEQ ID NO 38
<211> LENGTH: 2485
<212> TYPE: DNA
<213> ORGANISM: Rattus norvegicus

<400> SEQUENCE: 38

-continued

```
cccacgcgtc cgggggaact cacccagcat atggggagcc ctagaattct tcccttagct     60
tgactgggga aaaggaaggg aaggaggaag gaaagaggaa aggggcagaa aaggagagag    120
ggagggaact acagaaatca gttatcaacc ctggcaaaaa caaaagtgtg ctaaaagttt    180
aagtgtaata tgaaaagatg acagagaata gacattgagt tgctgacagg aaggaccact    240
aacgaagtaa ggcttcctgg tggtagaaag tagatgccac cctctctaaa tttccaaaac    300
atgacttgag gcaagtctat cacataaggc aagttgttaa tgagtagttg cagaaatgaa    360
caagagtatg gtgatgtatg cccgtacagc taaagcccaa tacttgagag gctcaggcag    420
gagaaggatc aagggcaaca cagtgagact ctgcctctaa acaaatgcac tgaaacacca    480
cattatagaa gcaaaacagg agactggaat ttggggaatg ttgatttttc aaccatagca    540
cctattagac aatcagagat cctgcctacg aggacgcctc acaggactca aggatctata    600
caagcttccg aagcctttcc ccaccaccct actatacatc tctgttccat tccctctcct    660
gtgtgctaaa agatgctatt cgtgtccttg tgatgctgaa tgactgtgta cacatgcagg    720
atgtgtgtct acaatgtcaa agttagttaa aaacaataat gaagtaaaca cattccctca    780
aaccaaaaaa acaaaaacaa aaacaaaaaa aaccaaatag taccttataa atgactatag    840
aataaacaaa attttaaaac ccacgaaaac ttagttgcag gcaaggcaaa tcaacaaaca    900
tccagatgta ctaggaatgt accaagtagt tatgcccttc agaatataag ataaagcaaa    960
gatattttta aatgtcgagt tttccttgtt catggggacc catttttaat ttgtatctac   1020
aagattagat gtacaaagca gctctcttcc aaagctagaa ccggcatagg tgtccattag   1080
caagtagtag ctatagaata ctgctccatt catgaggaaa atctactcct aattaaaata   1140
gggagtatgt gtctctcaca aacacccttt gggggtaaaa gaaaactttg cacgaaatat   1200
gacacactgc gtgatgtgat tgtgtggggc tctgaaacac acaaaagtag cctgtgcttt   1260
aaaggagcat tatagtcatt gtctttggga gacagaagcc tgattccatg caaaagggct   1320
agaggtcact ttctgagtca ctactgagtg tgctagatgg tcactgaggt acacagcttc   1380
tccagaattc aggcaaacgt atgctcacac cacatgtact ttgccttatg tagtggttct   1440
caacctgtgg gtcatgaatc atgttatgat tcaaaataat agagaagtat gaagtagtaa   1500
tgacataatg tcatggtcgg gggtgacggc atgaagaact gtaacaaagg gtcactgcat   1560
caggaaagtg gagagccact gccttaaaga aaccttagaa tatatttctg aagtgttcag   1620
gaatgaggga cattgaagtc tgacacttac tttaaaatat caggagacac tgataaaaat   1680
taagagatga gcagatgtgt gacaaagcaa acatgataaa atgtaggtgg tatgttaatg   1740
gtttgtatcc tataatggtc tcattttctg cgatagttca aattttattt taaagtgtaa   1800
aaaaaataaa ctctgacaga gctgacacaa ggctgacaca aggctgacac aaggctgtct   1860
cttcgccatg gtaaccattt cctttactgt gtatgagctt ttgaatttaa tatgatccta   1920
cttattaatt cttgaaatta ctccctctgc tgctggagtt ctttgcaaaa atgttcttgc   1980
ctttgccttt gccctgccag tatcttaaga gtatttttgt agatttttat cctgcagttt   2040
caattttcca agttctatac aaggttttgc tccattttga cttttgtgtg tgcaggatga   2100
ggaacgggaa tctagtttca ttgttttacg tgtgggtatt cagtttttcc agaacctgtt   2160
gttgaagagg gtgtctcttt caatgcatgt tttgttactt ttgtcaaaag ttaggtggct   2220
gtcactgtgt gggcttattt ctaagtcatc cactaagtat tccatcgctc tccatgcttg   2280
tctttgtgcc agtaccacat agtttctgtt attatcactt catgttataa tttaatatca   2340
gatatttcat cagcgtcttc ctgcttagaa tcattttggt attcagggtc ctttgcactt   2400
```

ctatatgaat acctaggacc tataaagtaa ctcaaaaatg aaacacccaa aaaaaaaaaa 2460
aaaaaaaaaa aaaaagggcg gccgc 2485

<210> SEQ ID NO 39
<211> LENGTH: 3381
<212> TYPE: DNA
<213> ORGANISM: Rattus norvegicus

<400> SEQUENCE: 39
gtcgacccac gcgtccgcgg acgcgtgggc cggtttgaga ggtgactgtg agctgggctc 60
agtgctgcca ccggtcacct aagggagcgc tggcgaggcg cagactctcg gcttagtcgg 120
ccgcggccca ggctcccggc gcggcgcgga acggagtggc agaaatctta aataattcca 180
tcagaatgac accttctcag gtcacctttg aaataagagg aactctttta ccaggagagg 240
tctttgcaat gtgtggaaac tgtgatgcct tgggaaactg gagtcctcaa aatgctgtgc 300
ctcttactga gagtgagaca ggcgaaagtg tatggaaagc agtgattgtt cttagtagag 360
gaatgtccgt gaagtaccgc tacttcagag gctgcttttt agaaccaaag actatcggtg 420
gtccatgtca agtcatagtt cacaagtggg agactcatct acaaccacga tcaataaccc 480
ctttagaaaa cgaaatcatt attgacgatg gacaatttgg aatccacaat ggtgttgaaa 540
cactggattc tggatggctt acctgtcaga ctgaaataag actgcgtctg catttttctg 600
agaaacctcc tgtttcaatt accaagaaaa agttcaaaaa atctagattt agggtaaagc 660
ttacactaga gggtctggag gaagatgatg acgacgatga taaggcatct cccactgttc 720
ttcacaagat gtccaatagc ctggagatat ccttaataag tgacaatgag ttcaagtgca 780
ggcactcaca gccagaatgt gggtatggct tacagcctga ccgctggaca gagtacagca 840
tacagacaat ggagccggac aaccttgaac tcatctttga ctttttttgag gaagatctca 900 gtgagcatgt agtccagggt gatgttcttc ctggacatgt gggcacagca tgcctcctgt 960
catctaccat tgctgagagt gagagaagcg ctggaatcct tactcttccc atcatgagca 1020
gaagttccag aaaaactata ggcaaagtca gagttgattt tatcatcatc aagccattac 1080
caggatatag ttgttctatg cagtcttcat tctccaagta ttggaaacca agaataccac 1140
tggatgttgg acatcgtggt gcagggaact caacaacaac tgccaagctg gctaaagtac 1200
aggaaaatac tattgcttct ttaagaaatg ctgccagcca tggtgcagca tttgtggaat 1260
ttgatgtcca cctttcaaag gacttagtgc ctgtagtgta tcatgatctc acctgctgtt 1320
taactatgaa aaggaaatat gaagctgatc cagttgaatt gtttgaaatc ccagtaaagg 1380
aattaacatt cgaccaactc cagttattga agctttctca tgtgactgca ctaaaaacca 1440
aagaccagaa acaatgtatg gctgaggagg aaaattcctt ttctgaaaac caaccatttc 1500
cttctcttaa gatggtttta gagtcattgc cagaaaatgt aggatttaat atagaaataa 1560
aatggatttg ccaacacagg gatggagtat gggacggcaa cttatcgaca tattttgata 1620
tgaatgcatt tttggatata attttaaaaa ctgttttaga aaattccggg aagaggagaa 1680
tagtattttc ttcatttgat gcagacatct gtacaatggt tcggcagaaa caaaacaaat 1740
atcccatatt atttttgacc caaggaaagt ctgacattta ccctgaactc atggacctca 1800
gatctcggac aacacccatt gcaatgagct ttgcacagtt tgaaaatatt ttggggataa 1860
atgcccatac tgaagatctc cttagaaacc catcctatgt ccaagaggca aaagataagg 1920
gattggtcat attctgctgg ggtgatgata ccaatgatcc tgaaaacaga aggaaactga 1980

-continued aggaatttgg agtaaatggt ctaatatatg ataggtattt gtttttttgta aaaaatctcc 2040 atggaattgt tcaaacagtg tagttttatc tattttaact attttaaaat tagatagttt 2100
agcctaaagt tttatcttga cactgtgacc tttcccaggt gttgagatat gtcaaaagcc 2160
acttaagaag ccctaaccca aatgtatttg ccttgaagtg agggtacttg cctgtctcac 2220
tcctgtctgt caaaactttt tctgcagttg tcttagttac attctattgc tgtgaagaag 2280
tactgtgatc aaggtgaatt gtttgcagtt ttggagggtg agcccatggc tgtcatggtg 2340
gggagtgtgg cagaaggcag gcatggcact ggagtagtta gtagctgtca gcttacttct 2400
gatccacaag caggagtcag agacacaggc agaaacagat tgtccctggt gtggactttt 2460
gtaacctcaa agtttactgc ctcataacaa acacacgagg ccatacatac ctcctaatct 2520
ttcccaaata gtccaactgg ggaccatact tcctcattca agggtctaca gtgatctctt 2580
cctgtgtggg ggtccttatc ttcactcata tccaactcag gacacttccc tgactttaaa 2640
acttttacgt cccttctctt gatttcagcc taaatggcca ctctgcttat tttgctttct 2700
caggccgaat ccttgaagtc ttccatggca gtgttcttga acctcttctt cattcctatt 2760
ttcccctggg atcttaactc acacaacatt cctcaatggg ctctttcttt ctgcttcaga 2820
gagtgactcc cgtacactga aatgtcactt gcacaaggac tacactattt aaaatggtag 2880
cttctgttca tagggtgctt cttaactttg cttgagataa tttatcacgg acaaacacag 2940
atatatgtaa cattgtattg tgtgtctttt ccttcctggc ctccccgttt cctaatgcat 3000
acacagagtg tgggctgcac aagaaccagg acactttcct ttttttgttt actatcgtca 3060
aaggctaaga caataatatg tagactgtgg gatcagatat ttgttgactg gatacagctt 3120
cctaggaatt ggtatgtaag atgtaagttt aatagctgct gatgttcaga aagttgcttt 3180
agtgtaaaga agctttaggt tgtaaaaaaa cgactcgatg gaggaagtac aaagttttga 3240
ccagaccttg agaaaaaaaa ccaaaataag ctttccttag atttaattcc tactactctt 3300
tatcctactg agttgtacca ttctttttaa taaagacttt actcccaaaa aaaaaaaaaa 3360
aaaaaaaaaa agggcggccg c 3381

<210> SEQ ID NO 40
<211> LENGTH: 1596
<212> TYPE: DNA
<213> ORGANISM: Rattus norvegicus

<400> SEQUENCE: 40
gcggccgccc tttttttttt tttttttttt tttttttttt tttttttttt tttttttttt 60
tttttttttt ttttttacta aaaacctttg accagtttta tttaacaagt gttgtacaaa 120
gagatttctg taccgaaatg tttaccacag gcaccatact agaaacacta gaaacattta 180
gaaatctttg aatggagaaa gcatacatgt ttagtcagta aacatgctgc aggtgtgggg 240
aaacacacca tgttaagtga aaaggtgtga caaaaccatc tgatacaatt taacatatat 300
atgtatgtat aaaaaacatc tatgtccatg catctcacca gccagccagc cccatcacca 360
ctggtggatc aggttgctgc tttccctatt gctactgcta tctagaatct gaagttgtct 420
aaaattaaag ttgcttacaa acaggtatta gttgtttcgt tcatgcccag gatgagcttc 480
ctgaccccca cgatcctgct gctggcgctg gtcgccgcca cccaggccga gcccctgcac 540
ttcaaggact gcggttctaa ggtgggagtt ataaaggaag tgaatgtgag cccatgccct 600
acccagccct gtcagctaca caaaggccag tcctacagtg tcaacgtcac ctttactagc 660
ggcactcagt cccagaacag cacggccttg gtccacggca tcttggcagg ggtcccagtc 720

-continued

```
tacttcccta ttcctgagcc tgacggttgt aaatgtggaa tcaactgccc catccagaaa    780
gacaaggtct acagctacct gaataagctg ccggtgaaga gcgaatatcc ctctctaaaa    840
ctggtggtgg aatggaaact tcaagatgac aaaaaggata acctcttctg ctgggagatc    900
ccagtagaga tcaaaggcta ggctgcttgg tgccctgtgt ctgtgcaggg tgagaggcca    960
tgggcggagg gaggggaagg aagagaaatc agacctgaaa ttgagtcggt gccataagac   1020
gaacagaact tcaagaatgc tgttttatgc ctttcagcct ccaaaaacat acctgcagcc   1080
ctactactct tgagagccag agccatggcc ccctgagata gcctttgtgg aggcttcggg   1140
agggaaaggg gagactggag agattagatt agtgtccatg gctgtttgct gttggattac   1200
gtcggcaggt ccaggcaaga tgaggcaggg atgcttgagg atgtcagata acctgtcaat   1260
ccactgtgaa ggatggcttc ccagaatctt ctggctggcc gggagtatta cctcttctgt   1320
atctaagtgc ctcctgagtc ccaagcaccc tgcttatcga tccgatgagt ctccatggta   1380
ccctctgccc aacgcttcaa cagcagtgac taactctcca tggtccagag acggcctgag   1440
ggaaggtctg cgcagaaact tagctctgac tggctgctgc tttgcggtta gctcttgttc   1500
tttggtagtt ttcattaaag ccaatacttg gttgcaaaaa aaaaaaaaaa aaaaaaaaaa   1560
aaaaaaaccc acgcgtccgc ggacgcgtgg gtcgac                             1596
```

<210> SEQ ID NO 41
<211> LENGTH: 3934
<212> TYPE: DNA
<213> ORGANISM: Rattus norvegicus

<400> SEQUENCE: 41

```
cggacgcgtg ggcggacgcg tgggctcaga aagccttaga cacgcagcgt gtggcagaac     60
taacctggcg tgtgagggtt aattctgctc agtgcctcca cccaagggac atggcccttc    120
cctgagggaa tatacacggt agtgggtggt gtctacagga tgctcacgag gtgggactgt    180
ccccacagct ccactcgggt gcctatgtgt cttgtgtgct ggcatcggga gtgtgtgaga    240
gtcgaatttc tcaaataggc tcaacacctt ccctgggctt ctttttgtaa attgttctaa    300
atttctgtgt agatcaagga agccttgatg atttccggtg catatattaa cagctatata    360
attaaaccat gttacataag gtgcctcatg tgggctgaca ggctgcgtga ccaggccaga    420
agagctcaaa gggctccctg gctcttaaca ccactctacc cagactgctt tctgcttgtc    480
tgcccttttt tttttttttt tgtctgtttt gtttgttttt tggtgttttt tgttttttaa    540
actcttaaca gccagctgtg aggaaagggc tctgatttgc tagttcggtg tggcaattag    600
cacctggcta gggagaacca gtggttctct gtgtctttgg gacgcacgtc ttatttccag    660
ttggataaaa ggagcctttg cctcttgtag tgtccccatg aggttgaagg gcctcgtgga    720
gacaaaggta cccatgcttt cagcagggaa tgctcatgtc acatcctcag gtacaagtcc    780
aagccaacct gtacgtggtg agcacaggcg tgccattatg ggacctaaac ctggccagat    840
ggagcaaggg cacgcgagac aaaaggcgta agggaaaaca gaggcaacag cgcccacccct    900
gctggctcta gcccttgatc ccctctgctg gctgaccttg ggcaaatgac tcaacttctc    960
tgatctttga caatcacata aaataatggg tgtactcaag gttggccgtg aatacaagaa   1020
atcaggcaga agggcctctg ctccaggcag gtgctcagca aactactaga aagtgtcact   1080
ggtgtgtcca ccattaagtt tcaaaaaaga agtcatctga ggcctggctg gattcctgca   1140
ttccagctca ggtatattgt gttttctaga acagagattc taggactttc taagaactca   1200
```

-continued

```
gtgctttgca ggactcaggc attagctctg cccgcaatcc atgagggaaa agctgggtca   1260
ggcaaggcag atctccaggt aaggccaggg cccggtcctg gagaaggact tcacttcaga   1320
ggttacttca tagctagact tcagtgacat tgttgcaagg cagtccctcg aggggttaac   1380
acagctgcat cccctgagtt acagctccag tgttcgtaaa ggcttcacct cagcctgagt   1440
ggctggccac tgtgtggaaa ctactgggct tgttccgtac tctgtggctg agctcgggag   1500
acattgcaca ctcattctcg ggaatatgac tgcctcctat tctgctgagg agtgtgtcgt   1560
acgtcgccat ctctggactc acaatctgaa tgcaatcttt agaagatgta tgtagaatct   1620
ttaatacaag acgggagaca gaagcccaga aggatccaaa cgattaaaaa gaacaacaca   1680
gaaagaaaag gagtgaagtc ccccaaggtg tgtctaggag gagtgtgccc gaggtctgcc   1740
tccttggttt ccttgccgct gctgtccctg taggctgcgc gacctctcga gctgattggg   1800
cgcgcttcat ttttaatttc aaacttagtg tctaaagagc catcaattca ggggttcaaa   1860
agccttgtcg tgcccgcatt cacacactcc cgtgtgttgc tagtgtcttt tggccacaga   1920
ggcaacagtg tactggcagg gtgctttccc tgtgcctggg gcagctctta cactcatcgg   1980
caccgaagcc actttcttga acaccctgtg gacagtggtc ccagtcccaa cttacactgt   2040
cctcaatctc ataactgaga aaataagaaa cagcttgttt ggagcaaaat aacaaagcta   2100
tagcgttctc cctgcaaagg caatgctgtg ggcgccttag acggactcac gccctgtggc   2160
tcagggtcaa ggggctttgc cttaaactac aaactccagt cagggctttc tgaaggaggg   2220
tctgagagat cgaccgacta taattctgtg tcctgggata ccacttccgg cccgaacggc   2280
ttgtgattgg acaaccacag aaccagcgct gtggagggaa agtgtcatcc tgcagccacg   2340
caggctcagt gcctaactcc tgtcttttcc ttttcccagg gaggaagaga cagccgctct   2400
ggatctccca tggcaagacg ctgagagcct ccctgctcag ccttcccgaa tcctgccctc   2460
ggcttcttaa tataactgcc ttaaacgttt aattctactt gcaccaaata gctagttaga   2520
gcagaccctc tcttaatccc gtggggctgt gaacgcggcg gggccaggcc cacggcaccc   2580
tgactggcta aaactgtttg tcccttttta tttgaagatt gagtttcctc ggggtcttct   2640
ctgccccgac ttgctccccg tgtaccttgg tcgactccgg aggttcaggt gcacggacac   2700
cctttcaagt tcacccctac tccatcctca gactttcttt tcacggcgag gcgcacccct   2760
ccagcttccg tgggcactgc ggatagacag gcacaccgcc aaggagccag agagcatggc   2820
gcaggggact gtgtggtcca ggcttccttt gttttctttc ccctaaagag ctttgttttt   2880
cctaacagga tcagacagtc ttggagtggc ttacacaacg ggggcttgtg gtatgtgagc   2940
acaggctggg cagctgtgag agtccagagt ggggtggccc tggggacgct tccaggccag   3000
cggttccctg caccccacca gctgatttcg agcgtggcag agggaaggaa aggggcgagc   3060
gggctgggca atggacccga caggaaacgg ggacttaggg gaacacgctg gagatgccat   3120
gtgtggctgc cgaaggtcac catctctcct cagtggctcc ccagagcagg tgcttttaag   3180
aaccctgttt cctctcagag cccagggaga gtccaaggac atggcgcatc aggaagtggg   3240
actgcaggag ttctctggtg gcctcgtgct gtccctctgg ccacttctca ctttagggtg   3300
gtcagcggca gctcgccatg gcagtgccca ttggtgcaca ctaacctcag tggaaaagta   3360
accattccct gcctcttaga aagaactcat tcttagtttt aggagggttc ctgtcgctga   3420
atcaagtcgc tgccctggat gcagggctgg cctgggcgac cctccaggga tgaggagctc   3480
agaattccag tcttctaatg tccacggaca cctccccatc cctctaacgt actgactatg   3540
tcttttgatt tagcatgtct tctatagacc ttccaaagag acccacactg gcactgtcac   3600
```

```
cccctaggag ggaaggtgat ggttgatgta gcccgacgcg catcttgtta atccgttcta   3660

attccgagga gagtgtgggt ttaagataac acctattaat gcattgccac aataatgtgg   3720

gggtaagaga aacgcaggga cgaaacttcc agaaacaaac cctccagatc gttccacagg   3780

agtgttcgcc ctccggtgtg actgaacgac cgaccttgcc catggcttca tccagacagc   3840

acagctgcag tatggctgga cagaagcacc tactgttctt ggatattgaa ataaaataat   3900

aaacttgcaa aaaaaaaaaa aaaagggcgg ccgc                               3934
```

```
<210> SEQ ID NO 42
<211> LENGTH: 1788
<212> TYPE: DNA
<213> ORGANISM: Rattus norvegicus

<400> SEQUENCE: 42

cggacgcgtg ggtcctggac aaggcaacag gtgaagggct gatccgggcc aaggagcctg     60

tggactgcga ggcccagaag gagcacacct ttaccatcca ggcttatgac tgtggagagg    120

ggcccgatgg tgccaatacc aagaagtctc acaaggcgac cgtgcatgtt cgggtcaacg    180

atgtgaatga gtttgcccca gtctttgtgg agcgtctcta ccgtgctgca gtgactgagg    240

ggaagctgta tgatcgcatc ttacgtgtgg aagccattga tggtgactgc tcccctcagt    300

acagccagat ctgctactat gagatcctta cacccaacac ccctttcctc attgacaatg    360

atggcaacat tgagaacaca gagaagttac agtacagtgg tgagaagctc tataagttca    420

cagtgacagc atatgactgt gggaagaagc gagcagcaga tgatgctgag gtggaaatcc    480

aggtgaagcc cacctgcaaa cccagctggc aaggctggaa caaaaggcat gaaggtgcac    540

gtgaacccct cgcagtccct gctcaccttg gagggggatg atgtggagac cttcaaccat    600

gccctgcagc acgtggctta catgaacact ctgcgctttg ccacgcccgg cgtcaggccc    660

ctgcgcctca ccaccgctgt caagtgcttt agtgaagagt cctgtgtctc catccctgaa    720

gtggagggct atgtggtggt tcttcagccc gatgcccccc agatccttct gagtggcaca    780

gctcattttg cccgcccagc tgtggacttt gagggacccg agggagtccc cttgttccct    840

gatcttcaga tcacctgctc catttctcac caggtggagg ccaaagcaga tgagagttgg    900

cagggcacag tgacagacac acggatgtca gatgagattg tacacaactt ggacggctgt    960

gagatttctc tggtggggga tgacctagac cctgaacgcg agagcctgct cttggacatg   1020

gcttccctgc agcagcgagg cctggagctc accaacacat ctgcctacct caccattgct   1080

ggggtggaga ccatcactgt gtatgaagag atcctgaggc aggttcatta tcagcttcgg   1140

cacggagcag ccctgtatgc caggaaattc cgtctctcct gttcggagat gaatggccga   1200

tactccagta acgaattcat tgtggaggtc aacgtcctgc acagcatgaa ccgggtggcc   1260

catcccagcc acgtgctcag ttcacagcag ttcctgcacc ggggtcacca gcctcctcct   1320

gagatggctg gacacagcct ggccagctcc caccggaact ccatggtccc cagtgctgcg   1380

actctcatca ttgtggtatg cgtgggcttt ctggtgctta tggtcatcct cggcctcgtg   1440

cggatccact cccttcatcg ccgtgtctca ggaactggtg gaccctcagg ggcttccgct   1500

gacccgaaag accctgacct cttctgggat gactctgctc tcaccattat cgtgaatccc   1560

atggagtcct accagaacca gcagactggt gtggcagggg ttgctggtgg ccagcaagag   1620

gaagaggaca gcagtgattc cgaagcagct gactccccca gcagcgatga aagacgcatc   1680

attgagagcc ccccacaccg ctattgaggc tccagccctg ccaaaagaga gagaggcctg   1740
```

```
ccctggggag acaggcaccc aggaaaaaaa aaaaaaaagg gcggccgc              1788


<210> SEQ ID NO 43
<211> LENGTH: 1403
<212> TYPE: DNA
<213> ORGANISM: Rattus norvegicus

<400> SEQUENCE: 43

gtcgacccac gcgtccgagc ggttcttggg ggcgcagggg gcgcgtcgcc ctctgccccc    60

gccggcaccc tggccatgac aggcaagtcg gtgaaggacg tggatcggta ccaggcggtc   120

ctggccaacc tgctgctgga ggaagataac aagttctgtg ctgactgcca gtccaaaggg   180

ccgagatggg cctcctggaa catcggcgtg tttatctgca ttcggtgtgc tggaatccac   240

aggaatctgg gggtgcatat atccagggta aaatcagtga acctcgacca gtggactcaa   300

gaacagattc agtgcatgca agagatgggg aatggaaaag caaaccgact ctatgaagcc   360

taccttcctg agacctttcg gcgacctcag atagacccag ctgttgaagg atttattcga   420

gataaatatg agaagaagaa atatatggac cgaagtctgg acatcaatgt ccttaggaaa   480

gagaaggatg ataagtggaa acgaggaagt gagcctgctc cagagaaaaa gatggaaccc   540

gttgtctttg agaaagtaaa aatgccacag aaaaaagaag acgcacagct acctcggaaa   600

agctccccga aatccgcagc ccctgtcatg gacttgttgg gccttgatgc tcctgtggcc   660

tgctctattg caaacagtaa gaccagcaat gccctagaaa aggatctaga tcttttggcc   720

tctgttccat ccccttcttc agtttccaga aaggctgtag gttccatgcc aactgccggg   780

agtgctggtt ctgtccctga aaacctgaac ctatttccag agccggggag caagtcagaa   840

gaaacaggca agaaacagct ctccaaggac tccatcctgt cactgtatgg atcccagacg   900

cctcaaatgc ctgcccaagc aatgttcatg gctcctgctc agatggcata tcccacagcg   960

taccccagct tccctggggt tacaccacct aacagcatca tggggagcat gatgccccca  1020

ccagtcggca tggtagctca cccaggagcc tctggaatgg tcacccccat ggccatgccc  1080

gcaggctata tgggggcat gcaggcttcc atggcgggca tgccgagcgg gatgatgacc  1140

actcagcagg ccggctacat ggcgagcatg gcagccatgc cccagactgt gtacggcgtt  1200

cagccagctc agcaactgca gtggaacctc actcagatga cccagcagat ggctgggatg  1260

aacttctacg gagccaacgg catgatgagc tatggacagt caatgggcgg tggaaatggc  1320

caggcagcca atcagactct cagtcctcag atgtggaaat aaaagcaaag cacctgtaaa  1380

aaaaaaaaaa aaagggcggc cgc                                           1403


<210> SEQ ID NO 44
<211> LENGTH: 1298
<212> TYPE: DNA
<213> ORGANISM: RAttus norvegicus

<400> SEQUENCE: 44

atcattttga ccagcaggtc tgcagacccc tcccccattg ctgaaagtcc tcccgtgctt    60

ggtgtgtggg accacaggct ccgccctccc tgcccatcac gcttgcagtt ttgcttagga   120

gctggccctt cctcccagtg caggggcccc acagcacctc agaccccaag tgtgtctgga   180

gtcccctgtc agccagggag aggacaccag cacctgggac ctccagagaa gccgcagtga   240

gcggacttgt cgacagaggg taaaaaatta ctcccacgca gtcatcattt ttcttcattt   300

ttaaaagttt ttattttat tttccaatat agtgcatgta taaagtggga gagcggggag   360

gggggttaa tatgtagatg accaactgac tttttaatat tttgtaaata aattgggatt    420
```

-continued

```
ctttgtgtcc tttgtgctag tgtagtccag gacaggaatg tgaagtcaga acatggggcc    480

aggaagagct cttcctccct tttccctccc aagaaaccag gttggaaagg tccaagtcac    540

agtggcccat gctggggttt ctgtacagcc atgtggccag ggccataggt tttgagtgct    600

gcctggggga gccagaccca cgcgctccca ccacattaga ggctgggaac agccaggatg    660

gtgccaaagc ccctggcctt ccttgtacac gcctgtgacc agcctcgtgg cttctgctaa    720

ttagcgtgtc tccctgttgg tgaaaacctg tagctgggaa ctgatggcaa agatggacaa    780

cagttctgag cagtctgcac tacagcaccc aagaggagaa cctgaggccc gaaaacaaac    840

tgctacaatg tttcaaaacg agctgcgctc tcctccccag agaccccacg ggatgccccc    900

gggatgcccc cttgctgtcg ggttttggct aagacctaag acccagcaga ggagagccag    960

ccggcttggg gggtgggggt gggggaggag acagcagcta aaacccacac agcacggctt   1020

gtcattcaca gtcacagttt agactcctcc agctggggaa tccggtcctc gctgctagtc   1080

ctaaggatgt tgacgctgtg ctgcctgtgg ccaccctccc gtgtcctgtt ccctgtagtc   1140

gctttataga tggaaacagg ctatgaagag ggacactgtc gtgtgttggt agccgcaggc   1200

tccccttaag atgtgtatat tgaccccagg tcaggaagtg tatgcgttat aataaagttc   1260

tggttctaac tccaaaaaaa aaaaaaaagg gcggccgc                           1298
```

<210> SEQ ID NO 45
<211> LENGTH: 4015
<212> TYPE: DNA
<213> ORGANISM: Rattus norvegicus

<400> SEQUENCE: 45

```
gcggccgcag cgccgcctgc tcagcgcccg ggtcagtagg agccagtcct tcgcaggcgt     60

cctcggcagc caagagcgcg ggcccaggaa cttcacggtc ttcagcccac cagggcctca    120

acggaagcct ttagtgctct cccgagtgtc aaggatgttt tctgtggccc acccagcccc    180

caaggtgcca cagcctgaga ggctggacct ggtatatgct gctcttaagc ggggactgac    240

ggcctacttg gaagtgcatc agcaagagca ggagaagctc cagcgccaga taaaggagtc    300

caagaggaat tcccgcctag gattcctgta tgacttggat aagcaagtca agtccattga    360

acgttttctt cgacgactgg aattccatgc cagtaagatt gatgagctgt atgaagcata    420

ctgtgtccag cggcgtctca gggatggtgc ctacaacatg gttcgtgctt atagcactgg    480

gtccccaggg agtcgagagg cccgagacag cctggctgag gccacccgag gccatcgaga    540

gtatacagag agcatgtgtc ttctggagaa tgagctggag gcacagctgg gcgagtttca    600

tctccggatg aaagggttgg ctgggttcgc caggctgtgt gtgggcgatc aatatgagat    660

ctgcatgaaa tacggccgcc agcgctggaa gttacgaggc cgaatagaga gtagtggaaa    720

gcaagtgtgg gacagtgaag agactgtctt tcttcctctg ctcacagaat tcctgtctat    780

caaggtgaca gaattaaaag gactggctaa ccatgtagtc gtgggcagtg tctcctgtga    840

gaccaaggac ctgtttgccg ccctgcccca ggttgtggct gtggatatca atgatctcgg    900

cactatcaag ctcagcctag aagtcatatg gagtcccttt gacaaggatg accagccttc    960

agctgcttct acagtcaaca aagcttccac agtcaccaag cggttttcca catatagcca   1020

gagtccacca gatacaccct cacttcggga gcaggctttt tataacatgt tacggcggca   1080

ggaggagtta gagaatggga cagcatggtc cctgtcatcc gaatcttctg atgattcatc   1140

cagcccgcag ctctcaggca ctgctcgata ctcatcaact cccaagcctc tggtgcaaca   1200
```

-continued

```
gcctgagccc ctgcctgtcc aagttacctt ccgaaggcca gagagcctct cctctggttc   1260
catggatgaa gagccacctc tgaccccagc cctggtcaat gggcatgccc cttacagtcg   1320
gactctcagc cacatcagtg aagccagcgt ggatgctgcc ttgactgagg ccatggaagc   1380
tgtggactta aaatgcccag ccccagggcc tagcccactt gtatatccag agtccaccca   1440
tgtggagcat gtcagtagtg ttcctcctgt tgcagacaat ggccgttctg ccacaagtcc   1500
tgccctaagt acagctggcc ctgcccccac atttatagac cctgcctcat ctacacagct   1560
agacttagtt cacaaagcca cagactctgg ctcttctgag ttgccaagca tcacacatac   1620
tatggcaagc tctacatata gtgctgtgag cccgatcaac agtgttccag gcctaacttc   1680
caccactgta ggttctaccc acaaacccat gccctctccc ctcacctcta caggctctat   1740
ccccagtgtc acagactcaa tccagactac cacaagccca actcacacca ccccaagccc   1800
tacccacact actgtaagcc ctacacatag cactccaagt cccacccata ccactgtaag   1860
tcccagcaat gctgctctaa gccccagcaa tgctactcca agcctcagcc acagtaccac   1920
tagtcctact caaaaagcca cgatgtcaac tcataccact agtgctgtgg gcccagtcca   1980
gaccactaca agtcccattt ctacaactgt aagcccctcc ccttctgtag acactgctat   2040
aatctccagt tcctctgcag taccctctgt cccaggccct gaagcacggc cttgtagtca   2100
cccaacctct actccctaca ctaaagcaga ccccacagca gcctgcacct cttctccgag   2160
tcttgcttcc tctggtccaa aacccctcac aagccctgcc ccagactcgc tagaacaaat   2220
ccttaagagc ccaagttcct ctccgtcatc catagtccct gaaccccaac gttcagaact   2280
tagcctggcc ttggttgctc aagccccagt ccctgaagcc actggaggag ctggggacag   2340
aaggctcgaa gaggctctca ggaccctaat ggctgccctg gatgattatc gaggtcagtt   2400
ccctgagctc cagggcctgg agcaggaggt gactcggctg gagagtctgc tcatgcagag   2460
gcaaggcctg actcgaagcc gggcctccag tcttagcatc accgtggagc atgccctgga   2520
gagcttcagc ttcctcaatg atgatgaaga tgaagacaat gacagtcctg gggacaggcc   2580
cacaagcagc ccagaggttg tggctgagga aagactagac tcatcaaatg cccagtgtct   2640
aagcacaggg tgttcagccc tggatgctac cttggtccag cacctgtacc actgcagctg   2700
cctcctgctg aaactgggca catttgggcc cctgcgctgc caggaggcat gggccctgga   2760
acggctgctg agggaagctc gagtgctcca ggaagtgtgt gagcacagca agctgtgggg   2820
aaatgctgtc acatctgccc aggaagtggt acagttctct gcctctcggc ccggtttcct   2880
gacctttttgg gaccagtgta cagagggact caacccccttc ctctgccctg tggagcaggt   2940
gctcctcact ttctgcagcc agtatggtgc ccgtctttcc ctgcgccagc caggcttagc   3000
cgaggctgtg tgtgtgaagt tcctggaaga tgctctgggg cagaagctgc ccaggaggcc   3060
ccactcaggc cccggggagc agctcaccat cttccaattc tggagttatg tagaagtctt   3120
ggacagcccc tccatggaag cctatgtgac agagaccgca gaggaggtgt tactggtaca   3180
gaacctgaac tccgatgacc aggcagttgt gctgaaggct ctaaggttag ccccagaggg   3240
gcgcctgagg aaggatgggc ttcgggctct tagctccctg ctggtccacg gcaatagcaa   3300
agtcatggct gctgtcagca cccagcttcg gagcctgtca cttggtcctg tcttccggga   3360
aagggctctt ctgtgcttcc tggaccagct tgaggatgag gatgtgcaga ctcgagtggc   3420
cgggtgcctg gctttgggct gtatcaaggc tcctgagggc attgagcccc tggtgtactt   3480
gtgtcaaaca gacacagaag ctgtgaggga agctgcccgg cagagcctcc agcagtgtgg   3540
ggaagaagga cagtctgctc atcgccagct agaggagtcc ctggatgccc tgccctgcct   3600
```

-continued

```
ctttgggccc agcagcatgg ccagcacagc attctgaact ctgattgcca gctcccagtg   3660

ctccttccct cattttcagg gctcactagg cactggcagg gagggtgagg gctggttcca   3720

gtcacctctc cccacaaatt cctatcaatg aaaatctaat atattcttct gttatcactg   3780

gggttggtag aatgcctgaa atgaagtgcc tcccagccgg ttctgcatag ccacaaacag   3840

tgtcaggggc ctgaccgttt ggtcagcttg ctctgcctca ccacatccct tggttttgta   3900

ttttatttac agagttttac agataataaa aaagcaaaat gtgaaaaaaa aaaaaaaaaa   3960

aaaaaaaaaa aaagttctag atcgcgatct agaactagcg gacgcgtggg tcgac        4015
```

```
<210> SEQ ID NO 46
<211> LENGTH: 1837
<212> TYPE: DNA
<213> ORGANISM: Rattus norvegicus

<400> SEQUENCE: 46

gtcgacccac gcgtccggaa aaacatttcc ttctcaaggg cagcattcca gcacctgctt     60

gcatctctca gccatctttc cttgatcctg tctgggaagt gtatctcagt gactccacaa    120

tttctctctt tgtccttttg ttttaaaagt aacactttct ataaaatagc taaatgtcct    180

tgaaggggtt taatcgtgca aaaagtaagc aatataatat ataatgtacg caacctttaa    240

tgacagtatc tattttctta ggggtattat tcagatacct tcccagatct ggatttaact    300

ttggtaattg ttatctatat agaaaatcaa caatatcaaa taaatatttc agtgttctgg    360

cataaagtcc tcgtgagtaa gaactaatga ttttggaatt tgctttgtgt ctattgttat    420

gtccctcatt tcatttctga tttttaattc atgtattgtg tctcttgtgc attgttagtt    480

tgaggaaggg gttgtctctc ttgtggatct tctccagaag aagaagaaga agaagaagaa    540

gaagaagaag aagaaaaaga agaagaagaa gaagaagaag aagaagaaga agaagaagta    600

gaaaagacag ctcttgcttt ccttgacttt gtatttttct ctttgtttct gaaggcttga    660

tttcaaccct gagttcattt cctttcatca gatcctacca gactctctat gggatgaggc    720

tttgcctcac tttgggcagg ctggatgatg acattcagtt gacaatgtgg acatctcaag    780

acagtcactg gacaatggct gacacacttg tctgaagact ggaaatgttt ctctatcttg    840

gagaggaaag aaggaccctc caactacact gaactctaag gaaggttatt cagatctcaa    900

gactggttaa ccccccaaaa ctgaccctgc taccagttga ctgtgattat aaagaagcca    960

acagccaaca gctgcacagc agagagatgg gggagatgct gggagagaaa catcatcccc   1020

tgaaactgcc ctaagcgaga agcaggctaa gaaggaaaaa gagaggctga tagaagagct   1080

gcagctcatt accgaggaga gaaatgacct gagagatcgc ctgaggtttc tgacagagag   1140

atccatgaac aacaggccac acttcaggcc aaatccatat tatgaagacc tggagagaat   1200

ggaggaggca gtcatgtcaa ttctgcacaa cttagagatg gagaacactg agatccatga   1260

gaacaaccat aagctgaaga aggagatgac cttctctaga aacctgctca gccagctcct   1320

gatggagaac acttttagga agaagttggt cccactgaag caggagagca aggaggtaca   1380

tcttgattgg gtaccgatcc agaaatattt ggttgaattc aacaagatcg ataaagacca   1440

gcaacctcca gaccccgcat catctggtct caaaaagtac aagagagctg aaattggaca   1500

cacactagta agagagcttc ctgaagaata agttgctttc tcaggagtcc ctgatgacca   1560

acatcctgaa tgaaaacacc acttgagaga caacttgggg gactgccttt cattatgtgt   1620

gctagaggag aaatagcaat acatctgtgc ttctaaatat tcctaaatgt tcttgttact   1680
```

attttttcact tttcaaatac tttaaaacat ttatatttat tcattttcat cctctgtctt 1740
tgtaaaacgt atttcttatg aataaaaatt gaattctatc tcctgaaaaa aaaaaaaaaa 1800
aaaaaaaaaa aaaaaaaaaa aaaaaaaaaa aaaaaaa 1837

<210> SEQ ID NO 47
<211> LENGTH: 1042
<212> TYPE: DNA
<213> ORGANISM: Rattus norvegicus

<400> SEQUENCE: 47
gtcgacccac gcgtccggcg gttacaagct aagacatgtt ttcccatctt cgcaagcgtt 60
ttgggagggg gaacgtcgat tctggagaga ctagagtgaa ggagtctggc ctttcgtctc 120
aaagtaatga tggagaaaga cagcacttct ggggaatgtg gaacgttggg agagaaacat 180
catcccctgg cactgaccta agcaagaatc aggccatgaa ggaaaaggag aggctgatta 240
aagagctgca gctcattacc gaggagagaa atgacctgag agatcgcctg aagtttctaa 300
cagagagatc catgaagaac aggccacact tcaggccaaa tccatattat gaagacctgg 360
agagaatgga ggaggcggtc atatcaattc tgcacaactt agagatggag aacactgagg 420
tccatgagaa caaccataag ctgaagaagg agatgacctt ctctagaaac ctgctcagcc 480
agcccctgat ggagaacaca tgtaggaaga agttgttccc cctgaagcag gagagcaagg 540
aggtacatct tgattgtgca ctgaaccaga aatatttggt tgacttcaac cagaaagata 600
aagaccatca acggccagaa ccagcattat caggtctcag aaagtgcaag agagctggaa 660
ttggacacac cccagtaaga gagcttcctg aagaataagt tgctttctca ggagtccctg 720
atgacaaata tcctgaatga aaacagcact tgagagacaa cttgggggac cgcctttcat 780
tatgtgtgct agaggagaaa cagcaatatg tctgtgcttc taaatgttcg ttaagaatat 840
gcttttagaa atatttttgt tatgatttta attgaagttt tctttttgtt gtttcatatt 900
tatatgttct tgttactatt tttactttca aatattttta aatattttta ttcattttaa 960
tcctgttttg ttgtaaaaat gtatttgtta tgaataaaaa ttgaattcta aaaaaaaaaa 1020
aaaaaaaaaa aagggcggcc gc 1042

<210> SEQ ID NO 48
<211> LENGTH: 2393
<212> TYPE: DNA
<213> ORGANISM: Rattus norvegicus

<400> SEQUENCE: 48
gtcgacccac gcgtccggtg caaacattca aaaatagtaa aacagattga tctctccctt 60
tttctaatag aaatatgaag ctgatccagt tgaattgttt gaaatcccag taaaggaatt 120
aacattcgac caactccagt tattgaagct ttctcatgtg actgcactaa aaaccaaaga 180
ccagaaacaa tgtatggctg aggaggaaaa ttcctttttct gaaaaccaac catttccttc 240
tcttaagatg gttttagagt cattgccaga aaatgtagga tttaatatag aaataaaatg 300
gatttgccaa cacagggatg gagtatggga cggcaactta tcgacatatt ttgatatgaa 360
tgcatttttg gatataattt taaaaactgt tttagaaaat tccgggaaga ggagaatagt 420
attttcttca tttgatgcag acatctgtac aatggttcgg cagaaacaaa acaaatatcc 480
catattattt ttgacccaag gaaagtctga catttaccct gaactcatgg acctcagatc 540
tcggacaaca cccattgcaa tgagctttgc acagtttgaa aatattttgg ggataaatgc 600
ccatactgaa gatctcctta gaaacccatc ctatgtccaa gaggcaaaag ataagggatt 660

```
ggtcatattc tgctggggtg atgataccaa tgatcctgaa aacagaagga aactgaagga    720

atttggagta aatggtctaa tatatgatag gatatacgat tggatgcctg aacaaccaaa    780

tatattccaa gtggagcaac tggagcgcct gaagcgagaa ttgccagagc ttaagaactg    840

tttgtgtccc actgttagcc acttcattcc tccttctttc tgtatggagt ctaaaatcca    900

tgtggatgct aacggcattg ataatgtgga gaacgcttag ttcctagtgc acagaggaca    960

ttcagaggct ctcccctgcg ctgaggttcc gtctccacca ctgaacaccg gtcgcctctt   1020

aggtttctca gtccaatgaa gcaataatga agtattttac tatcattaca gttcccgcaa   1080

gaatatcaag tacactattt atcacttgtc caggtataat taccaatcag tctctgtaca   1140

aatgttaaac actttaaatg agagatctaa gcctataatg gtgaatcttc attaaaagca   1200

taatacttgg aaattagcta tataaatatc tcatagttca ggcttttcat ttgattaggt   1260

cttaaatctt cagtgcttga gaaaaatgac tgcataatta tacctgacca tggaaataat   1320

aagtacctca agtgcatgca tttgcactgg tggctccagc tgcacaagtc tgtgtcatcc   1380

atgtacatag gtgtctttac atgggttgat agaaacatgc actaggctcc tttagtataa   1440

acctcagact gctgccattt cccacctgac ccaaaccagc ctgcagatga acctcaaaac   1500

ttgtttcata gactgttcaa agattttaaa agttccagaa tgctgcaggg taacttaatg   1560

tataaagtat ttgtaagagg tatatattgc atatatagtc gtgtagatca gaatgtgtaa   1620

atttgactcc gtgcatgctt taggtttgtt ttaagcatga ggttgtacat gtttactgtc   1680

cttgcatctg gtgctaggtg agtgagatgt taaggactga aaatattttg tcgcctaaaa   1740

agagtatgcc tatttagtgt ctcactacct agtaagcaat tgccgtgtgt gctccacagt   1800

agttaacccc catgcagaaa aataaatgtc ctgaattctc aaattgctat tctttattgt   1860

ttaatatata tcatgtatgt aatttattta ggaatgtaga aattactgta tataaatgca   1920

tgcttttagg attatactaa gatttcatta gaagcagatt gtattgataa aactgtaact   1980

tcagaatgaa tgttaaataa aatgacagat ttattttttc ctcatcttaa aatgaaattt   2040

gaagaaggta ttttgtagaa ttgttttata atcgtatctg tctgacaata gtcatttatt   2100

cattttgtat ggctggctca ccgcacgctc tgtgttcctg ctggggtagt ttgttcatgt   2160

attgacattt tgacagaagc taaaatccta agacttgaga tgacaagttg taccttttat   2220

ttttttaatt ttttgggaca acctgtgtag ccttggctgt ccaggaactc actgtgtaaa   2280

ccagctggct ttgaactccc agatcatctg cctctgcttc ctaagtggta ttaaagtcat   2340

gcgccaccaa aaaaaaaaaa aaaaaaaaaa aaaaaaaaaa aaagggcggc cgc          2393
```

<210> SEQ ID NO 49
<211> LENGTH: 3604
<212> TYPE: DNA
<213> ORGANISM: Rattus norvegicus

<400> SEQUENCE: 49

```
gcctggagga gtgagccagg cagtgagact ggctcgggcg ggccgggacg cgtcgttgca     60

gcagcggctc ccagctccca gccaggattc cgcgcgcccc ttcacgcgcc ctgctcctga    120

acttcagctc ctgcacagtc ctccccaccg caaggctcaa ggcgccgccg gcgtggaccg    180

cgcacggcct ctaggtctcc tcgccaggac agcaacctct cccctggccc tcatgggcac    240

cgtcagctcc aggcggtcct ggtggccgct gccactgctg ctgctgctgc tgctgctcct    300

gggtcccgcg ggcgcccgtg cgcaggagga cgaggacggc gactacgagg agctggtgct    360
```

-continued

```
agccttgcgt tccgaggagg acggcctggc cgaagcaccc gagcacggaa ccacagccac    420
cttccaccgc tgcgccaagg atccgtggag gttgcctggc acctacgtgg tggtgctgaa    480
ggaggagacc cacctctcgc agtcagagcg cactgcccgc cgcctgcagg cccaggctgc    540
ccgccgggga tacctcacca agatcctgca tgtcttccat ggccttcttc ctggcttcct    600
ggtgaagatg agtggcgacc tgctggagct ggccttgaag ttgccccatg tcgactacat    660
cgaggaggac tcctctgtct ttgcccagag catcccgtgg aacctggagc ggattacccc    720
tccacggtac cgggcggatg aataccagcc ccccgacgga ggcagcctgg tggaggtgta    780
tctcctagac accagcatac agagtgacca ccgggaaatc gagggcaggg tcatggtcac    840
cgacttcgag aatgtgcccg aggaggacgg gacccgcttc cacagacagg ccagcaagtg    900
tgacagtcat ggcacccacc tggcaggggt ggtcagcggc cgggatgccg gcgtggccaa    960
gggtgccagc atgcgcagcc tgcgcgtgct caactgccaa gggaagggca cggttagcgg   1020
caccctcata ggcctggagt ttattcggaa aagccagctg gtccagcctg tggggccact   1080
ggtggtgctg ctgcccctgg cgggtgggta cagccgcgtc ctcaacgccg cctgccagcg   1140
cctggcgagg gctggggtcg tgctggtcac cgctgccggc aacttccggg acgatgcctg   1200
cctctactcc ccagcctcag ctcccgaggt catcacagtt ggggccacca atgcccagga   1260
ccagccggtg accctgggga ctttggggac caactttggc cgctgtgtgg acctctttgc   1320
cccaggggag gacatcattg gtgcctccag cgactgcagc acctgctttg tgtcacagag   1380
tgggacatca caggctgctg cccacgtggc tggcattgca gccatgatgc tgtctgccga   1440
gccggagctc accctggccg agttgaggca gagactgatc cacttctctg ccaaagatgt   1500
catcaatgag gcctggttcc ctgaggacca gcgggtactg acccccaacc tggtggccgc   1560
cctgcccccc agcacccatg ggcaggttgg gcagctgttt tgcaggactg tgtggtcagc   1620
acactcgggg cctacacgga tggccacagc catcgcccgc tgcgccccag atgaggagct   1680
gctgagctgc tccagtttct ccaggagtgg gaagcggcgg ggcgagcgca tggaggccca   1740
agggggcaag ctggtctgcc gggcccacaa cgcttttggg ggtgagggtg tctacgccat   1800
tgccaggtgc tgcctgctac cccaggccaa ctgcagcgtc cacacagctc caccagctga   1860
ggccagcatg ggggacccgtg tccactgcca ccaacagggc cacgtcctca caggctgcag   1920
ctcccactgg gaggtggagg accttggcac ccacaagccg cctgtgctga ggccacgagg   1980
tcagcccaac cagtgcgtgg gccacaggga ggccagcatc cacgcttcct gctgccatgc   2040
cccaggtctg gaatgcaaag tcaaggagca tggaatcccg gcccctcagg agcaggtgac   2100
cgtggcctgc gaggagggct ggaccctgac tggctgcagt gccctccctg ggacctccca   2160
cgtcctgggg gcctacgccg tagacaacac gtgtgtagtc aggagccggg acgtcagcac   2220
tacaggcagc accagcgaag aggccgtgac agccgttgcc atctgctgcc ggagccggca   2280
cctggcgcag gcctcccagg agctccagtg acagccccat cccaggatgg gtgtctgggg   2340
agggtcaagg gctggggctg agctttaaaa tggttccgac ttgtccctct ctcagccctc   2400
catggcctgg cacgagggga tggggatgct tccgcctttc cggggctgct ggcctggccc   2460
ttgagtgggg cagcctcctt gcctggaact cactcactct gggtgcctcc tccccaggtg   2520
gaggtgccag gaagctccct ccctcactgt ggggcatttc accattcaaa caggtcgagc   2580
tgtgctcggg tgctgccagc tgctcccaat gtgccgatgt ccgtgggcag aatgactttt   2640
attgagctct tgttccgtgc caggcattca atcctcaggt ctccaccaag gaggcaggat   2700
tcttcccatg gataggggag gggcggtag gggctgcagg gacaaacatc gttgggggt   2760
```

```
gagtgtgaaa ggtgctgatg gccctcatct ccagctaact gtggagaagc ccctgggggc   2820

tccctgatta atggaggctt agctttctgg atggcatcta gccagaggct ggagacaggt   2880

gtgcccctgg tggtcacagg ctgtgccttg gtttcctgag ccacctttac tctgctctat   2940

gccaggctgt gctagcaaca cccaaaggtg gcctgcgggg agccatcacc taggactgac   3000

tcggcagtgt gcagtggtgc atgcactgtc tcagccaacc cgctccacta cccggcaggg   3060

tacacattcg cacccctact tcacagagga agaaacctgg aaccagaggg ggcgtgcctg   3120

ccaagctcac acagcaggaa ctgagccaga aacgcagatt gggctggctc tgaagccaag   3180

cctcttctta cttcacccgg ctgggctcct catttttacg ggtaacagtg aggctgggaa   3240

ggggaacaca gaccaggaag ctcggtgagt gatggcagaa cgatgcctgc aggcatggaa   3300

ctttttccgt tatcacccag gcctgattca ctggcctggc ggagatgctt ctaaggcatg   3360

gtcgggggag agggccaaca actgtccctc cttgagcacc agccccaccc aagcaagcag   3420

acatttatct tttgggtctg tcctctctgt tgccttttta cagccaactt ttctagacct   3480

gttttgcttt tgtaacttga agatatttat tctgggtttt gtagcatttt tattaatatg   3540

gtgacttttt aaaataaaaa caaacaaacg ttgtcctaaa aaaaaaaaaa aaaaaaaaaa   3600

aaaa                                                                3604
```

<210> SEQ ID NO 50
<211> LENGTH: 3583
<212> TYPE: DNA
<213> ORGANISM: Homo Sapiens

<400> SEQUENCE: 50

```
cggacgcgtg ggcgcaaggc tcaaggcgcc gccggcgtgg accgcgcacg gcctctaggt     60

ctcctcgcca ggacagcaac ctctcccctg gccctcatgg gcaccgtcag ctccaggcgg    120

tcctggtggc cgctgccact gctgctgctg ctgctgctgc tcctgggtcc cgcgggcgcc    180

cgtgcgcagg aggacgagga cggcgactac gaggagctgg tgctagcctt gcgttccgag    240

gaggacggcc tggccgaagc acccgagcac ggaaccacag ccaccttcca ccgctgcgcc    300

aaggatccgt ggaggttgcc tggcacctac gtggtggtgc tgaaggagga gacccacctc    360

tcgcagtcag agcgcactgc ccgccgcctg caggcccagg ctgcccgccg gggatacctc    420

accaagatcc tgcatgtctt ccatggcctt cttcctggct tcctggtgaa gatgagtggc    480

gacctgctgg agctggcctt gaagttgccc catgtcgact acatcgagga ggactcctct    540

gtctttgccc agagcatccc gtggaacctg gagcggatta cccctccacg gtaccgggcg    600

gatgaatacc agccccccga cggaggcagc ctggtggagg tgtatctcct agacaccagc    660

atacagagtg accaccggga aatcgagggc agggtcatgg tcaccgactt cgagaatgtg    720

cccgaggagg acgggacccg cttccacaga caggccagca agtgtgacag tcatggcacc    780

cacctggcag gggtggtcag cggccgggat gccggcgtgg ccaagggtgc cagcatgcgc    840

agcctgcgcg tgctcaactg ccaagggaag ggcacggtta gcggcaccct cataggcctg    900

gagtttattc ggaaaagcca gctggtccag cctgtggggc cactggtggt gctgctgccc    960

ctggcgggtg ggtacagccg cgtcctcaac gccgcctgcc agcgcctggc gagggttggg   1020

gtcgtgctgg tcaccgctgc cggcaacttc cgggacgatg cctgcctcta ctccccagcc   1080

tcagctcccg aggtcatcac agttggggcc accaatgccc aggaccagcc ggtgaccctg   1140

gggactttgg ggaccaactt tggccgctgt gtggacctct ttgccccagg ggaggacatc   1200
```

-continued

```
attggtgcct ccagcgactg cagcacctgc tttgtgtcac agagtgggac atcacaggct   1260
gctgcccacg tggctggcat tgcagccatg atgctgtctg ccgagccgga gctcaccctg   1320
gccgagttga ggcagagact gatccacttc tctgccaaag atgtcatcaa tgaggcctgg   1380
ttccctgagg accagcgggt actgaccccc aacctggtgg ccgccctgcc ccccagcacc   1440
catggggcag gttggcagct gttttgcagg actgtgtggt cagcacactc ggggcctaca   1500
cggatggcca cagccatcgc ccgctgcgcc ccagatgagg agctgctgag ctgctccagt   1560
ttctccagga gtgggaagcg gcggggcgag cgcatggagg cccaaggggg caagctggtc   1620
tgccgggccc acaacgcttt tgggggtgag ggtgtctacg ccattgccag gtgctgcctg   1680
ctaccccagg ccaactgcag cgtccacaca gctccaccag ctgaggccag catggggacc   1740
cgtgtccact gccaccaaca gggccacgtc ctcacaggtt tcctagctct tgcctcagac   1800
cttaaagaga gagggtctga tggggatggg cactggagac ggagcatccc agcatttcac   1860
atctgagctg gctttcctct gccccaggct gcagctccca ctgggaggtg gaggaccttg   1920
gcacccacaa gccgcctgtg ctgaggccac gaggtcagcc caaccagtgc gtgggccaca   1980
gggaggccag catccacgct tcctgctgcc atgccccagg tctggaatgc aagtcaagga   2040
gcatggaatc ccggcccctc aggagcaggt gaccgtggcc tgcgaggagg gctggaccct   2100
gactggctgc agtgccctcc ctgggacctc ccacgtcctg gggcctacg ccgtagacaa   2160
cacgtgtgta gtcaggagcc gggacgtcag cactacaggc agcaccagcg aagaggccgt   2220
gacagccgtt gccatctgct gccggagccg gcacctggcg caggcctccc aggagctcca   2280
gtgacagccc catcccagga tgggtgtctg ggagggtca agggctgggg ctgagcttta   2340
aaatggttcc gacttgtccc tctctcagcc ctccatggcc tggcacgagg ggatggggat   2400
gcttccgcct ttccggggct gctggcctgg cccttgagtg gggcagcctc cttgcctgga   2460
actcactcac tctgggtgcc tcctccccag gtggaggtgc caggaagctc cctccctcac   2520
tgtggggcat ttcaccattc aaacaggtcg agctgtgctc gggtgctgcc agctgctccc   2580
aatgtgccga tgtccgtggg cagaatgact tttattgagc tcttgttccg tgccaggcat   2640
tcaatcctca ggtctccacc aaggaggcag gattcttccc atggataggg gagggggcgg   2700
taggggctgc agggacaaac atcgttgggg ggtgagtgtg aaaggtgctg atggccctca   2760
tctccagcta actgtggaga agcccctggg ggctccctga ttaatggagg cttagctttc   2820
tggatggcat ctagccagag gctggagaca ggtgtgcccc tggtggtcac aggctgtgcc   2880
ttggtttcct gagccacctt tactctgctc tatgccaggc tgtgctagca acacccaaag   2940
gtggcctgcg gggagccatc acctaggact gactcggcag tgtgcagtgg tgcatgcact   3000
gtctcagcca acccgctcca ctacccggca gggtacacat tcgcacccct acttcacaga   3060
ggaagaaacc tggaaccaga gggggcgtgc ctgccaagct cacacagcag gaactgagcc   3120
agaaacgcag attgggctgg ctctgaagcc aagcctcttc ttacttcacc cggctgggct   3180
cctcattttt acgggtaaca gtgaggctgg gaaggggaac acagaccagg aagctcggtg   3240
agtgatggca gaacgatgcc tgcaggcatg gaacttttc cgttatcacc caggcctgat   3300
tcactggcct ggcggagatg cttctaaggc atggtcgggg gagagggcca acaactgtcc   3360
ctccttgagc accagcccca cccaagcaag cagacattta tcttttgggt ctgtcctctc   3420
tgttgccttt ttacagccaa cttttctaga cctgttttgc ttttgtaact tgaagatatt   3480
tattctgggt tttgtagcat ttttattaat atggtgactt tttaaaataa aaacaaacaa   3540
acgttgtcct aaaaaaaaaa aaaaaaaaaa aaagggcggc cgc                     3583
```

<210> SEQ ID NO 51
<211> LENGTH: 5145
<212> TYPE: DNA
<213> ORGANISM: Homo Sapiens

<400> SEQUENCE: 51

```
ggcggcggga gagctgctgg ctcgcccgga tcccgggagc tgcctggagg cgggcccggc     60
ccggggaagg tgagcggctg cgggacccag cccctcgccg ggagcgggca ccatggtgct    120
gtcggtgcct gtgatcgcgc tgggcgccac gctgggcaca gccaccagca tcctcgcgtt    180
gtgcggggtc acctgcctgt gtcggcacat gcaccccaag aaggggctgc tgccgcggga    240
ccaggacccc gacctggaga aggcgaagcc cagcttgctc gggtctgcac aacagttcaa    300
tgttaaaaag tccacggaac ctgttcagcc ccgtgccctc ctcaagttcc cagacatcta    360
tggacccagg ccagctgtga cggctccaga ggtcatcaac tatgcagact attcactgag    420
gtctacggag gagcccactg cacctgccag cccccaaccc ccgaatgaca gtcgcctcaa    480
gaggcaggtc acagaggagc tgttcatcct ccctcagaat ggtgtggtgg aggatgtctg    540
tgtcatggag acctggaacc cagagaaggc tgccagttgg aaccaggccc ccaaactcca    600
ctactgcctg gactatgact gtcagaaggc agaattgttt gtgactcgcc tggaagctgt    660
gaccagcaac cacgacggag gctgtgactg ctacgtccaa gggagtgtgg ccaataggac    720
cggctctgtg gaggctcaga cagccctaaa gaagcggcag ctgcacacca cctgggagga    780
gggcctggtg ctcccccctgg cggaggagga gctccccaca gccaccctga cgctgacctt    840
gaggacctgc gaccgcttct cccgtcacag cgtggccggg gagctccgcc tgggcctgga    900
cgggacatct gtgcctctag ggctgcccca gtggggcgag ctgaagactt cagcgaagga    960
gccatctgca ggagctggag aggtcctact atccatcagc tacctcccgg ctgccaaccg   1020
cctcctggtg gtgctgatta aagccaagaa cctccactct aaccagtcca aggagctcct   1080
ggggaaggat gtctctgtca aggtgacctt gaagcaccag gctcggaagc tgaagaagaa   1140
gcagactaaa cgagctaagc acaagatcaa ccccgtgtgg aacgagatga tcatgtttga   1200
gctgcctgac gacctgctgc aggcctccag tgtggagctg gaagtgctgg gccaggacga   1260
ttcagggcag agctgtgcgc ttggccactg cagcctgggc ctgcacacct cgggctctga   1320
gcgcagccac tgggaggaga tgctcaaaaa ccctcgccgg cagattgcca tgtggcacca   1380
gctgcacctg taaccagctg cccagctgcc tcccttcttg gacagccctg acccgtcctc   1440
tgcaacctcc tttctgtgcc cctttcctca ttctgacacc cagaagacag tgacagatgt   1500
gtttgcaagg ctgggatggc tctctcatca tactcttgtt tcttagaaat aagcaagaca   1560
gagcaggaaa tggaatatgc gggtcacact gaggaatgca ttttgctcat ctgtgttatt   1620
gaaggaggtg cttattaaat acagttccta tgcctgtttt ataggtgggg ttaggccaga   1680
tgcagagaaa gctaaatgtg ggaatcatgg atgcaaagaa gaatttggct ttttgaaaaa   1740
caagcatttc aaaaatgatg aaggaagtga aagtatcctg gatcaactcc tagagttaga   1800
gattgcccag gtggaaagaa accttagcca gcgttcaatc aagctcacca tgcagggcag   1860
tcacccggca gttctcaaac tttagcatgt gaagagtcac cagcagattc ctgggctcgc   1920
ctggagacat tcctagtcgg tattcctggt cgaagcccag gagccttcct ttttaacaag   1980
ctgatgtaga gggtggagca ctgtatgtgg agaaattcct tctacaatat tccacacagg   2040
tttttggcca cagtccttga tggagtccca aaaccatggt gcagccagtt ccaatgctgg   2100
```

-continued

```
acacctcaac catcagggtg aaatctgggg cctcagcttt ttaatttaat tattttaatt   2160
cttaatactt taatttgtgc atttcataag ccccctgctc ttggactgaa ttttgtgctt   2220
tttattgaag aattttattg tttttatctt aaaatcagtt tctattatcc ttggggagac   2280
catccctaac aaagtacagg tgggatctcc tgtgagtcat tggctgggtt ctgattgcta   2340
gatgtcacac ccaccagcat caccaaagtg actctgagat agaccggtcc cttctcagcg   2400
ttccagtcac ttcaggagga atttagttat tgacttagtc tatgacatct ggctacatgt   2460
aggtagagaa gaaagacaat tttaaaaagg aaatcaggtc ttttgcaact gtgcctccct   2520
ctgtctgttt tcacttgaat gggtaaataa ccagcagcta ggttttgaat tcctaccttg   2580
ttattctaaa cagatgtcca cattgttaat taaatctaaa ttatgagcct tgctgagtgg   2640
atacggtact tacacctgaa ccaggattcc tgggttctgt tgttgacatt gcccttcagc   2700
acctgtttgg ccagctgtat aagataggac taatgactag gaagcctacc ccaatgaatg   2760
atatactaga tgaaatagtg ttcaaaacct gtaggcactc tctggctaaa aacaaactct   2820
gaggccacca gcagatcatc tttaagctaa gttactattt ttcacctttt tttttagacg   2880
gagttttgct ctttgttgcc caggctggag tgcagtggca cgatctcggc tcactgcaac   2940
ctccgcctcc caagttcaag cgattctcct gtctcagcct cctgggtagc tgggattaca   3000
ggtgcccacc aacatgcctg gctaattttt gtacttttag tagagatggg gtttcaccat   3060
gttggccagg ctggtcttca actccagatc tcaggtgatc taccctcctc ggcctcccaa   3120
agtactggga ttacaggcct gagccaccgc gcccggccta tttttcactt taatttggca   3180
gctgagaatg cccaaaaagt gccagaagca tcgtggcatt tccagaacca tggattctgc   3240
ctttggaccc ctctctatta atattaaaac tctgggcctt cagatgtcac cctaatccac   3300
tgccctaaga cagaatttct ggacaagatg ggtaagggct tcattccttc aacaagtcaa   3360
gtcatacttg gcctctccct gagaatctga gcaggagcct tataacctgt ggtcattatt   3420
ttttcttttct gtacagaaat agaaaagcat tagaaataac ttctaaccat cctctgaaaa   3480
aacagaaaaa atatcgaatc cctctttcat gagaagtctt ttggataatt ggaaaccttc   3540
atcactgagg ttggccagcc cctgccaagt gttgtgtagg caaagcactt gttagtggct   3600
tcctatgaaa tgttttagag atctcttcac catactggtt tcttctcttt ggttggtgtg   3660
ggtaaaagaa aacaaaacat ttcctataag ctgaaagctg accagcattc tcttcttggt   3720
aacatctact actccaacct agaaaatttg gattctagac caaaaatcag gaaacatggc   3780
tccttataaa tctgtgcagc tgccttatag taccatcaaa ggaatttcag gtgggctggg   3840
cggggccccg atcccagaat tatcaactcc acccatcatc atttggtcat gaagcatcct   3900
ttcattcttc ttcttctttt ttttgggggg ggcggggcgg gggagggatc tcaaagtttt   3960
agtcttccag aatccaaatt aaaggttgcc cctgatgggg gccaggttcc gccacagaac   4020
atcttagatg tcagccttga cctcacttag cagggattac agaaatgaga tacattttga   4080
aggagagttg tctgttatgt tcactgtatt ctaagtgcct gggataaagc tgtctcatgg   4140
gtgctccata tatattcata tatatttgtt gagtgaatta atgaattaag agtggctggc   4200
agagtaggca gaaaaagaca ctgcaaatgg cataaaaatt aaagtcctag ctgagttctc   4260
aatggtaaag gcatcagatg tcttagcagt caagctagaa attcatgaca atgagtatta   4320
ctatttgcct aatgacaact cattgctctc catgtaaatg taatcaacag atgaagagaa   4380
tataattgct ctgcttttcc actaaaactc catcttagtg aattttaaat tatccagaga   4440
tgtcaaactg ccaaataaaa atatttcagt agtctttgca tcagcttacc ttgtaccaga   4500
```

-continued

```
aacatttcca atttactatc aaattatagt aactgagcct gtgtgaagta tctcatcatt   4560

ttcgaaagga acaccttgtg tgatgccagt gagcatttct aaaaagggtg tgaggtagag   4620

gtaaaaataa ggtgagagac catttcagaa tgcactgttg ctcaaaaagg tgatctggtt   4680

ctttcttcag agatttctac ggggatagaa aatcgggagt ctgccctcat taatctgtga   4740

ctccacctct tgcatcaaat caatatctat ttgttgagca cttattgatt aagaccttgc   4800

atatgtctgt ccattttgat ttgagataca actttttgtg tgggttgaat gacaaatcac   4860

tccaaacaaa actgggcaca gagaatcagc taggagacca gttattcagg gtccatttct   4920

cttggatgta aaggagtcct gggtaaaatg tggctgtaac ctaaaccaac tagtccttgt   4980

gatttgtttc tgccctctgt gtttcctgtt gtcaaatgct aagtgtgtgt tttgcagtca   5040

tgaactaaag cacaaaaaga tgcatgagac attgtagtca tatgtctggt gtgacacttt   5100

ggagcaaaaa ccttgcagtg gtaaataaaa aatttccaac agggt                   5145


<210> SEQ ID NO 52
<211> LENGTH: 454
<212> TYPE: PRT
<213> ORGANISM: Homo Sapiens

<400> SEQUENCE: 52

Met Phe Leu Ala Gln Arg Ser Leu Cys Ser Leu Ser Gly Arg Ala Lys
1               5                   10                  15

Phe Leu Lys Thr Ile Ser Ser Ser Lys Ile Leu Gly Phe Ser Thr Ser
            20                  25                  30

Ala Lys Met Ser Leu Lys Phe Thr Asn Ala Lys Arg Ile Glu Gly Leu
        35                  40                  45

Asp Ser Asn Val Trp Ile Glu Phe Thr Lys Leu Ala Ala Asp Pro Ser
    50                  55                  60

Val Val Asn Leu Gly Gln Gly Phe Pro Asp Ile Ser Pro Pro Thr Tyr
65                  70                  75                  80

Val Lys Glu Glu Leu Ser Lys Ile Ala Ala Ile Asp Ser Leu Asn Gln
                85                  90                  95

Tyr Thr Arg Gly Phe Gly His Pro Ser Leu Val Lys Ala Leu Ser Tyr
            100                 105                 110

Leu Tyr Glu Lys Leu Tyr Gln Lys Gln Ile Asp Ser Asn Lys Glu Ile
        115                 120                 125

Leu Val Thr Val Gly Ala Tyr Gly Ser Leu Phe Asn Thr Ile Gln Ala
    130                 135                 140

Leu Ile Asp Glu Gly Asp Glu Val Ile Leu Ile Val Pro Phe Tyr Asp
145                 150                 155                 160

Cys Tyr Glu Pro Met Val Arg Met Ala Gly Ala Thr Pro Val Phe Ile
                165                 170                 175

Pro Leu Arg Ser Lys Pro Val Tyr Gly Lys Arg Trp Ser Ser Ser Asp
            180                 185                 190

Trp Thr Leu Asp Pro Gln Glu Leu Glu Ser Lys Phe Asn Ser Lys Thr
        195                 200                 205

Lys Ala Ile Ile Leu Asn Thr Pro His Asn Pro Leu Gly Lys Val Tyr
    210                 215                 220

Asn Arg Glu Glu Leu Gln Val Ile Ala Asp Leu Cys Ile Lys Tyr Asp
225                 230                 235                 240

Thr Leu Cys Ile Ser Asp Glu Val Tyr Glu Trp Leu Val Tyr Ser Gly
                245                 250                 255
```

```
Asn Lys His Leu Lys Ile Ala Thr Phe Pro Gly Met Trp Glu Arg Thr
            260                 265                 270

Ile Thr Ile Gly Ser Ala Gly Lys Thr Phe Ser Val Thr Gly Trp Lys
        275                 280                 285

Leu Gly Trp Ser Ile Gly Pro Asn His Leu Ile Lys His Leu Gln Thr
    290                 295                 300

Val Gln Gln Asn Thr Ile Tyr Thr Cys Ala Thr Pro Leu Gln Glu Ala
305                 310                 315                 320

Leu Ala Gln Ala Phe Trp Ile Asp Ile Lys Arg Met Asp Asp Pro Glu
                325                 330                 335

Cys Tyr Phe Asn Ser Leu Pro Lys Glu Leu Glu Val Lys Arg Asp Arg
            340                 345                 350

Met Val Arg Leu Leu Glu Ser Val Gly Leu Lys Pro Ile Val Pro Asp
        355                 360                 365

Gly Gly Tyr Phe Ile Ile Ala Asp Val Ser Leu Leu Asp Pro Asp Leu
    370                 375                 380

Ser Asp Met Lys Asn Asn Glu Pro Tyr Asp Tyr Lys Phe Val Lys Trp
385                 390                 395                 400

Met Thr Lys His Lys Lys Leu Ser Ala Ile Pro Val Ser Ala Phe Cys
                405                 410                 415

Asn Ser Glu Thr Lys Ser Gln Phe Glu Lys Phe Val Arg Phe Cys Phe
            420                 425                 430

Ile Lys Lys Asp Ser Thr Leu Asp Ala Ala Glu Glu Ile Ile Lys Ala
        435                 440                 445

Trp Ser Val Gln Lys Ser
    450
```

<210> SEQ ID NO 53
<211> LENGTH: 1975
<212> TYPE: DNA
<213> ORGANISM: Homo Sapiens

<400> SEQUENCE: 53

```
caaaaaaaca cccctcatcc agtctcttcc agcctagaga tcctggccta cccctccgcc      60

aaagcgcgca ctgagtgcaa accccagagt caatccctgt cccggctccg ccccccgcgt     120

ccgaatcccg cccagccggg ccctcaagcc cagtcgggac tcgagcctag ggaggcgagg     180

ttcccgcacc ggatagcatg tttttggccc agaggagcct ctgctctctt agcggtagag     240

caaaattcct gaagacaatt tcttcttcca aaatcctcgg attctctact tctgctaaaa     300

tgtcactgaa attcacaaat gcaaaacgga ttgaaggact tgatagtaat gtgtggattg     360

aatttaccaa attggctgca gacccttctg ttgtgaatct tggccaaggc tttccagata     420

tatcccctcc tacatatgta aaagaagaat tatcaaagat tgcagcaatc gatagcctga     480

atcagtatac acgaggcttt ggccatccat cacttgtgaa agctctgtcc tatctgtatg     540

aaaagcttta tcaaaagcaa attgattcaa ataaagaaat ccttgtgaca gtaggagcat     600

atggatctct ttttaacacc attcaagcat taattgatga gggagatgaa gtcatactaa     660

tagtgccttt ctatgactgc tatgagccca tggtgagaat ggctggagca acacctgttt     720

ttattcccct gagatctaaa cctgtttatg gaaaaagatg gtctagttct gactggacat     780

tagatcctca agaactggaa agtaaattta attccaaaac caaagctatt atactaaata     840

ctccacataa cccacttggc aaggtgtata acagagagga actgcaagta attgctgacc     900

tttgcatcaa atatgacaca ctctgcatca gtgatgaggt ttatgaatgg cttgtatatt     960
```

-continued

```
ctggaaataa gcacttaaaa atagctactt ttccaggtat gtgggagaga acaataacaa   1020

taggaagtgc tggaaagact ttcagtgtaa ctggctggaa gcttggctgg tccattggtc   1080

caaatcattt gataaaacat ttacagacag ttcaacaaaa cacgatttat acttgtgcaa   1140

ctcctttaca ggaagccttg gctcaagctt tctggattga catcaagcgc atggatgacc   1200

cagaatgtta ctttaattct ttgccaaaag agttagaagt aaaaagagat cggatggtac   1260

gtttacttga aagtgttggc ctaaaaccca tagttcctga tggaggatac ttcatcatcg   1320

ctgatgtgtc tttgctagat ccagacctct ctgatatgaa gaataatgag ccttatgact   1380

ataagtttgt gaaatggatg actaaacata agaaactatc agccatcccc gtttcagcat   1440

tctgtaactc agagactaaa tcacagtttg agaagtttgt gcgtttttgc ttcattaaaa   1500

aagacagcac actggatgct gctgaagaaa tcatcaaggc atggagtgta cagaagtctt   1560

gatttgtgca gaatggatta atgtttctgt tagatgacct agtatggaat tgttacttag   1620

tgctgccacc tgctggatgt taaaaggtat ttcagtacaa ctggaattta aatatttcca   1680

ttgtttttcc aaagcagtta acccaactcc taacaacatt ttcgggggat ctgacctttt   1740

ttttccagtt gaaatgtatt aacacacctt ccacaatcat tttataagag tcagcataac   1800

atagtggata agaactgtga gatgtttaac ctctcagtaa ctcggttctc tcattataaa   1860

ataggaataa aatcagtacc tgtttcatat gaaggtcgtt tctgagaatt aaatggacta   1920

atgtatgcaa aaagcctggc aaacaataaa cactcatctg actttaaaaa aaaaa        1975
```

<210> SEQ ID NO 54
<211> LENGTH: 274
<212> TYPE: PRT
<213> ORGANISM: Homo Sapiens

<400> SEQUENCE: 54

```
Met Pro Arg Asn Leu Leu Tyr Ser Leu Leu Ser Ser His Leu Ser Pro
 1               5                  10                  15

His Phe Ser Thr Ser Val Thr Ser Ala Lys Val Ala Val Asn Gly Val
            20                  25                  30

Gln Leu His Tyr Gln Gln Thr Gly Glu Gly Asp His Ala Val Leu Leu
        35                  40                  45

Leu Pro Gly Met Leu Gly Ser Gly Glu Thr Asp Phe Gly Pro Gln Leu
    50                  55                  60

Lys Asn Leu Asn Lys Lys Leu Phe Thr Val Val Ala Trp Asp Pro Arg
65                  70                  75                  80

Gly Tyr Gly His Ser Arg Pro Pro Asp Arg Asp Phe Pro Ala Asp Phe
                85                  90                  95

Phe Glu Arg Asp Ala Lys Asp Ala Val Asp Leu Met Lys Ala Leu Lys
            100                 105                 110

Phe Lys Lys Val Ser Leu Leu Gly Trp Ser Asp Gly Gly Ile Thr Ala
        115                 120                 125

Leu Ile Ala Ala Ala Lys Tyr Pro Ser Tyr Ile His Lys Met Val Ile
    130                 135                 140

Trp Gly Ala Asn Ala Tyr Val Thr Asp Glu Asp Ser Met Ile Tyr Glu
145                 150                 155                 160

Gly Ile Arg Asp Val Ser Lys Trp Ser Glu Arg Thr Arg Lys Pro Leu
                165                 170                 175

Glu Ala Leu Tyr Gly Tyr Asp Tyr Phe Ala Arg Thr Cys Glu Lys Trp
            180                 185                 190

Val Asp Gly Ile Arg Gln Phe Lys His Leu Pro Asp Gly Asn Ile Cys
```

-continued

```
        195                 200                 205

Arg His Leu Leu Pro Arg Val Gln Cys Pro Ala Leu Ile Val His Gly
    210                 215                 220

Glu Lys Asp Pro Leu Val Pro Arg Phe His Ala Asp Phe Ile His Lys
225                 230                 235                 240

His Val Lys Gly Ser Arg Leu His Leu Met Pro Glu Gly Lys His Asn
                245                 250                 255

Leu His Leu Arg Phe Ala Asp Glu Phe Asn Lys Leu Ala Glu Asp Phe
            260                 265                 270

Leu Gln
```

<210> SEQ ID NO 55
<211> LENGTH: 1521
<212> TYPE: DNA
<213> ORGANISM: Homo Sapiens

<400> SEQUENCE: 55

```
ggatccacgt cccacgggcc ggacccgcgg ccgcgttcgg aaatcagcct gagcctgagt     60

accgctaagg ctttaatcac gggtcccgag agccctaagt cttctctttg cttgctgatc    120

tcgtacctta atgtgcaaaa gaatcacgtt gggaactgaa aattcagaat cctgggcctc    180

actcccagag gatctgatct acatgtgtgg agatgcccag gaatctgctt tattctcttt    240

tgtcctccca cctgtccccc catttcagca cctcggtaac ctctgccaaa gtggctgtga    300

atggcgttca gctgcattac cagcagactg gagagggaga tcacgcagtc ctgctacttc    360

ctgggatgtt aggaagtgga gagactgatt ttggacctca gctcaagaac ctcaataaga    420

agctcttcac ggtggtcgcc tgggatcctc gaggctatgg acattccagg cccccagatc    480

gcgatttccc agcagacttt tttgaaaggg atgcaaaaga tgctgttgat ttgatgaagg    540

cgctgaagtt taagaaggtt tctctgctgg ggtggagtga tgggggcata accgcactca    600

ttgctgctgc aaaatatcca tcttacatcc acaagatggt gatctggggc gccaacgcct    660

acgtcactga cgaagacagc atgatatatg agggcatccg agatgtttcc aaatggagtg    720

agagaacaag aaagcctcta gaagccctct atgggtatga ctactttgcc agaacctgtg    780

aaaagtgggt ggatggcata agacagttta aacatctccc agatggtaac atctgccggc    840

acctgctgcc ccgggtccag tgccccgcct tgattgtgca cggtgagaag gatcctctgg    900

tcccacggtt tcatgccgac ttcattcata agcacgtgaa aggctcacgg ctgcatttga    960

tgccagaagg caaacacaac ctgcatttgc gttttgcaga tgaattcaac aagttagcag   1020

aagacttcct acaatgagaa tgcacactcc agtcttggtg gttccttcgt gtggggcttg   1080

atcgtgttgc tgcctgttaa catgatgcct ttgaaactct ccgcctttga aactttctac   1140

ccctcccttc aatcttatcc taaccaaatg agaataatga catattgaaa acagcctcta   1200

gcttcaggct gggcacggtg gctcacagct ataatctcag cactttggga ggctgaggtg   1260

ggagaattgc ctgagcccag gagttcaaga ccagcttgtg caatataggg agactccggc   1320

tctacaaaaa agagtttttc aaaattagcc aggcgaagtg gcacacatct gtggtcccag   1380

gtgctcagga agctgaggtg ggaggatcac ttgagcccaa ttcaaagctg cagtgagctg   1440

taattgcatc actgcactcc aacctgggca acagagtaag accttgtctt aaaaaaaaat   1500

aaaaacataa aaaaaaaaaa a                                             1521
```

<210> SEQ ID NO 56
<211> LENGTH: 1521

-continued

```
<212> TYPE: DNA
<213> ORGANISM: Homo Sapiens

<400> SEQUENCE: 56

ggatccacgt cccacgggcc ggacccgcgg ccgcgttcgg aaatcagcct gagcctgagt      60
accgctaagg ctttaatcac gggtcccgag agccctaagt cttctctttg cttgctgatc     120
tcgtacctta atgtgcaaaa gaatcacgtt gggaactgaa aattcagaat cctgggcctc     180
actcccagag gatctgatct acatgtgtgg agatgcccag gaatctgctt tattctcttt     240
tgtcctccca cctgtccccc catttcagca cctcggtaac ctctgccaaa gtggctgtga     300
atggcgttca gctgcattac cagcagactg gagagggaga tcacgcagtc ctgctacttc     360
ctgggatgtt aggaagtgga gagactgatt ttggacctca gctcaagaac ctcaataaga     420
agctcttcac ggtggtcgcc tgggatcctc gaggctatgg acattccagg cccccagatc     480
gcgatttccc agcagacttt tttgaaaggg atgcaaaaga tgctgttgat ttgatgaagg     540
cgctgaagtt taagaaggtt tctctgctgg ggtggagtga tgggggcata accgcactca     600
ttgctgctgc aaaatatcca tcttacatcc acaagatggt gatctggggc gccaacgcct     660
acgtcactga cgaagacagc atgatatatg agggcatccg agatgtttcc aaatggagtg     720
agagaacaag aaagcctcta gaagccctct atgggtatga ctactttgcc agaacctgtg     780
aaaagtgggt ggatggcata agacagttta aacatctccc agatggtaac atctgccggc     840
acctgctgcc ccgggtccag tgccccgcct tgattgtgca cggtgagaag gatcctctgg     900
tcccacggtt tcatgccgac ttcattcata agcacgtgaa aggctcacgg ctgcatttga     960
tgccagaagg caaacacaac ctgcatttgc gttttgcaga tgaattcaac aagttagcag    1020
aagacttcct acaatgagaa tgcacactcc agtcttggtg gttccttcgt gtggggcttg    1080
atcgtgttgc tgcctgttaa catgatgcct ttgaaactct ccgcctttga aactttctac    1140
ccctcccttc aatcttatcc taaccaaatg agaataatga catattgaaa acagcctcta    1200
gcttcaggct gggcacggtg gctcacagct ataatctcag cactttggga ggctgaggtg    1260
ggagaattgc ctgagcccag gagttcaaga ccagcttgtg caatataggg agactccggc    1320
tctacaaaaa agagtttttc aaaattagcc aggcgaagtg gcacacatct gtggtcccag    1380
gtgctcagga agctgaggtg ggaggatcac ttgagcccaa ttcaaagctg cagtgagctg    1440
taattgcatc actgcactcc aacctgggca acagagtaag accttgtctt aaaaaaaaat    1500
aaaaacataa aaaaaaaaaa a                                              1521
```